(12) United States Patent
Fukushima et al.

(10) Patent No.: US 12,216,401 B2
(45) Date of Patent: Feb. 4, 2025

(54) SULFONIUM SALT, CHEMICALLY AMPLIFIED RESIST COMPOSITION, AND PATTERNING PROCESS

(71) Applicant: Shin-Etsu Chemical Co., Ltd., Tokyo (JP)

(72) Inventors: Masahiro Fukushima, Joetsu (JP); Kazuhiro Katayama, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 238 days.

(21) Appl. No.: 17/487,201

(22) Filed: Sep. 28, 2021

(65) Prior Publication Data

US 2022/0107560 A1  Apr. 7, 2022

(30) Foreign Application Priority Data

Oct. 1, 2020 (JP) .................. 2020-166632

(51) Int. Cl.

| | | |
|---|---|---|
| *G03F 7/004* | (2006.01) | |
| *C07C 309/12* | (2006.01) | |
| *C07C 381/12* | (2006.01) | |
| *C07D 307/93* | (2006.01) | |
| *C08F 220/22* | (2006.01) | |
| *C08F 220/24* | (2006.01) | |
| *C08F 220/38* | (2006.01) | |
| *G03F 7/038* | (2006.01) | |
| *G03F 7/039* | (2006.01) | |
| *G03F 7/20* | (2006.01) | |
| *G03F 7/30* | (2006.01) | |

(52) U.S. Cl.
CPC .......... *G03F 7/0045* (2013.01); *C07C 309/12* (2013.01); *C07C 381/12* (2013.01); *C07D 307/93* (2013.01); *C08F 220/22* (2013.01); *C08F 220/24* (2013.01); *C08F 220/382* (2020.02); *G03F 7/038* (2013.01); *G03F 7/039* (2013.01); *G03F 7/2041* (2013.01); *G03F 7/30* (2013.01); *C07C 2603/74* (2017.05)

(58) Field of Classification Search
CPC .... G03F 7/0045; G03F 7/0392; G03F 7/0397; G03F 7/30; G03F 7/2041; C07C 381/12; C07C 303/32; C07C 309/06; C08F 220/382; C08F 220/22; C08F 220/24
See application file for complete search history.

(56) References Cited

U.S. PATENT DOCUMENTS

| | | | |
|---|---|---|---|
| 6,215,021 B1 | 4/2001 | Shreeve et al. | |
| 11,746,085 B2 * | 9/2023 | Qian | C07C 381/12 |
| | | | 430/270.1 |
| 2011/0177453 A1 | 7/2011 | Masubuchi et al. | |
| 2011/0269070 A1 | 11/2011 | Aqad et al. | |
| 2015/0017586 A1 * | 1/2015 | Hatakeyama | G03F 7/38 |
| | | | 430/326 |
| 2015/0338732 A1 * | 11/2015 | Yoshino | G03F 7/11 |
| | | | 430/325 |
| 2016/0349619 A1 | 12/2016 | Tsubaki et al. | |
| 2017/0038685 A1 | 2/2017 | Goto et al. | |
| 2020/0249571 A1 | 8/2020 | Fujiwara et al. | |
| 2021/0188770 A1 | 6/2021 | Fujiwara et al. | |

FOREIGN PATENT DOCUMENTS

| | | | | |
|---|---|---|---|---|
| CN | 111187130 A | | 5/2020 | |
| CN | 110283274 | * | 8/2021 | ............. G03F 7/004 |
| JP | 2007-145797 A | | 6/2007 | |
| JP | 2008-281974 A | | 11/2008 | |
| JP | 2008-281975 A | | 11/2008 | |
| JP | 4554665 B2 | | 9/2010 | |
| JP | 5061484 B2 | | 10/2012 | |
| JP | 2014-153432 A | | 8/2014 | |
| JP | 5573098 B2 | | 8/2014 | |
| JP | 2015-63472 A | | 4/2015 | |
| JP | 2016-147879 A | | 8/2016 | |
| JP | 6461919 B2 | | 1/2019 | |
| JP | 2020-126143 A | | 8/2020 | |
| JP | 2021-091666 A | | 6/2021 | |
| TW | 201026653 A | | 7/2010 | |

(Continued)

OTHER PUBLICATIONS

"Introduction to Fluorochemistry 2010—basic and advanced application", Japan Society for the Promotion of Science, 2010, Fluorochemistry No. 155 Committee, Sankyo Publishing, pp. 488-491, cited in Specification, w/English partial translation (9 pages).
Office Action dated Sep. 21, 2022, issued in counterpart TW Application No. 110136144. (7 pages).
Office Action date Aug. 22, 2023, issued in counterpart JP Application No. 2020-166632, with English Translation. (8 pages).
Magnier, Emmanuel et al., "Straightforward One-Pot Synthesis of Trifluoromethyl Sulfonium Salts", Angewandte Chemie. InterScience. Ed., year. 2006, 45, 8, pp. 1279-1282; Cited in KR Office Action dated Jul. 19, 2023.
Office Action dated Jul. 19, 2023, issued in counterpart to KR Application No. 10-2021-0129001, with English Translation. (8 pages).

*Primary Examiner* — John S. Chu
(74) *Attorney, Agent, or Firm* — WHDA, LLP

(57) ABSTRACT

A sulfonium salt having formula (1) is novel. A chemically amplified resist composition comprising the sulfonium salt as a PAG has advantages including solvent solubility and improved lithography properties such as EL and LWR when processed by photolithography using high-energy radiation such as KrF or ArF excimer laser, EB or EUV.

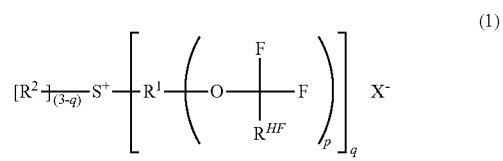

(1)

19 Claims, 5 Drawing Sheets

(56) References Cited

FOREIGN PATENT DOCUMENTS

| | | | |
|---|---|---|---|
| WO | WO-2008007539 A1 * | 1/2008 | ........... B41C 1/1008 |
| WO | WO-2016051985 A1 * | 4/2016 | ................ C08F 8/12 |

* cited by examiner

SULFONIUM SALT, CHEMICALLY AMPLIFIED RESIST COMPOSITION, AND PATTERNING PROCESS

CROSS-REFERENCE TO RELATED APPLICATION

This non-provisional application claims priority under 35 U.S.C. § 119(a) on Patent Application No. 2020-166632 filed in Japan on Oct. 1, 2020, the entire contents of which are hereby incorporated by reference.

TECHNICAL FIELD

This invention relates to a sulfonium salt, a chemically amplified resist composition, and a pattern forming process.

BACKGROUND ART

While a number of recent efforts are being made to achieve a finer pattern rule in the drive for higher integration and operating speeds in LSIs, DUV and EUV lithography processes are thought to hold particular promise as the next generation in microfabrication technology. In particular, photolithography using an ArF excimer laser is requisite to the micropatterning technique capable of achieving a feature size of 0.13 µm or less.

The ArF lithography started partial use from the fabrication of 130-nm node devices and became the main lithography since 90-nm node devices. Although lithography using $F_2$ laser (wavelength 157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Non-Patent Document 1. The ArF immersion lithography is now implemented on the commercial stage. The immersion lithography requires a resist material which is substantially insoluble in water.

In the photolithography using an ArF excimer laser (wavelength 193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polymers of acrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Recently a highlight is put on the negative tone resist adapted for organic solvent development as well as the positive tone resist adapted for alkaline development. It would be desirable if a very fine hole pattern, which is not achievable with the positive tone, is resolvable through negative tone exposure. To this end, a positive resist material featuring a high resolution is subjected to organic solvent development to form a negative pattern. An attempt to double a resolution by combining two developments, alkali development and organic solvent development is under study. As the ArF resist material for negative tone development with organic solvent, positive ArF resist compositions of the prior art design may be used. Such pattern forming processes are described in Patent Documents 1 to 3.

To meet the current rapid progress of microfabrication technology, development efforts are put on not only the process, but also the resist material. Studies have also been made on photoacid generators (PAGs). Commonly used are sulfonium salts of triphenylsulfonium cation with perfluoroalkanesulfonic acid anion. These salts generate perfluoroalkanesulfonic acids, especially perfluorooctanesulfonic acid (PFOS), which are considered problematic with respect to their non-degradability, biological concentration and toxicity. It is rather restricted to apply these salts to the resist material. Instead, PAGs capable of generating perfluorobutanesulfonic acid are currently used, but are awkward to achieve a high resolution because of substantial diffusion of the generated acid in the resist material. To address the problem, partially fluorinated alkane sulfonic acids and salts thereof are developed. For instance, Patent Document 1 describes the prior art PAGs capable of generating $\alpha,\alpha$-difluoroalkanesulfonic acid, such as di(4-tert-butylphenyl) iodonium 1,1-difluoro-2-(1-naphthyl)ethanesulfonate and PAGs capable of generating $\alpha,\alpha,\beta,\beta$-tetrafluoroalkanesulfonic acid. Despite a reduced degree of fluorine substitution, these PAGs still have the following problems. Since they do not have a decomposable substituent group such as ester structure, they are unsatisfactory from the aspect of environmental safety or ease of decomposition. The molecular design to change the size of alkanesulfonic acid is limited. Fluorine-containing starting reactants are expensive.

As the circuit line width is reduced, the degradation of contrast by acid diffusion becomes more serious for the resist material. The reason is that the pattern feature size is approaching the diffusion length of acid. This invites a lowering of mask fidelity and a degradation of pattern rectangularity because a dimensional shift on wafer (known as mask error factor (MEF)) relative to a dimensional shift on mask is exaggerated. Accordingly, to gain more benefits from a reduction of exposure light wavelength and an increase of lens NA, the resist material is required to increase a dissolution contrast or restrain acid diffusion, as compared with the prior art materials. One approach is to lower the bake temperature for suppressing acid diffusion and hence, improving MEF. A low bake temperature, however, inevitably leads to a low sensitivity.

Incorporating a bulky substituent or polar group into PAG is effective for suppressing acid diffusion. Patent Document 4 discloses a PAG capable of generating 2-acyloxy-1,1,3,3,3-pentafluoropropane-1-sulfonic acid which is fully soluble and stable in resist solvents and allows for a wide span of molecular design. In particular, a PAG having a bulky substituent incorporated therein or capable of generating 2-(1-adamantyloxy)-1,1,3,3,3-pentafluoropropane-1-sulfonic acid is characterized by slow acid diffusion. Patent Documents 5 to 7 describe PAGs having fused ring lactone, sultone or thiolactone incorporated as the polar group. Although some improvement in performance is observed due to the acid diffusion suppressing effect of the polar group incorporated, they are still insufficient in precise control of acid diffusion. Their lithography performance is unsatisfactory when evaluated totally in terms of MEF, pattern profile and sensitivity.

Incorporating a polar group into an anion of PAG is effective for suppressing acid diffusion, but disadvantageous from the standpoint of solvent solubility. Attempting to improve solvent solubility, Patent Documents 8 and 9 propose to incorporate an alicyclic group into a cation moiety of a PAG. Specifically, a cyclohexane ring or adamantane ring is incorporated. While incorporating such an alicyclic group achieves an improvement in solubility, a relatively large number of carbon atoms is necessary to insure a satisfactory solubility. This means that the molecular structure of PAG becomes bulky, causing to degrade lithography performance factors such as LWR and CDU in forming small-size patterns.

Fluorine atom is sterically smaller next to hydrogen atom and hydrophobic and lipophilic. Among others, a trifluoromethoxy group is known as a substituent group which is highly hydrophobic as compared with a methoxy group (Non-Patent Document 1). It is thus believed that incorporating a trifluoromethoxy group into a cation of a PAG provides a smaller steric contribution than the alicyclic group, imparting a satisfactory solvent solubility. PAG having such a substituent group incorporated in its cation is not known in the art. To meet the demand for further miniaturization, it is crucial to develop a novel PAG. There is the desire to have a PAG capable of meeting fully suppressed acid diffusion and high solvent solubility.

CITATION LIST

Patent Document 1: JP-A 2008-281974
Patent Document 2: JP-A 2008-281975
Patent Document 3: JP 4554665
Patent Document 4: JP-A 2007-145797
Patent Document 5: JP 5061484
Patent Document 6: JP-A 2016-147879
Patent Document 7: JP-A 2015-063472
Patent Document 8: JP 5573098
Patent Document 9: JP 6461919
Non-Patent Document 1: "Introduction to Fluorochemistry 2010—basic and advanced application", Japan Society for the Promotion of Science, Fluorochemistry No. 155 Committee, Sankyo Publishing, 2010

DISCLOSURE OF INVENTION

While it is recently demanded to form resist patterns at a high resolution, a resist composition using a conventional PAG of sulfonium salt type shows an uneven acid generation behavior because the salt compound has an insufficient solvent solubility to prevent agglomeration in a solvent. As a result, lithography performance factors such as contrast and LWR are degraded. Possible precipitation during storage is another concern.

An object of the invention is to provide a novel sulfonium salt and a chemically amplified resist composition comprising the same as a photoacid generator, the resist composition having a high solvent solubility and a high sensitivity and being improved in lithography properties such as EL and LWR when processed by photolithography using high-energy radiation such as KrF or ArF excimer laser, EB or EUV; and a pattern forming process using the resist composition.

The inventors have found that a sulfonium salt of specific structure has a high solvent solubility and that a chemically amplified resist composition comprising the sulfonium salt as a photoacid generator has a high sensitivity, is improved in lithography properties such as EL and LWR, and thus best suited for precise micropatterning.

In one aspect, the invention provides a sulfonium salt having the formula (1).

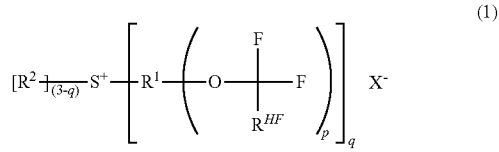

Herein p is an integer of 1 to 5, q is an integer of 1 to 3. $R^{HF}$ is hydrogen or fluorine. $R^1$ is a $C_1$-$C_{20}$ (p+1)-valent hydrocarbon group which may contain a heteroatom. $R^2$ is a $C_1$-$C_{20}$ hydrocarbyl group which may contain a heteroatom. In case of q=1, any two of $R^1$ and two $R^2$ may bond together to form a ring with the sulfur atom to which they are attached; in case of q=2, any two of two $R^1$ and $R^2$ may bond together to form a ring with the sulfur atom to which they are attached; in case of q=3, any two of three $R^1$ may bond together to form a ring with the sulfur atom to which they are attached. $X^-$ is a non-nucleophilic anion.

In a preferred embodiment, the sulfonium salt has the formula (1A):

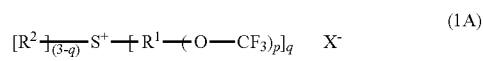

wherein $R^1$, $R^2$, p, q, and $X^-$ are as defined above.

In a more preferred embodiment, the sulfonium salt has the formula (1B):

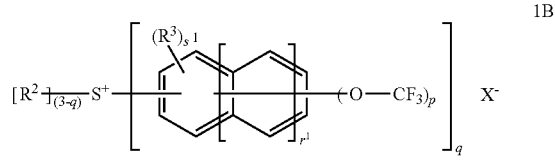

wherein $R^2$, p, q, and $X^-$ are as defined above, $R^3$ is a $C_1$-$C_{20}$ hydrocarbyl group which may contain a heteroatom, $r^1$ is an integer of 0 to 2, and $s^1$ is an integer of 0 to $(2r^1+4)$.

In a further preferred embodiment, the sulfonium salt has the formula (1C):

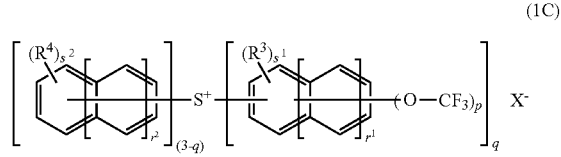

wherein $R^3$, p, q, $r^1$, $s^1$, and $X^-$ are as defined above, $R^4$ is a $C_1$-$C_{20}$ hydrocarbyl group which may contain a heteroatom, $r^2$ is an integer of 0 to 2, and $s^2$ is an integer of 0 to $(2r^2+4)$.

In a preferred embodiment, $X^-$ is an anion selected from the formulae (2A) to (2D).

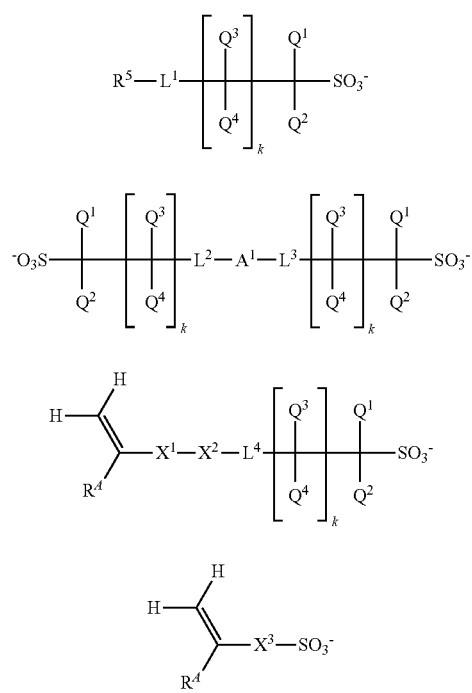

(2A)

(2B)

(2C)

(2D)

Herein $Q^1$ and $Q^2$ are each independently fluorine or a $C_1$-$C_6$ fluorinated alkyl group; $Q^3$ and $Q^4$ are each independently hydrogen, fluorine or a $C_1$-$C_6$ fluorinated alkyl group; k is an integer of 0 to 4; $L^1$ to $L^4$ are each independently a single bond, ether bond, ester bond, sulfonic ester bond, carbonate bond or carbamate bond; $R^5$ is a $C_1$-$C_{30}$ hydrocarbyl group which may contain a heteroatom; $A^1$ is a $C_1$-$C_{30}$ hydrocarbylene group which may contain a heteroatom; $R^4$ is each independently hydrogen, fluorine, methyl or trifluoromethyl.

$X^1$ is a single bond, phenylene, naphthylene or (backbone)-C(=O)—O—$X^{11}$—, wherein $X^{11}$ is a $C_1$-$C_{10}$ aliphatic hydrocarbylene group which may contain a hydroxy moiety, ether bond, ester bond or lactone ring, or phenylene or naphthylene group. $X^2$ is a single bond or —$X^{21}$—C(=O)—O—, wherein $X^{21}$ is a $C_1$-$C_{20}$ hydrocarbylene group which may contain a heteroatom. $X^3$ is a single bond, methylene, ethylene, phenylene, fluorinated phenylene, trifluoromethyl-substituted phenylene, —O—$X^{31}$—, —C(=O)—O—$X^{31}$—, or —C(=O)—NH—$X^{31}$—, wherein $X^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety.

In a more preferred embodiment, $X^-$ is an anion selected from the formulae (2A-1) to (2C-1):

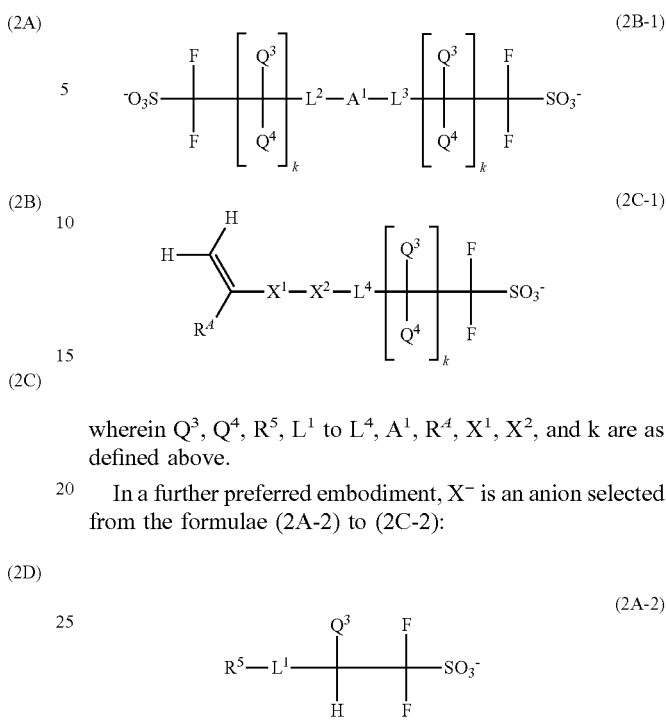

(2A-1)

(2B-1)

(2C-1)

wherein $Q^3$, $Q^4$, $R^5$, $L^1$ to $L^4$, $A^1$, $R^4$, $X^1$, $X^2$, and k are as defined above.

In a further preferred embodiment, $X^-$ is an anion selected from the formulae (2A-2) to (2C-2):

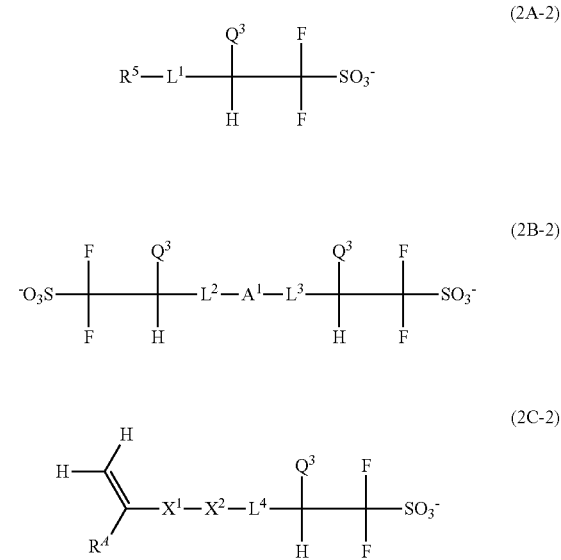

(2A-2)

(2B-2)

(2C-2)

wherein $Q^3$, $R^5$, $L^1$ to $L^4$, $A^1$, $R^4$, $X^1$, and $X^2$ are as defined above.

Also provided is a photoacid generator comprising the sulfonium salt defined above.

In another aspect, the invention provides a chemically amplified resist composition comprising the photoacid generator defined above and a base polymer comprising repeat units having the formula (a1) or (a2).

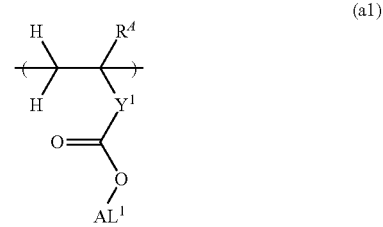

(a1)

(a2)

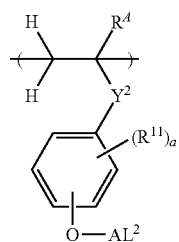

(a4)

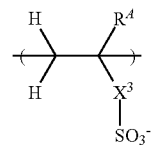

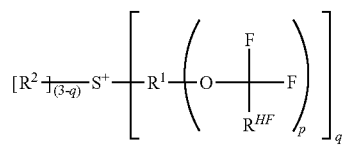

Herein $R^A$ is each independently hydrogen, fluorine, methyl or trifluoromethyl. $Y^1$ is a single bond, phenylene, naphthylene or (backbone)-C(=O)—O—$Y^{11}$—, wherein $Y^{11}$ is a $C_1$-$C_{10}$ alkanediyl group which may contain a hydroxy moiety, ether bond, ester bond or lactone ring, or phenylene or naphthylene group. $Y^2$ is a single bond or (backbone)-C(=O)—O—. $AL^1$ and $AL^2$ are each independently an acid labile group. $R^{11}$ is a $C_1$-$C_{20}$ hydrocarbyl group which may contain a heteroatom, and a is an integer of 0 to 4.

Another embodiment of the invention is a chemically amplified resist composition comprising a base polymer comprising repeat units having the formula (a1) or (a2) and repeat units having the formula (a3) or (a4).

Herein p is an integer of 1 to 5, q is an integer of 1 to 3. $R^{HF}$ is hydrogen or fluorine. $R^1$ is a $C_1$-$C_{20}$ (p+1)-valent hydrocarbon group which may contain a heteroatom. $R^2$ is a $C_1$-$C_{20}$ hydrocarbyl group which may contain a heteroatom. In case of q=1, any two of $R^1$ and two $R^2$ may bond together to form a ring with the sulfur atom to which they are attached; in case of q=2, any two of two $R^1$ and $R^2$ may bond together to form a ring with the sulfur atom to which they are attached; in case of q=3, any two of three $R^1$ may bond together to form a ring with the sulfur atom to which they are attached. $L^4$ is each independently a single bond, ether bond, ester bond, sulfonic ester bond, carbonate bond or carbamate bond. $R^A$ is each independently hydrogen, fluorine, methyl or trifluoromethyl.

$X^1$ is a single bond, phenylene, naphthylene or (backbone)-C(=O)—O—$X^{11}$—, wherein $X^{11}$ is a $C_1$-$C_{10}$ aliphatic hydrocarbylene group which may contain a hydroxy moiety, ether bond, ester bond or lactone ring, or phenylene or naphthylene group. $X^2$ is a single bond or —$X^{21}$—C(=O)—O—, wherein $X^{21}$ is a $C_1$-$C_{20}$ hydrocarbylene group which may contain a heteroatom. $X^3$ is a single bond, methylene, ethylene, phenylene, fluorinated phenylene, trifluoromethyl-substituted phenylene, —O—$X^{31}$—, —C(=O)—O—$X^{31}$—, or —C(=O)—NH—$X^{31}$—, wherein $X^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety, and k is an integer of 0 to 4.

In a preferred embodiment, the base polymer further comprises repeat units having the formula (b1) or (b2).

(a1)

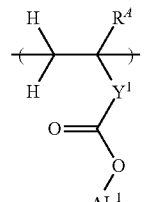

(a2)

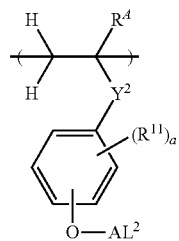

Herein $R^A$, $Y^1$, $Y^2$, $AL^1$, $AL^2$, $R^{11}$, and a are as defined above.

(a3)

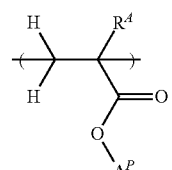

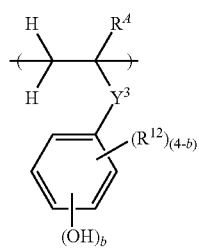

(b1)

(b2)

Herein $R^A$ is each independently hydrogen, fluorine, methyl or trifluoromethyl. $A^P$ is hydrogen or a polar group containing at least one structure selected from the group consisting of hydroxy, cyano, carbonyl, carboxy, ether bond, ester bond, sulfonic ester bond, carbonate bond, lactone ring, sultone ring and carboxylic anhydride. $Y^3$ is a single bond or (backbone)-C(=O)—O—. $R^{12}$ is halogen, cyano, a $C_1$-$C_{20}$ hydrocarbyl group which may contain a heteroatom, a $C_1$-$C_{20}$ hydrocarbyloxy group which may contain a heteroatom, or a $C_2$-$C_{20}$ hydrocarbylcarbonyl group which may contain a heteroatom, and b is an integer of 1 to 4.

In a further preferred embodiment, the base polymer further comprises repeat units of at least one type selected from repeat units having the formulae (c1) to (c3).

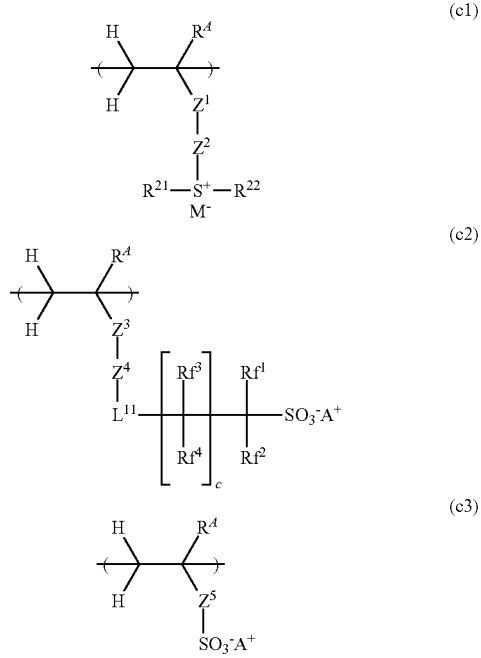

Herein $R^A$ is each independently hydrogen, fluorine, methyl or trifluoromethyl. $Z^1$ is a single bond or phenylene group. $Z^2$ is —C(=O)—O—$Z^{21}$—, —C(=O)—NH—$Z^{21}$—, or —O—$Z^1$—, wherein $Z^{21}$ is a $C_1$-$C_6$ aliphatic hydrocarbylene group, phenylene group or a divalent group obtained by combining the foregoing, which may contain a carbonyl moiety, ester bond, ether bond or hydroxy moiety. $Z_3$ is a single bond, phenylene, naphthylene, or (backbone)-C(=O)—O—$Z^{31}$—, wherein $Z^{31}$ is a $C_1$-$C_{10}$ aliphatic hydrocarbylene group which may contain a hydroxy moiety, ether bond, ester bond or lactone ring, or phenylene or naphthylene group. $Z^4$ is a single bond or —$Z^{41}$—C(=O)—O—, wherein $Z^{41}$ is a $C_1$-$C_{20}$ hydrocarbylene group which may contain a heteroatom. $Z^5$ is a single bond, methylene, ethylene, phenylene, fluorinated phenylene, trifluoromethyl-substituted phenylene, —C(=O)—O—$Z^{51}$—, —C(=O)—NH—$Z^{51}$—, or —O—$Z^{51}$—, wherein $Z^{51}$ is a $C_1$-$C_6$ aliphatic hydrocarbylene group, phenylene group, fluorinated phenylene group or trifluoromethyl-substituted phenylene group, which may contain a carbonyl moiety, ester bond, ether bond or hydroxy moiety. $R^{21}$ and $R^{22}$ are each independently a $C_1$-$C_{20}$ hydrocarbyl group which may contain a heteroatom, $R^{21}$ and $R^{22}$ may bond together to form a ring with the sulfur atom to which they are attached. $L^{11}$ is a single bond, ether bond, ester bond, carbonyl group, sulfonic ester bond, carbonate bond or carbamate bond. $Rf^1$ and $Rf^2$ are each independently fluorine or a $C_1$-$C_6$ fluorinated alkyl group. $Rf^3$ and $Rf^4$ are each independently hydrogen, fluorine, or a $C_1$-$C_6$ fluorinated alkyl group. $M^-$ is a non-nucleophilic counter ion. $A^+$ is an onium cation, and c is an integer of 0 to 3.

The resist composition may further comprise an organic solvent and/or a quencher.

The resist composition may further comprise a surfactant which is insoluble or substantially insoluble in water and soluble in alkaline developer, and/or a surfactant which is insoluble or substantially insoluble in water and alkaline developer.

In a further aspect, the invention provides a pattern forming process comprising the steps of applying the chemically amplified resist composition defined above to form a resist film on a substrate, exposing a selected region of the resist film to KrF excimer laser, ArF excimer laser, EB or EUV, and developing the exposed resist film in a developer.

In a preferred embodiment, the developing step uses an alkaline aqueous solution as the developer, thereby forming a positive pattern in which an exposed region of the resist film is dissolved away and an unexposed region of the resist film is not dissolved.

In another preferred embodiment, the developing step uses an organic solvent as the developer, thereby forming a negative pattern in which an unexposed region of the resist film is dissolved away and an exposed region of the resist film is not dissolved.

In a further preferred embodiment, the exposure step is carried out by immersion lithography while a liquid having a refractive index of at least 1.0 is held between the resist film and a projection lens.

The process may further comprise the step of forming a protective film on the resist film prior to the exposure step, wherein immersion lithography is carried out while the liquid is held between the protective film and the projection lens.

Advantageous Effects of Invention

When the chemically amplified resist composition comprising a sulfonium salt of specific structure as a photoacid generator is processed by lithography, patterns having improved properties including sensitivity, MEF and LWR can be formed.

DESCRIPTION OF EMBODIMENTS

Figure 1:
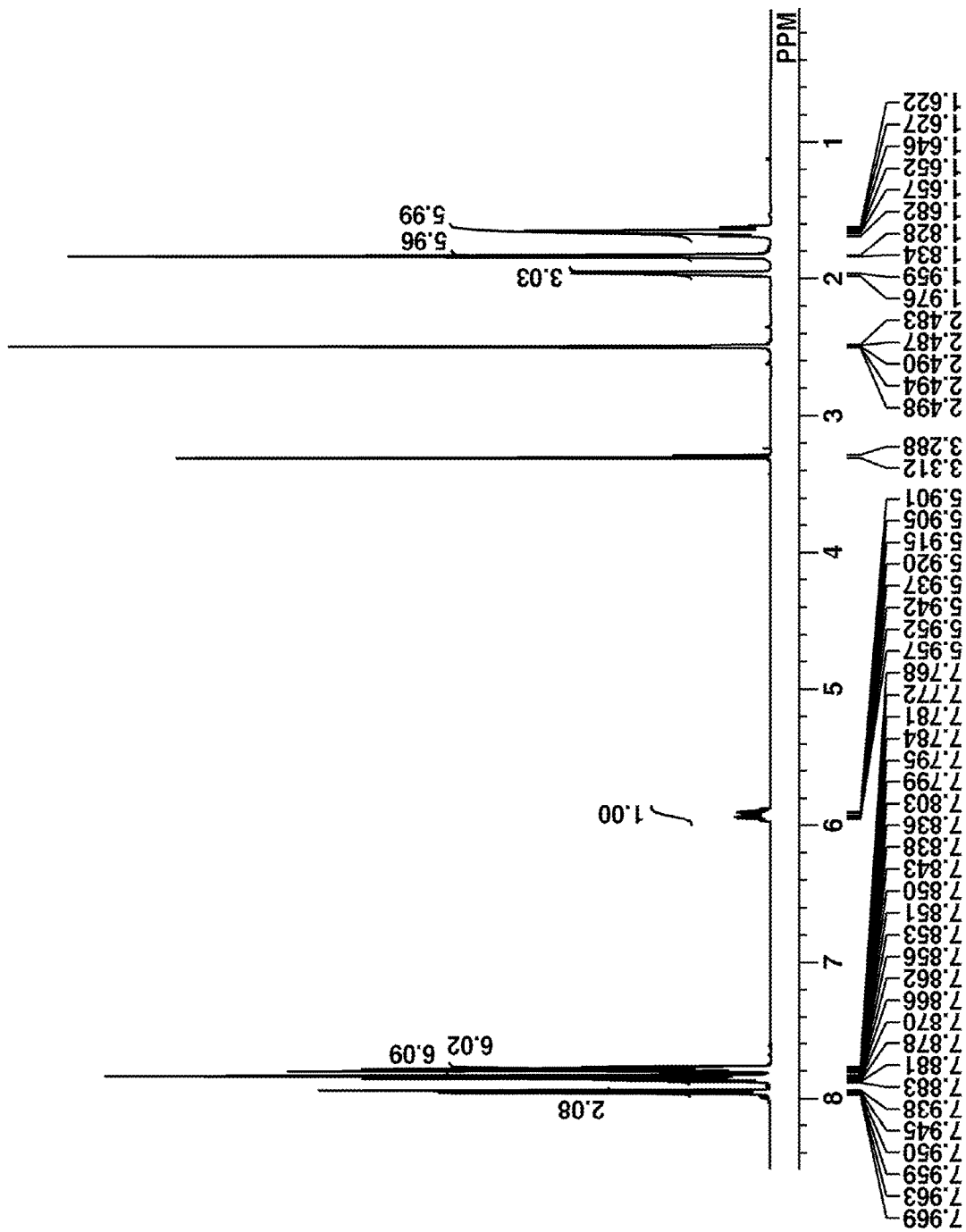
FIG. 1 is a diagram showing the $^1$H-NMR spectrum of the compound in Example 1-1.

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, Me stands for methyl, Ac for acetyl, and the broken line designates a valence bond.

The abbreviations and acronyms have the following meaning.
EB: electron beam
EUV: extreme ultraviolet
Mw: weight average molecular weight
Mn: number average molecular weight
Mw/Mn: molecular weight dispersity
GPC: gel permeation chromatography
PEB: post-exposure bake
PAG: photoacid generator
EL: exposure latitude
LWR: line width roughness
MEF: mask error factor
CDU: critical dimension uniformity
DOF: depth of focus Sulfonium Compound The invention provides a sulfonium compound having the formula (1).

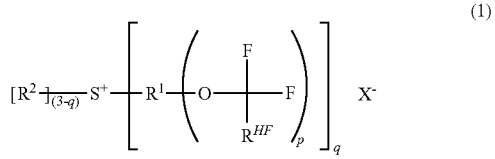

(1)

In formula (1), p which is representative of the number of fluorinated alkoxy groups bonded to $R^1$ is an integer of 1 to 5, preferably in view of availability of reactants, an integer of 1 to 3, more preferably 1 or 2; and q is an integer of 1 to 3.

In formula (1), $R^{HF}$ is hydrogen or fluorine, preferably in view of solvent solubility, fluorine.

In formula (1), $R^3$ is a $C_1$-$C_{20}$ (p+1)-valent hydrocarbon group which may contain a heteroatom. The (p+1)-valent hydrocarbon group may be saturated or unsaturated and straight, branched or cyclic. Examples thereof include $C_1$-$C_{20}$ hydrocarbylene groups and groups obtained by removing (p−1) number of hydrogen atoms from the hydrocarbylene groups. Suitable hydrocarbylene groups include $C_1$-$C_{30}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; $C_3$-$C_{30}$ cyclic saturated hydrocarbylene groups such as cyclopentanediyl, cyclohexanediyl, norbornanediyl, and adamantanediyl; arylene groups such as phenylene, methylphenylene, ethylphenylene, n-propylphenylene, isopropylphenylene, n-butylphenylene, isobutylphenylene, sec-butylphenylene, tert-butylphenylene, naphthylene, methylnaphthylene, ethylnaphthylene, n-propylnaphthylene, isopropylnaphthylene, n-butylnaphthylene, isobutylnaphthylene, sec-butylnaphthylene, and tert-butylnaphthylene; and combinations thereof.

In the (p+1)-valent hydrocarbon group, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain a hydroxy, cyano, fluorine, chlorine, bromine, iodine, carbonyl, ether bond, ester bond, sulfonic ester bond, carbonate bond, lactone ring, sultone ring, carboxylic anhydride or haloalkyl moiety.

In formula (1), $R^2$ is a $C_1$-$C_{20}$ hydrocarbyl group which may contain a heteroatom. The hydrocarbyl group may be saturated or unsaturated and straight, branched or cyclic. Examples thereof include $C_1$-$C_{20}$ alkyl groups such as methyl, ethyl, n-propyl, isopropyl, n-butyl, and tert-butyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl: $C_2$-$C_{20}$ alkenyl groups such as vinyl, allyl, propenyl, butenyl, and hexenyl; $C_3$-$C_{20}$ cyclic unsaturated hydrocarbyl groups such as cyclohexenyl; $C_6$-$C_{20}$ aryl groups such as phenyl and naphthyl; $C_7$-$C_{20}$ aralkyl groups such as benzyl, 1-phenylethyl, and 2-phenylethyl; and combinations thereof. Of these, aryl groups are preferred. In the hydrocarbyl group, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain a hydroxy, cyano, fluorine, chlorine, bromine, iodine, carbonyl, ether bond, ester bond, sulfonic ester bond, carbonate bond, lactone ring, sultone ring, carboxylic anhydride or haloalkyl moiety.

In case of q=1, any two of $R^1$ and two $R^2$ may bond together to form a ring with the sulfur atom to which they are attached. In case of q=2, any two of two $R^1$ and $R^2$ may bond together to form a ring with the sulfur atom to which they are attached. In case of q=3, any two of three $R^1$ may bond together to form a ring with the sulfur atom to which they are attached. Examples of the sulfonium cation in this embodiment include the following.

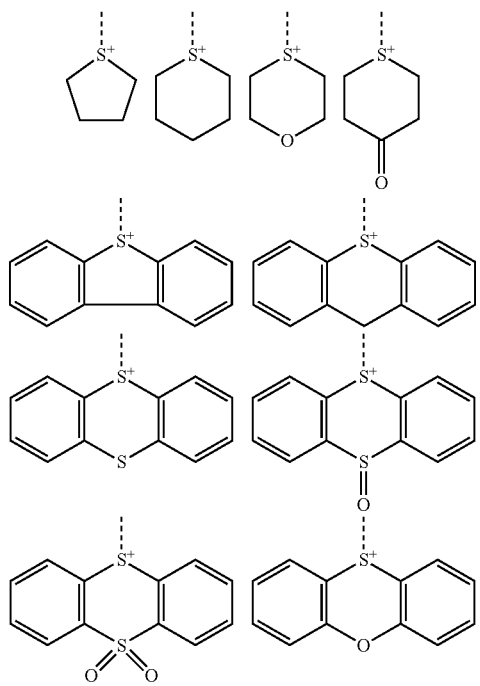

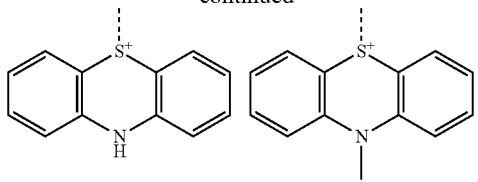

Notably, the broken line designates a point of attachment to $R^1$ or $R^3$.

Of the sulfonium salts having formula (1), those salts having the formula (1A) are preferred.

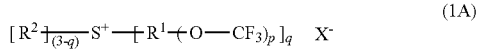
(1A)

In formula (1A), $R^1$, $R^2$, p, q, and $X^-$ are as defined above.

Of the sulfonium salts having formula (1A), those salts having the formula (1B) are more preferred.

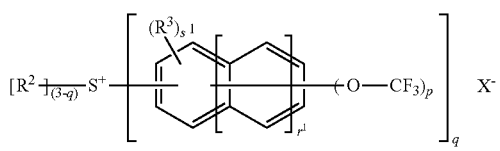
(1B)

In formula (1B), $R^2$, p, q, and $X^-$ are as defined above.

In formula (1B), $R^3$ is a $C_1$-$C_{20}$ hydrocarbyl group which may contain a heteroatom. The hydrocarbyl group may be saturated or unsaturated and straight, branched or cyclic. Examples thereof include alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl, and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; aryl groups such as phenyl, naphthyl and anthracenyl; and combinations thereof. In the hydrocarbyl group, some or all of the hydrogen atoms may be substituted by a moiety containing a heteroatom such as oxygen, sulfur, nitrogen or halogen, and any constituent —CH$_2$— may be replaced by a moiety containing a heteroatom such as oxygen, sulfur or nitrogen, so that the group may contain a hydroxy, cyano, fluorine, chlorine, bromine, iodine, carbonyl, ether bond, ester bond, sulfonic ester bond, carbonate bond, carbamate bond, amide bond, imide bond, lactone ring, sultone ring, thiolactone ring, lactam ring, sultam ring, carboxylic anhydride or haloalkyl moiety.

In formula (1B), $r^1$ is an integer of 0 to 2. The relevant structure is a benzene ring in case of $r^1$=0, naphthalene ring in case of $r^1$=1, and anthracene ring in case of $r^1$=2. Of these, a benzene ring corresponding to $r^1$=0 is preferred from the standpoint of solvent solubility.

In formula (1B), $s^1$ is an integer of 0 to 8. In case of $s^1 \geq 2$ two or more $R^3$ may be the same or different and two or more $R^3$ may bond together to form a ring. Exemplary rings include cyclopropane, cyclobutane, cyclopentane, cyclohexane, norbornane, and adamantane rings.

Of the sulfonium salts having formula (1B), those salts having the formula (1C) are even more preferred.

(1C)

In formula (1C), $R^3$, p, q, $r^1$, $s^1$, and $X^-$ are as defined above.

In formula (1C), $R^4$ is a $C_1$-$C_{20}$ hydrocarbyl group which may contain a heteroatom. The hydrocarbyl group may be saturated or unsaturated and straight, branched or cyclic. Examples thereof are as exemplified above for the hydrocarbyl group $R^3$.

In formula (1C), $r^2$ is an integer of 0 to 2. The relevant structure is a benzene ring in case of $r^2$=0, naphthalene ring in case of $r^2$=1, and anthracene ring in case of $r^2$=2. Of these, a benzene ring corresponding to $r^2$=0 is preferred from the standpoint of solvent solubility.

In formula (1C), $s^2$ is an integer of 0 to 8. In case of $s^2 \geq 2$, two or more $R^4$ may be the same or different and two or more $R^4$ may bond together to form a ring. Exemplary rings include cyclopropane, cyclobutane, cyclopentane, cyclohexane, norbornane, and adamantane rings.

Examples of the cation in the sulfonium salt having formula (1) are shown below, but not limited thereto.

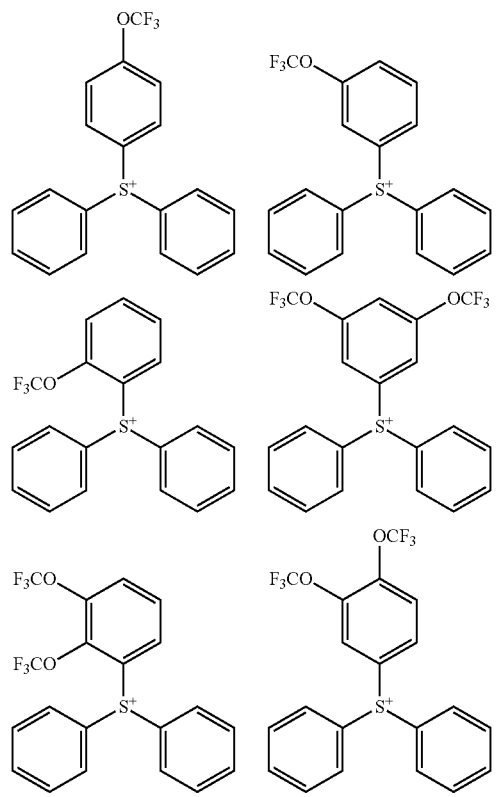

-continued
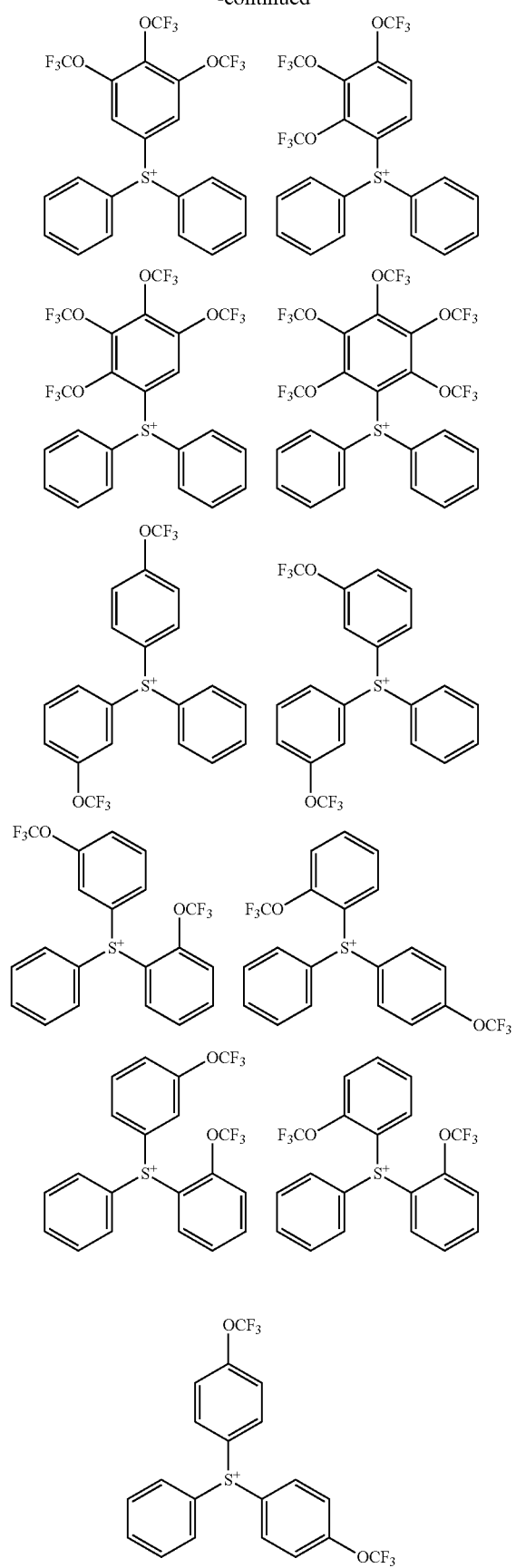
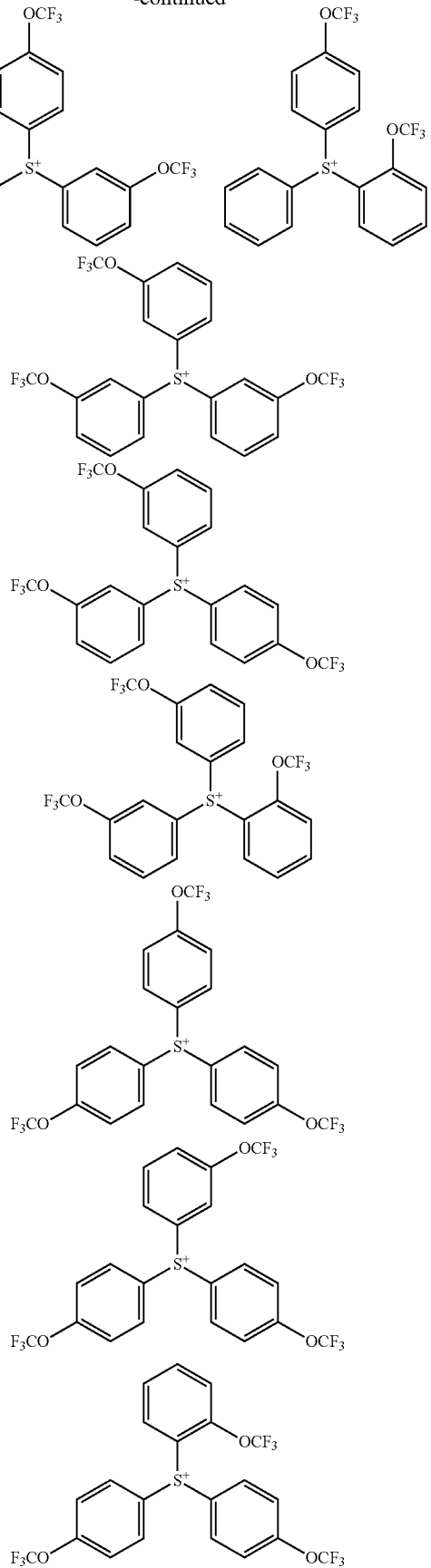

-continued
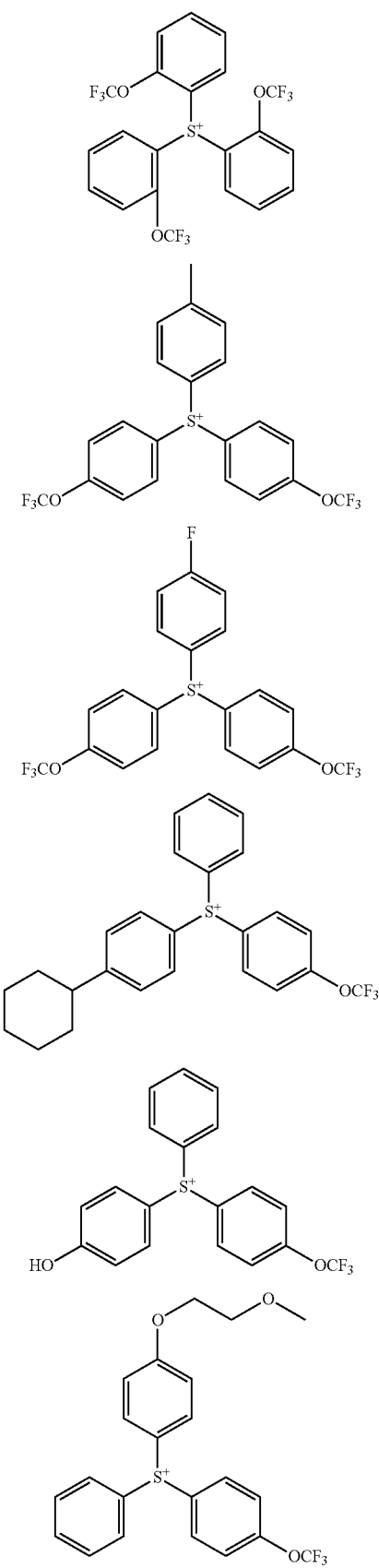
-continued
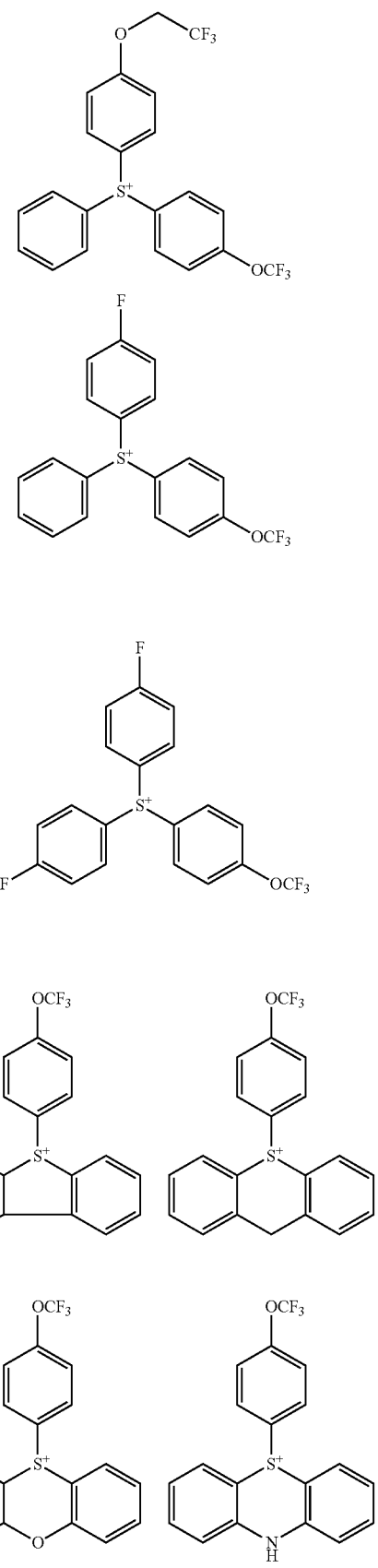

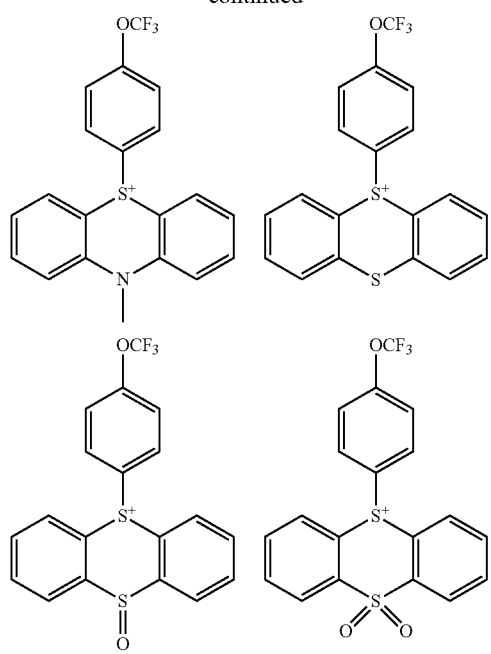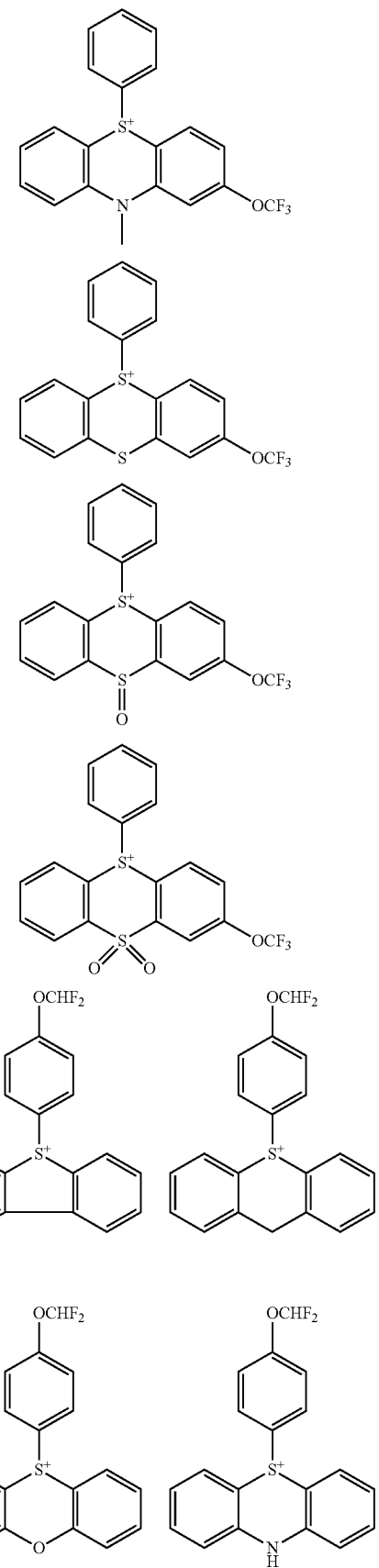

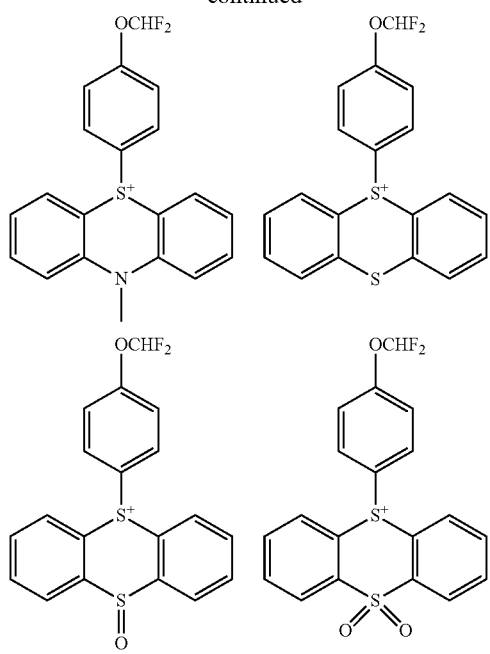
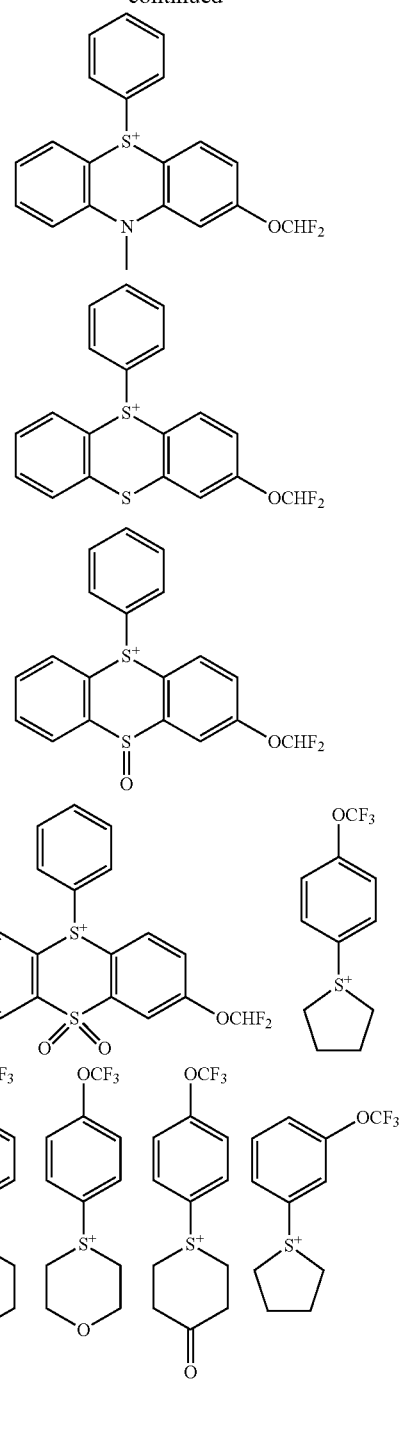
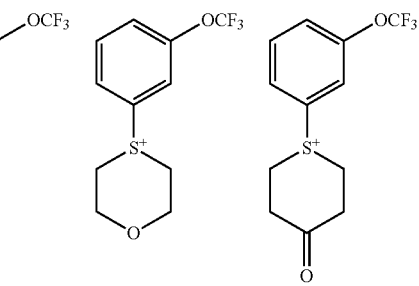

-continued
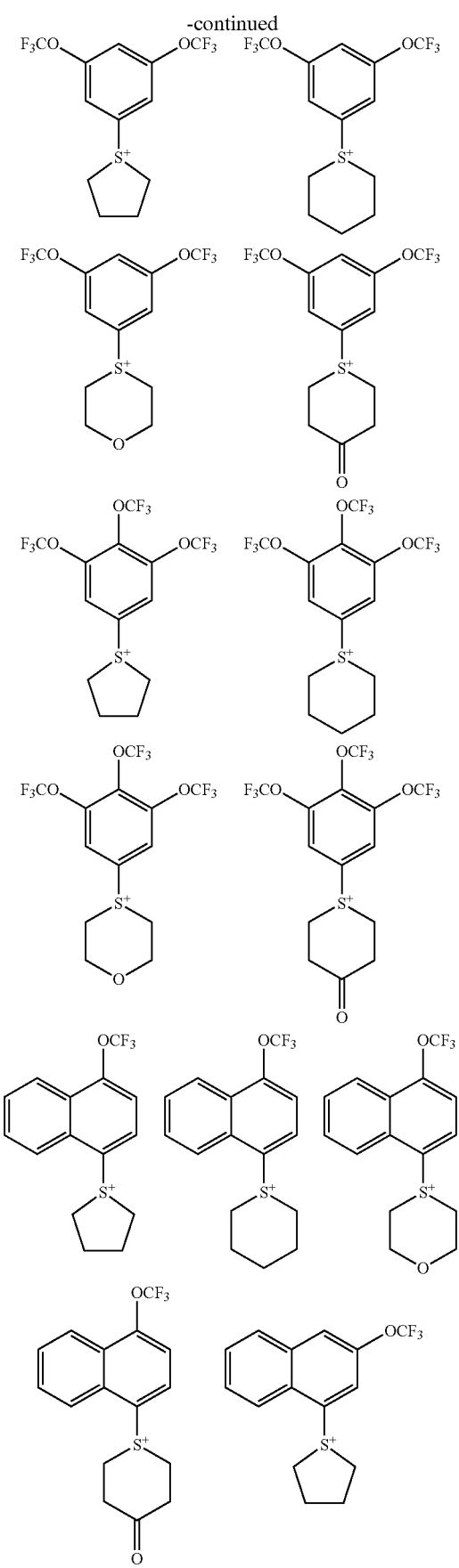
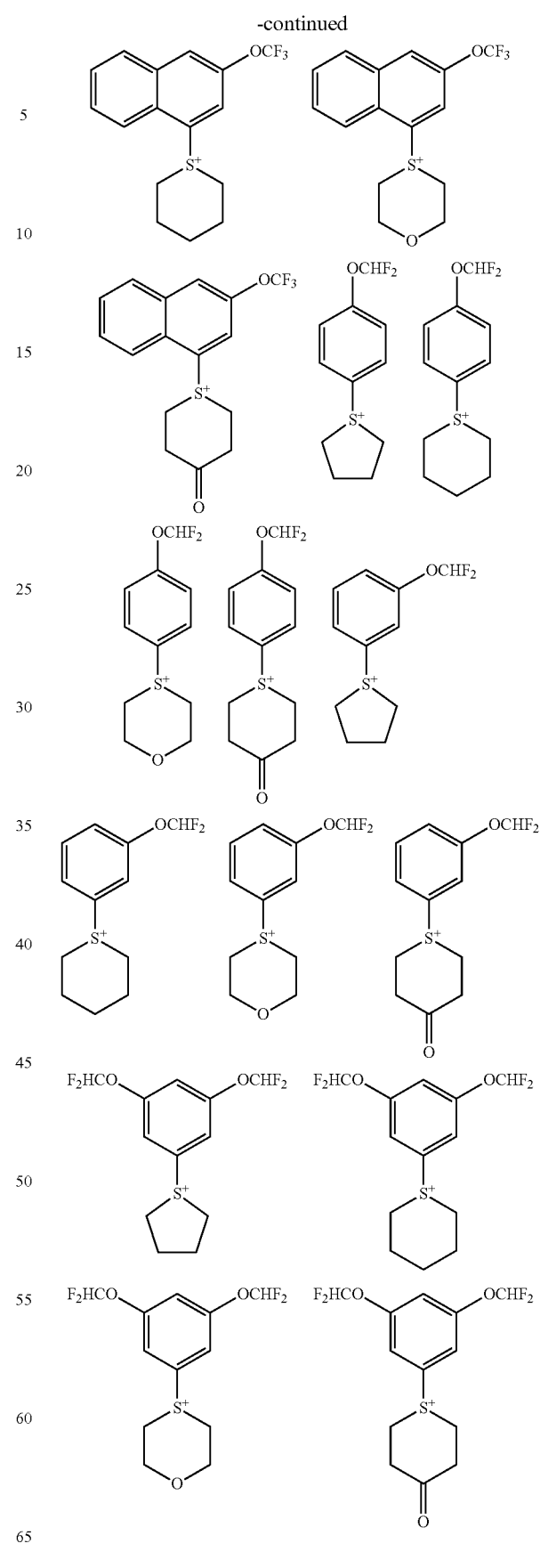

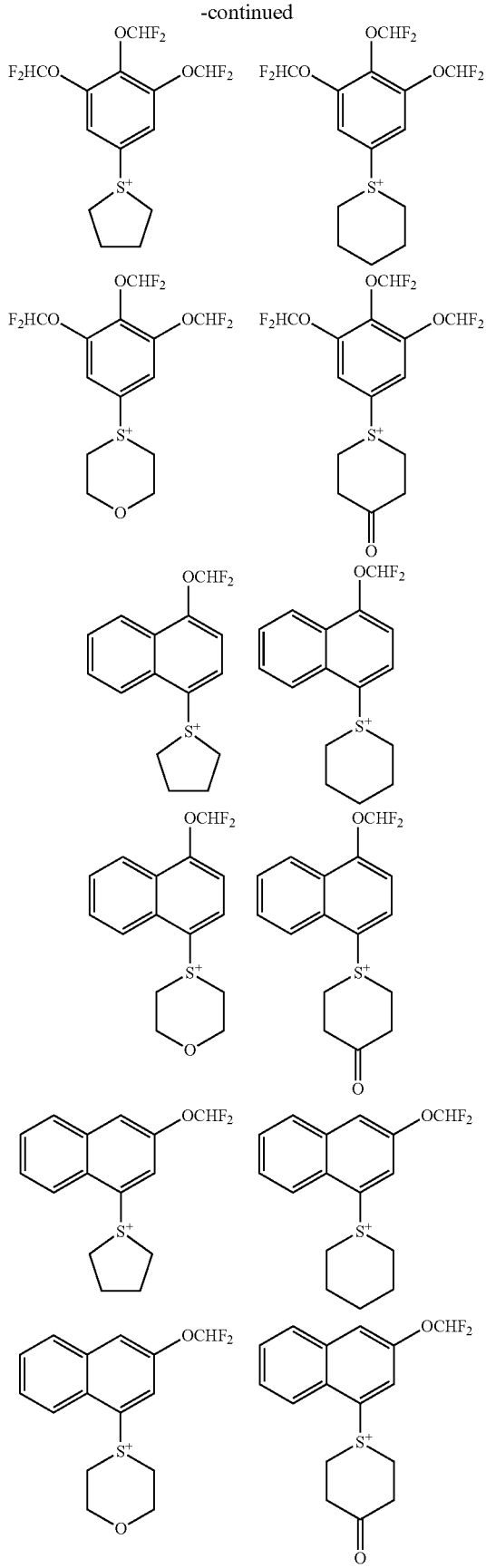

In formula (1), X⁻ is a non-nucleophilic anion, which is preferably selected from anions having the following formulae (2A) to (2D).

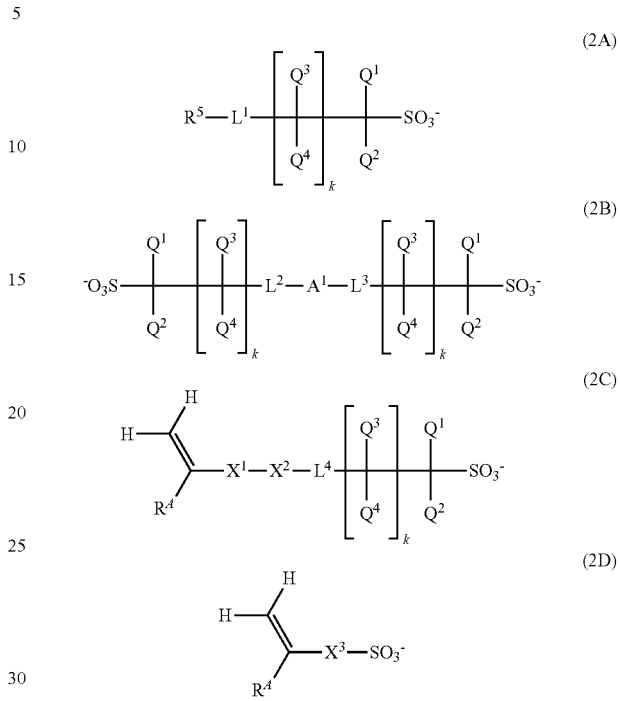

In formulae (2A) to (2C), $Q^1$ and $Q^2$ are each independently fluorine or a $C_1$-$C_6$ fluorinated alkyl group. It is preferred for enhancing the acid strength of the generated acid that both $Q^1$ and $Q^2$ be fluorine.

In formulae (2A) to (2C), $Q^3$ and $Q^4$ are each independently hydrogen, fluorine or a $C_1$-$C_6$ fluorinated alkyl group. It is preferred for improving solvent solubility that at least one of $Q^3$ and $Q^4$ be trifluoromethyl. The subscript k is an integer of 0 to 4, most preferably 1.

In formulae (2A) to (2C), $L^1$ to $L^4$ are each independently a single bond, ether bond, ester bond, sulfonic ester bond, carbonate bond or carbamate bond. From the standpoint of synthesis, $L^1$ to $L^4$ each are preferably an ether bond or ester bond, more preferably an ester bond.

In formula (2A), $R^5$ is a $C_1$-$C_{30}$ hydrocarbyl group which may contain a heteroatom. The hydrocarbyl group is preferably of 6 to 30 carbon atoms from the standpoint of gaining a high resolution in small size pattern formation.

The $C_1$-$C_{30}$ hydrocarbyl group $R^5$ may be saturated or unsaturated and straight, branched or cyclic. Examples thereof include $C_1$-$C_{30}$ alkyl groups such as methyl, ethyl, propyl, isopropyl, butyl, isobutyl, sec-butyl, tert-butyl, pentyl, neopentyl, hexyl, heptyl, octyl, 2-ethylhexyl, nonyl, decyl, undecyl, dodecyl, tridecyl, pentadecyl, heptadecyl and icosyl; $C_3$-$C_{30}$ cyclic saturated hydrocarbyl groups such as cyclopentyl, cyclohexyl, 1-adamantyl, 2-adamantyl, 1-methyl-1-adamantyl, 1-adamantylmethyl, norbornyl, norbornylmethyl, tricyclodecanyl, tetracyclododecanyl, tetracyclododecanylmethyl, dicyclohexylmethyl; $C_2$-$C_{30}$ unsaturated aliphatic hydrocarbyl groups such as allyl and 3-cyclohexenyl; $C_6$-$C_{30}$ aryl groups such as phenyl, 1-naphthyl and 2-naphthyl; $C_7$-$C_{30}$ aralkyl groups such as benzyl and diphenylmethyl; and combinations thereof.

In the foregoing hydrocarbyl groups, some or all of the hydrogen atoms may be substituted by a moiety containing a heteroatom such as oxygen, sulfur, nitrogen or halogen, and any constituent —CH$_2$— may be replaced by a moiety containing a heteroatom such as oxygen, sulfur or nitrogen, so that the group may contain a hydroxy, cyano, fluorine, chlorine, bromine, iodine, carbonyl, ether bond, ester bond, sulfonic ester bond, carbonate bond, lactone ring, sultone ring, carboxylic anhydride or haloalkyl moiety. Examples of the heteroatom-containing hydrocarbyl group include tetrahydrofuryl, methoxymethyl, ethoxymethyl, methylthiomethyl, acetamidomethyl, trifluoroethyl, (2-methoxyethoxy) methyl, acetoxymethyl, 2-carboxy-1-cyclohexyl, 2-oxopropyl, 4-oxo-1-adamantyl, 5-hydroxy-1-adamantyl, 5-tert-butylcarbonyloxy-1-adamantyl, 4-oxatricyclo [4.2.1.0$^{3,7}$]nonan-5-on-2-yl, and 3-oxocyclohexyl.

In formula (2B), A$^1$ is a C$_1$-C$_{30}$ hydrocarbylene group which may contain a heteroatom. The hydrocarbylene group may be saturated or unsaturated and straight, branched or cyclic. Examples thereof include alkanediyl groups such as methanediyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; cyclic saturated hydrocarbylene groups such as cyclopentanediyl, cyclohexanediyl, norbornanediyl and adamantanediyl; arylene groups such as phenylene, methylphenylene, ethylphenylene, n-propylphenylene, isopropylphenylene, n-butylphenylene, isobutylphenylene, sec-butylphenylene, tert-butylphenylene, naphthylene, methylnaphthylene, ethylnaphthylene, n-propylnaphthylene, isopropylnaphthylene, n-butylnaphthylene, isobutylnaphthylene, sec-butylnaphthylene and tert-butylnaphthylene; and combinations thereof. In the hydrocarbylene groups, some or all of the hydrogen atoms may be substituted by a moiety containing a heteroatom such as oxygen, sulfur, nitrogen or halogen, or any constituent —CH$_2$— may be replaced by a moiety containing a heteroatom such as oxygen, sulfur or nitrogen, so that the group may contain a hydroxy, cyano, fluorine, chlorine, bromine, iodine, carbonyl, ether bond, ester bond, sulfonic ester bond, carbonate bond, lactone ring, sultone ring, carboxylic anhydride or haloalkyl moiety. From the standpoint of availability of reactants, A$^1$ is preferably selected from unsubstituted alkanediyl groups and unsubstituted cyclic saturated hydrocarbylene groups.

In formula (2C), R$^4$ is each independently hydrogen, fluorine, methyl or trifluoromethyl.

In formula (2C), X$^1$ is a single bond, phenylene group, naphthylene group, or (backbone)-C(=O)—O—X$^{11}$—. X$^{11}$ is a C$_1$-C$_{11}$ aliphatic hydrocarbylene group which may contain a hydroxy moiety, ether bond, ester bond or lactone ring, or phenylene or naphthylene group.

In formula (2C), X$^2$ is a single bond or —X$^{21}$—C(=O)—O—. X$^{21}$ is a C$_1$-C$_{20}$ hydrocarbylene group which may contain a heteroatom.

Examples of the C$_1$-C$_{20}$ hydrocarbylene group which may contain a heteroatom, represented by X$^{11}$, are shown below, but not limited thereto.

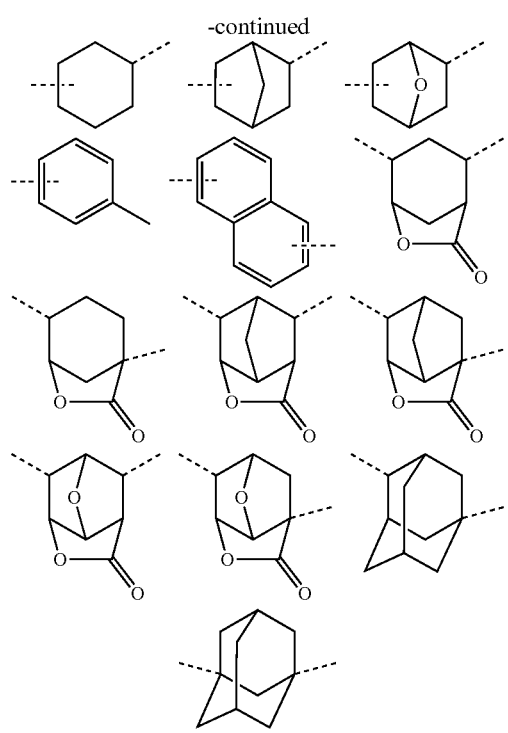

In formula (2D), X$^3$ is a single bond, methylene group, ethylene group, phenylene group, fluorinated phenylene group, trifluoromethyl-substituted phenylene group, —O—X$^{31}$—, —C(=O)—O—X$^{31}$— or —C(=O)—NH—X$^{31}$—. X$^{31}$ is a C$_1$-C$_6$ aliphatic hydrocarbylene group, phenylene group, fluorinated phenylene group, or trifluoromethyl-substituted phenylene group, which may contain a carbonyl moiety, ester bond, ether bond or hydroxy moiety.

Of the anions having formula (2A), those having the formula (2A-1) are preferred.

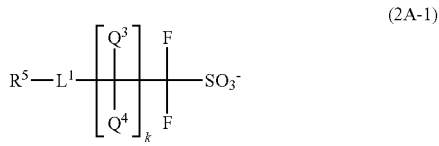

Herein Q$^3$, Q$^4$, R$^5$ and L$^1$ are as defined above.

Of the anions having formula (2A-1), those having the formula (2A-2) are more preferred.

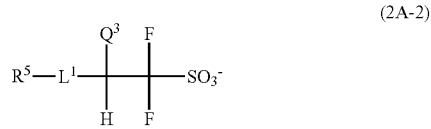

Herein Q$^3$, R$^5$ and L$^1$ are as defined above.

Examples of the anion having formula (2A) are shown below, but not limited thereto. Herein Q$^3$ is as defined above

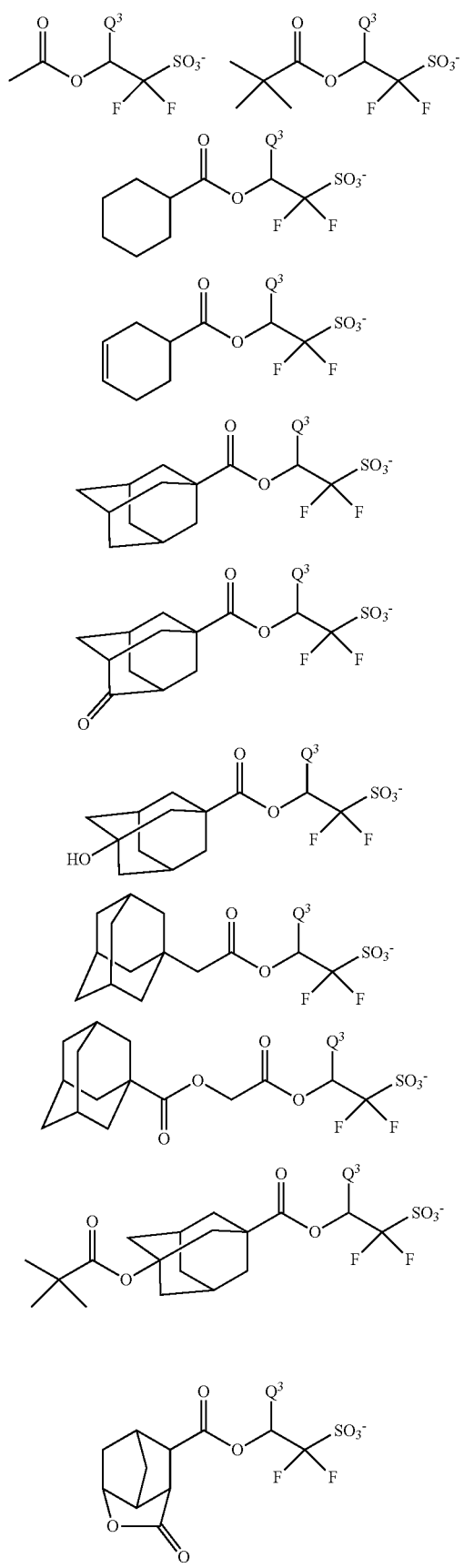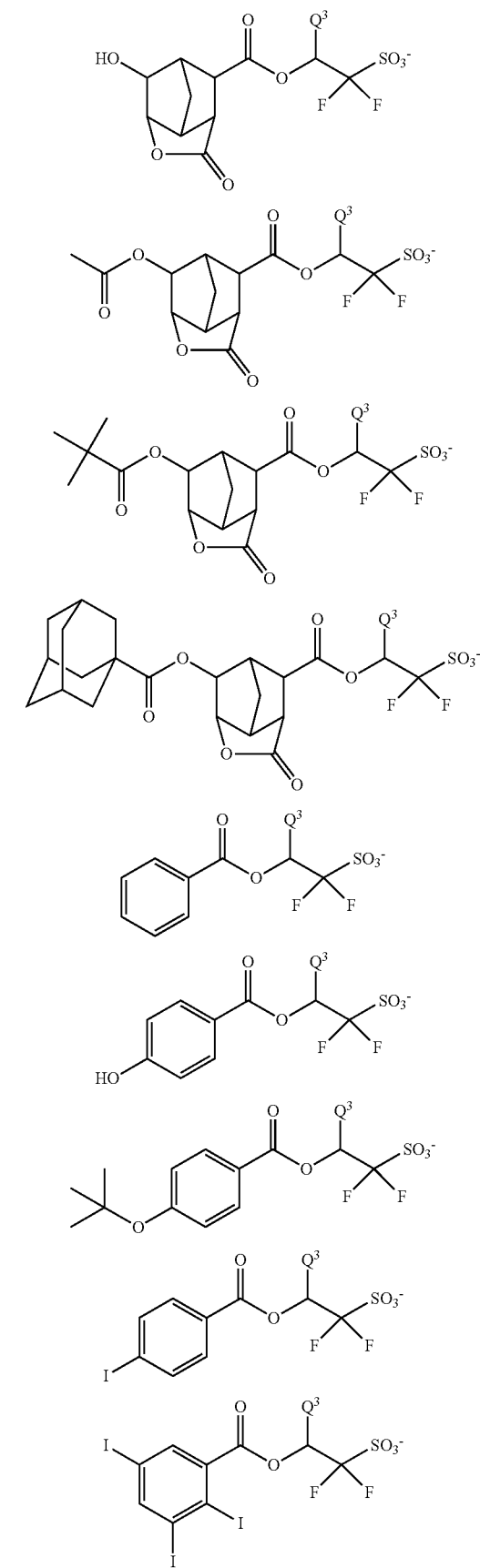

31
-continued
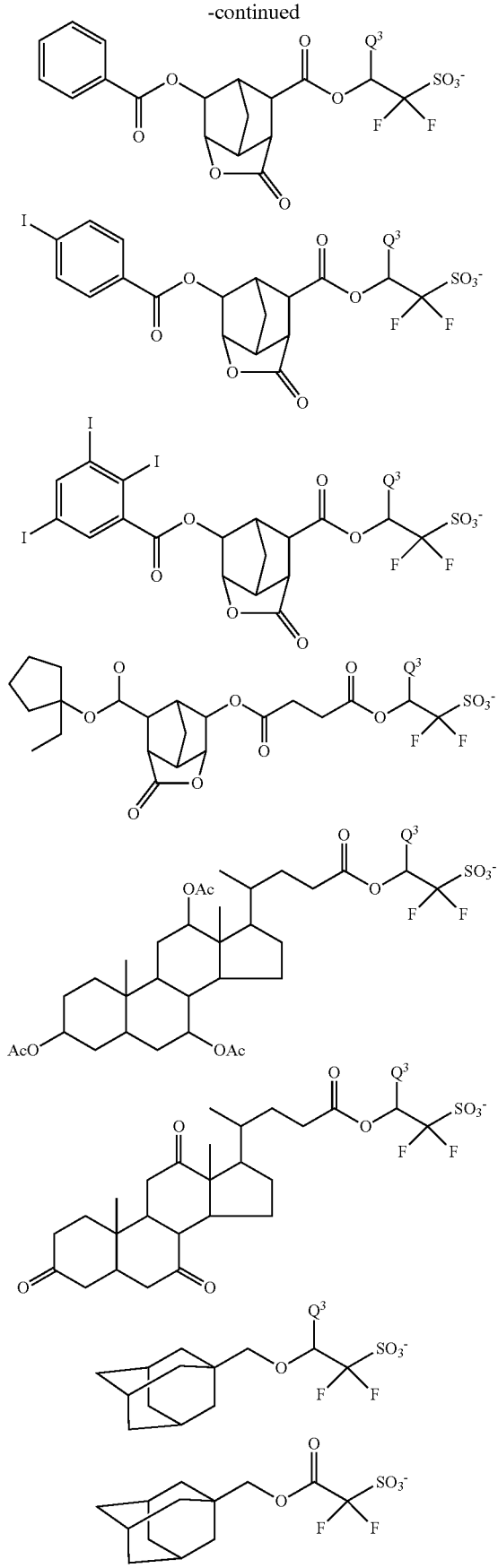
32
-continued
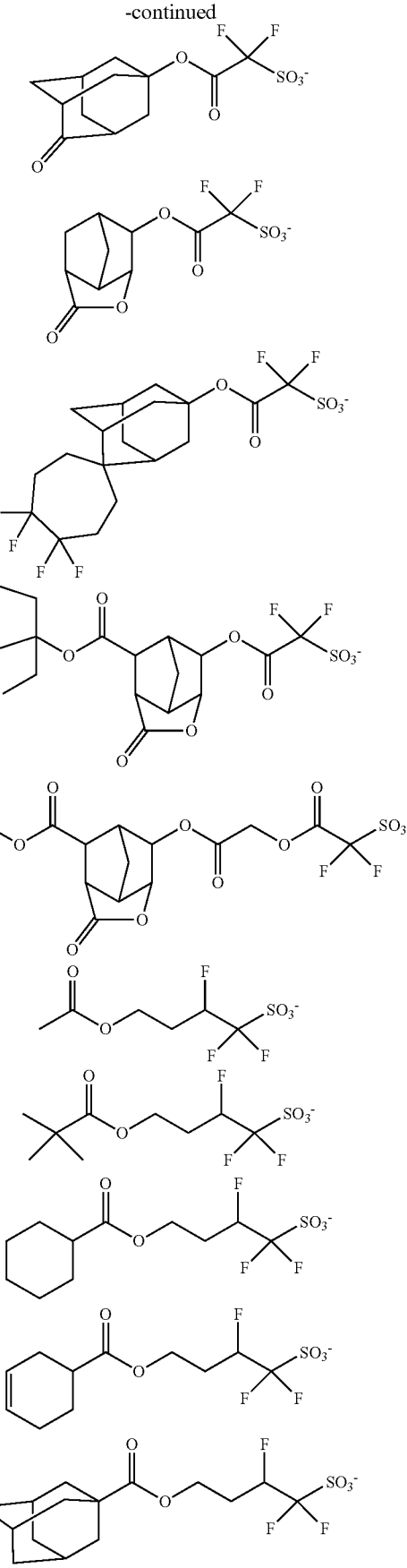

33
-continued
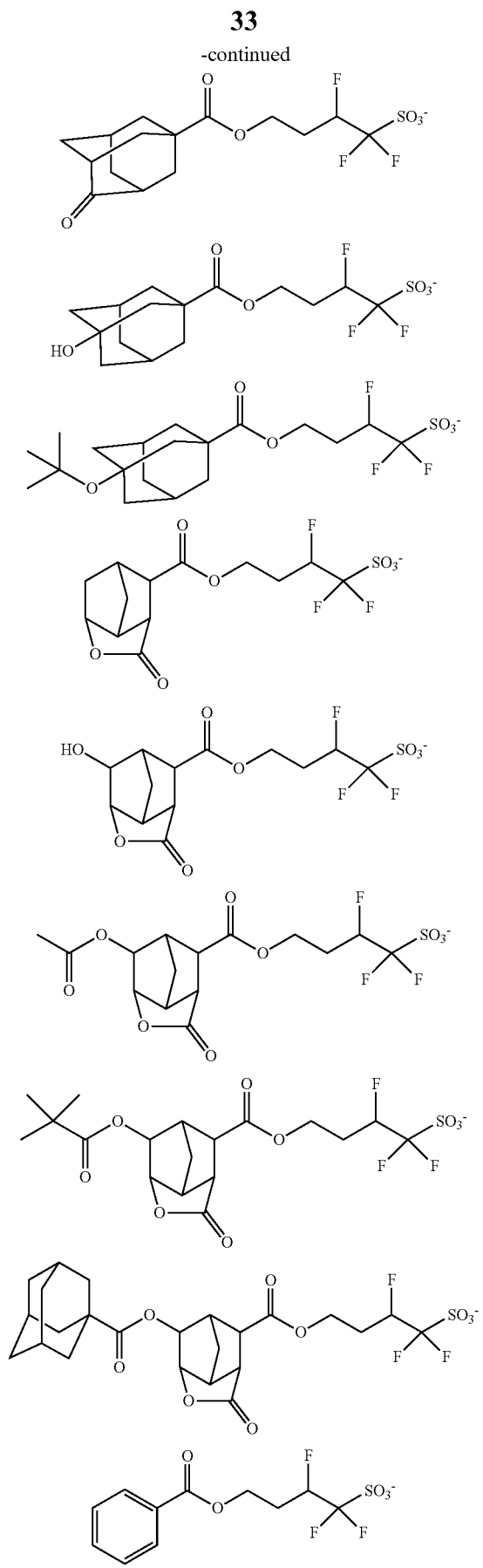
34
-continued
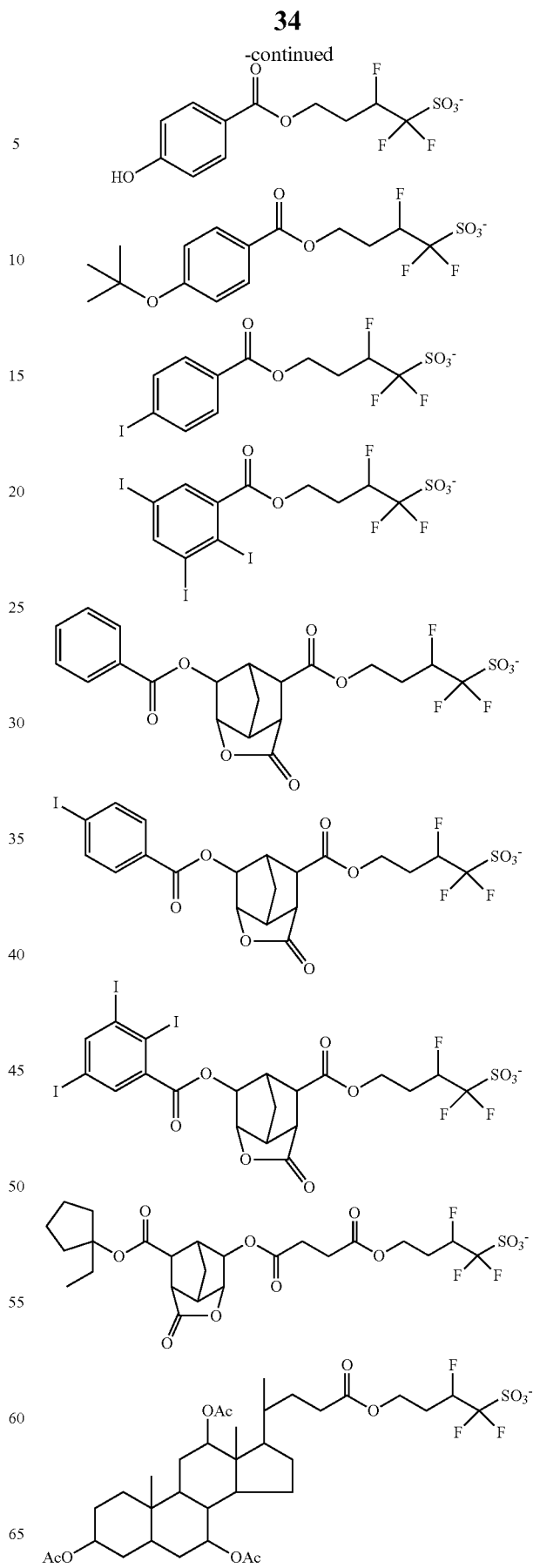

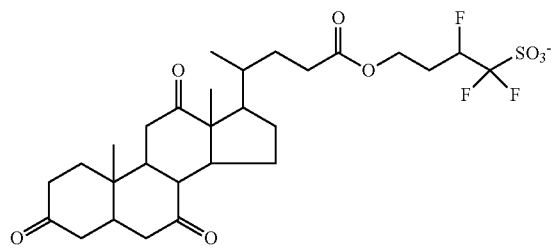
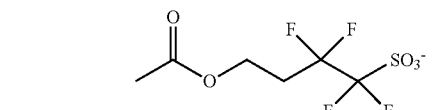
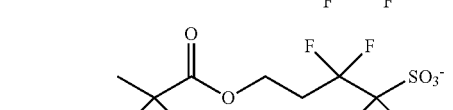
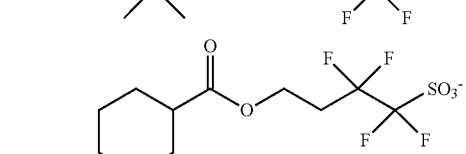
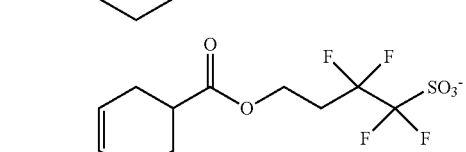
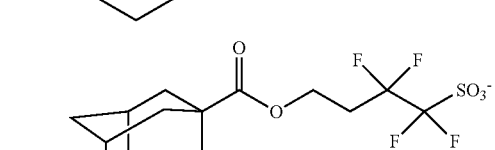
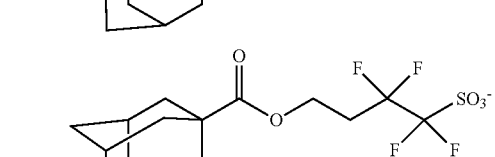
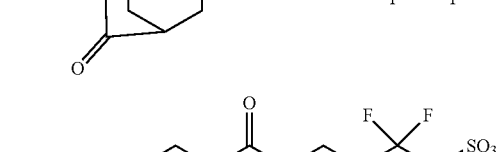
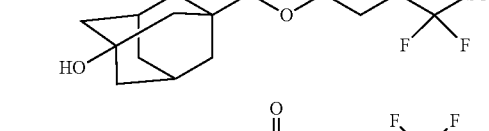
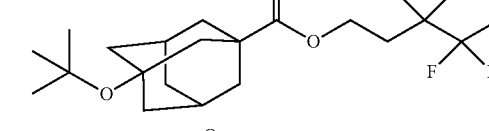
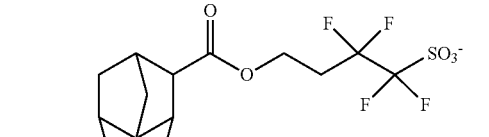
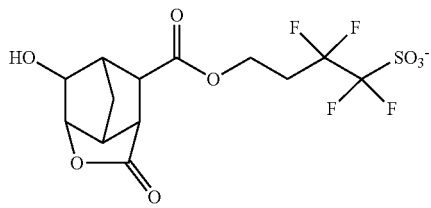
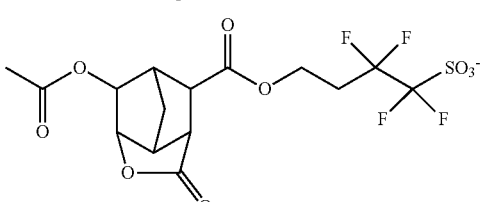
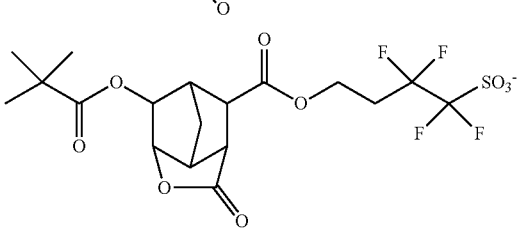
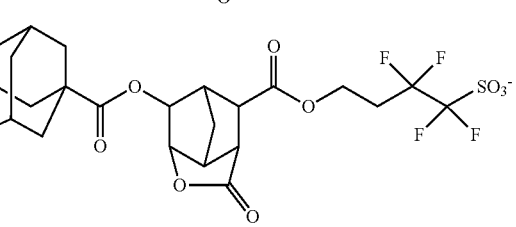
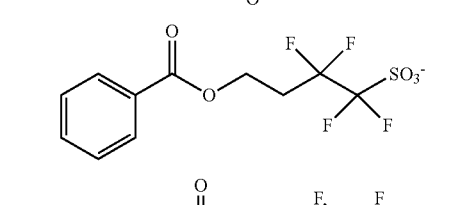
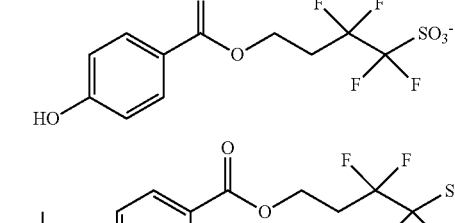
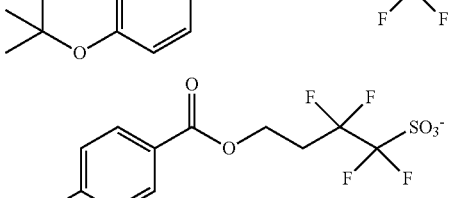
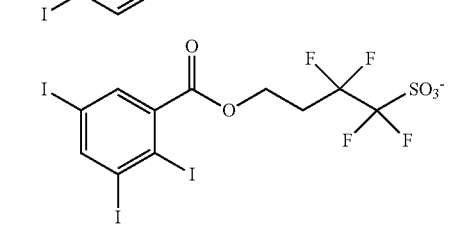

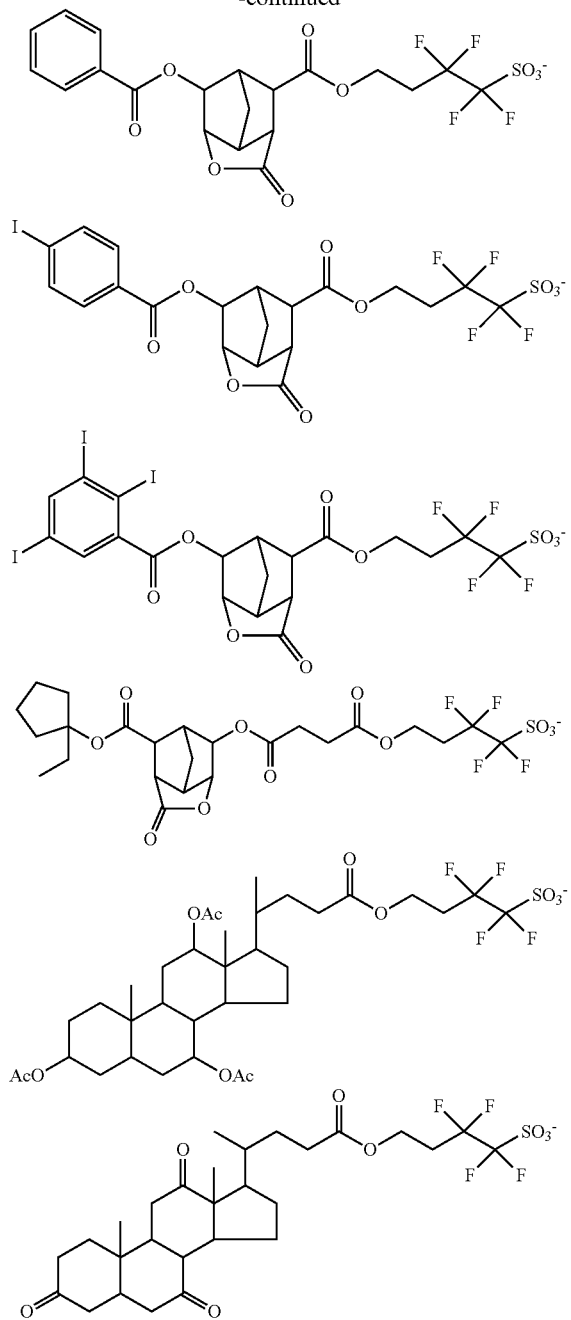

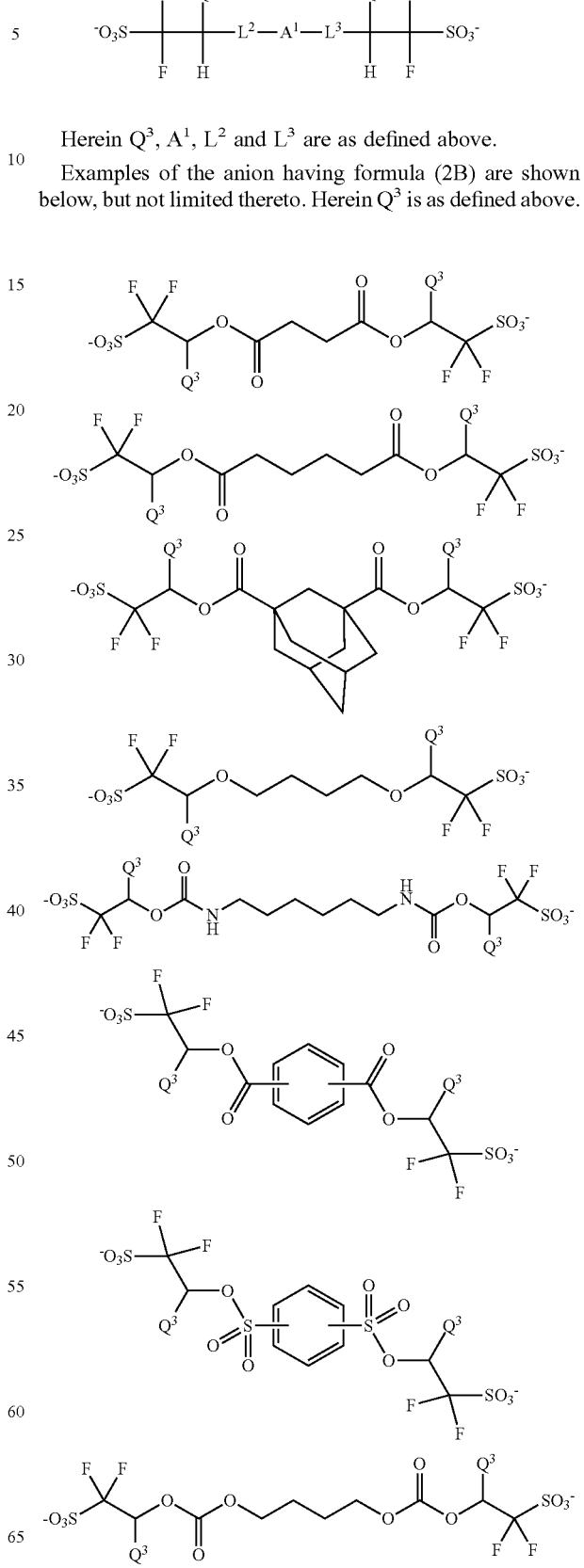

Herein $Q^3$, $A^1$, $L^2$ and $L^3$ are as defined above.

Examples of the anion having formula (2B) are shown below, but not limited thereto. Herein $Q^3$ is as defined above.

Of the anions having formula (2B), those having the formula (2B-1) are preferred.

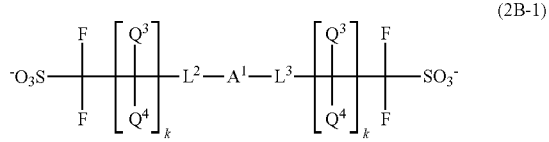

Herein $Q^3$, $Q^4$, $A^1$, $L^2$ and $L^3$ are as defined above.

Of the anions having formula (2B-1), those having the formula (2B-2) are more preferred.

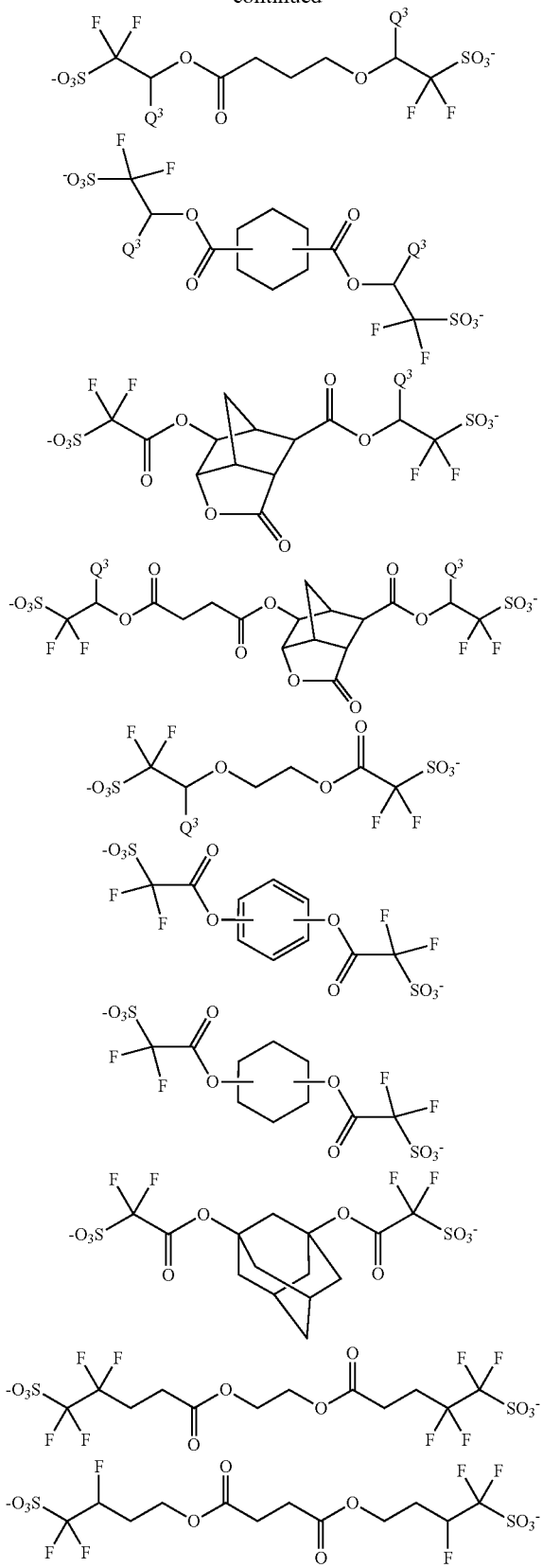

Of the anions having formula (2C), those having the formula (2C-1) are preferred.

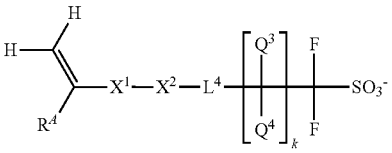
(2C-1)

Herein $Q^3$, $Q^4$, $L^4$, $R^A$, $X^1$, $X^2$ and k are as defined above.

Of the anions having formula (2C-1), those having the formula (2C-2) are more preferred.

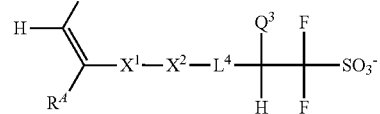
(2C-2)

Herein $Q^3$, $L^4$, $R^A$, $X^1$, and $X^2$ are as defined above.

Examples of the anion having formula (2C) are shown below, but not limited thereto. Herein $R^A$ is as defined above.

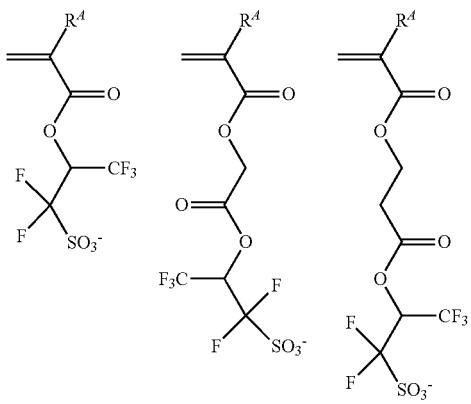

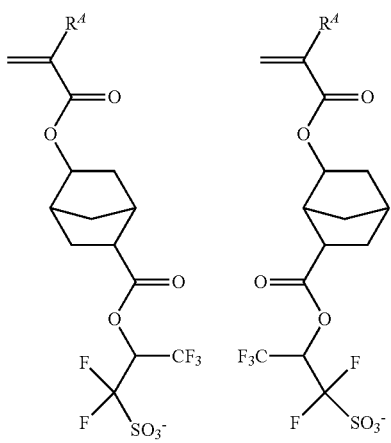

-continued
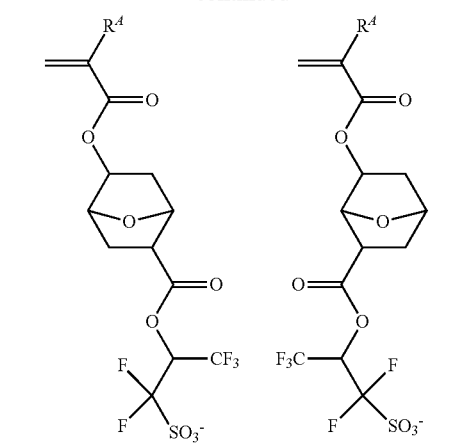
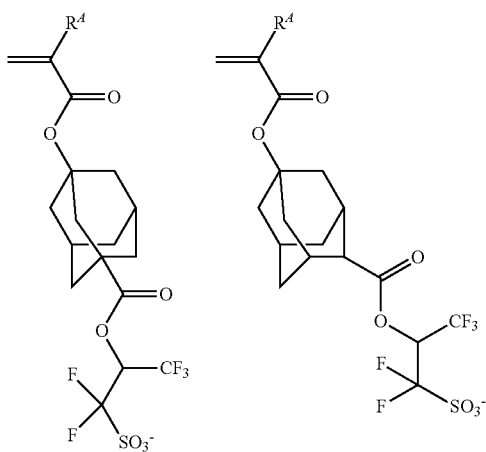
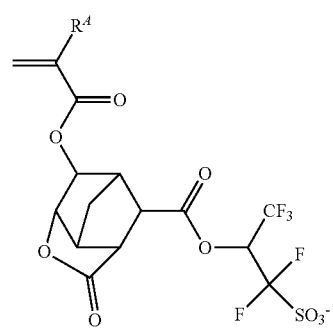
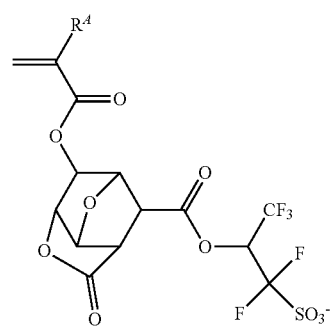
-continued
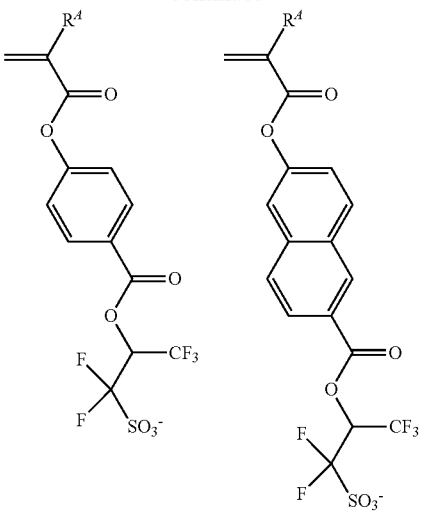
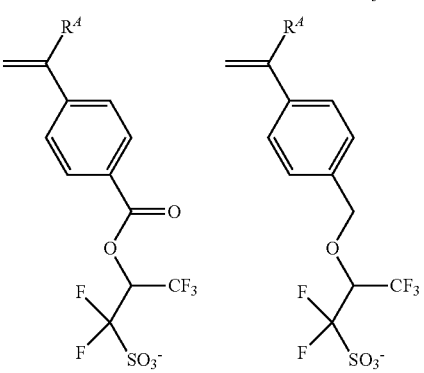
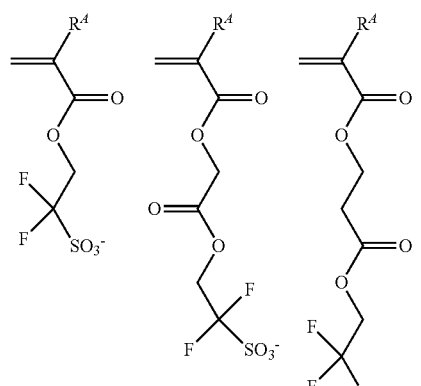
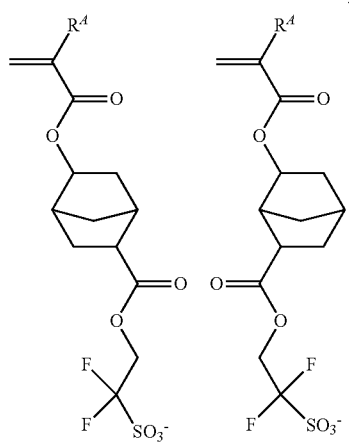

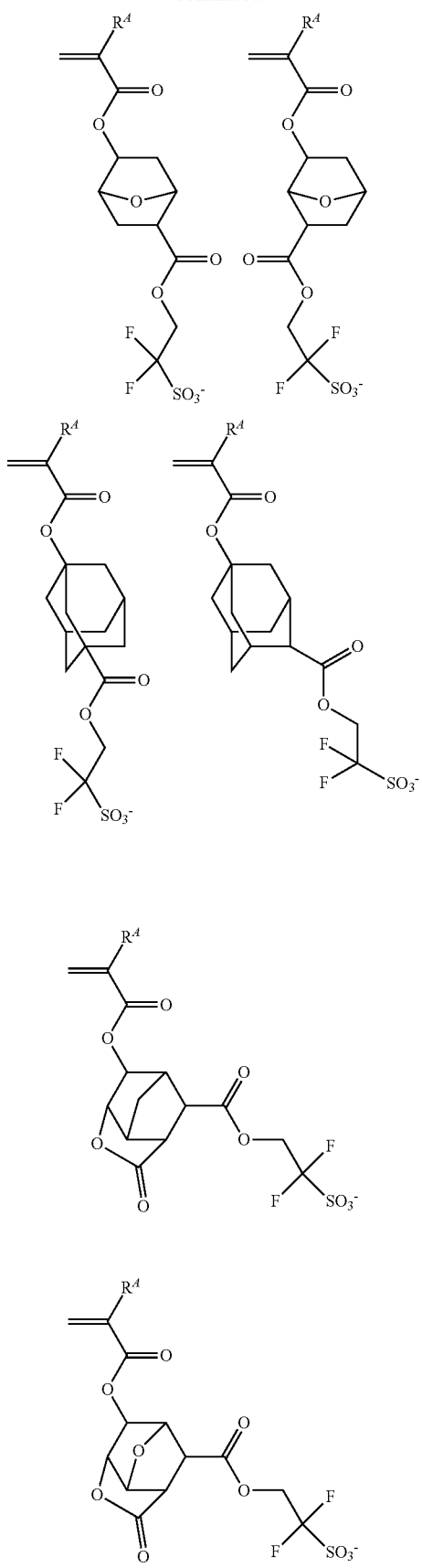
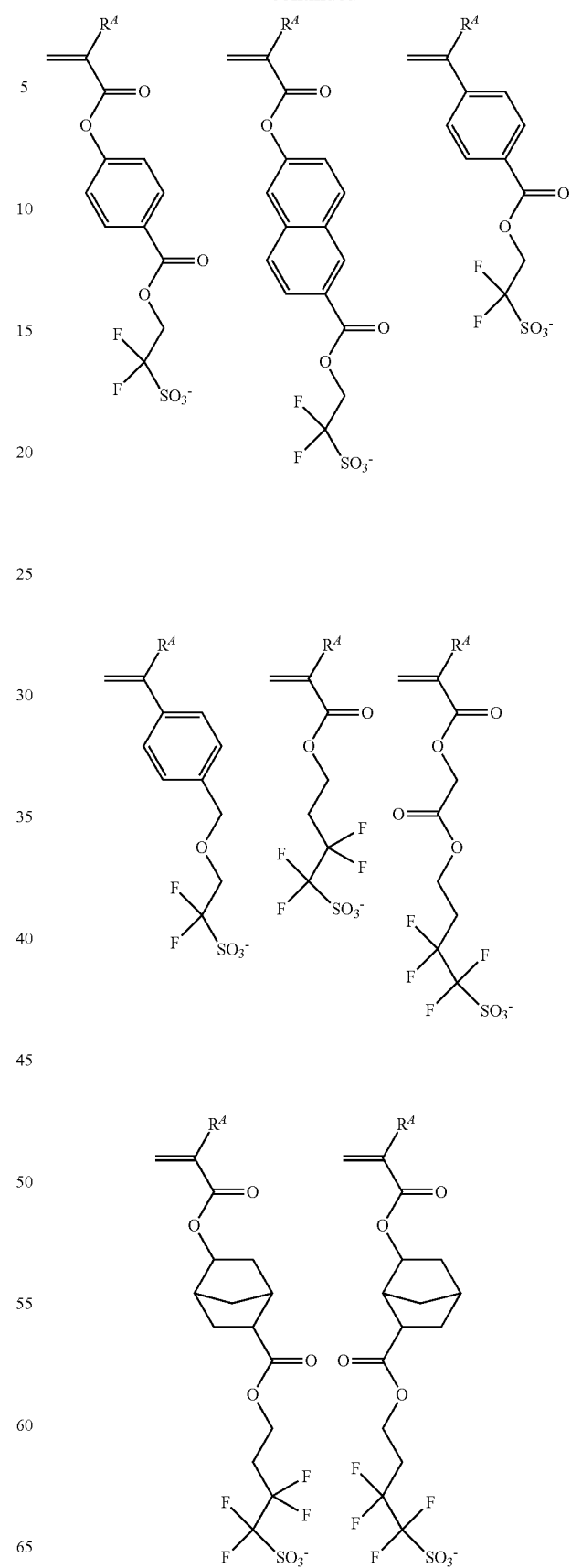

-continued
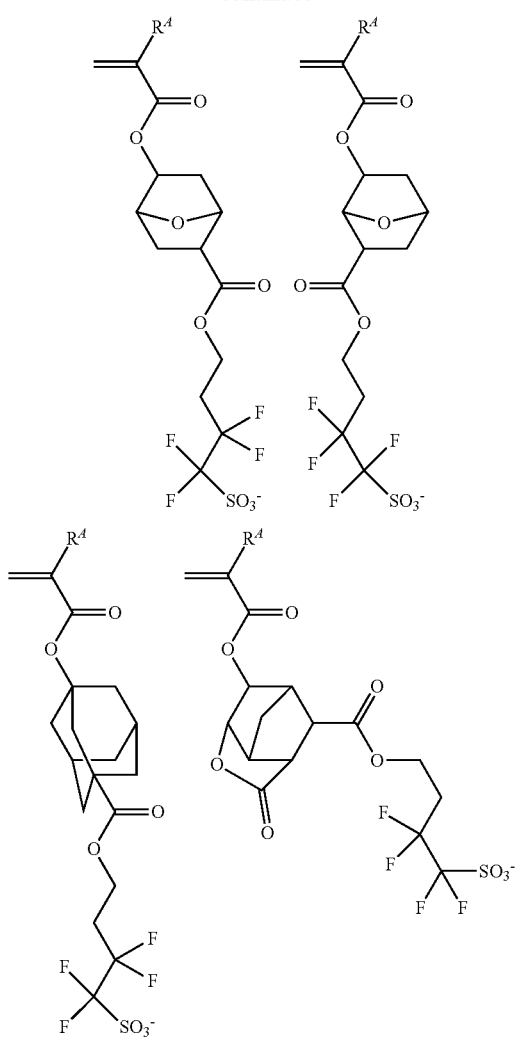
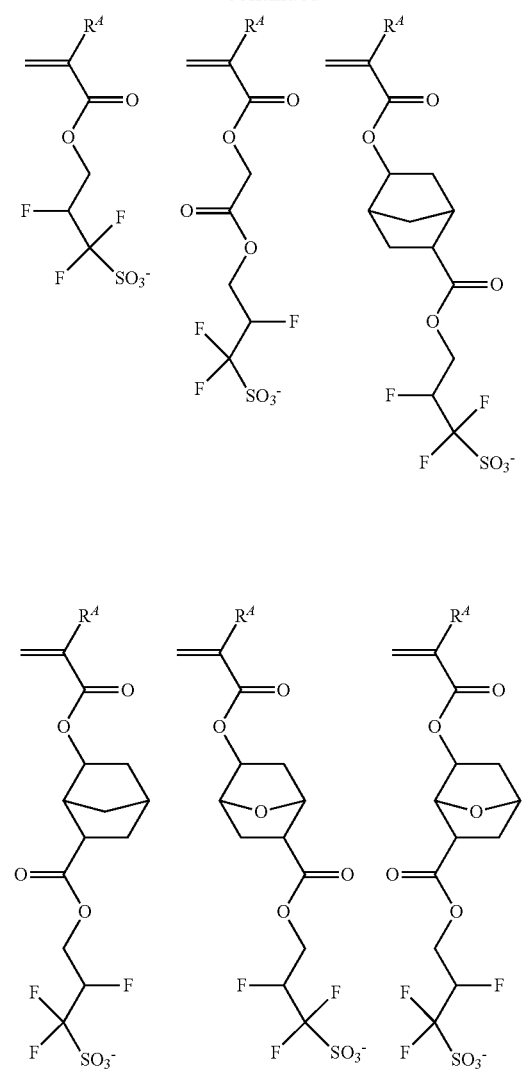
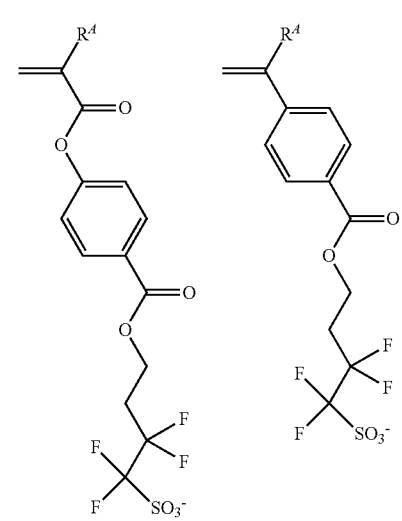
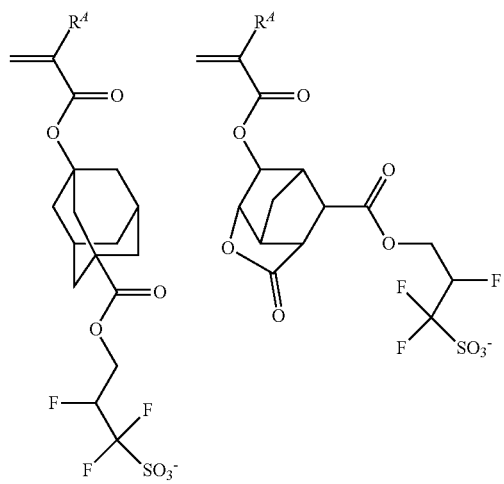

-continued
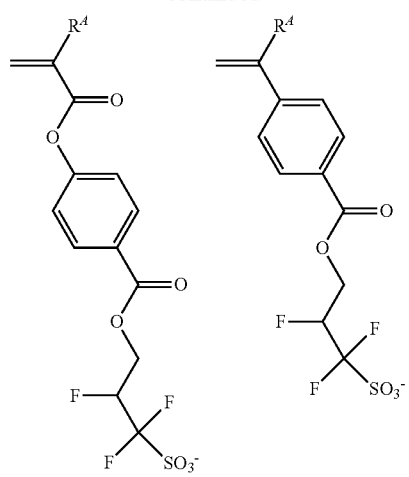
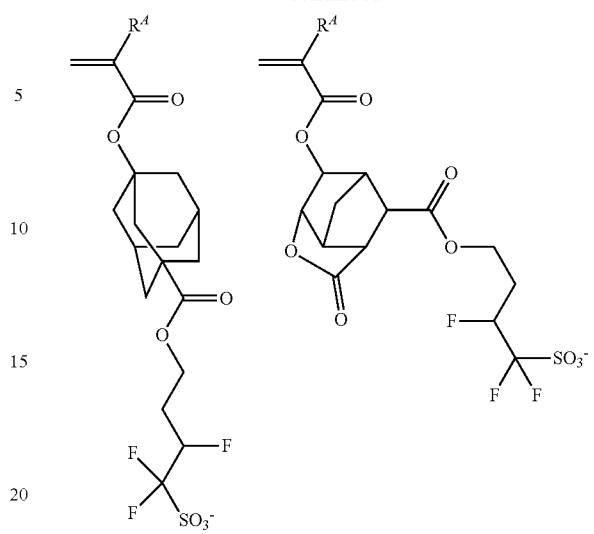
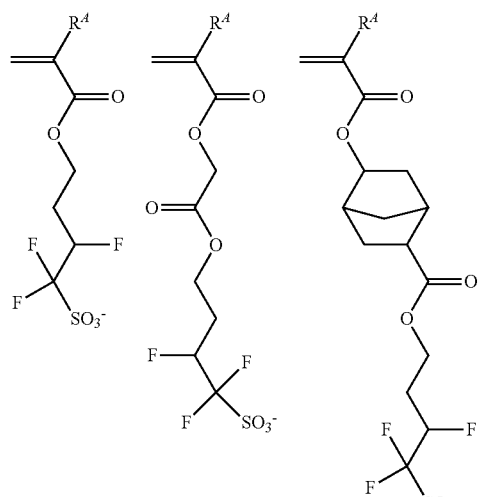
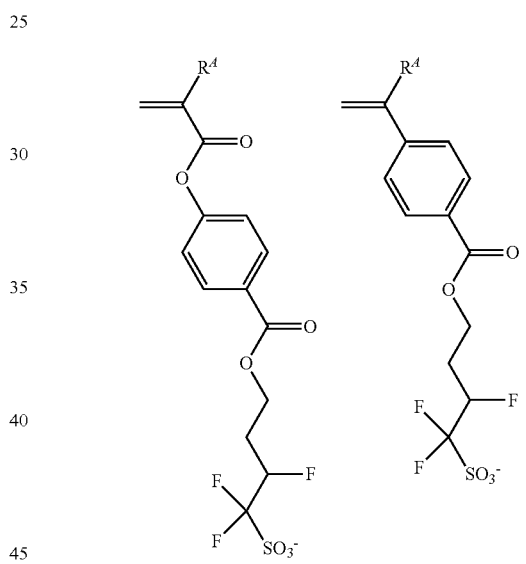
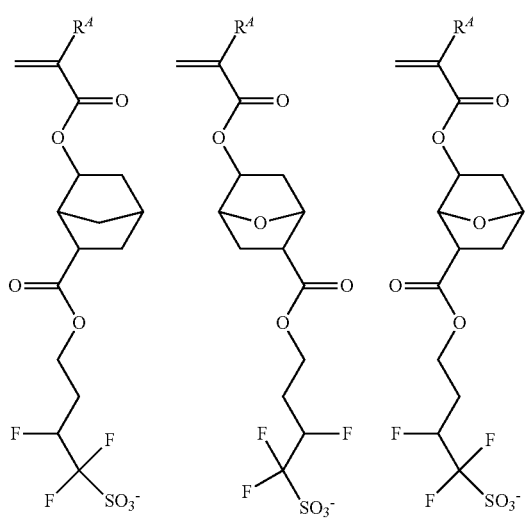
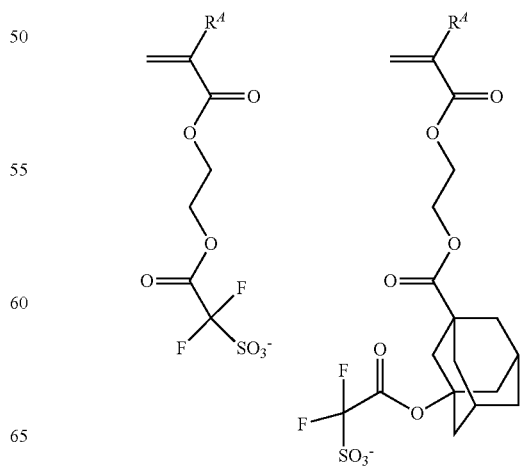

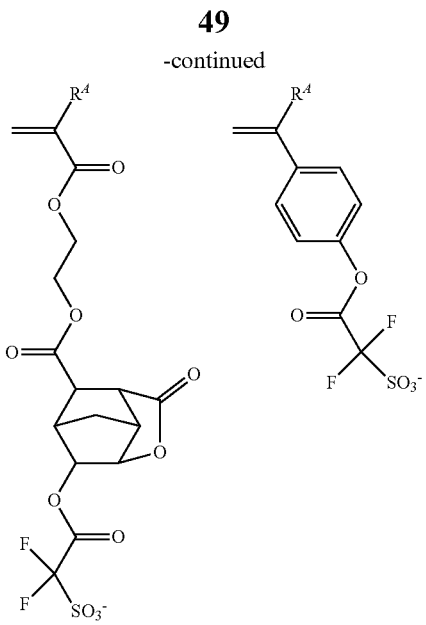

Examples of the anion having formula (2D) are shown below, but not limited thereto. Herein $R^A$ is as defined above.

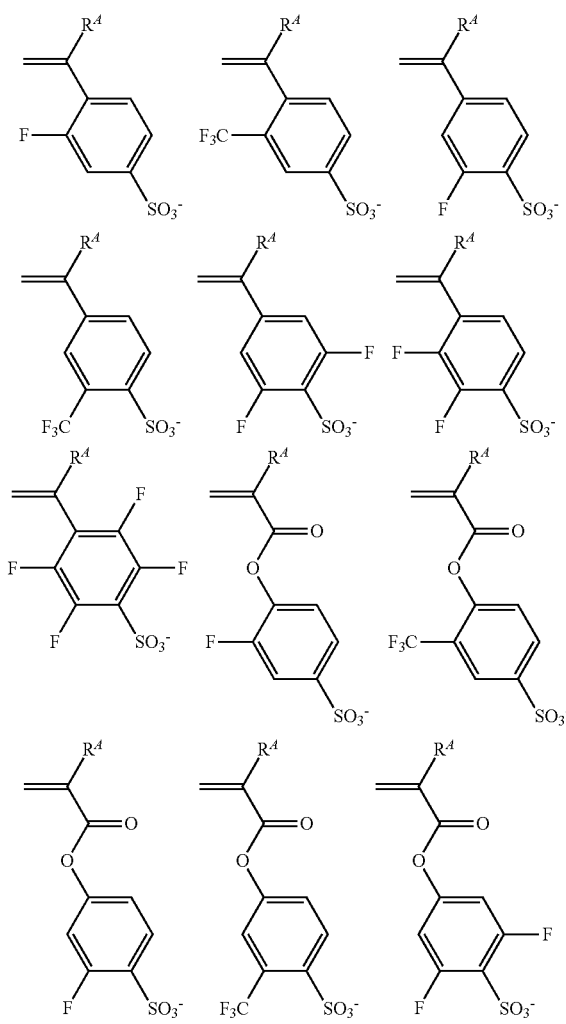

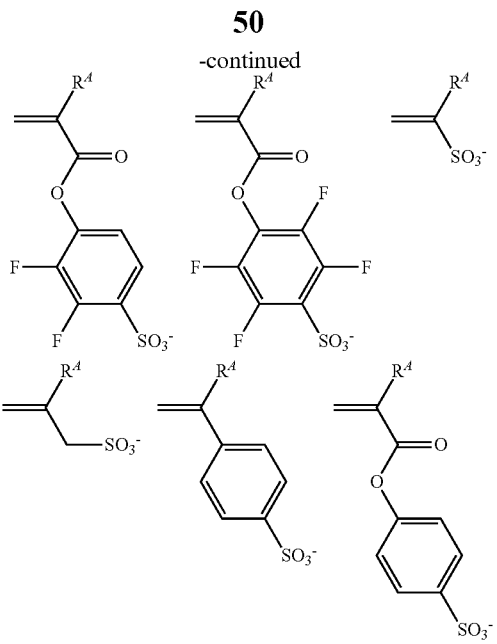

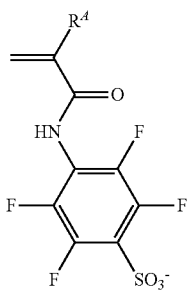

Examples of the sulfonium salt include arbitrary combinations of anions with cations, both as exemplified above.

One of the structural features of the inventive sulfonium salt is that the sulfonium cation contains a fluorinated alkoxy group having a very high solvent solubility. Particularly when the fluorinated alkoxy group is trifluoromethoxy, the sulfonium salt has a high solvent solubility and maintains a satisfactory solvent solubility even when it forms a salt with an anion having a low solvent solubility. Because of a high solvent solubility, the sulfonium salt dissolves uniformly in the solvent without agglomeration and is uniformly distributed in a resist film when used as a photoacid generator. Since an acid is generated from the uniformly distributed photoacid generator upon exposure, an increase of sensitivity and improvements in LWR and CDU are expectable.

The sulfonium salt can be synthesized by well-known methods. For example, first a corresponding sulfoxide is reacted with a Grignard reagent in the presence of a halo-silicon reagent to synthesize a sulfonium salt containing the sulfonium cation. The sulfonium salt thus synthesized is then converted to the desired sulfonium salt through salt exchange reaction with a corresponding anion. The salt exchange with a corresponding anion is readily carried out by a well-known method, for example, with reference to JP-A 2007-145797.

The above synthesis method is merely exemplary, and the preparation of the inventive sulfonium salt is not limited thereto.

Photoacid Generator

The sulfonium salt is advantageously used as a PAG. While the sulfonium salt itself may be used as a PAG, it may also be used in the form of a base polymer comprising repeat units derived from the sulfonium salt, i.e., polymer-bound PAG when $X^-$ is an anion having formula (2C) or (2D).

Resist Composition

Another embodiment of the invention is a chemically amplified resist composition comprising (A) a photoacid generator in the form of the sulfonium salt having formula (1), (B) a base polymer, and (C) an organic solvent.

An alternative embodiment is a chemically amplified resist composition comprising (B') a base polymer comprising repeat units derived from the sulfonium salt having formula (1) wherein $X^-$ is an anion having formula (2C) or (2D), and (C) an organic solvent. In this embodiment, the composition may or may not contain (A) the photoacid generator in the form of the sulfonium salt having formula (1).

If necessary, the resist composition may further comprise at least one component selected from (D) another photoacid generator, (E) a quencher, (F) a surfactant which is insoluble or substantially insoluble in water and soluble in alkaline developer, and/or a surfactant which is insoluble or substantially insoluble in water and alkaline developer, and (G) another component.

The amount of the PAG in the form of the sulfonium salt having formula (1) as component (A) is preferably 0.1 to 20 parts by weight, more preferably 0.5 to 15 parts by weight per 80 parts by weight of the base polymer as component (B). As long as the amount of component (A) is in the range, good sensitivity and resolution are achievable and the risk of foreign particles being formed after development or during stripping of resist film is avoided. The PAG may be used alone or in admixture as component (A).

(B) Base Polymer

The base polymer as component (B) preferably contains repeat units having the formula (a1) or repeat units having the formula (a2). These units are simply referred to as repeat units (a1) and (a2).

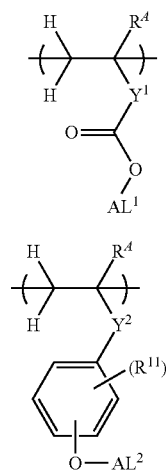

In formulae (a1) and (a2), $R^A$ is each independently hydrogen, fluorine, methyl or trifluoromethyl. $Y^1$ is a single bond, phenylene, naphthylene or (backbone)-C(=O)—O—$Y^{11}$—, wherein $Y^{11}$ is a $C_1$-$C_{11}$ alkanediyl group which may contain a hydroxy moiety, ether bond, ester bond or lactone ring, or a phenylene or naphthylene group. $Y^2$ is a single bond or (backbone)-C(=O)—O—. $AL^1$ and $AL^2$ are each independently an acid labile group.

In formula (a2), $R^{11}$ is a $C_1$-$C_{20}$ hydrocarbyl group which may contain a heteroatom. The hydrocarbyl group may be saturated or unsaturated and straight, branched or cyclic, and examples thereof are as exemplified above for $R^3$. The subscript "a" is an integer of 0 to 4, preferably 0 or 1.

Examples of the structure of formula (a1) wherein $Y^1$ is a variant are illustrated below, but not limited thereto. Herein $R^A$ and $AL^1$ are as defined above.

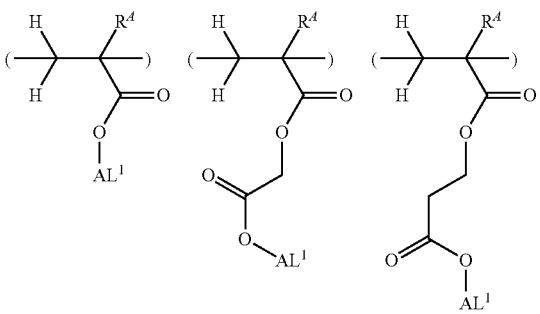

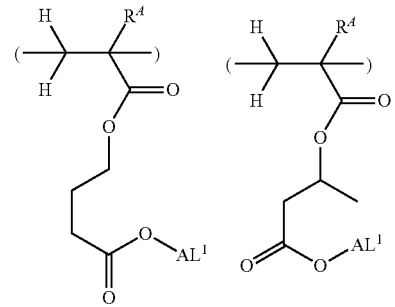

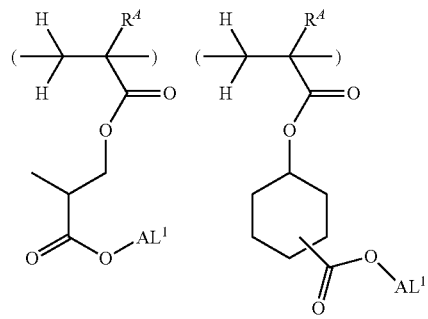

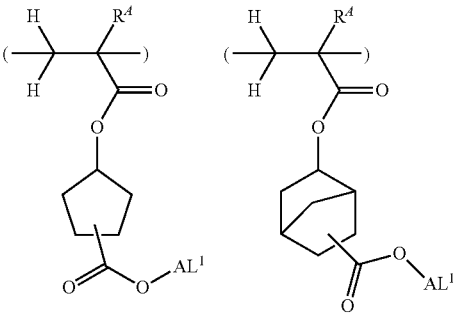

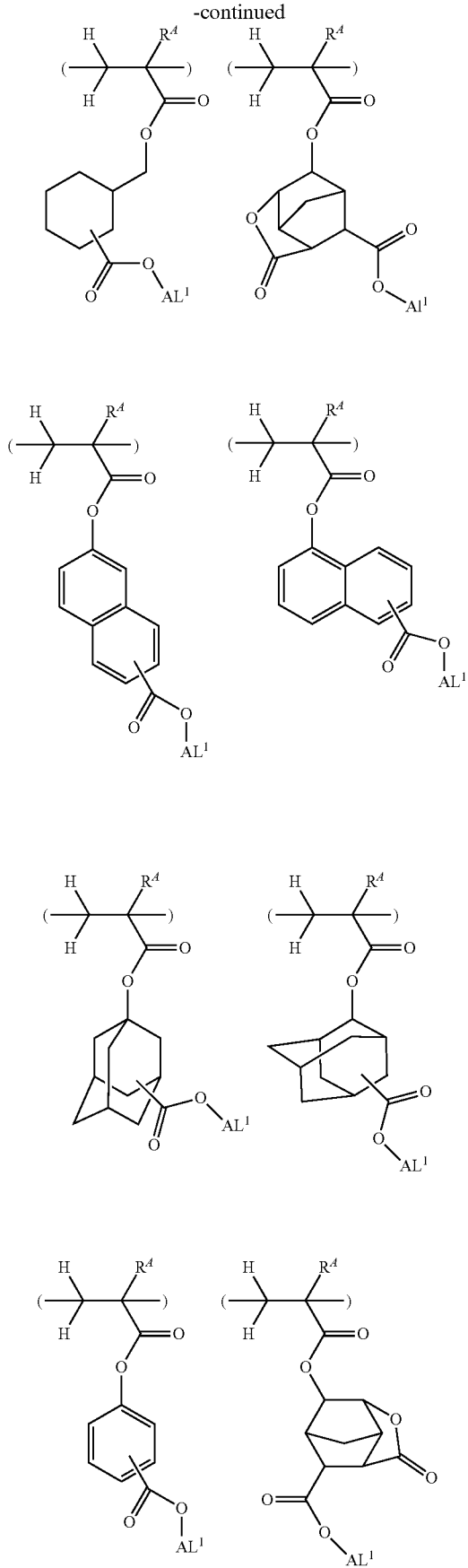
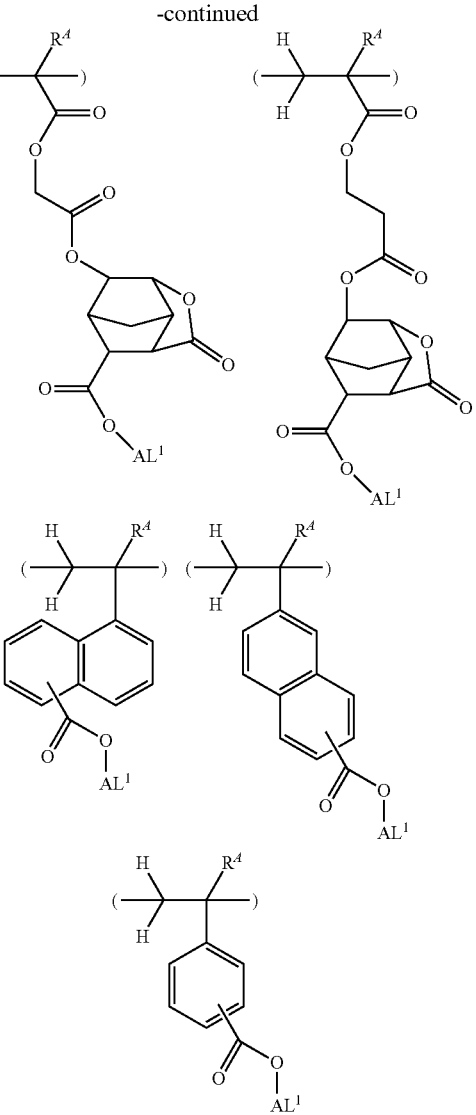

A polymer comprising repeat units having formula (a1) turns alkali soluble through the mechanism that it is decomposed under the action of acid to generate a carboxy group.

The acid labile groups represented by $AL^1$ and $AL^2$ may be selected from a variety of such groups. Preferred examples of the acid labile group are groups of the following formulae (L1) to (L4), $C_4$-$C_{20}$, preferably $C_4$-$C_{15}$ tertiary hydrocarbyl groups, trialkylsilyl groups in which each alkyl moiety has 1 to 6 carbon atoms, and $C_4$-$C_{20}$ saturated hydrocarbyl groups containing a carbonyl moiety, ether bond or ester bond.

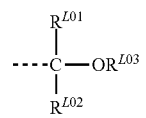

(L1)

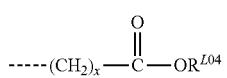

(L2)

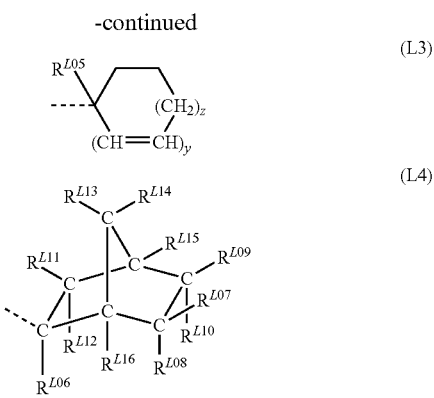

In formula (L1), $R^{L01}$ and $R^{L02}$ are each independently hydrogen or a $C_1$-$C_{18}$ saturated hydrocarbyl group. The saturated hydrocarbyl group may be straight, branched or cyclic and examples thereof include alkyl groups such as methyl, ethyl, propyl, isopropyl, n-butyl, sec-butyl, tert-butyl, n-octyl, and 2-ethylhexyl, and cyclic saturated hydrocarbyl groups such as cyclopentyl, cyclohexyl, norbornyl, tricyclodecanyl, tetracyclododecanyl, and adamantyl. Of the saturated hydrocarbyl groups, those of 1 to 10 carbon atoms are preferred.

$R^{L03}$ is a $C_1$-$C_{18}$, preferably $C_1$-$C_{10}$ hydrocarbyl group which may contain a moiety containing a heteroatom. The hydrocarbyl group may be saturated or unsaturated and straight, branched or cyclic. Saturated hydrocarbyl groups are preferred. In the saturated hydrocarbyl group, some or all of the hydrogen atoms may be substituted by hydroxy, saturated hydrocarbyloxy, oxo, amino, saturated hydrocarbylamino or the like, or any constituent —CH$_2$— may be replaced by a moiety containing a heteroatom, typically oxygen. Suitable saturated hydrocarbyl groups are as exemplified above for the saturated hydrocarbyl groups $R^{L01}$ and $R^{L02}$. Examples of the substituted saturated hydrocarbyl group are shown below.

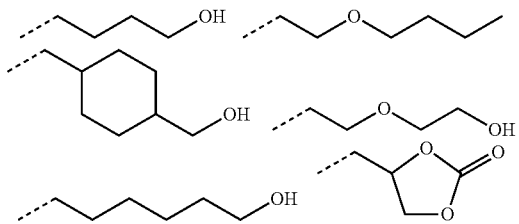

Any two of $R^{L01}$, $R^{L02}$, and $R^{L03}$ may bond together to form a ring with the carbon atom or the carbon and oxygen atoms to which they are attached. When they form a ring, any pair among $R^{L01}$, $R^{L02}$ and $R^{L03}$ is a $C_1$-$C_{18}$, preferably $C_1$-$C_{10}$ alkanediyl group.

In formula (L2), $R^{L04}$ is a $C_4$-$C_{20}$, preferably $C_4$-$C_{15}$ tertiary hydrocarbyl group, a trialkylsilyl group in which each alkyl moiety has 1 to 6 carbon atoms, a $C_4$-$C_{20}$ saturated hydrocarbyl group containing a carbonyl moiety, ether bond or ester bond, or a group of formula (L1). The subscript x is an integer of 0 to 6.

Of the groups $R^{L04}$, the tertiary hydrocarbyl group may be branched or cyclic, and examples thereof include tert-butyl, tert-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopen- tyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups include trimethylsilyl, triethylsilyl, and dimethyl-tert-butylsilyl. Exemplary saturated hydrocarbyl groups containing a carbonyl, ether bond or ester bond include 3-oxocyclohexyl, 4-methyl-2-oxooxan-4-yl, and 5-methyl-2-oxooxolan-5-yl.

In formula (L3), $R^{L05}$ is an optionally substituted $C_1$-$C_8$ saturated hydrocarbyl group or an optionally substituted $C_6$-$C_{20}$ aryl group. The optionally substituted saturated hydrocarbyl group may be straight, branched or cyclic and examples thereof include alkyl groups such as methyl, ethyl, propyl, isopropyl, n-butyl, sec-butyl, tert-butyl, tert-pentyl, n-pentyl, n-hexyl, cyclic saturated hydrocarbyl groups such as cyclopentyl and cyclohexyl, and substituted forms of the foregoing in which some or all of the hydrogen atoms are substituted by hydroxy, $C_1$-$C_6$ saturated hydrocarbyloxy, carboxy, $C_1$-$C_6$ saturated hydrocarbylcarbonyl, oxo, amino, $C_1$-$C_6$ saturated hydrocarbylamino, cyano, mercapto, $C_1$-$C_6$ saturated hydrocarbylthio, sulfo or the like. Examples of the optionally substituted aryl group include phenyl, methylphenyl, naphthyl, anthryl, phenanthryl, and pyrenyl, and substituted forms of the foregoing in which some or all of the hydrogen atoms are substituted by hydroxy, $C_1$-$C_{10}$ saturated hydrocarbyloxy, carboxy, $C_1$-$C_{10}$ saturated hydrocarbylcarbonyl, oxo, amino, $C_1$-$C_{10}$ saturated hydrocarbylamino, cyano, mercapto, $C_1$-$C_{10}$ saturated hydrocarbylthio, sulfo or the like.

In formula (L3), y is equal to 0 or 1, z is an integer of 0 to 3, and 2y+z is equal to 2 or 3.

In formula (L4), $R^{L06}$ is an optionally substituted $C_1$-$C_8$ saturated hydrocarbyl group or an optionally substituted $C_6$-$C_{20}$ aryl group. Examples of the optionally substituted saturated hydrocarbyl and optionally substituted aryl groups are the same as exemplified above for $R^{L05}$.

$R^{L07}$ to $R^{L16}$ are each independently hydrogen or an optionally substituted $C_1$-$C_{15}$ hydrocarbyl group. The hydrocarbyl group may be saturated or unsaturated and straight, branched or cyclic, with saturated hydrocarbyl groups being preferred. Examples of the hydrocarbyl group include alkyl groups such as methyl, ethyl, propyl, isopropyl, n-butyl, sec-butyl, tert-butyl, tert-pentyl, n-hexyl, n-octyl, n-nonyl, n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl and cyclohexylbutyl; and substituted forms of the foregoing in which some or all of the hydrogen atoms are substituted by hydroxy, $C_1$-$C_{10}$ saturated hydrocarbyloxy, carboxy, $C_1$-$C_{10}$ saturated hydrocarbyloxycarbonyl, oxo, amino, $C_1$-$C_{10}$ saturated hydrocarbylamino, cyano, mercapto, $C_1$-$C_{10}$ saturated hydrocarbylthio, sulfo or the like. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each combination of two of $R^{L07}$ to $R^{L16}$ represents a $C_1$-$C_{18}$ hydrocarbylene group when they form a ring, examples of which are the ones exemplified above for the hydrocarbyl groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, $R^{L14}$ and $R^{L15}$, or a similar pair).

Of the acid labile groups having formula (L1), the straight and branched ones are exemplified by the following groups, but not limited thereto.

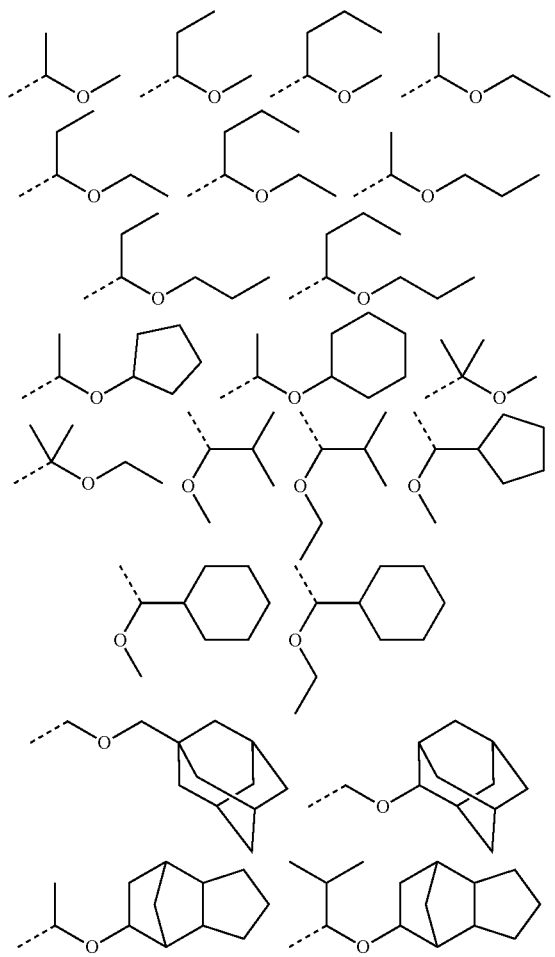

Of the acid labile groups having formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile group having formula (L2) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile group having formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl. 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulae (L4-1) to (L4-4) are preferred.

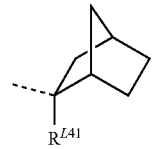

(L4-1)

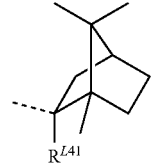

(L4-2)

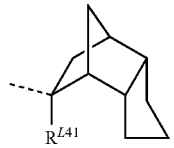

(L4-3)

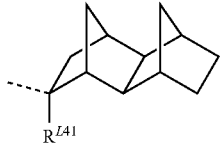

(L4-4)

In formulae (L4-1) to (L4-4), the broken line denotes a bonding site and direction. $R^{L41}$ is each independently a $C_1$-$C_{10}$ hydrocarbyl group. The hydrocarbyl group may be saturated or unsaturated and straight, branched or cyclic, and examples thereof include alkyl groups such as methyl, ethyl, propyl, isopropyl, n-butyl, sec-butyl, tert-butyl, tert-pentyl, n-pentyl, n-hexyl, and cyclic saturated hydrocarbyl groups such as cyclopentyl and cyclohexyl.

For formulae (L4-1) to (L4-4), there can exist stereoisomers (enantiomers or diastereomers). Each of formulae (L4-1) to (L4-4) collectively represents all such stereoisomers. When the acid labile group is of formula (L4), there may be contained a plurality of stereoisomers.

For example, the formula (L4-3) represents one or a mixture of two selected from groups having the following formulae (L4-3-1) and (L4-3-2).

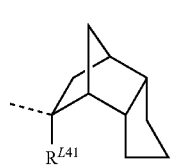

(L4-3-1)

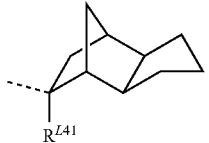

(L4-3-2)

Herein $R^{L41}$ is as defined above.

Similarly, the formula (L4-4) represents one or a mixture of two or more selected from groups having the following formulae (L4-4-1) to (L4-4-4).

(L4-4-1)

(L4-4-2)

(L4-4-3)

(L4-4-4)

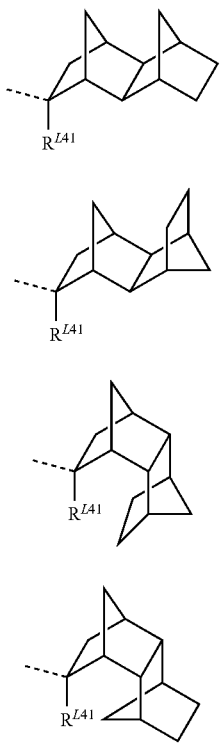

Herein $R^{L41}$ is as defined above.

Each of formulae (L4-1) to (L4-4), (L4-3-1), (L4-3-2), and (L4-4-1) to (L4-4-4) collectively represents an enantiomer thereof and a mixture of enantiomers.

It is noted that in the above formulae (L4-1) to (L4-4), (L4-3-1), (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-saturated hydrocarbyl group of bicyclo[2.2.1]heptane skeleton as a substituent group, there may be contained monomers substituted with an endo-alkyl group as represented by the following formulae (L4-1-endo) to (L4-4-endo). For good reactivity, an exo proportion of at least 50 mol % is preferred, with an exo proportion of at least 80 mol % being more preferred.

(L4-1-endo)

(L4-2-endo)

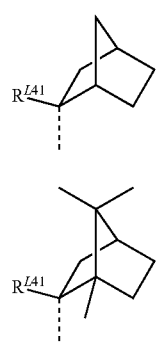

(L4-3-endo)

(L4-4-endo)

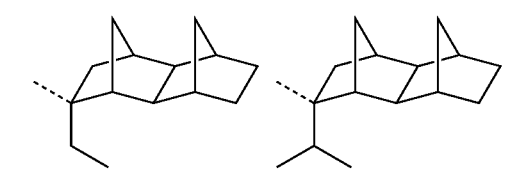

Herein $R^{L41}$ is as defined above.

Illustrative examples of the acid labile group having formula (L4) are given below Of the acid labile groups represented by $AL^1$ and $AL^2$, examples of the $C_4$-$C_{20}$ tertiary hydrocarbyl groups, trialkylsilyl groups in which each alkyl moiety has 1 to 6 carbon atoms, and $C_4$-$C_{20}$ saturated hydrocarbyl groups containing carbonyl, ether bond or ester bond are as exemplified above for $R^{LO4}$.

Illustrative examples of the repeat units of formula (a1) are given below, but not limited thereto. Herein $R^A$ is as defined above.

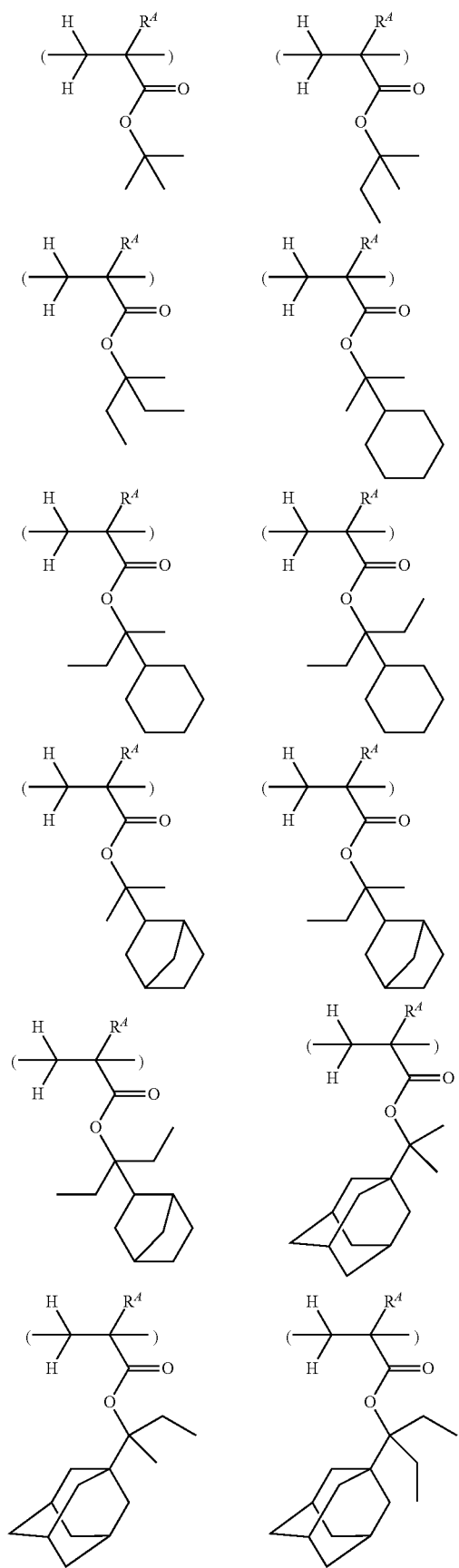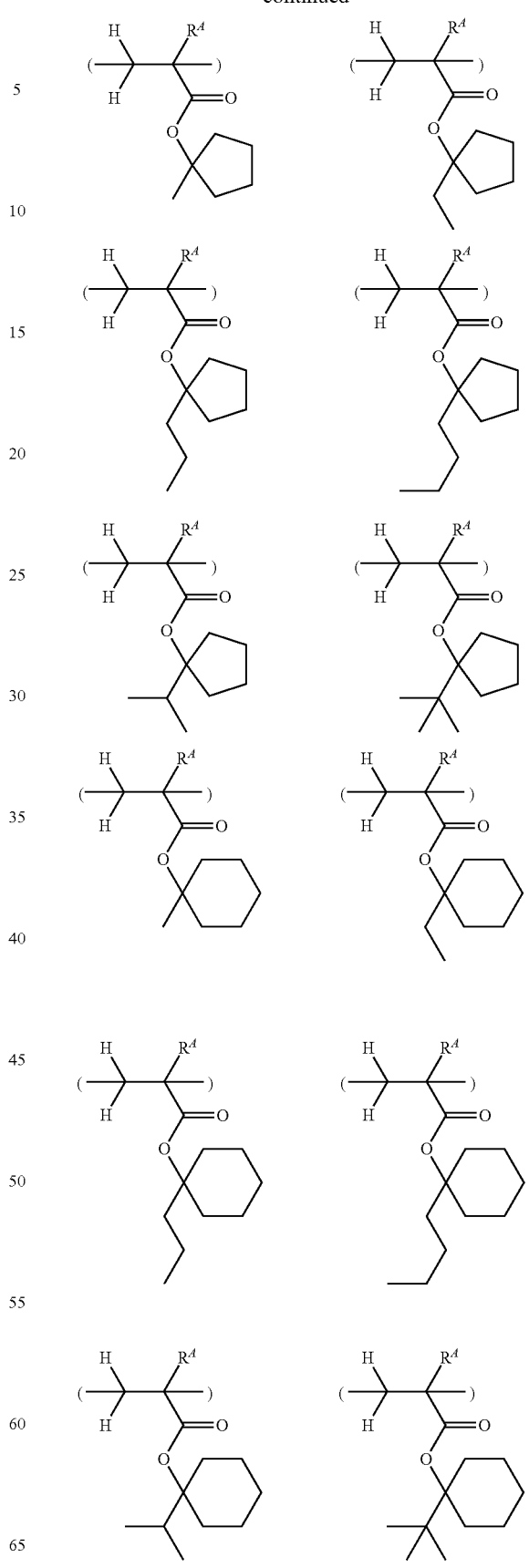

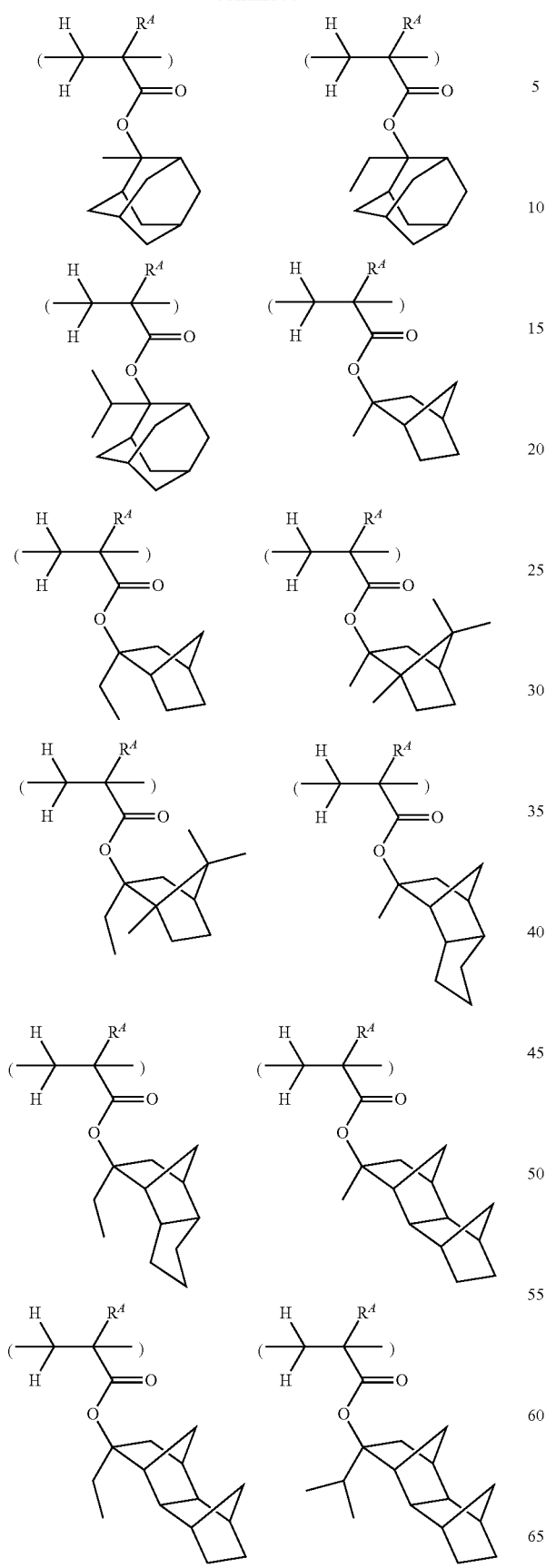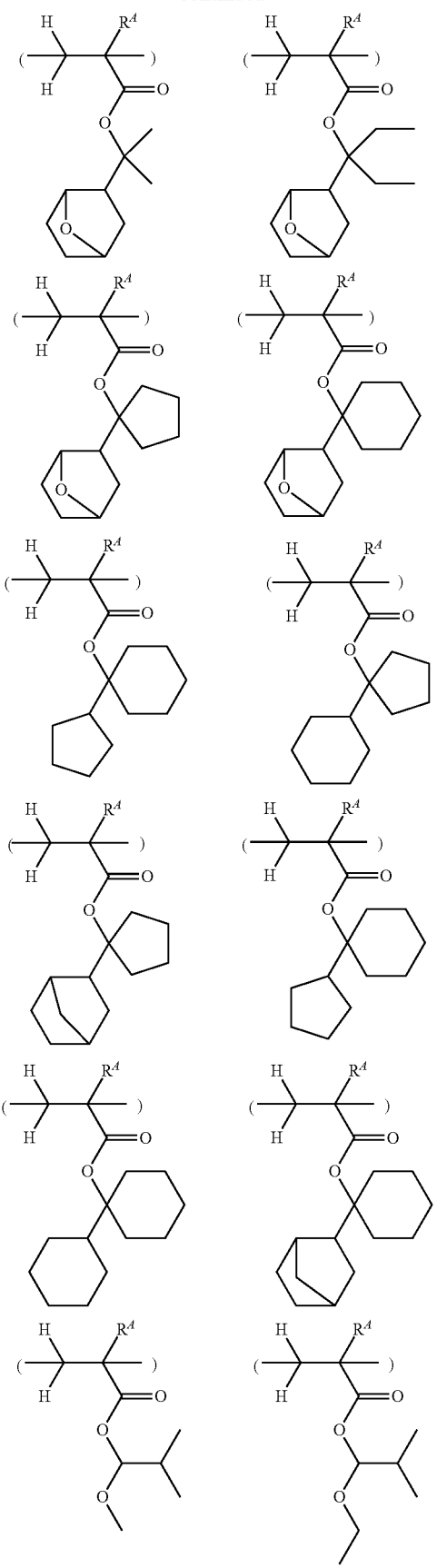

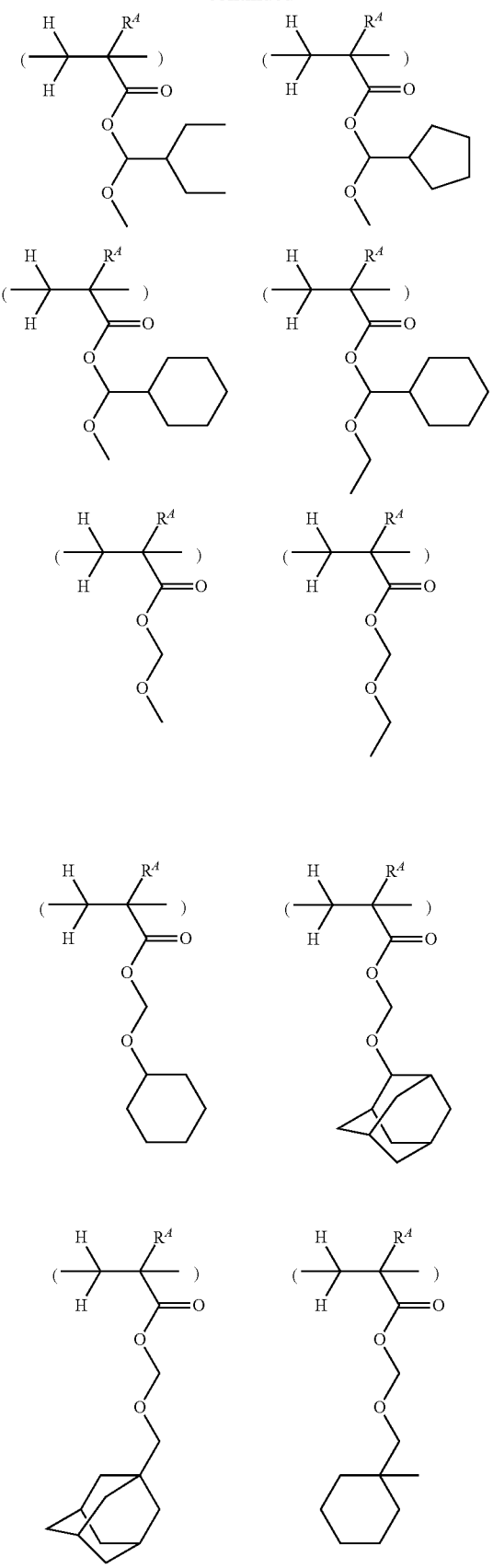
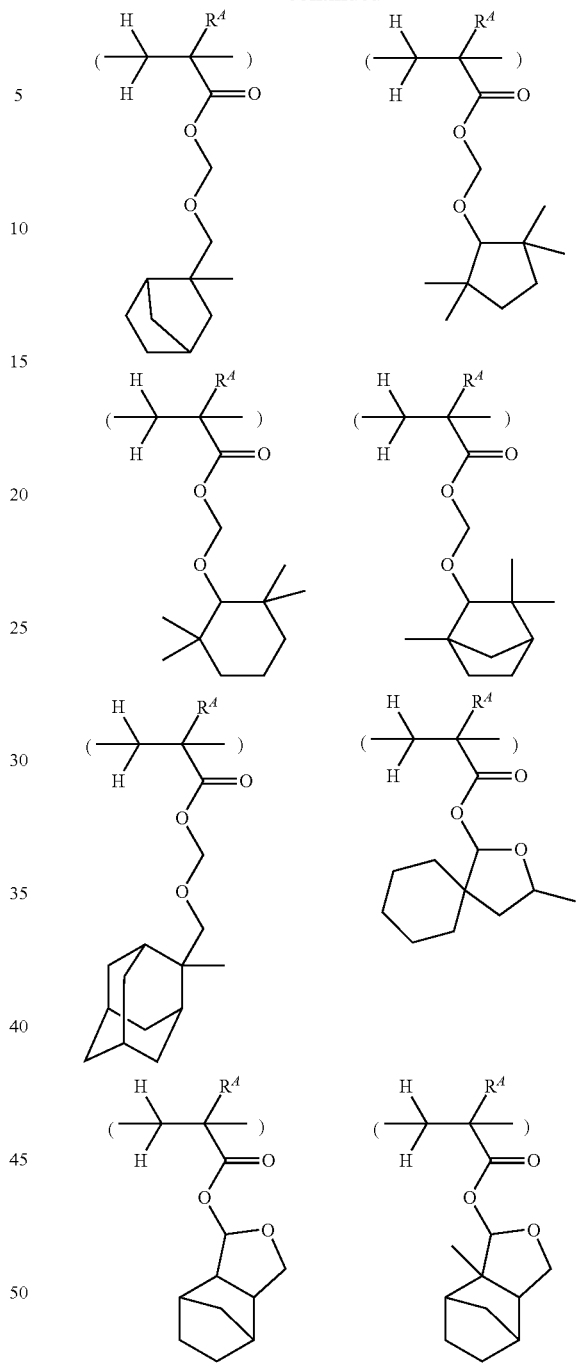

The above examples correspond to those units of formula (a1) wherein $Y^1$ is a single bond. Where $Y^1$ is other than a single bond, a combination with a similar acid labile group is possible. Thus examples of the repeat units of formula (a1) wherein $Y^1$ is other than a single bond are as illustrated above.

Like the repeat units having formula (a1), a polymer comprising repeat units having formula (a2) turns alkali soluble through the mechanism that it is decomposed under the action of acid to generate a hydroxy group. Illustrative examples of the repeat units of formula (a2) are given below, but not limited thereto. Herein $R^4$ is as defined above.

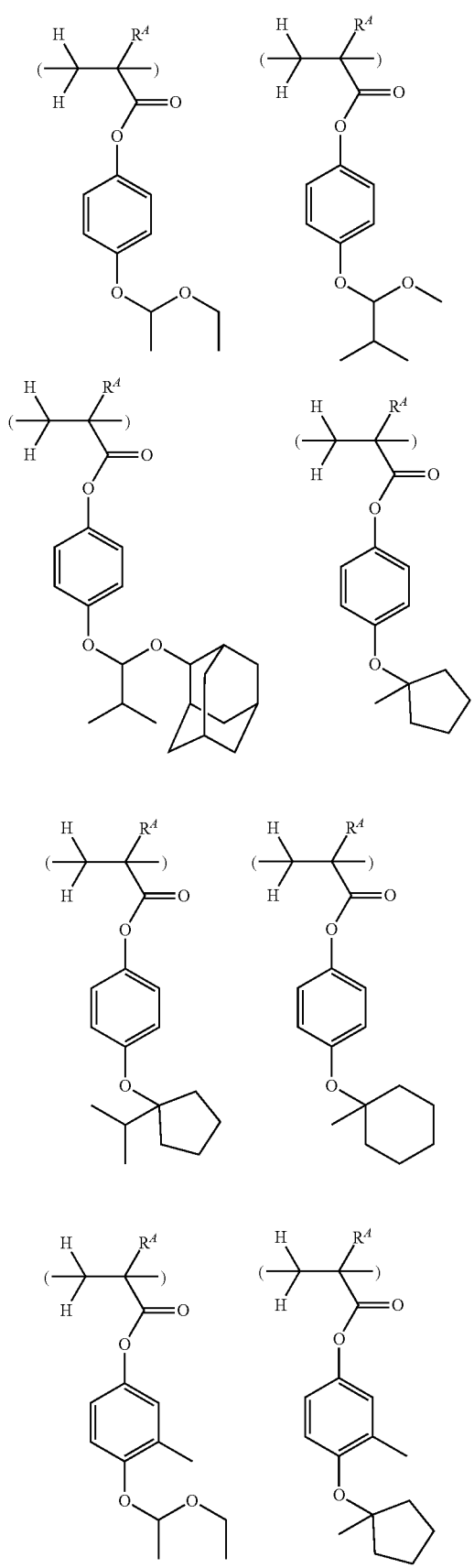
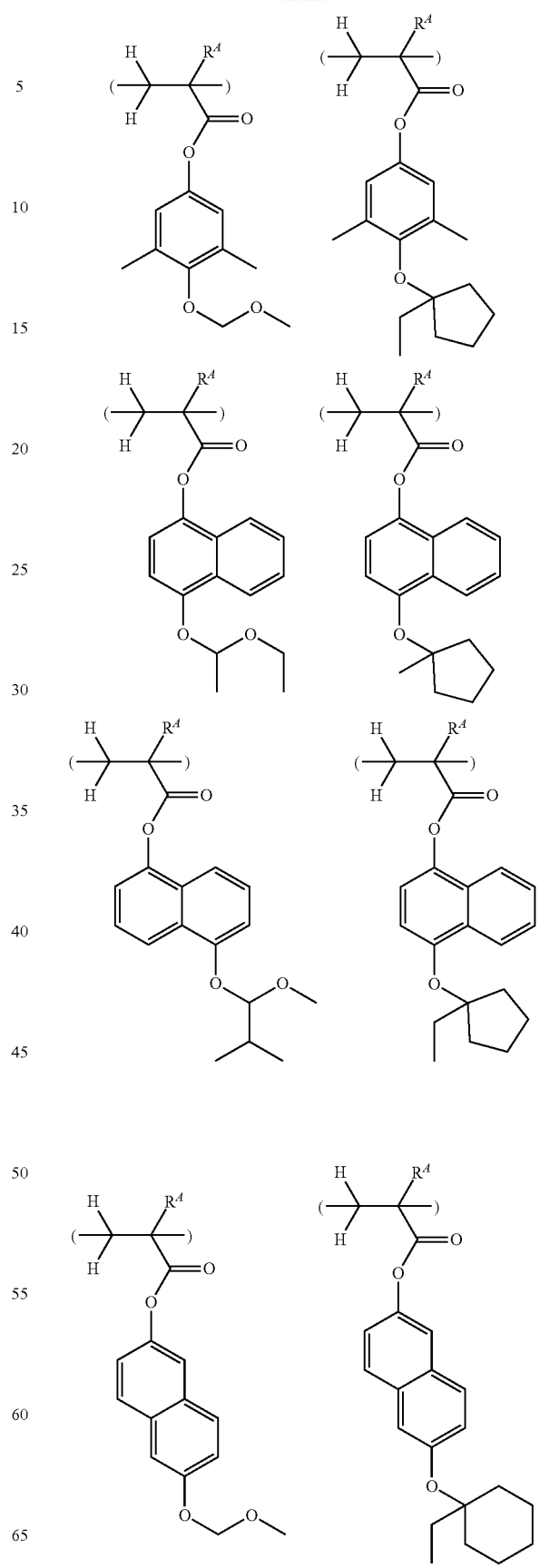

-continued

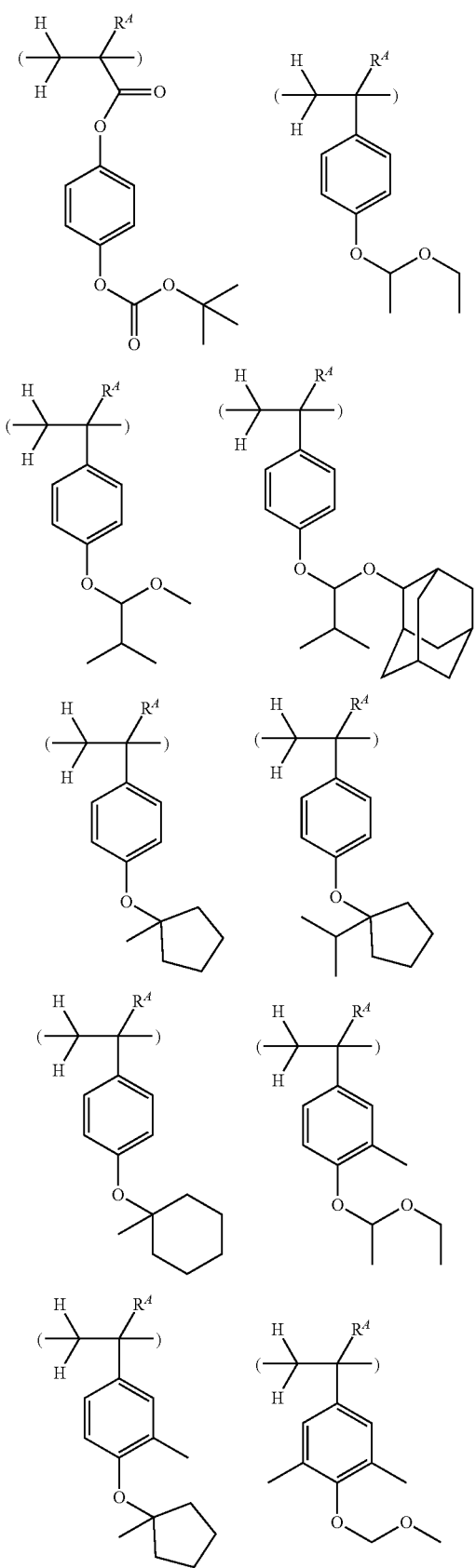

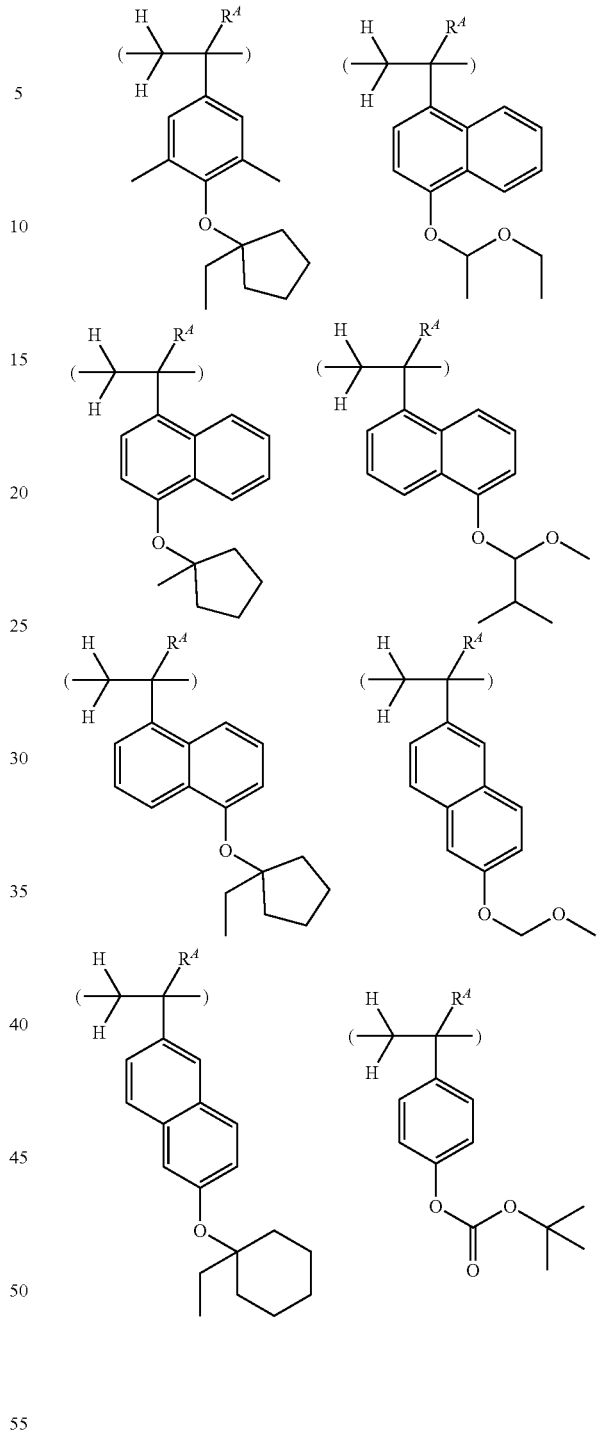

In the case of the base polymer comprising repeat units derived from the sulfonium salt having formula (1) wherein $X^-$ is an anion having formula (2C) or (2D), the base polymer contains repeat units having the formula (a3) or repeat units having the formula (a4) as well as repeat units (a1) or (a2). The repeat units having formula (a3) and repeat units having formula (a4) are simply referred to as repeat units (a3) and repeat units (a4), respectively. The polymer in this embodiment is also referred to as polymer-bound photoacid generator A.

(a3)

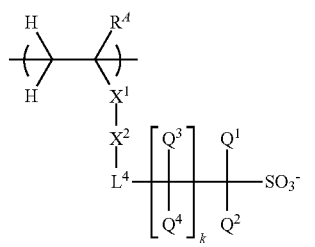

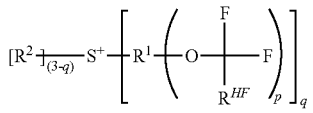

(a4)

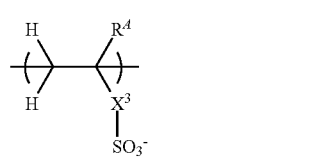

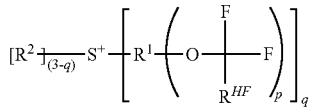

Herein, $R^A$, $R^1$, $R^2$, $R^{HF}$, $X^1$ to $X^3$, $L^4$, $Q^1$ to $Q^4$, k, p, and q are as defined above.

In a preferred embodiment, the base polymer further comprises repeat units having the formula (b1) or repeat units having the formula (b2), which are simply referred to as repeat units (b1) or (b2).

(b1)

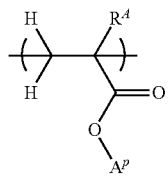

(b2)

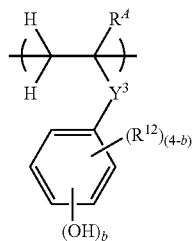

In formulae (b1) and (b2), $R^A$ is each independently hydrogen, fluorine, methyl or trifluoromethyl. $A^P$ is hydrogen or a polar group containing at least one structure selected from among hydroxy, cyano, carbonyl, carboxy, ether bond, ester bond, sulfonic ester bond, carbonate bond, lactone ring, sultone ring and carboxylic anhydride. $Y^3$ is a single bond or (backbone)—C(=O)—O—. $R^{12}$ is halogen, cyano, a $C_1$-$C_{20}$ hydrocarbyl group which may contain a heteroatom, $C_1$-$C_{20}$ hydrocarbyloxy group which may contain a heteroatom, or $C_2$-$C_{20}$ hydrocarbylcarbonyl group which may contain a heteroatom. The subscript b is an integer of 1 to 4.

Examples of the repeat unit having formula (b1) are shown below, but not limited thereto. Herein, $R^A$ is as defined above.

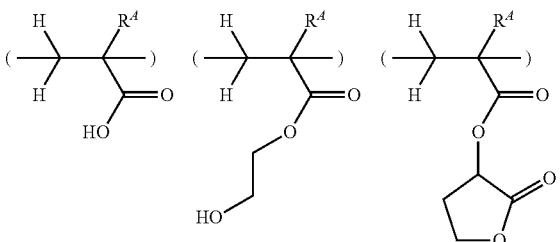

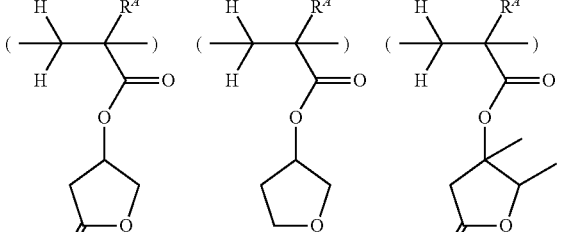

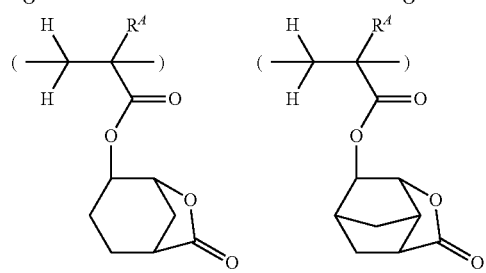

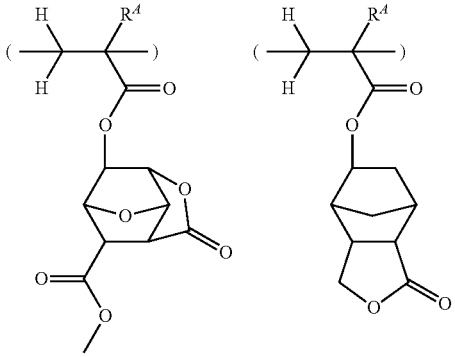

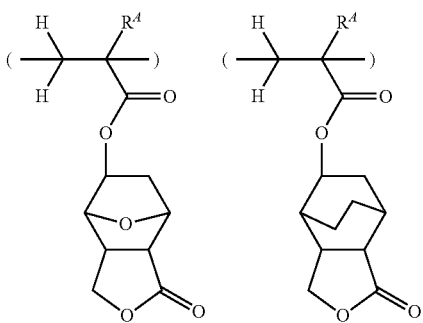

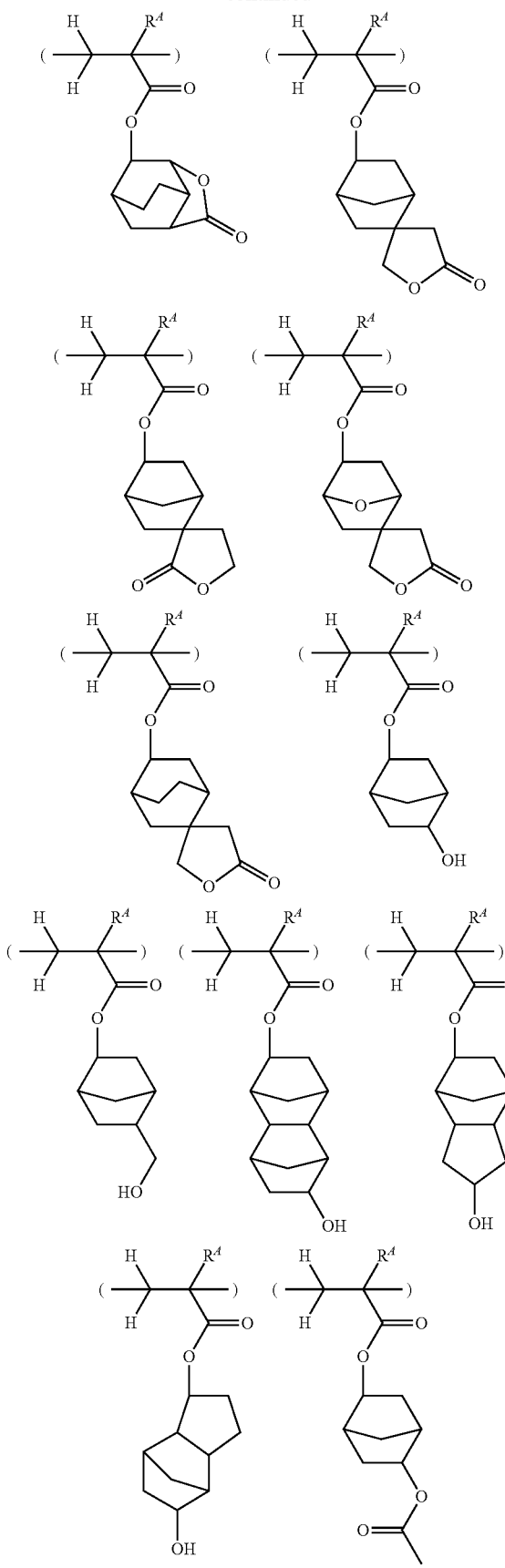
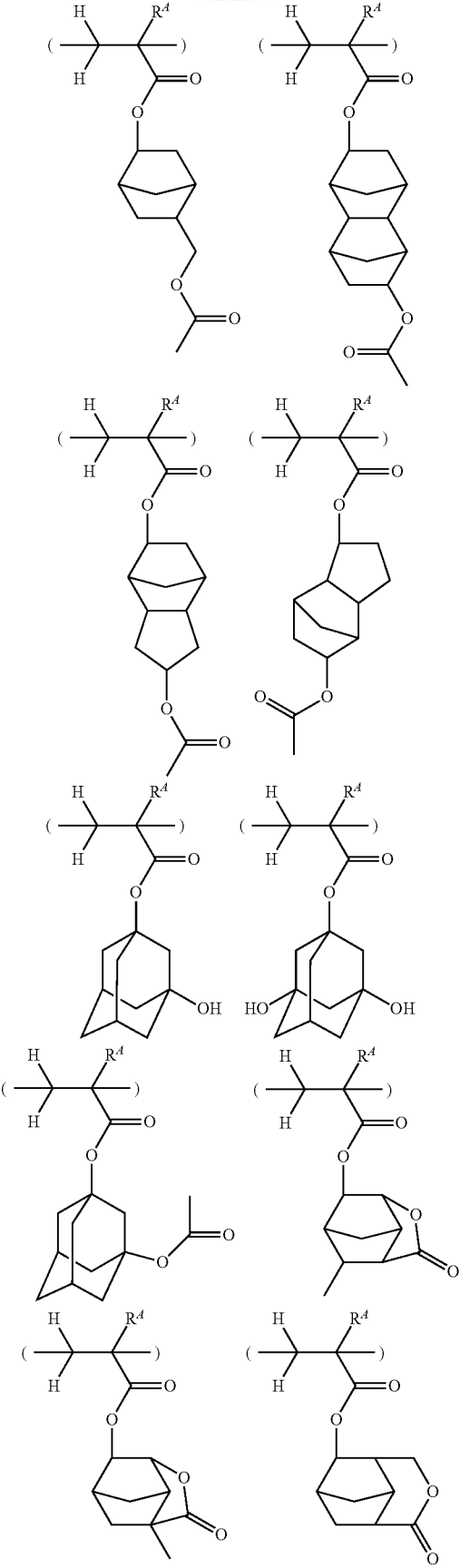

75
-continued
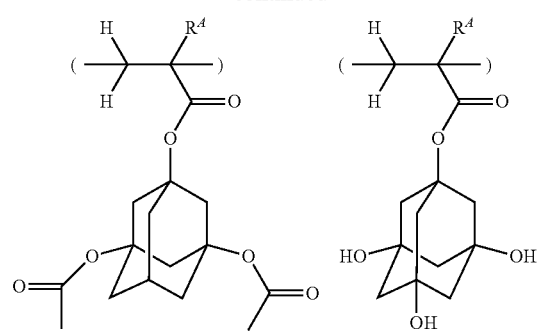
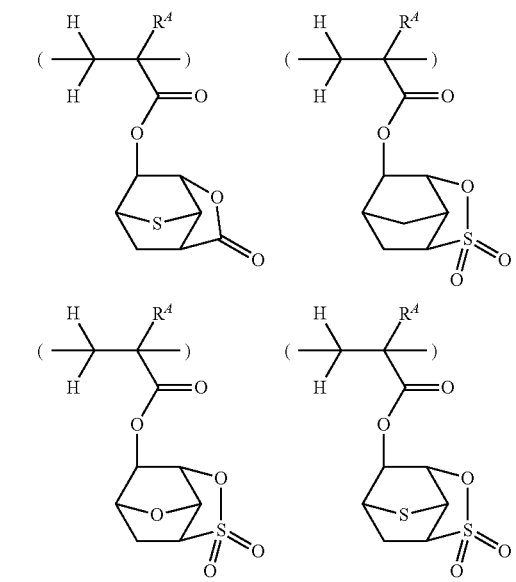
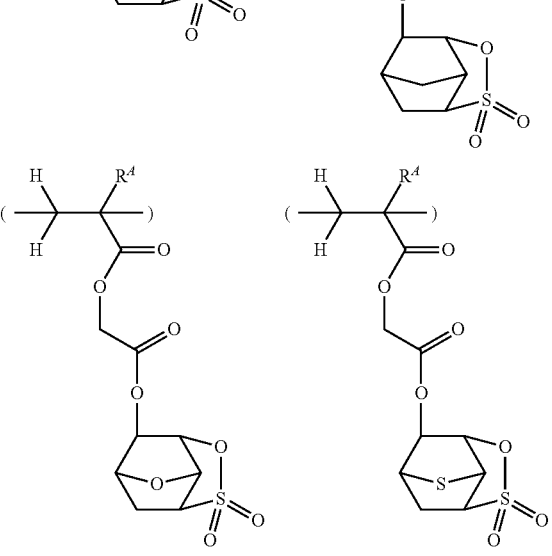
76
-continued
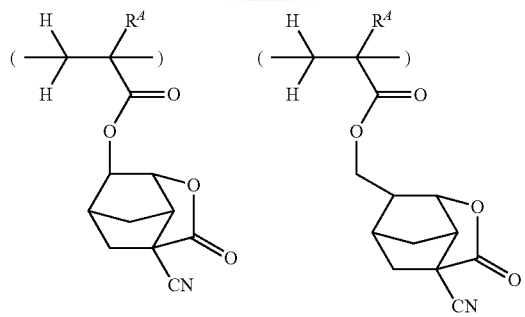
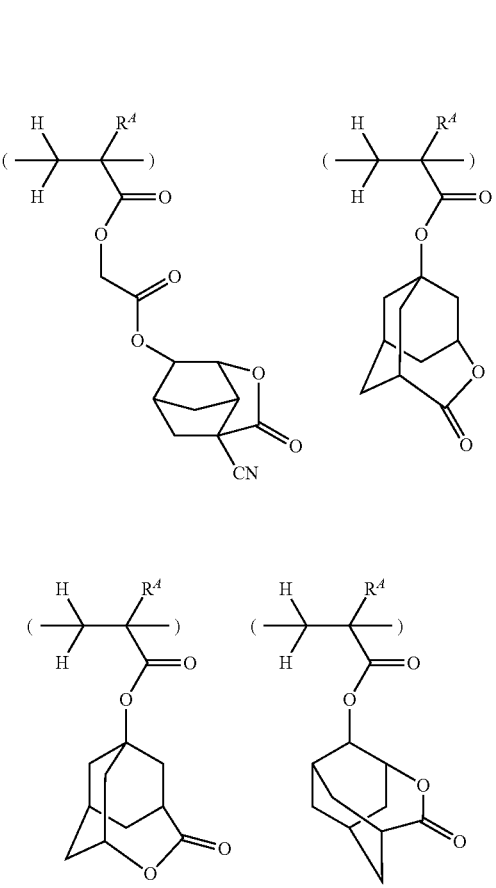
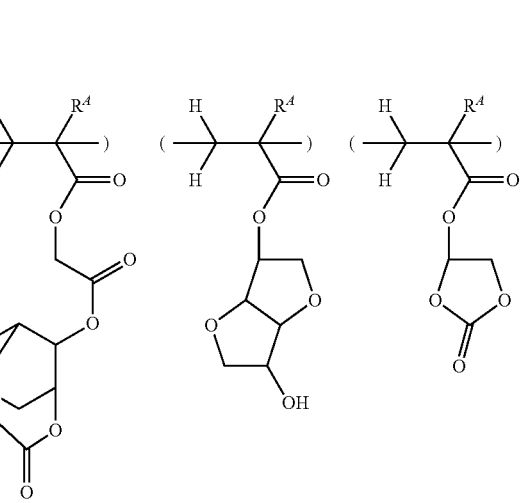

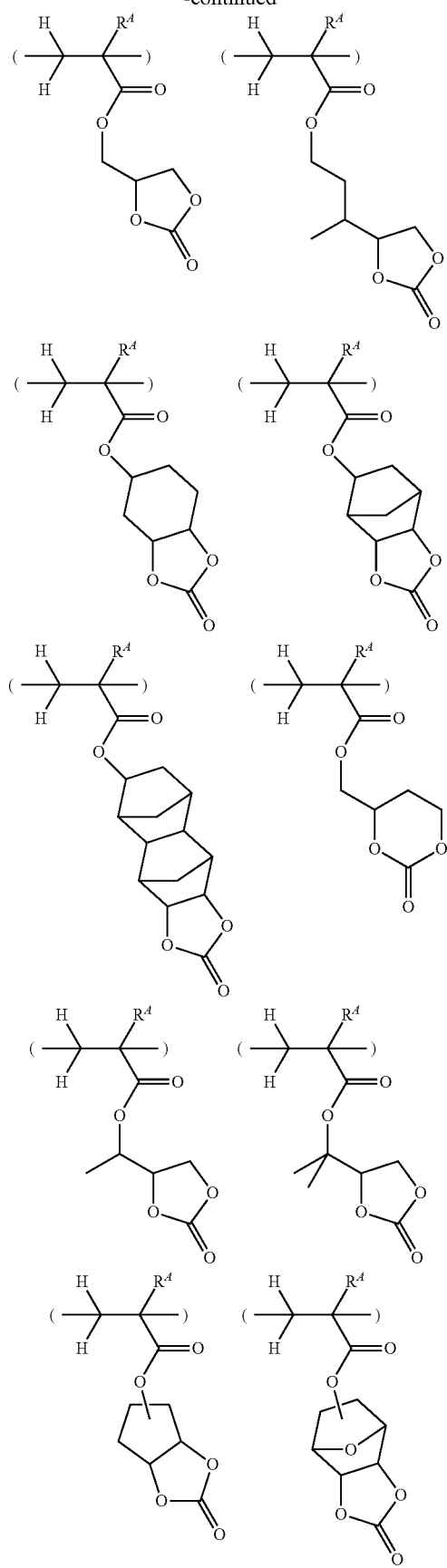
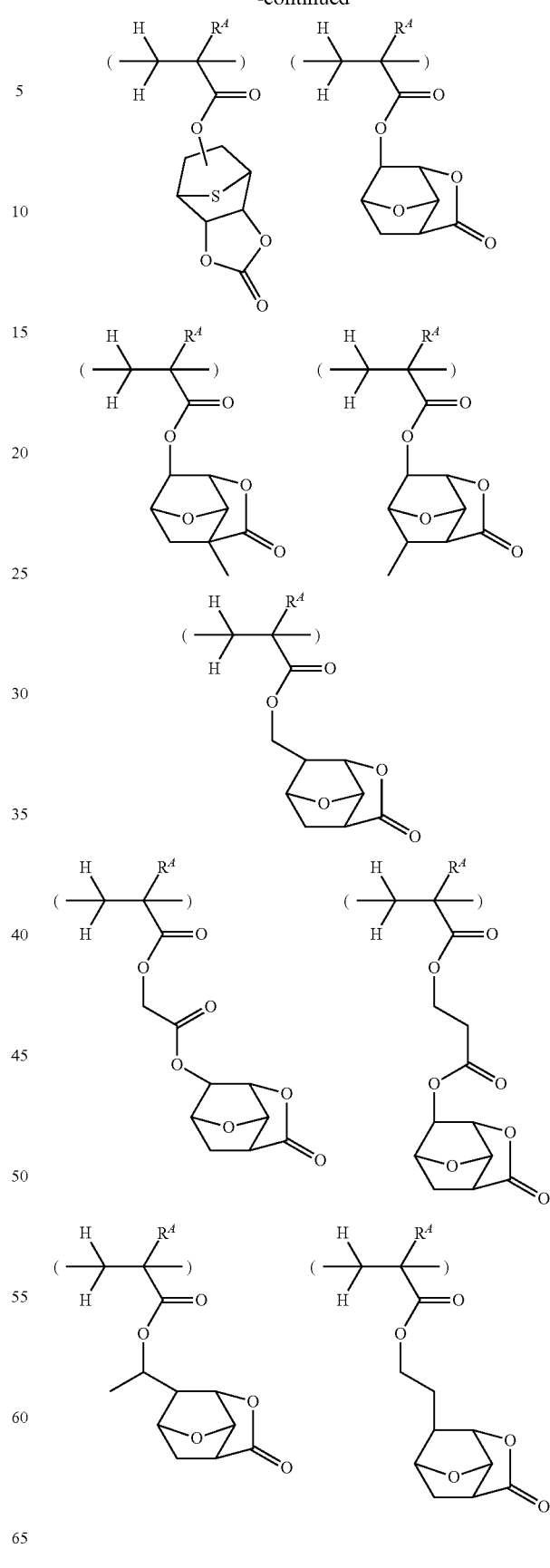

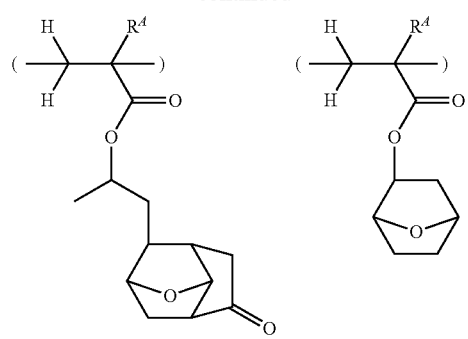
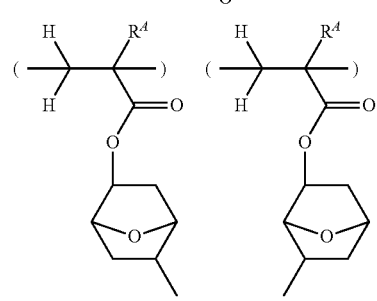
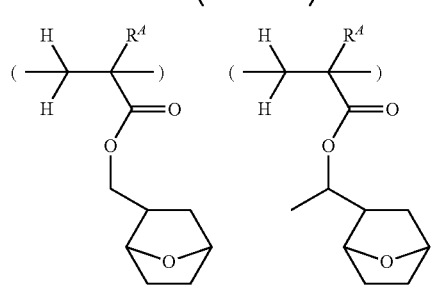
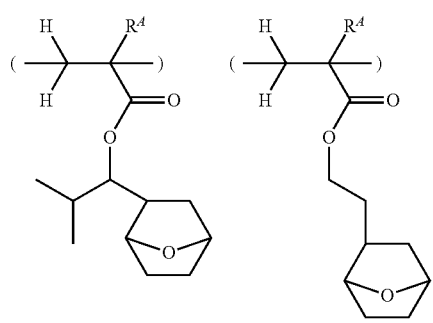
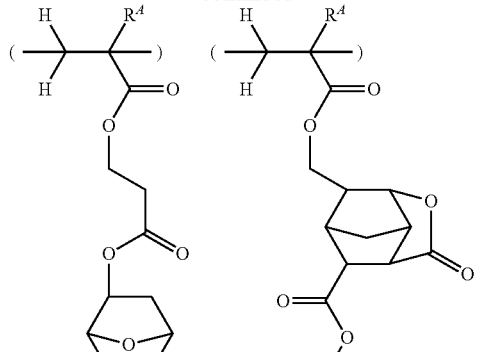
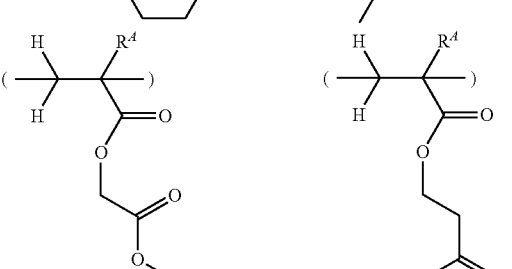
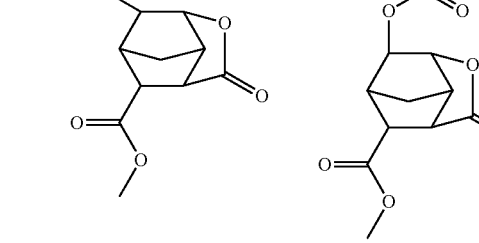

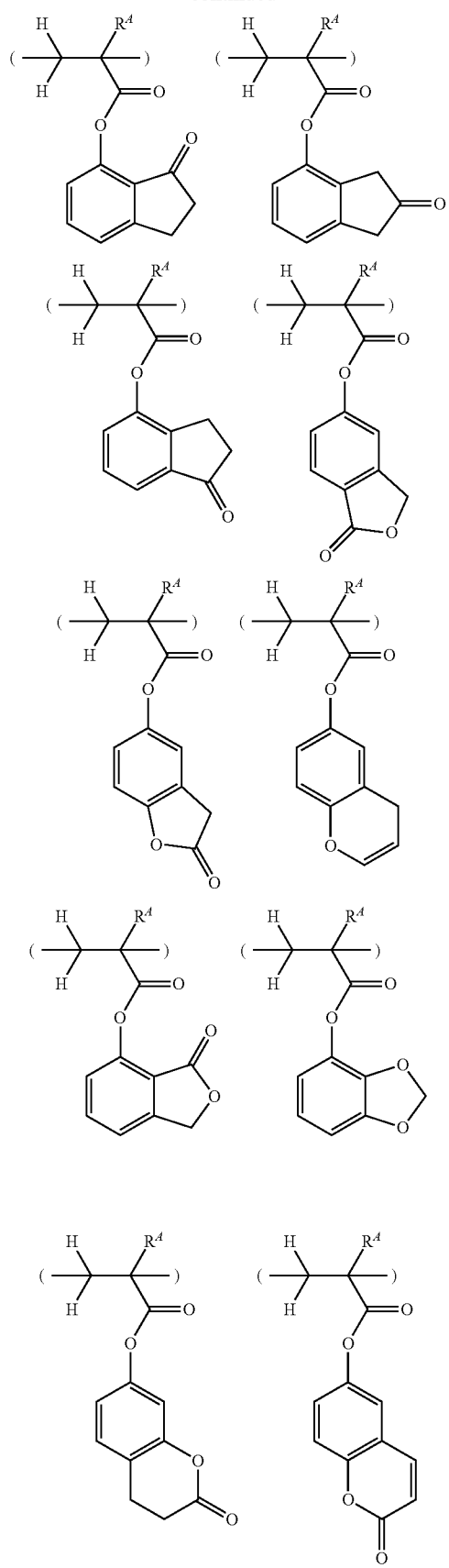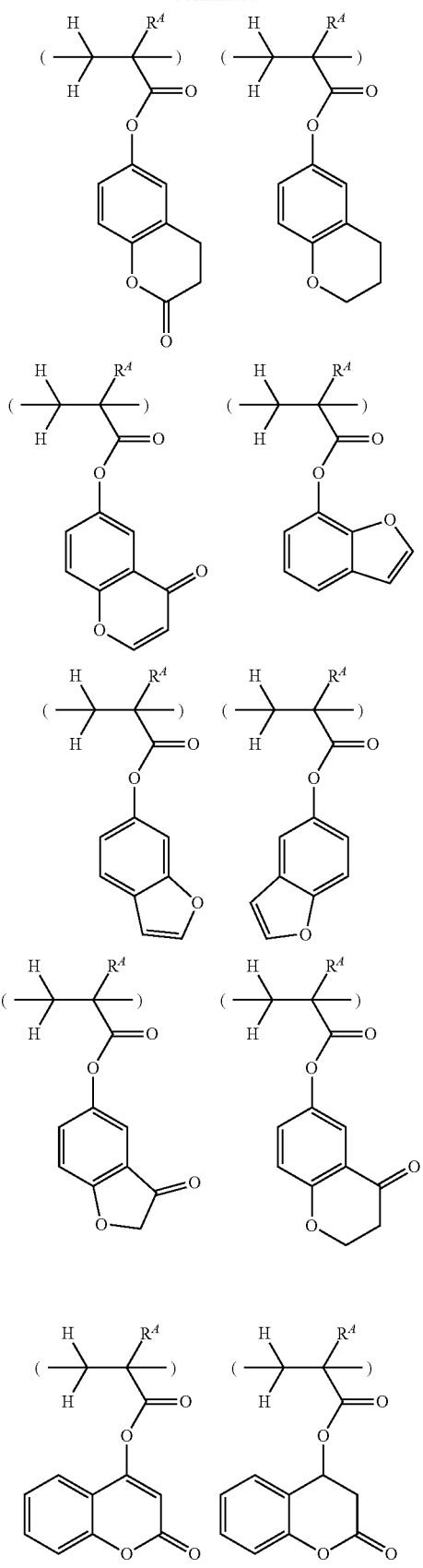

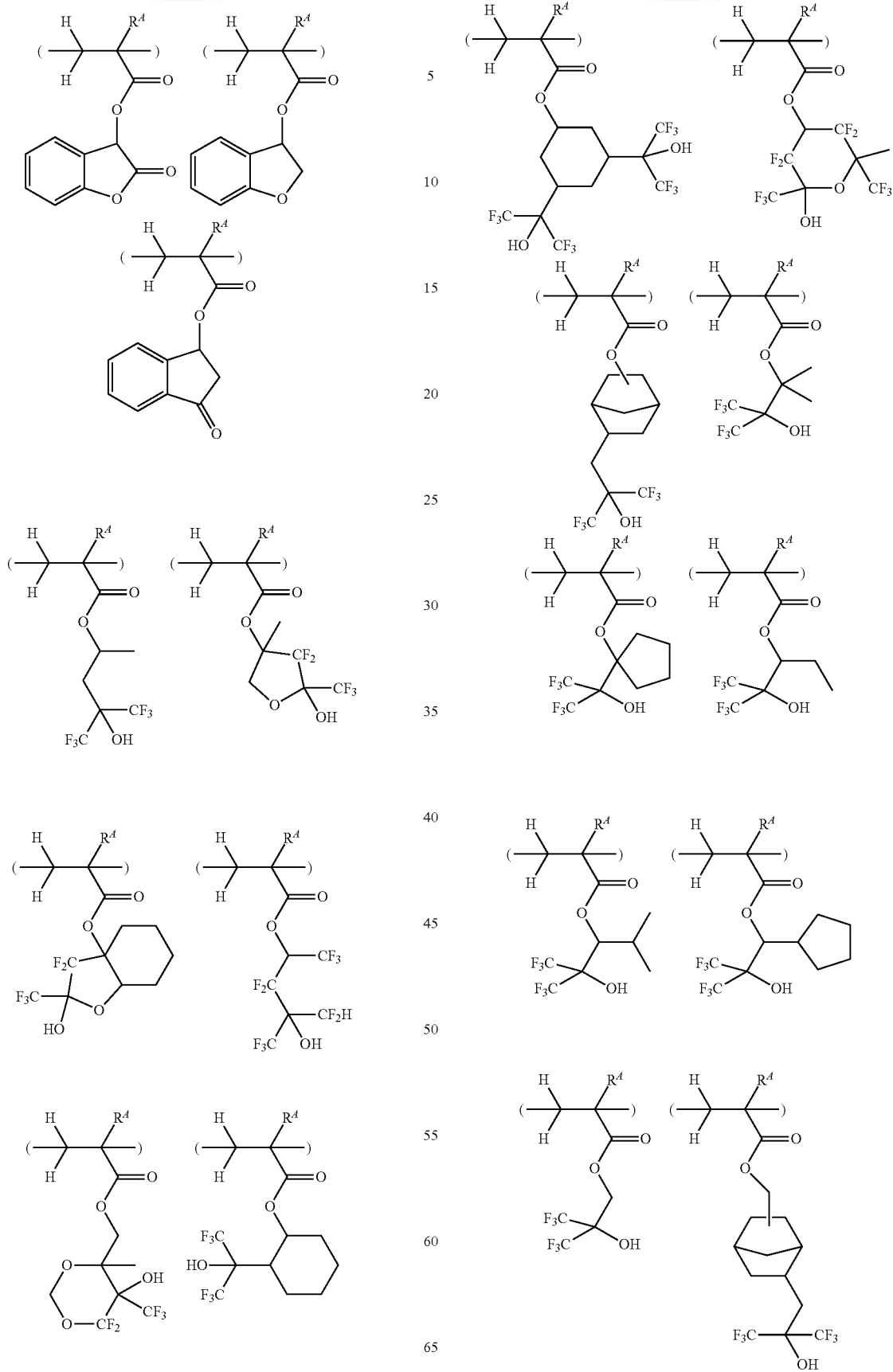

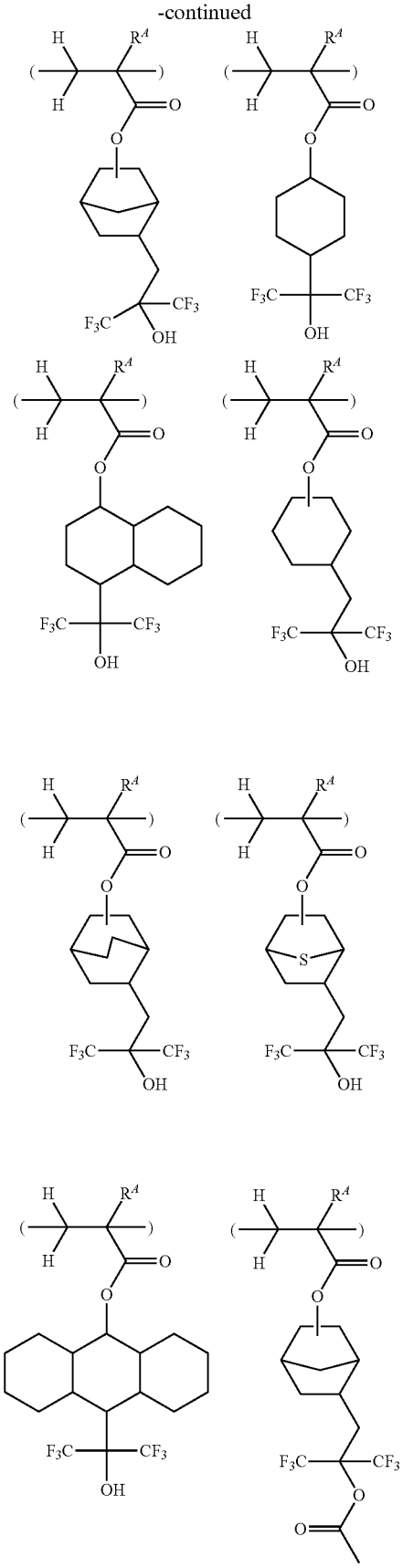
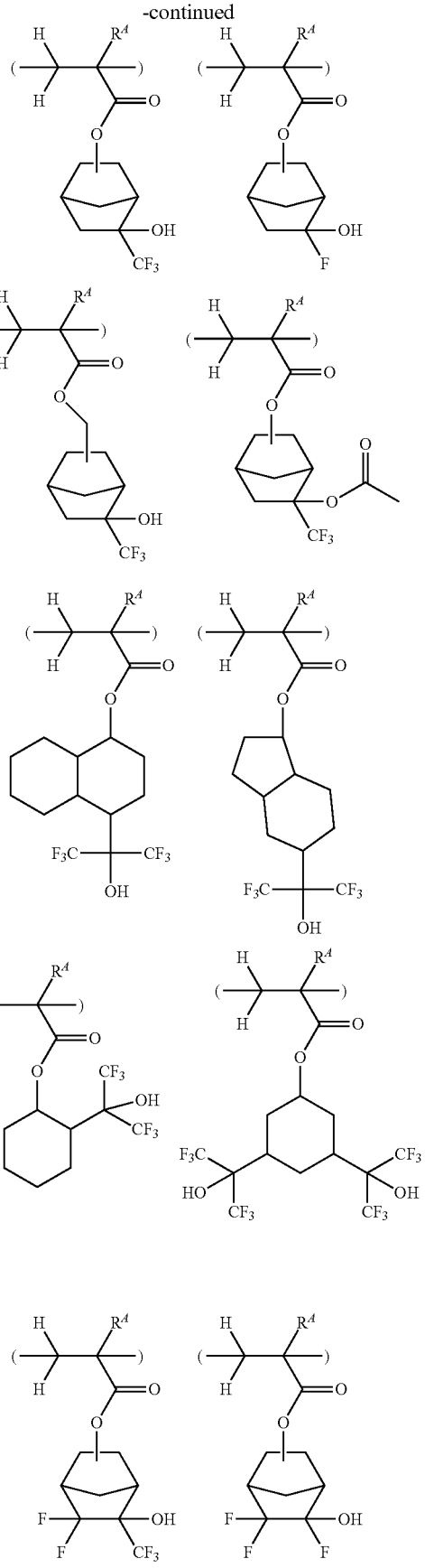

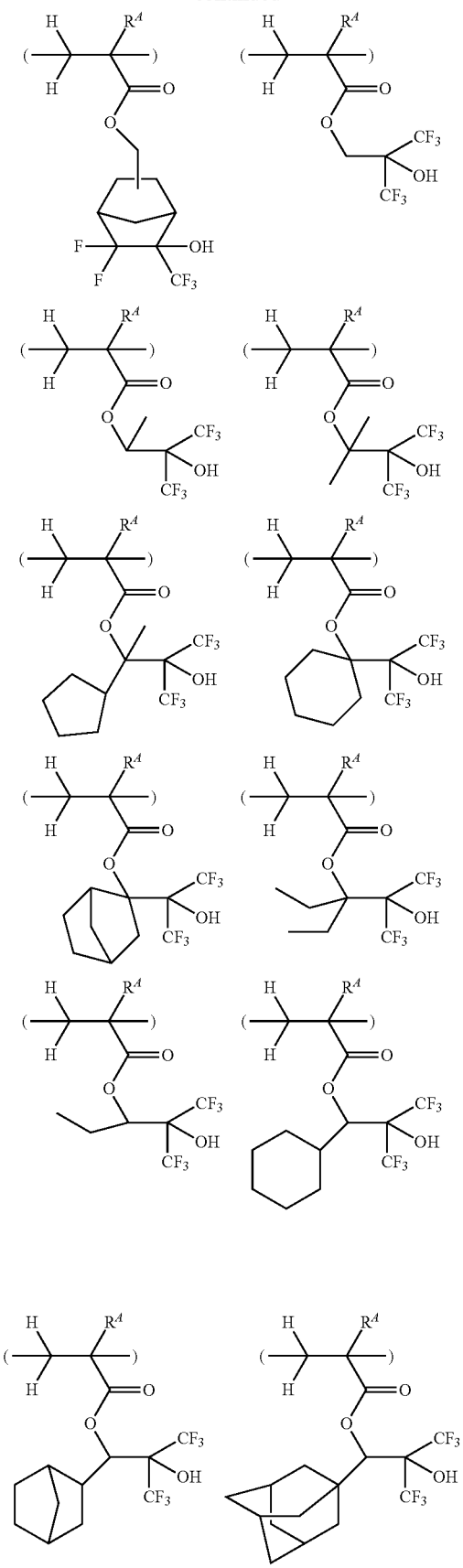
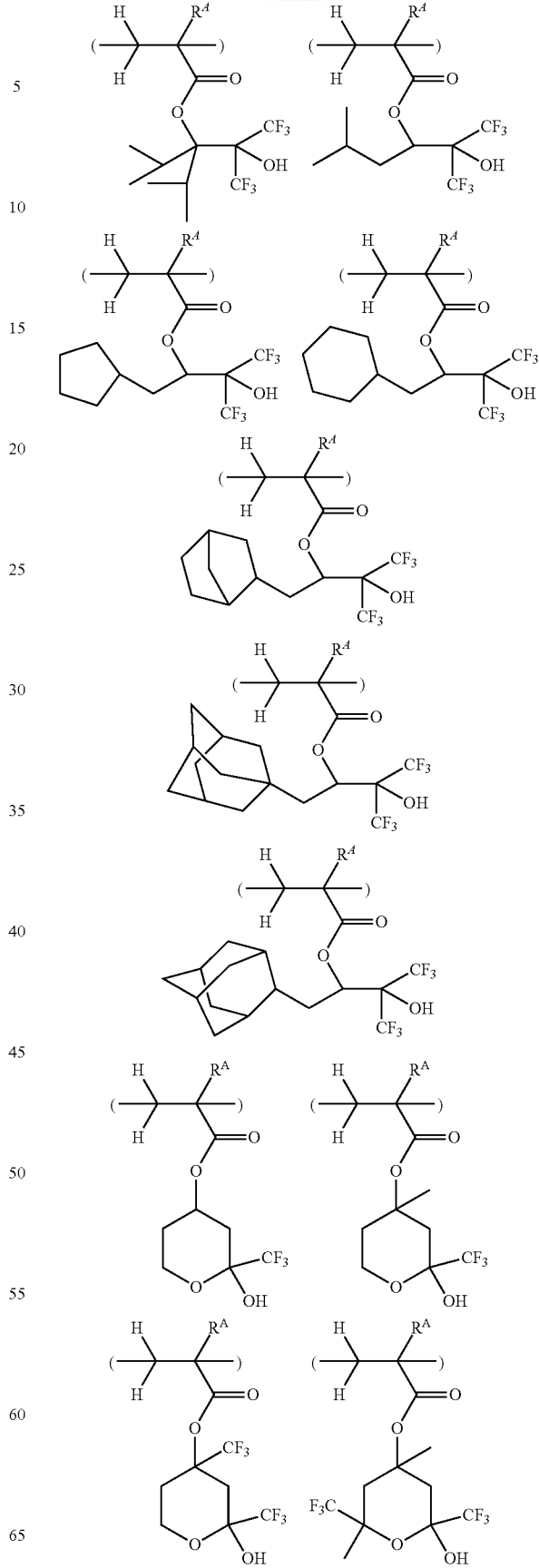

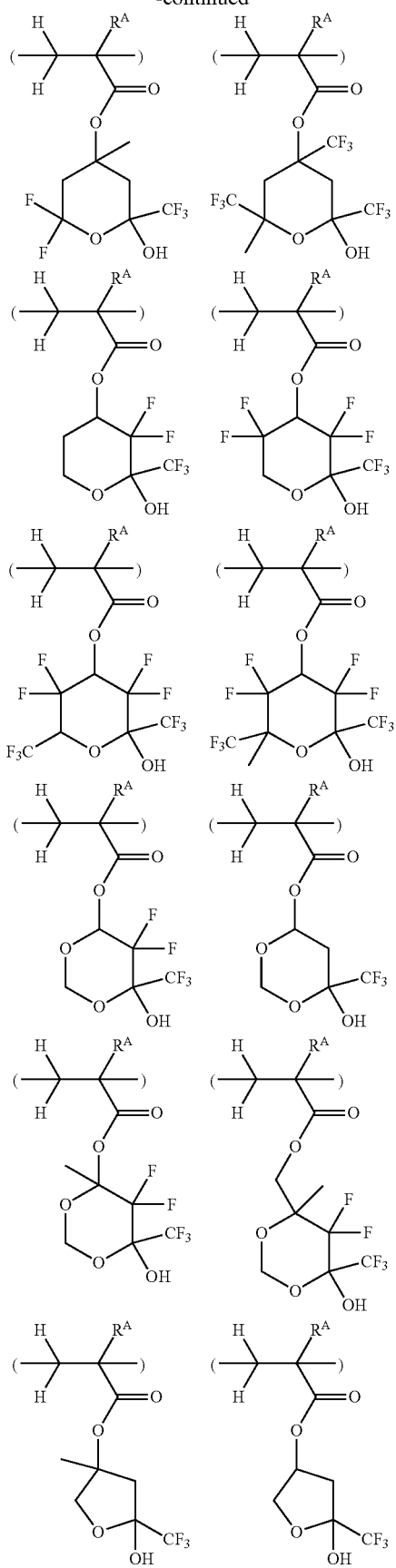
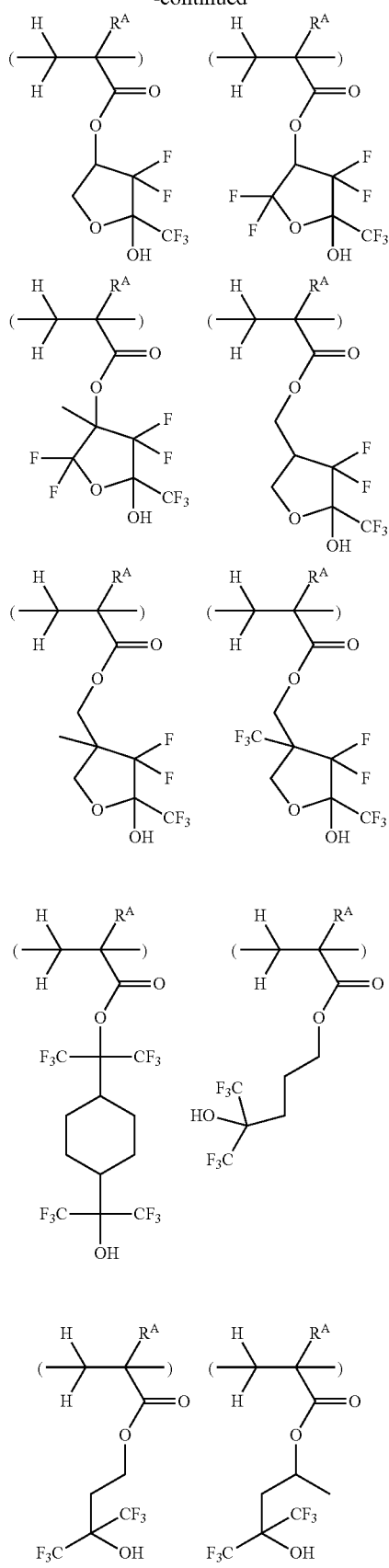

-continued
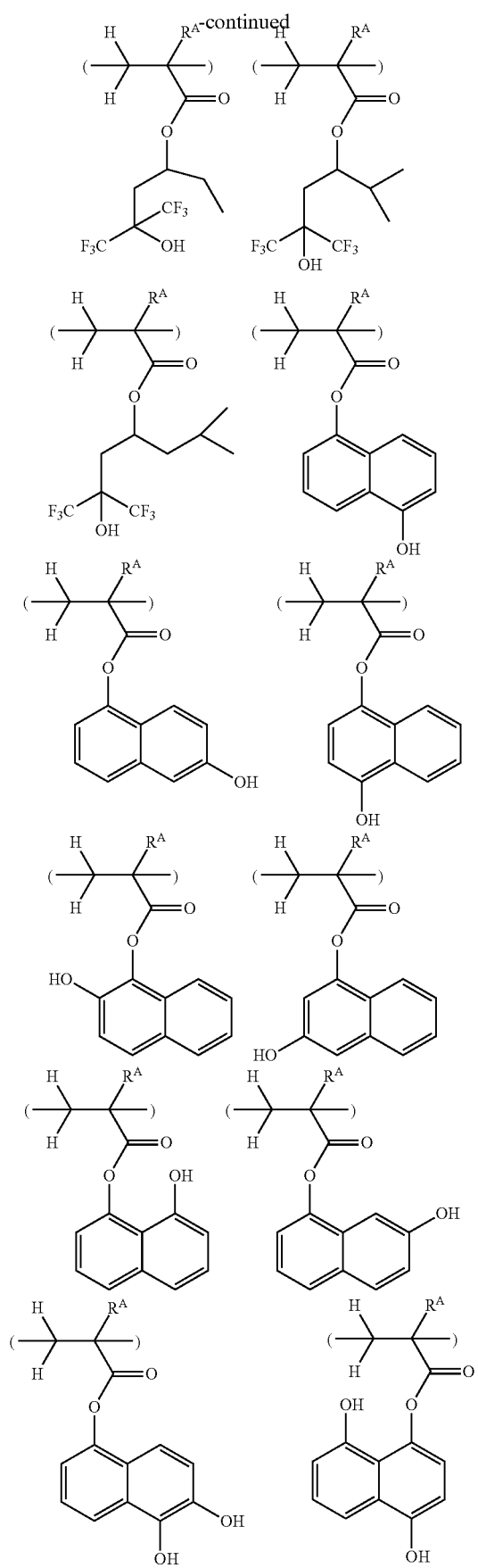
-continued
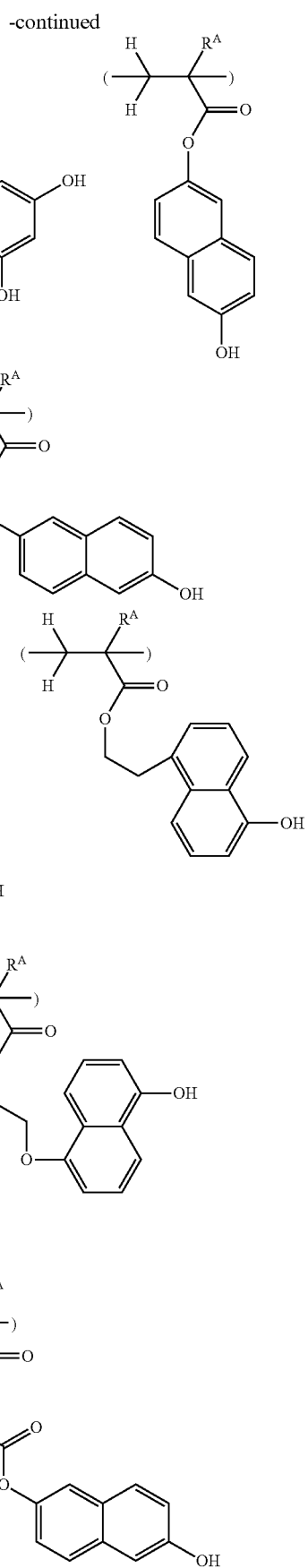

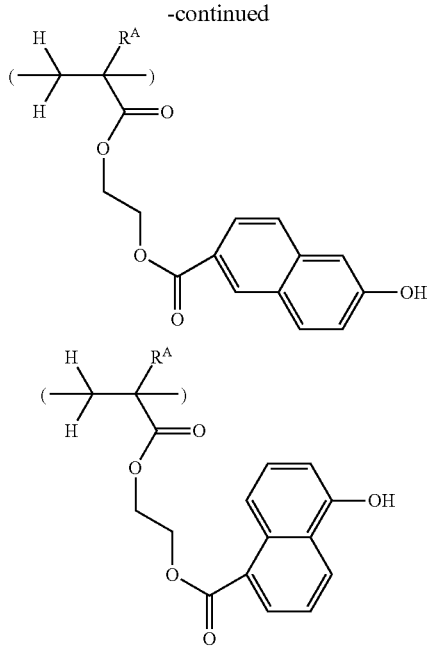
Examples of the repeat unit having formula (b2) are shown below, but not limited thereto. Herein, $R^A$ is as defined above.
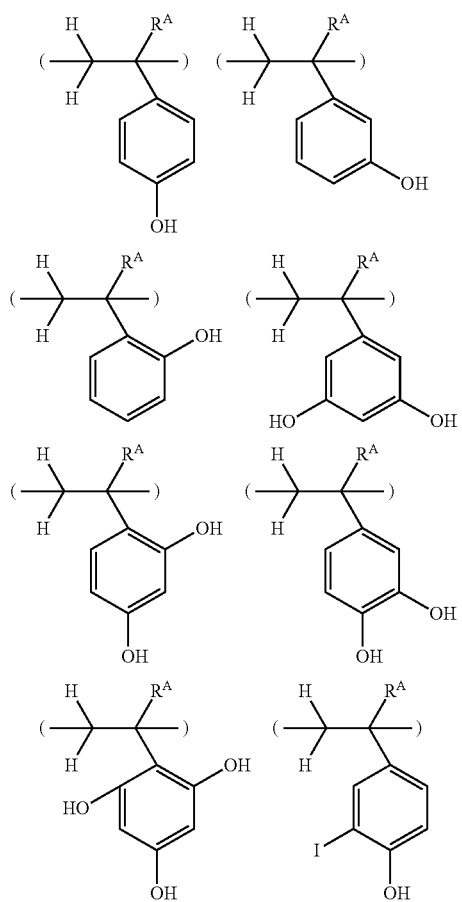
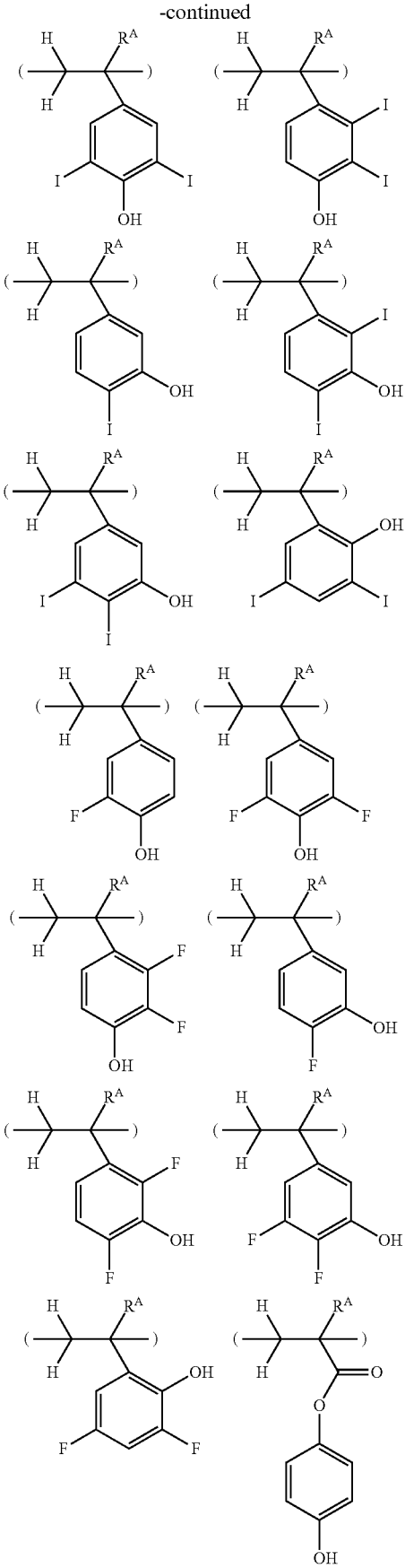

-continued
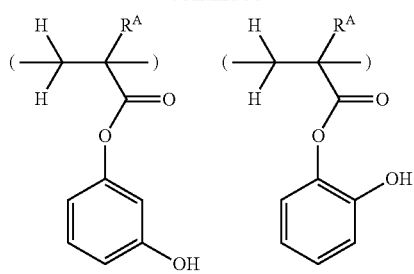
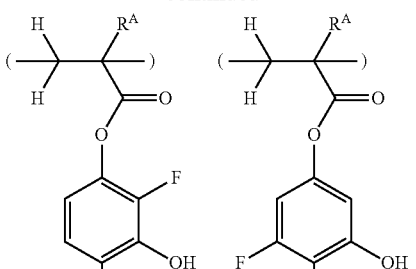
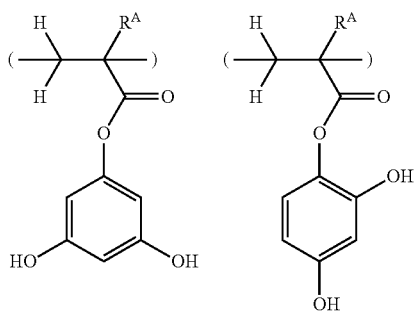
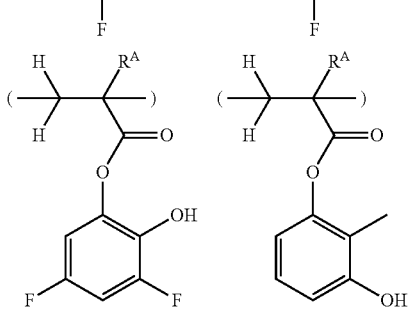
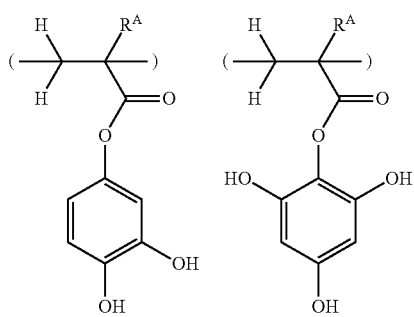
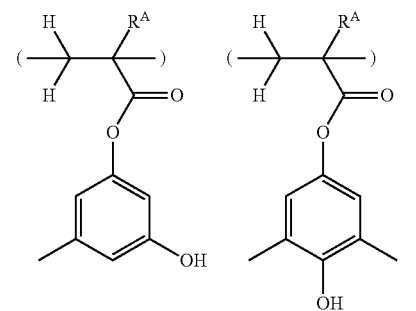
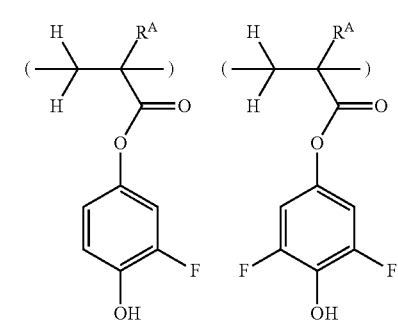
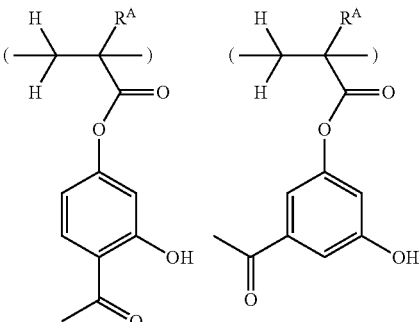
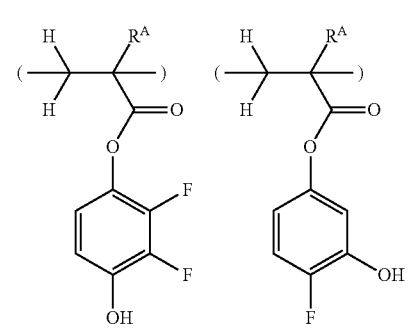
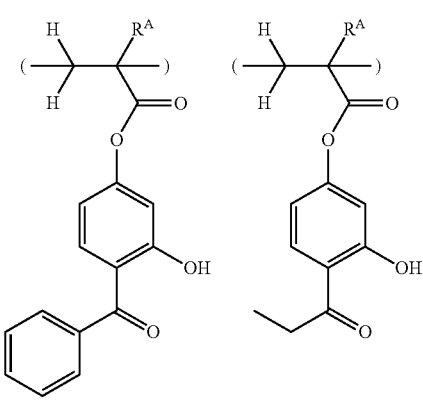

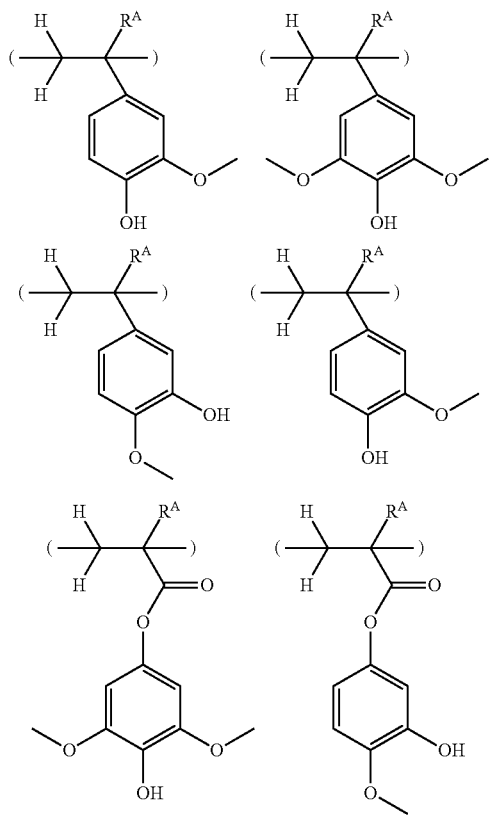

Of the repeat units (b1) and (b2), those units having a lactone ring as the polar group are preferred in the ArF lithography and those units having a phenolic site are preferred in the KrF, EB and EUV lithography.

The base polymer may further comprise repeat units of at least one type selected from repeat units having the formulae (c1) to (c3), which are simply referred to as repeat units (c1) to (c3).

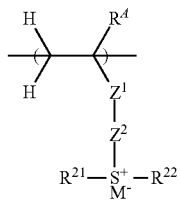

(c1)

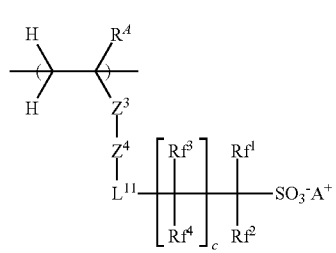

(c2)

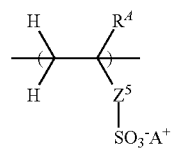

(c3)

In formulae (c1) to (c3), $R^A$ is as defined above. $Z^1$ is a single bond or phenylene group. $Z^2$ is —C(=O)—O—$Z^{21}$—, —C(=O)—NH—$Z^{21}$— or —O—$Z^{21}$—. $Z^{21}$ is a $C_1$-$C_6$ aliphatic hydrocarbylene group, a phenylene group or a divalent group obtained by combining the foregoing, which may contain a carbonyl moiety, ester bond, ether bond or hydroxy moiety. $Z^3$ is a single bond, phenylene group, naphthylene group or (backbone)-C(=O)—O—$Z^{31}$—. $Z^{31}$ is a $C_1$-$C_{10}$ aliphatic hydrocarbylene group which may contain a hydroxy moiety, ether bond, ester bond or lactone ring, or phenylene or naphthylene group. $Z^4$ is a single bond or —$Z^{41}$—C(=O)—O—. $Z^{41}$ is a $C_1$-$C_{20}$ hydrocarbylene group which may contain a heteroatom. $Z^5$ is a single bond, methylene, ethylene, phenylene, fluorinated phenylene, trifluoromethyl-substituted phenylene group, —C(=O)—O—$Z^{51}$—, —C(=O)—NH—$Z^{51}$—, or —O—$Z^{51}$—. $Z^{51}$ is a $C_1$-$C_6$ aliphatic hydrocarbylene group, phenylene group, fluorinated phenylene group or trifluoromethyl-substituted phenylene group, which may contain a carbonyl moiety, ester bond, ether bond or hydroxy moiety.

In formula (c1), $R^{21}$ and $R^{22}$ are each independently a $C_1$-$C_{20}$ hydrocarbyl group which may contain a heteroatom. $R^{21}$ and $R^{22}$ may bond together to form a ring with the sulfur atom to which they are attached.

The hydrocarbyl groups $R^{21}$ and $R^{27}$ may be saturated or unsaturated and straight, branched or cyclic. Examples thereof include alkyl groups such as methyl, ethyl, n-propyl, isopropyl, n-butyl, tert-butyl; cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl; alkenyl groups such as vinyl, allyl, propenyl, butenyl, hexenyl; cyclic unsaturated hydrocarbyl groups such as cyclohexenyl; aryl groups such as phenyl and naphthyl; aralkyl groups such as benzyl, 1-phenylethyl and 2-phenylethyl, and combinations thereof. Inter alia, aryl groups are preferred. In these hydrocarbyl groups, some or all of the hydrogen atoms may be substituted by a moiety containing a heteroatom such as oxygen, sulfur, nitrogen or halogen, and any constituent —CH$_2$— may be replaced by a moiety containing a heteroatom such as oxygen, sulfur or nitrogen, so that the group may contain a hydroxy moiety, cyano moiety, fluorine, chlorine, bromine, iodine, carbonyl moiety, ether bond, ester bond, sulfonic ester bond, carbonate bond, lactone ring, sultone ring, carboxylic anhydride or haloalkyl moiety.

Examples of the cation in the repeat units having formula (c1) are shown below, but not limited thereto. Herein, $R^A$ is as defined above.

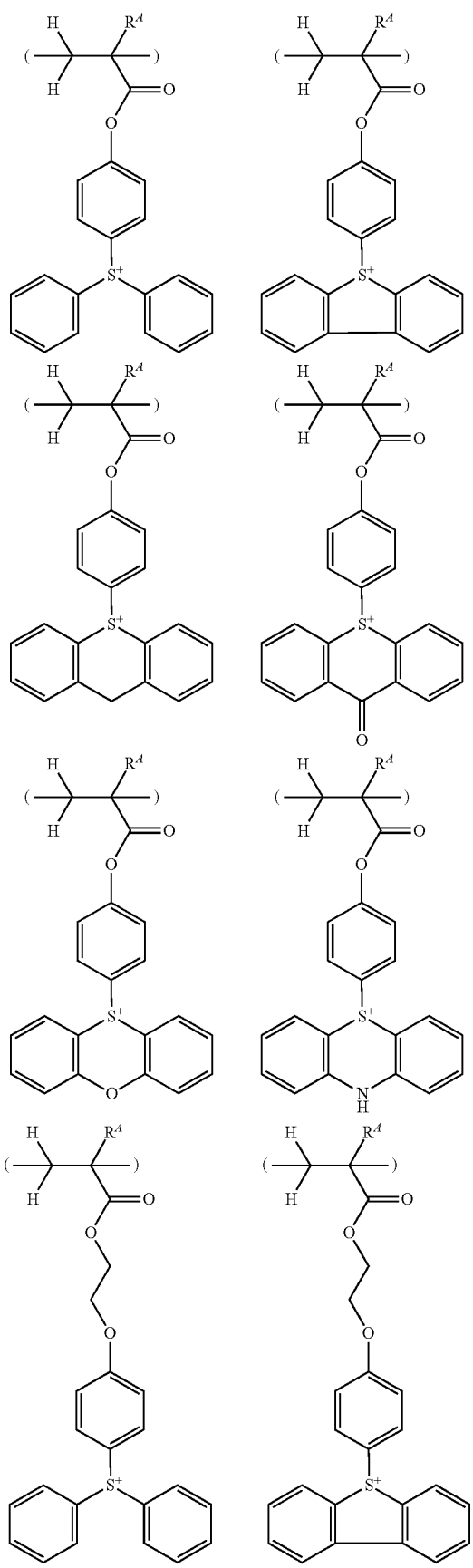
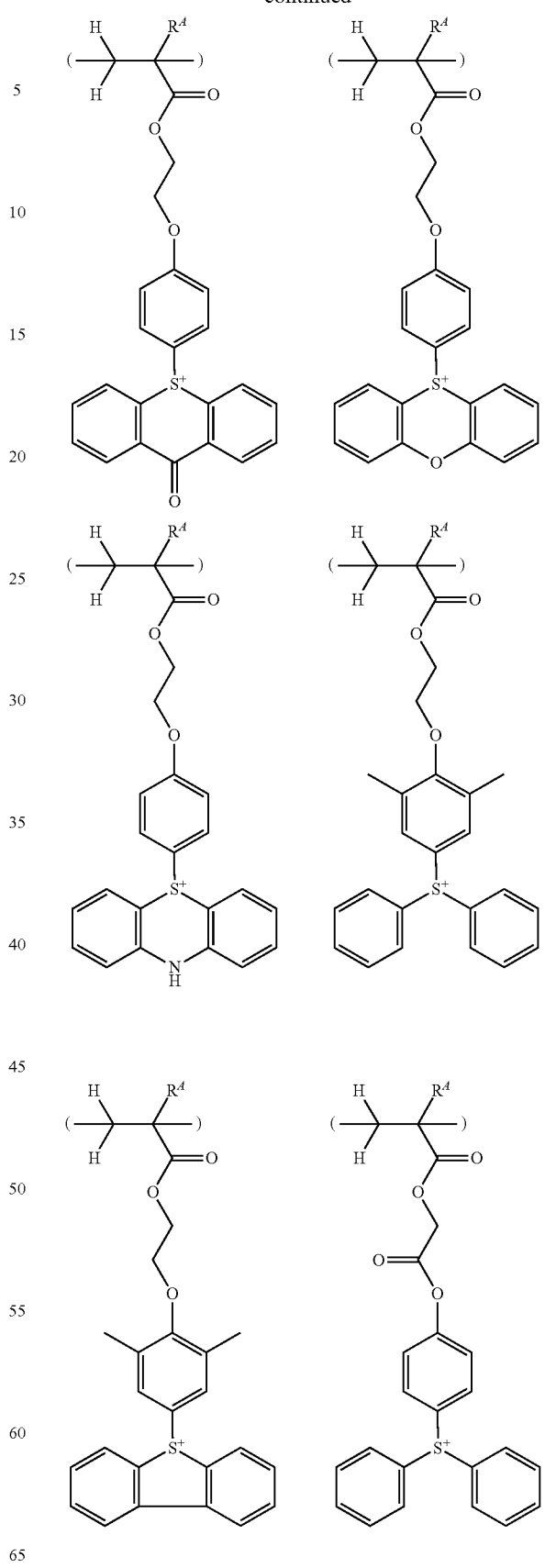

101
-continued
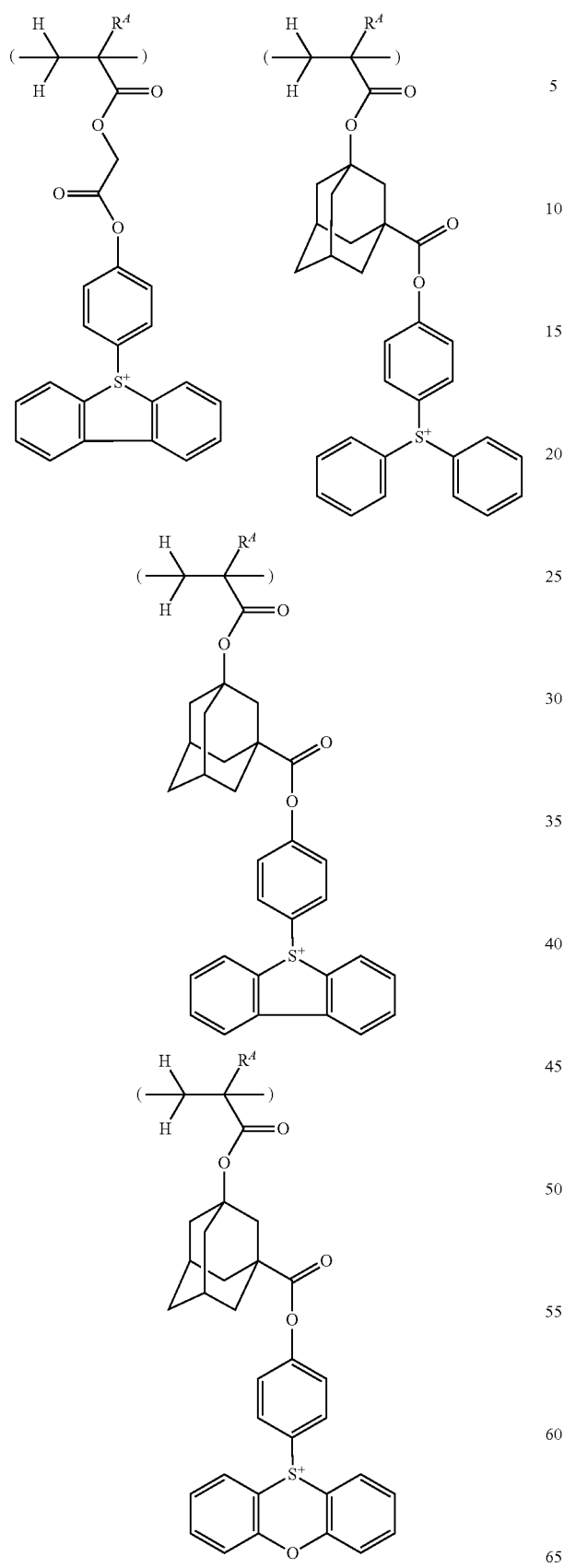
102
-continued

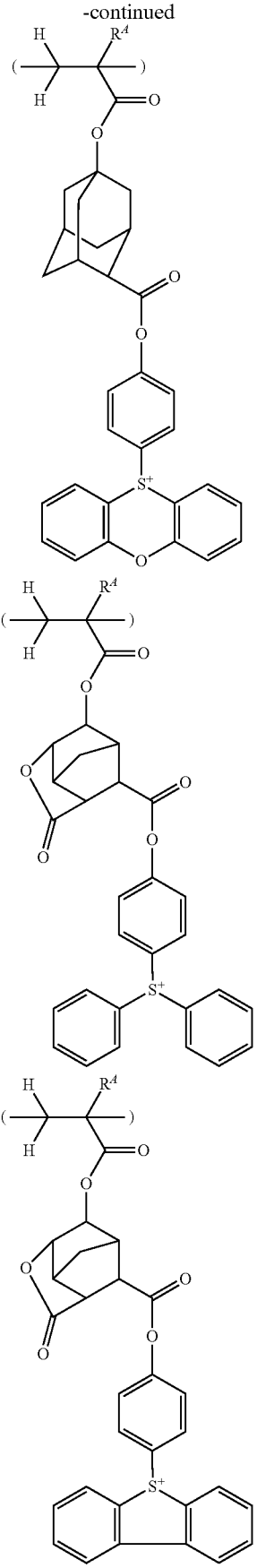
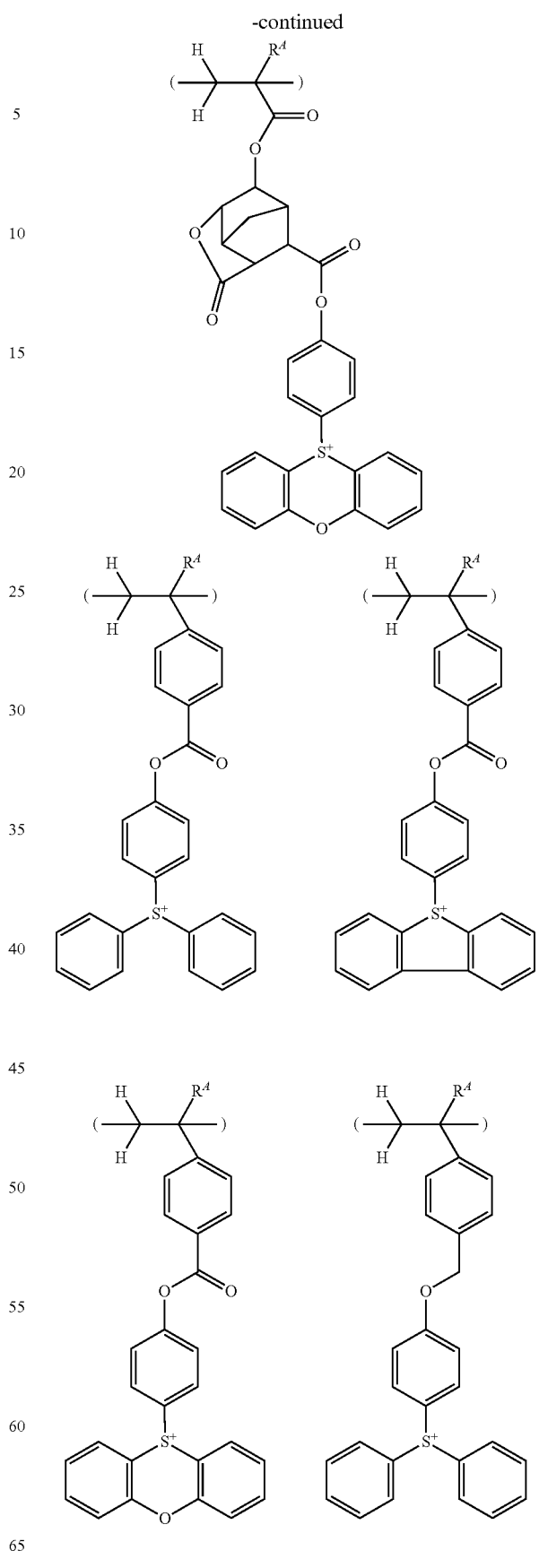

-continued

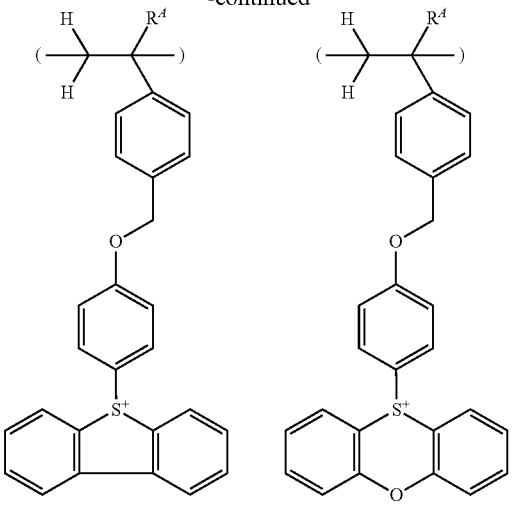

In formula (c1), M⁻ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl) imide and bis(perfluorobutylsulfonyl)imide; and methide ions such as tris(trifluoromethylsulfonyl)methide and tris (perfluoroethylsulfonyl)methide.

Also included are a sulfonate anion which is fluorinated at α-position as represented by the formula (c1-1) and a sulfonate anion which is substituted with fluorine at α-position and trifluoromethyl at β-position as represented by the formula (c1-2).

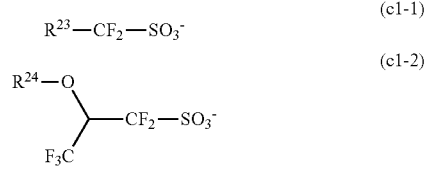

In formula (c1-1), $R^{23}$ is hydrogen or a hydrocarbyl group which may contain an ether bond, ester bond, carbonyl moiety, lactone ring or fluorine atom. The hydrocarbyl group may be saturated or unsaturated and straight, branched or cyclic, and examples thereof are as will be exemplified later for $R^{111}$ in formula (3A').

In formula (c1-2), $R^{24}$ is hydrogen, a $C_1$-$C_{30}$ hydrocarbyl group, or $C_6$-$C_{20}$ hydrocarbylcarbonyl group. The hydrocarbyl group and hydrocarbylcarbonyl group may contain an ether bond, ester bond, carbonyl moiety or lactone ring. The hydrocarbyl group and hydrocarbyl moiety in the hydrocarbylcarbonyl group may be saturated or unsaturated and straight, branched or cyclic, and examples thereof are as will be exemplified later for $R^{111}$ in formula (3A').

Examples of the sulfonate anions having formulae (c1-1) and (c1-2) are as exemplified above for the anion having formula (2A).

In formula (c2), examples of the optionally heteroatom-containing $C_1$-$C_{20}$ hydrocarbylene group $Z^{41}$ are shown below, but not limited thereto.

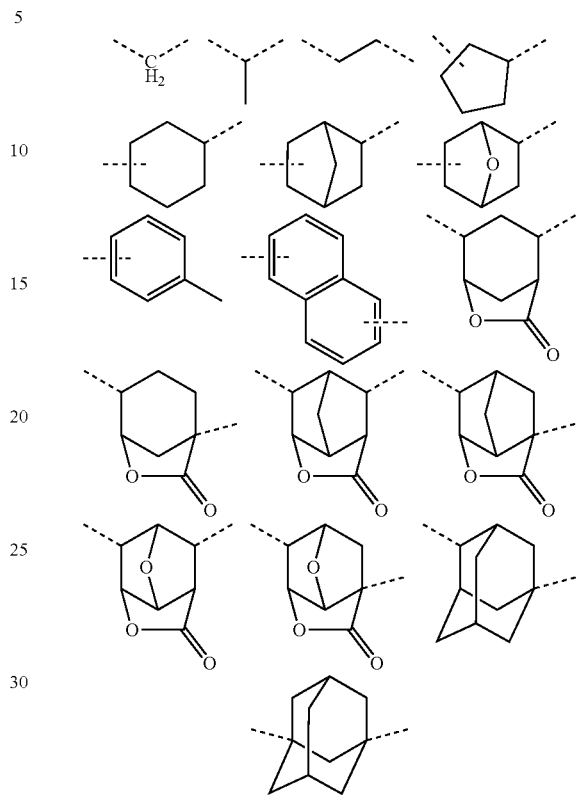

In formula (c2), $Rf^1$ and $Rf^2$ are each independently fluorine or a $C_1$-$C_6$ fluorinated alkyl group. It is preferred for enhancing the acid strength of the generated acid that both $Rf^1$ and $Rf^2$ be fluorine. $Rf^3$ and $Rf^4$ are each independently hydrogen, fluorine or a $C_1$-$C_6$ fluorinated alkyl group. It is preferred for enhancing solvent solubility that at least one of $Rf^3$ and $Rf^4$ be trifluoromethyl. The subscript c is an integer of 0 to 3, preferably 1.

Examples of the monomer from which the anion in repeat unit having formula (c2) is derived are as exemplified for the anion having formula (2C).

Examples of the monomer from which the anion in repeat unit having formula (c3) is derived are as exemplified for the anion having formula (2D).

In formulae (c2) and (c3), $A^+$ is an onium cation. Suitable onium cations include sulfonium, iodonium and ammonium cations, with the sulfonium and iodonium cations being preferred. More preferred are sulfonium cations having the formula (c4) and iodonium cations having the formula (c5).

In formulae (c4) and (c5), $R^{31}$ to $R^{35}$ are each independently a $C_1$-$C_{20}$ hydrocarbyl group which may contain a heteroatom. The hydrocarbyl group may be saturated or unsaturated and straight, branched or cyclic. Examples thereof include alkyl groups such as methyl, ethyl, n-propyl, isopropyl, n-butyl, and tert-butyl; cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl: alkenyl groups such as vinyl, allyl, propenyl, butenyl, and hexenyl; cyclic unsaturated hydrocarbyl groups such as cyclohexenyl; aryl groups such as phenyl and naphthyl; and aralkyl groups such as benzyl, 1-phenylethyl, and 2-phenylethyl. Of these, aryl groups are preferred. In the hydrocarbyl group, some or all of the hydrogen atoms may be substituted by a moiety containing a heteroatom such as oxygen, sulfur, nitrogen or halogen, and a moiety containing a heteroatom such as oxygen, sulfur or nitrogen may intervene between carbon atoms, so that the group may contain a hydroxy, cyano, fluorine, chlorine, bromine, iodine, carbonyl, ether bond, ester bond, sulfonic ester bond, carbonate bond, lactone ring, sultone ring, carboxylic anhydride or haloalkyl moiety.

$R^{31}$ and $R^{32}$ may bond together to form a ring with the sulfur atom to which they are attached. Examples of the sulfonium cation having formula (c4) wherein $R^{31}$ and $R^{32}$, form a ring are shown below.

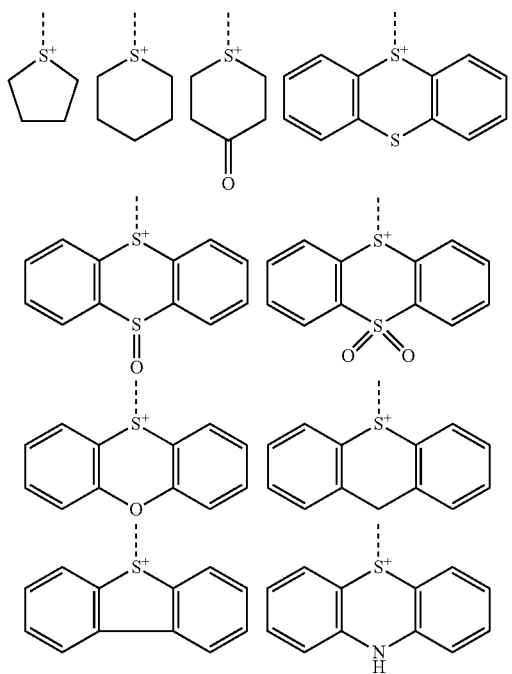

Herein, the broken line designates a point of attachment to $R^{33}$.

Examples of the sulfonium cation having formula (c4) are given below, but not limited thereto.

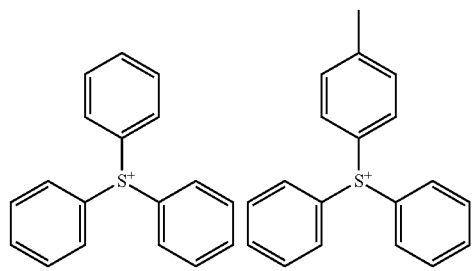

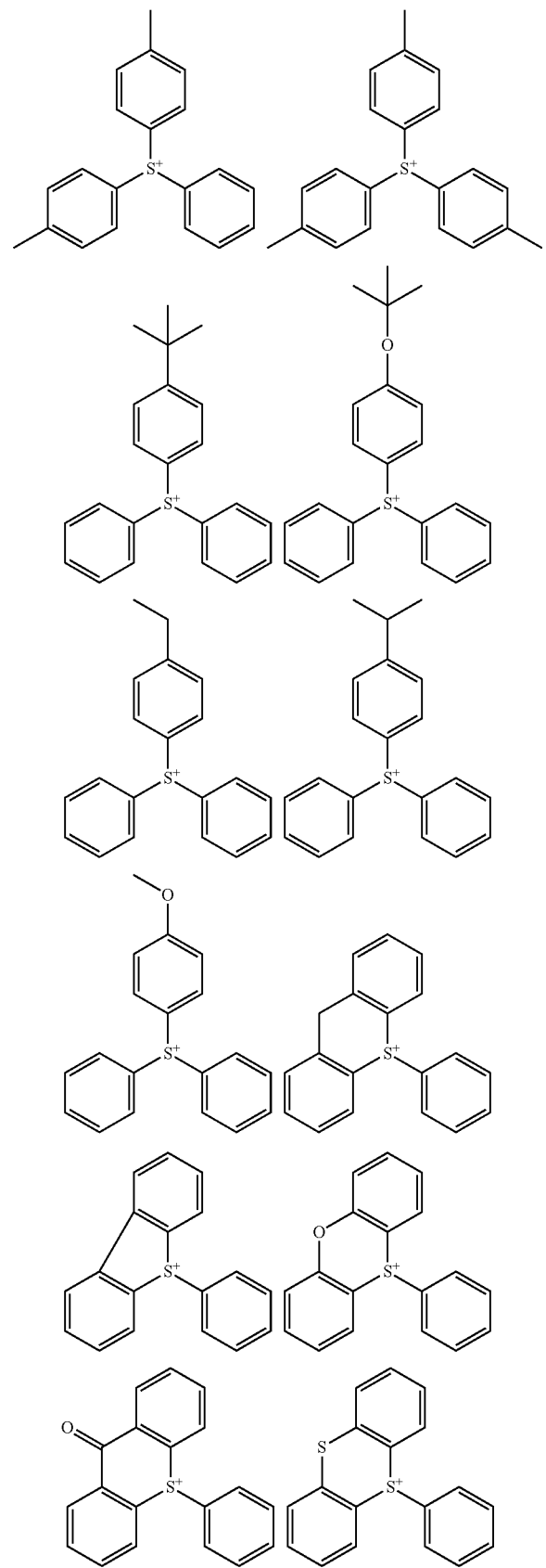

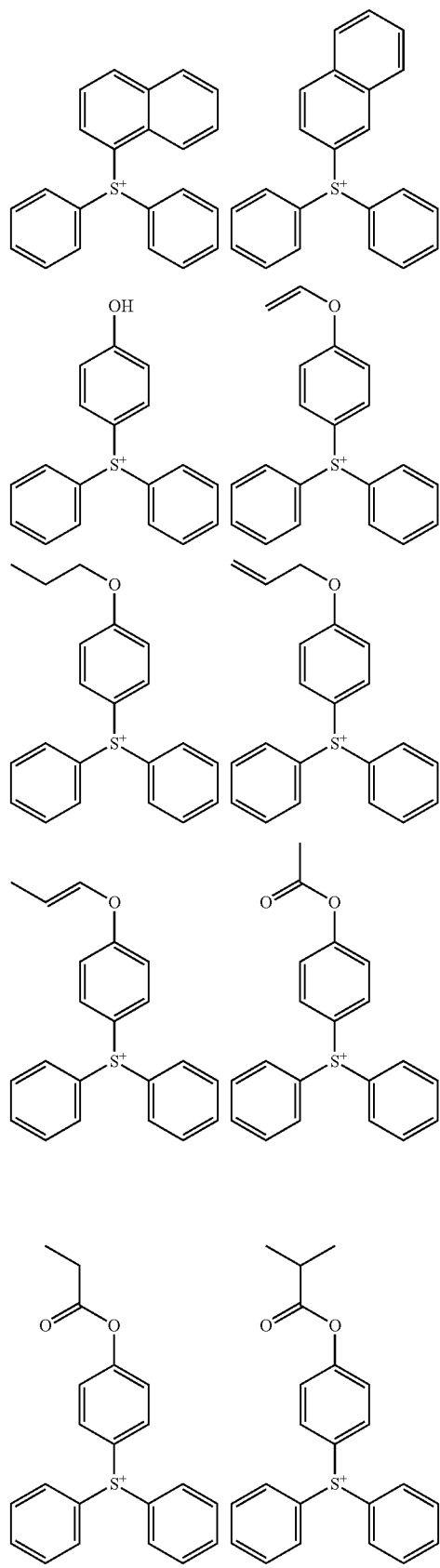
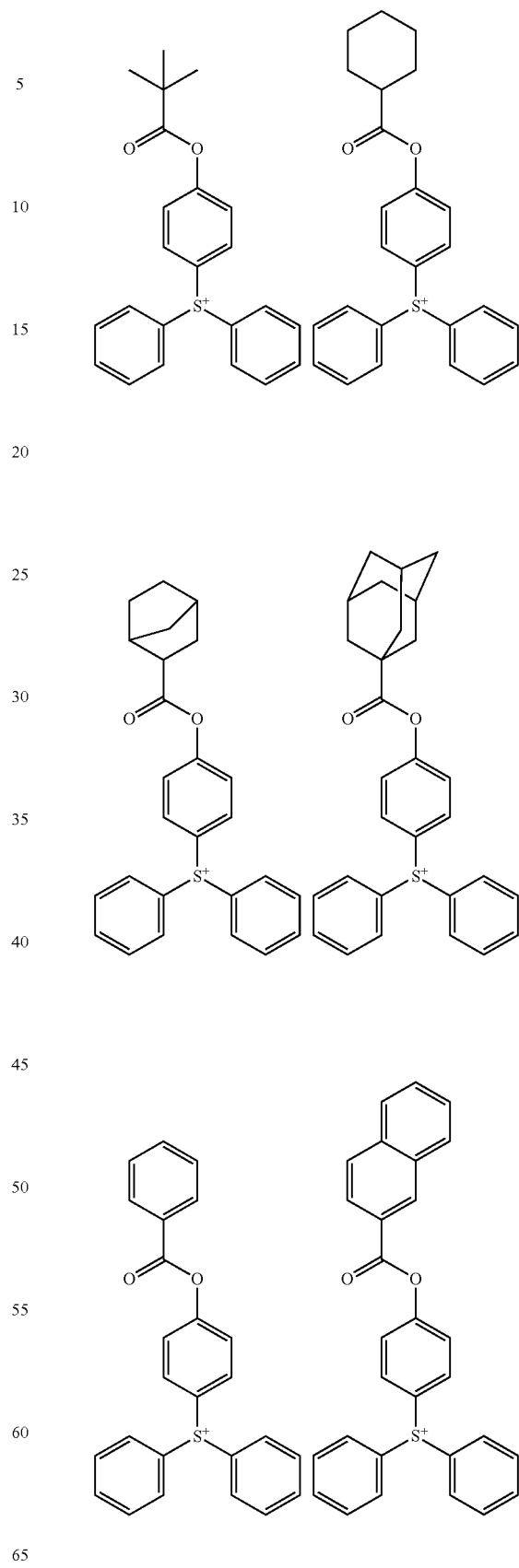

111
-continued
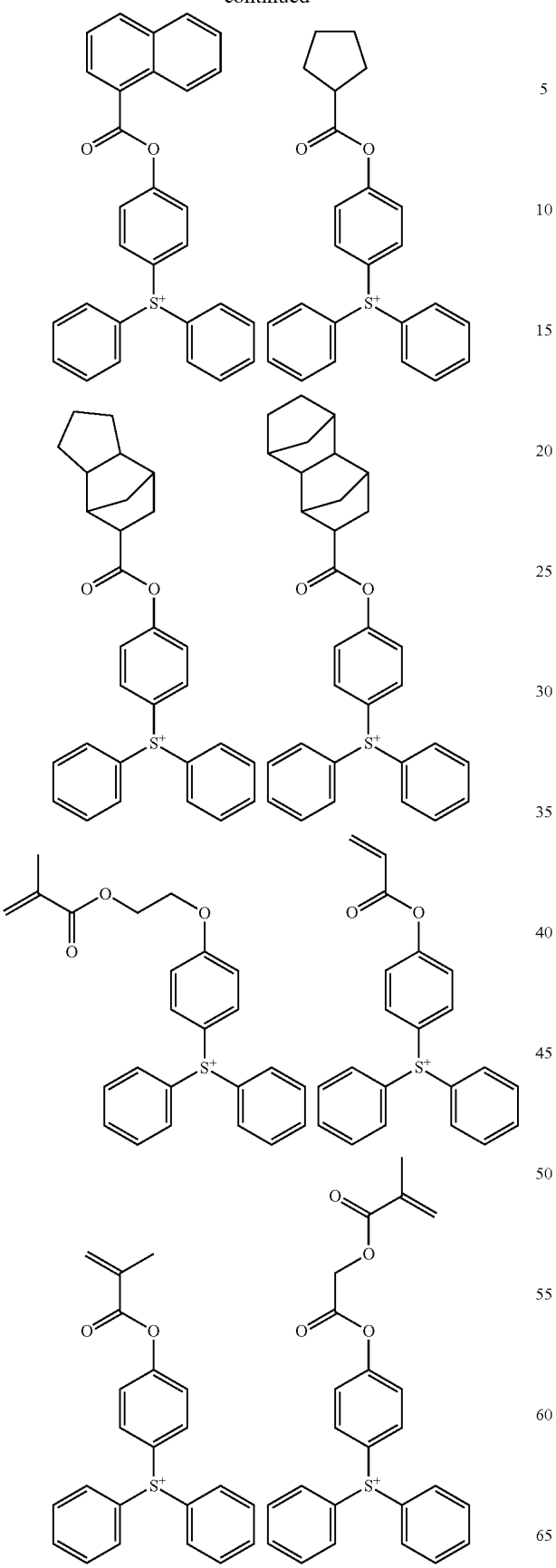
112
-continued
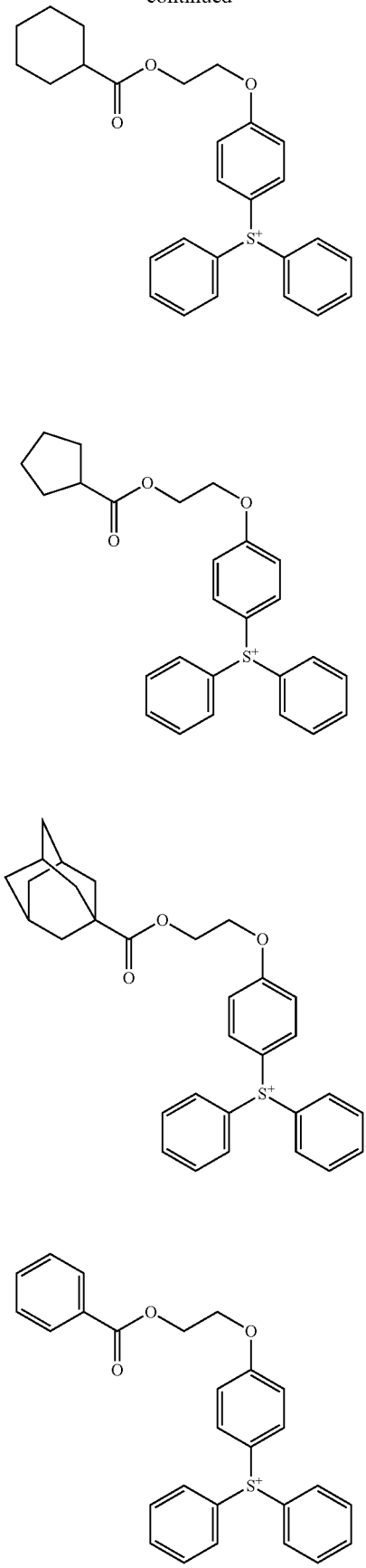

113
-continued
114
-continued
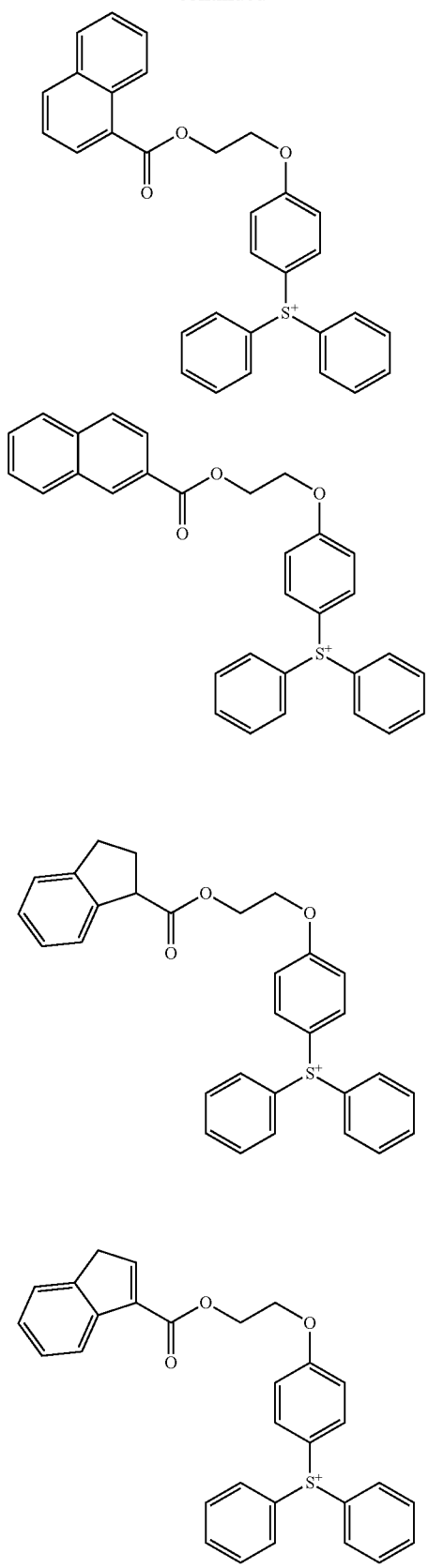

115
-continued
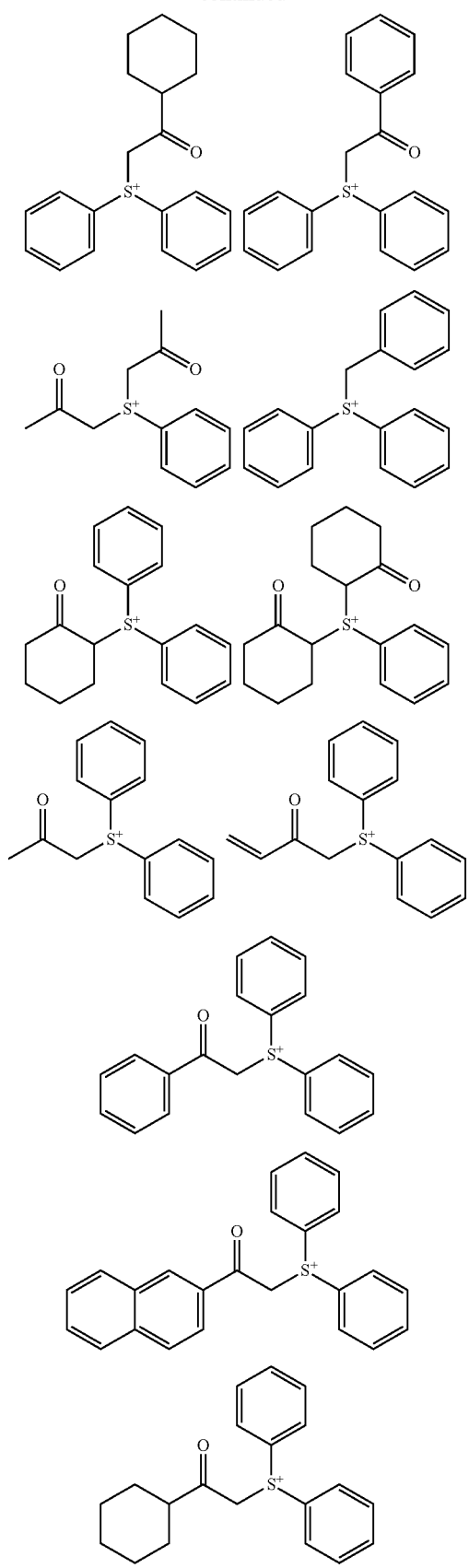
116
-continued
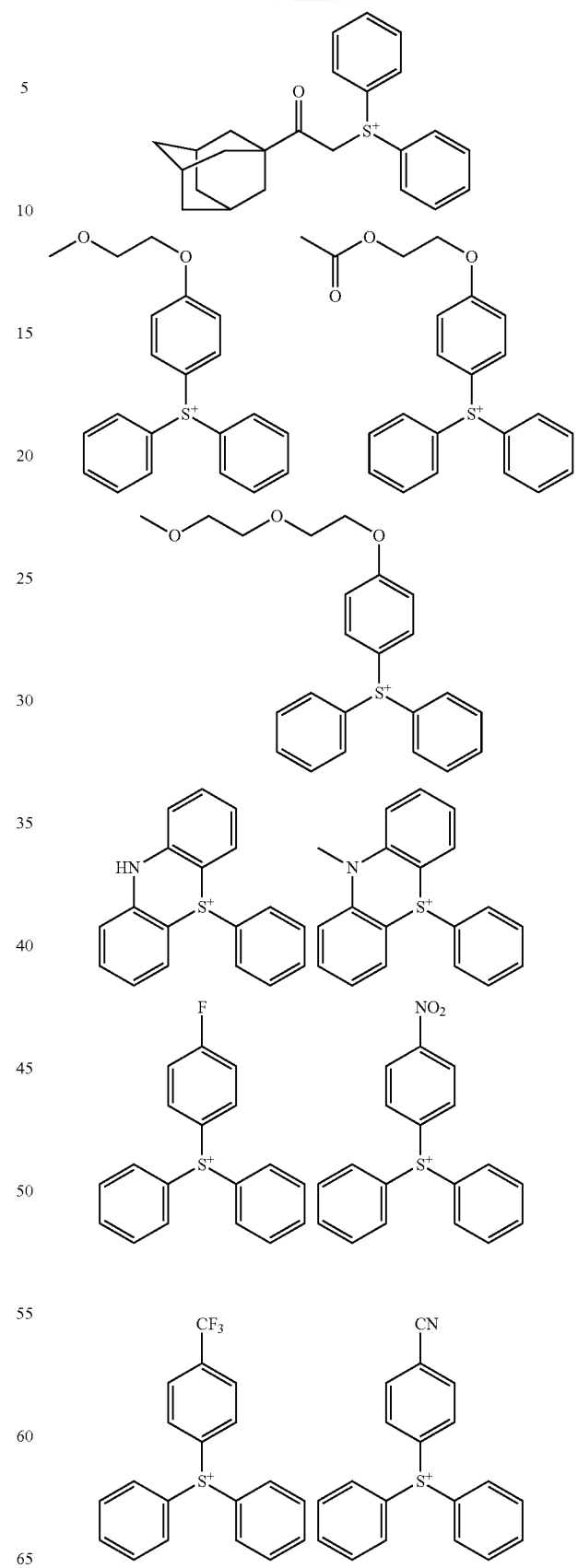

-continued
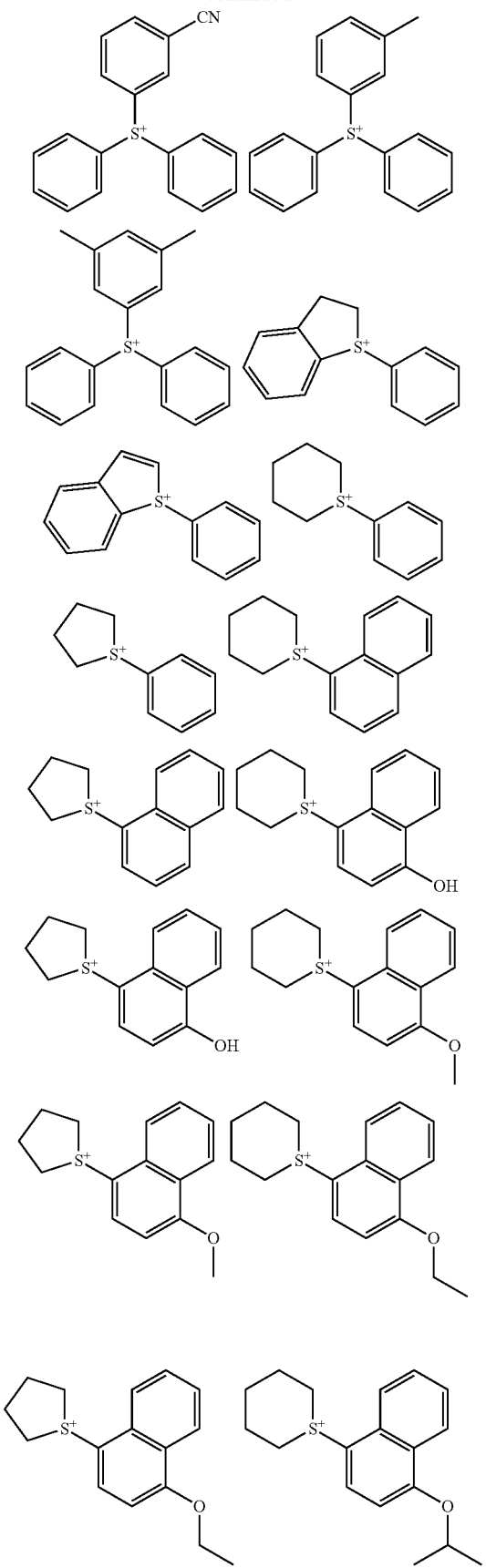
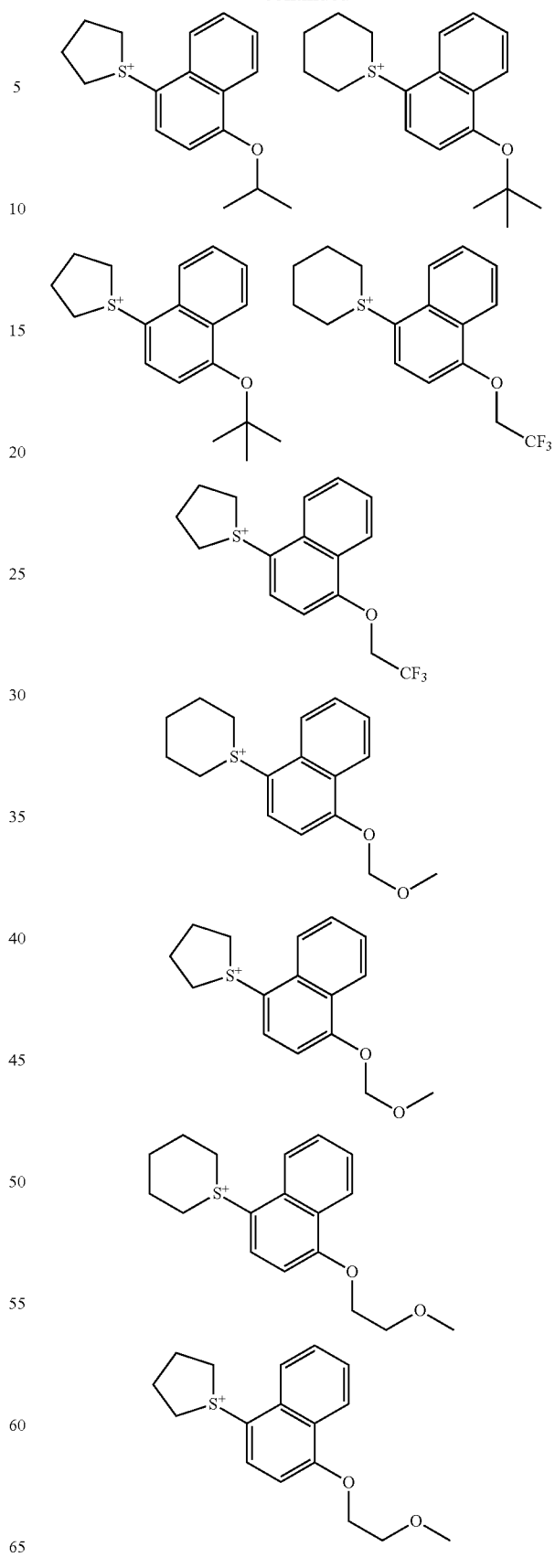

119
-continued
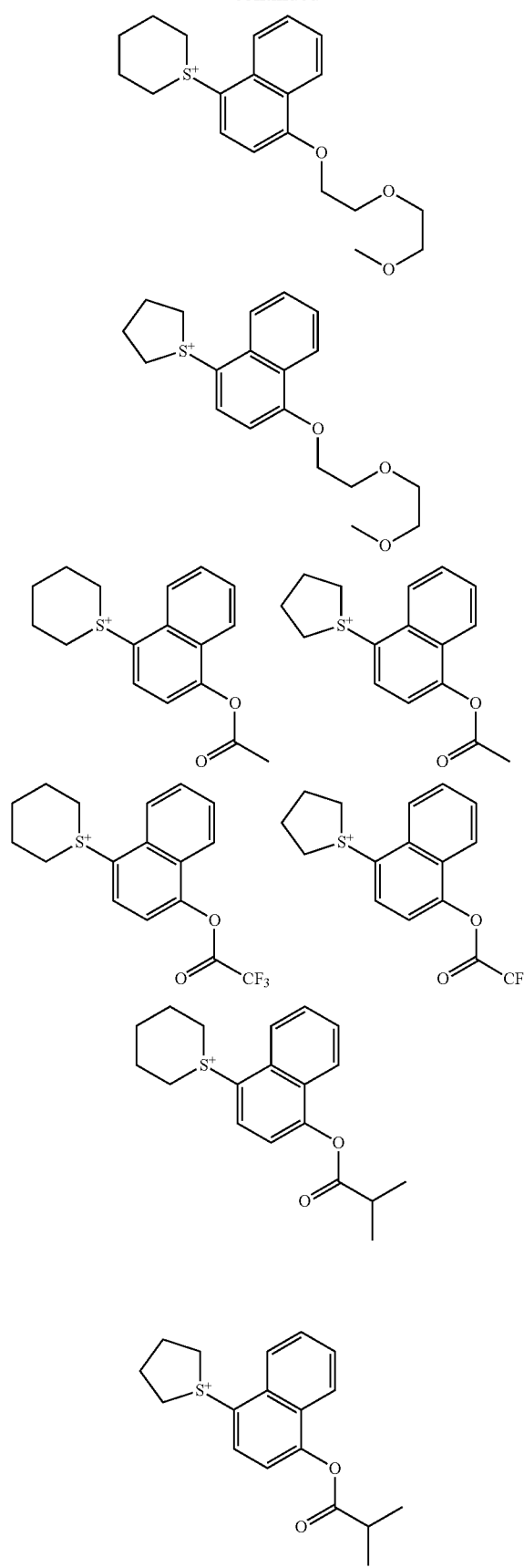
120
-continued
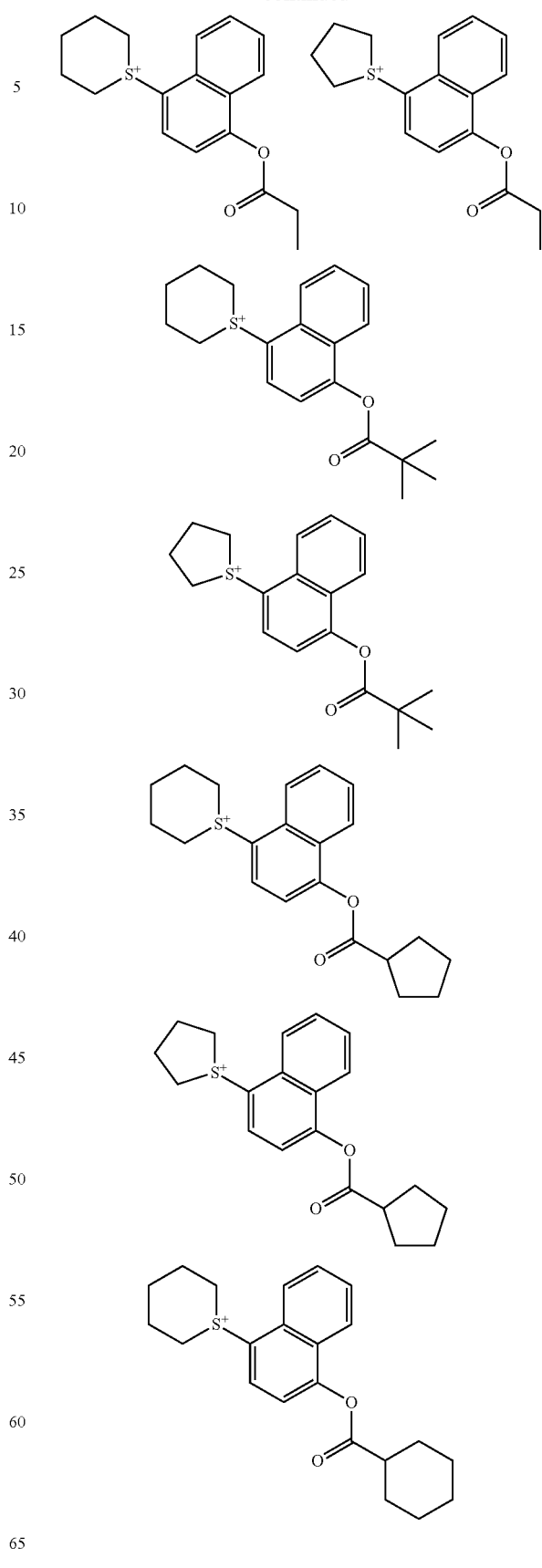

121
-continued
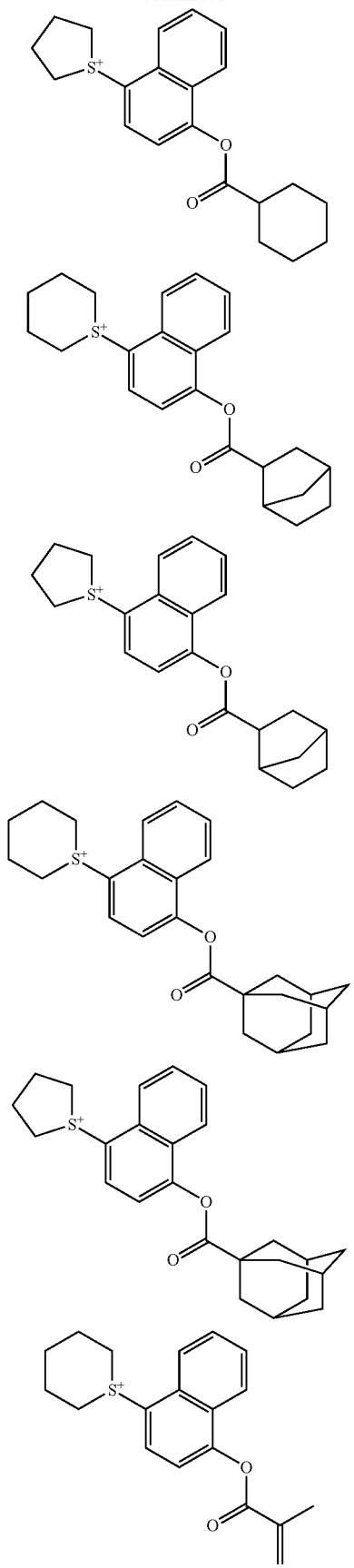
122
-continued
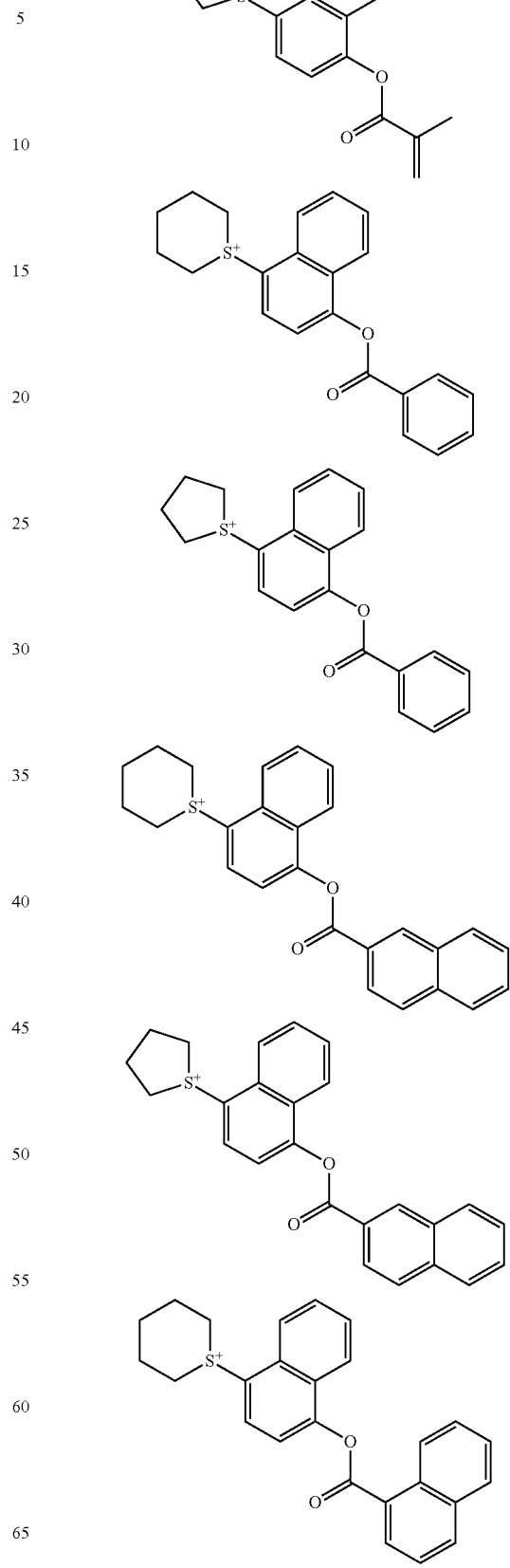

123
-continued
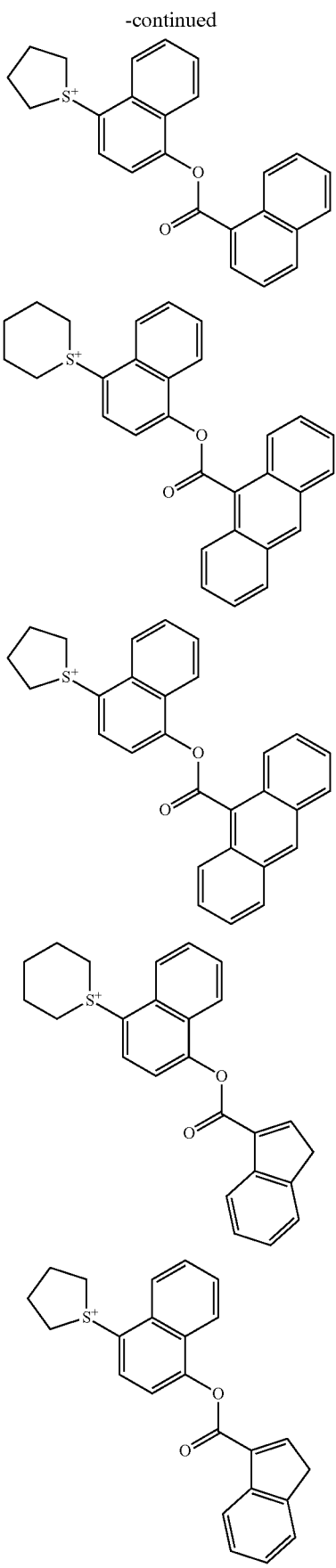
124
-continued
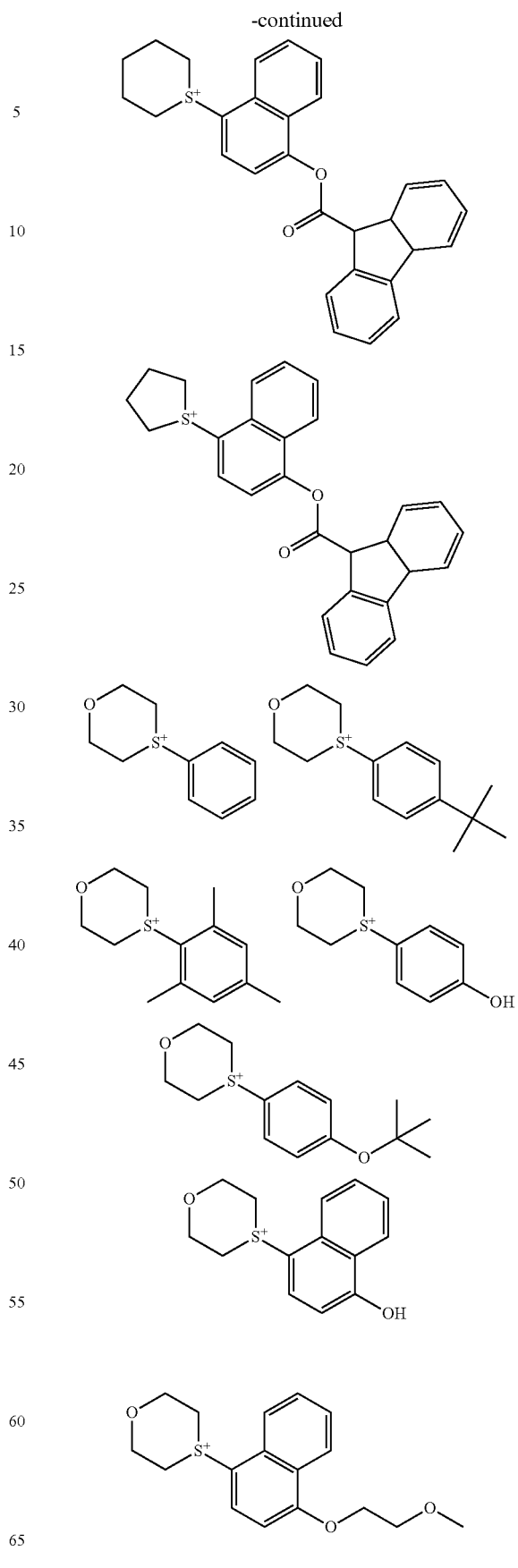

125
-continued
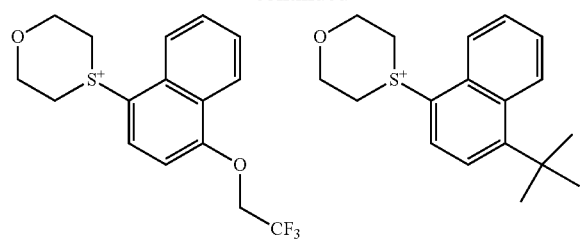
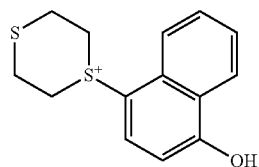
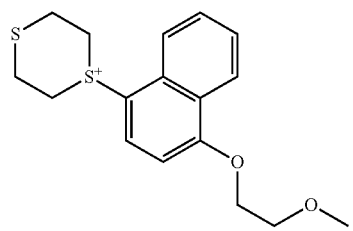
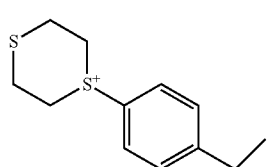
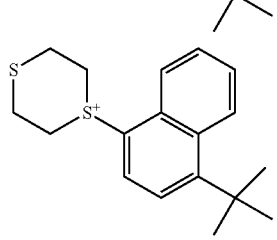
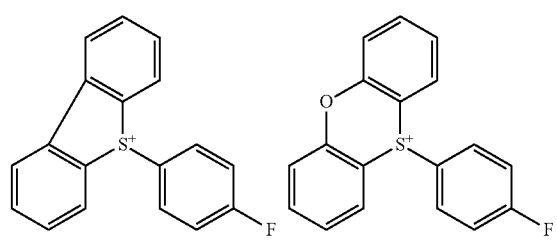
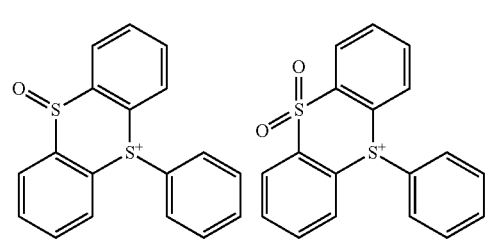
126
-continued
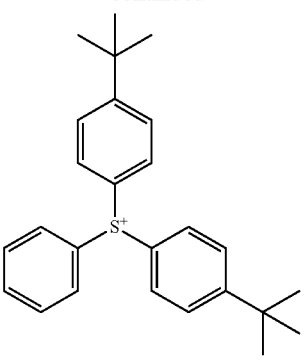
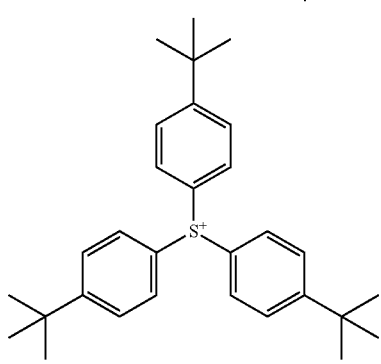
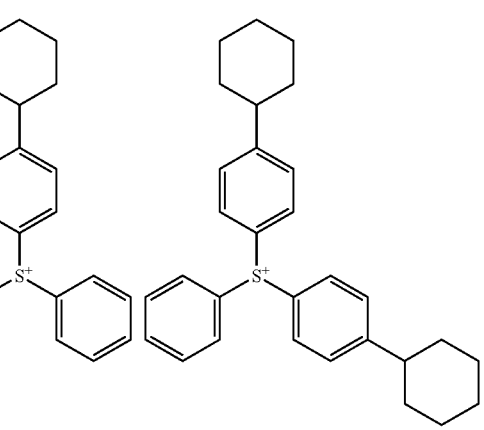
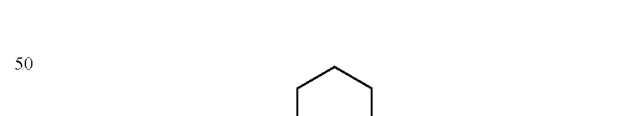
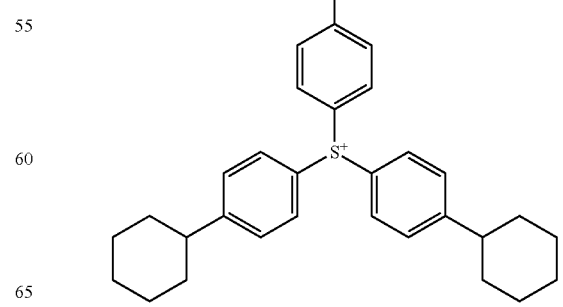

127
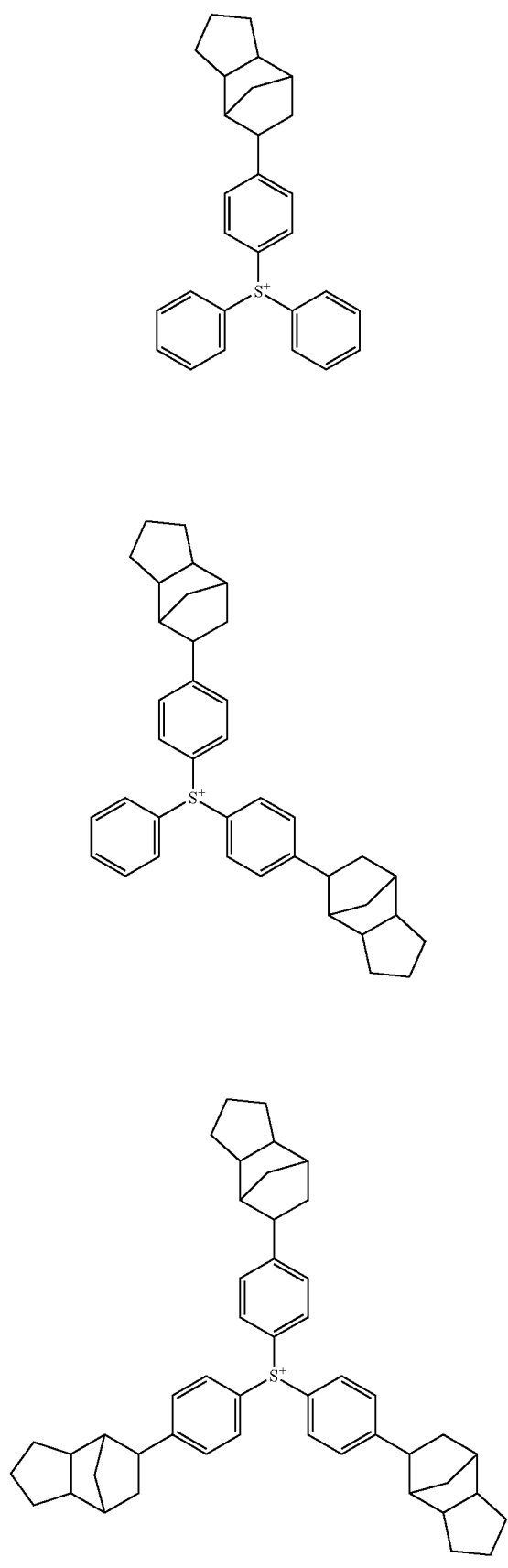 [SMILES: c1ccc([S+](c2ccccc2)c2ccc(C3CC4CC3C3CCCC43)cc2)cc1 ; c1ccc([S+](c2ccc(C3CC4CC3C3CCCC43)cc2)c2ccc(C3CC4CC3C3CCCC43)cc2)cc1 ; c1cc([S+](c2ccc(C3CC4CC3C3CCCC43)cc2)c2ccc(C3CC4CC3C3CCCC43)cc2)ccc1C1CC2CC1C1CCCC21]
128
-continued
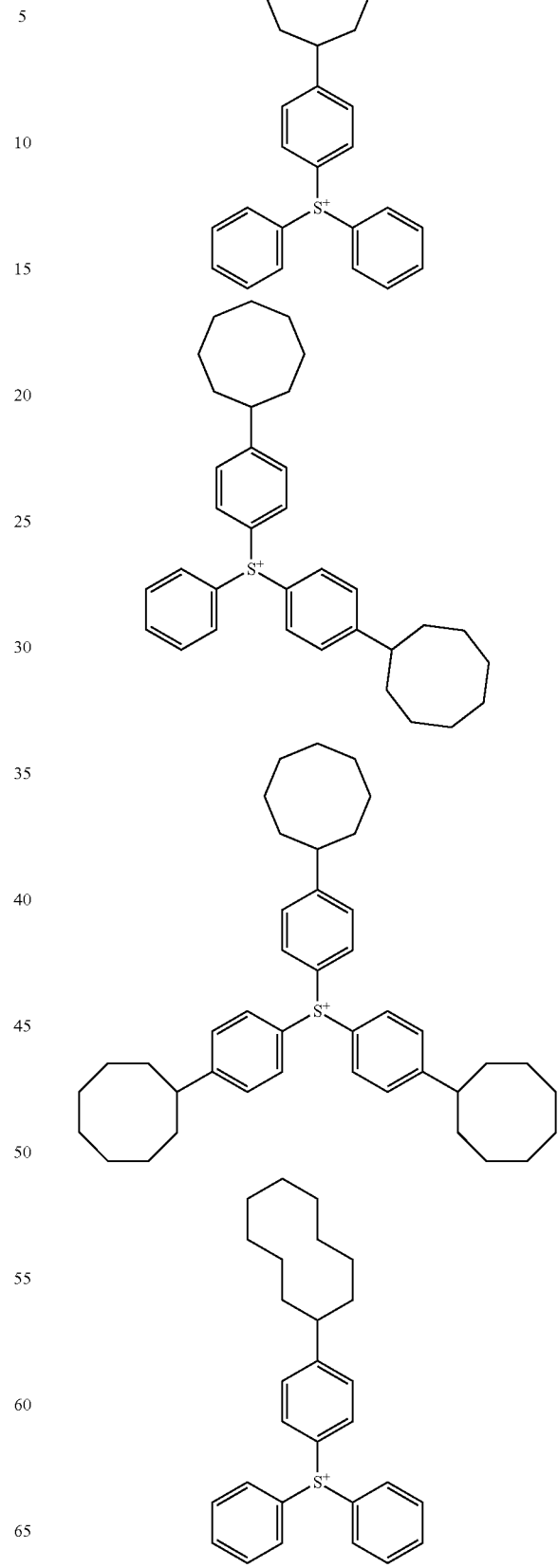

129
-continued
130
-continued
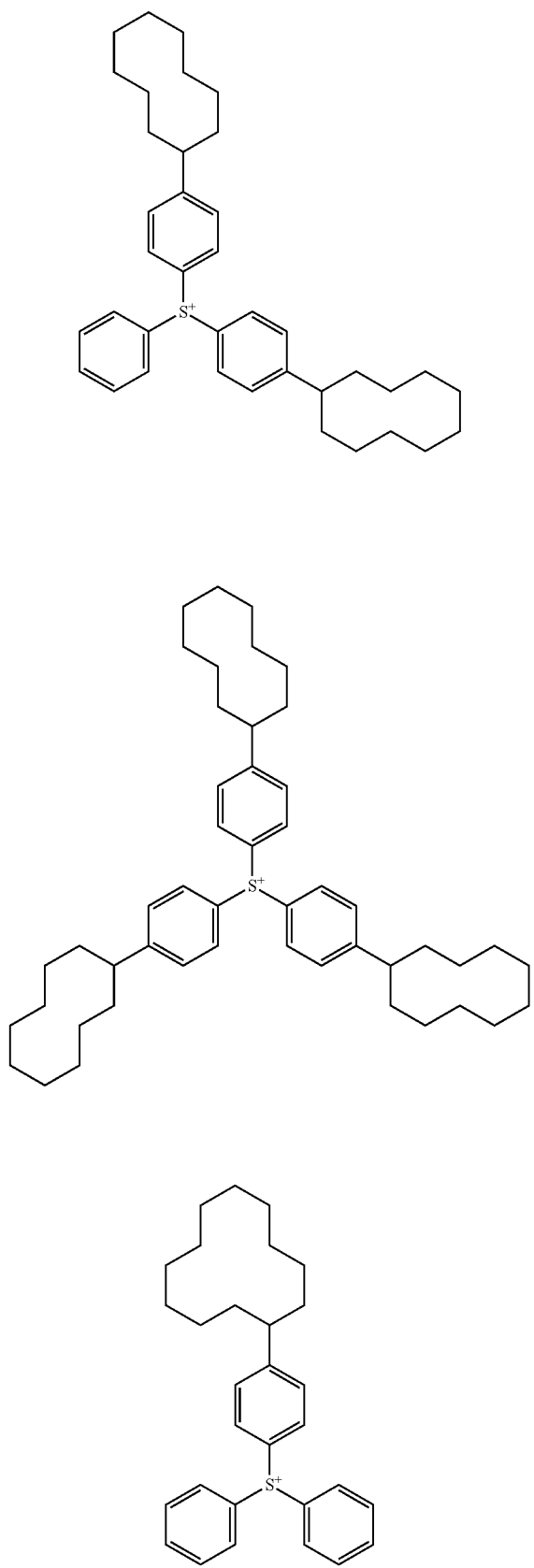
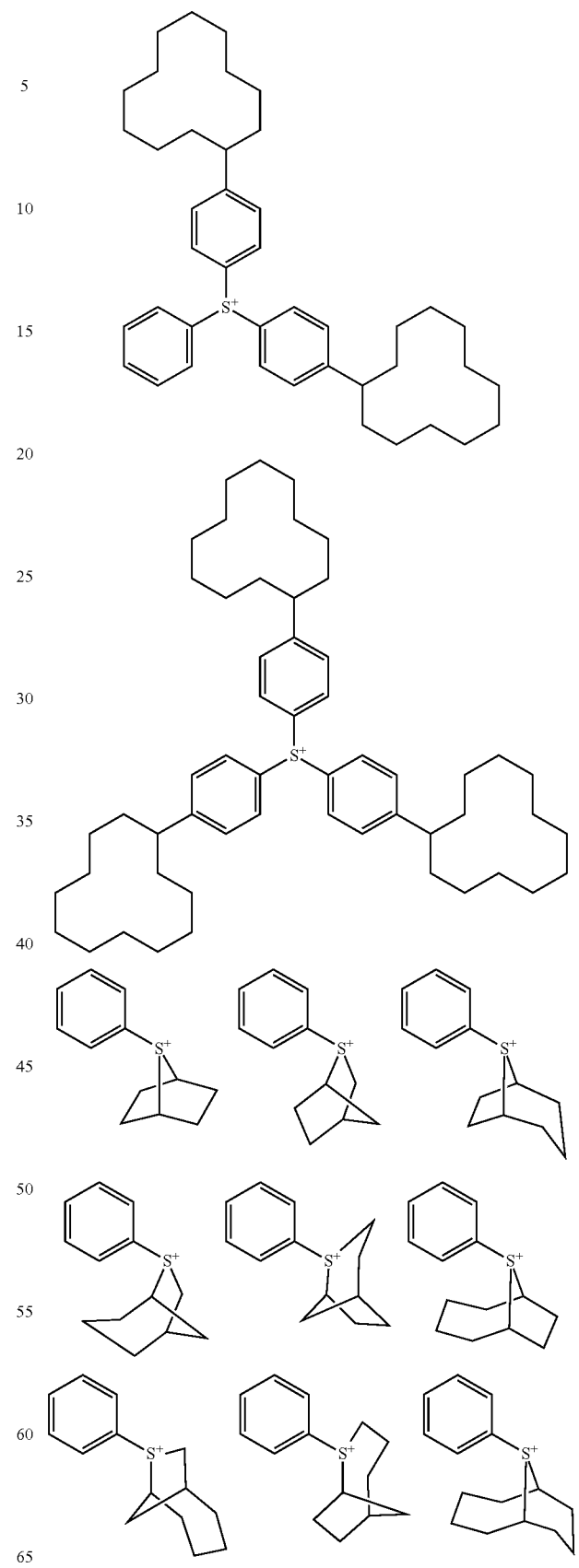

131
-continued
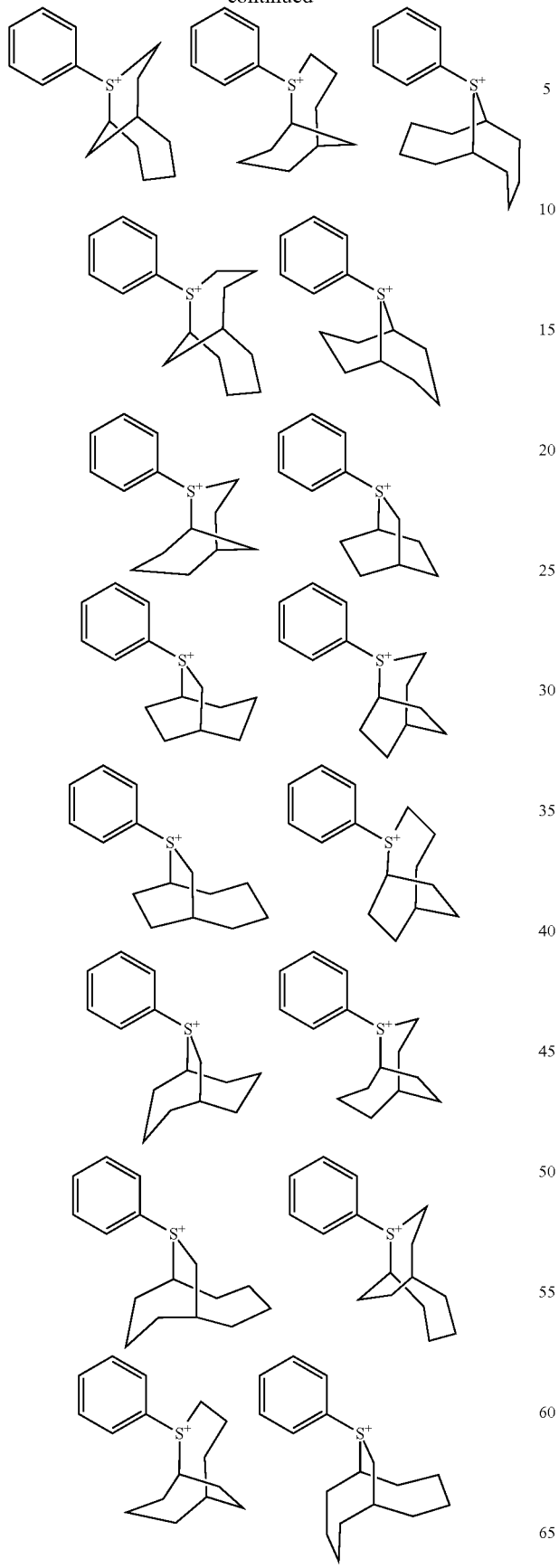
132
-continued
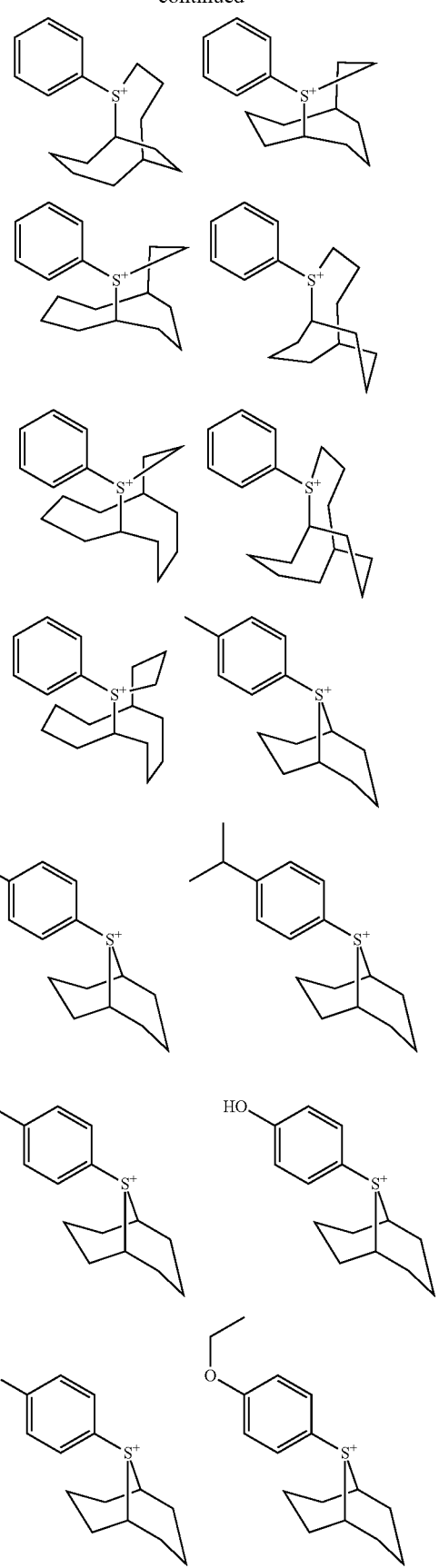

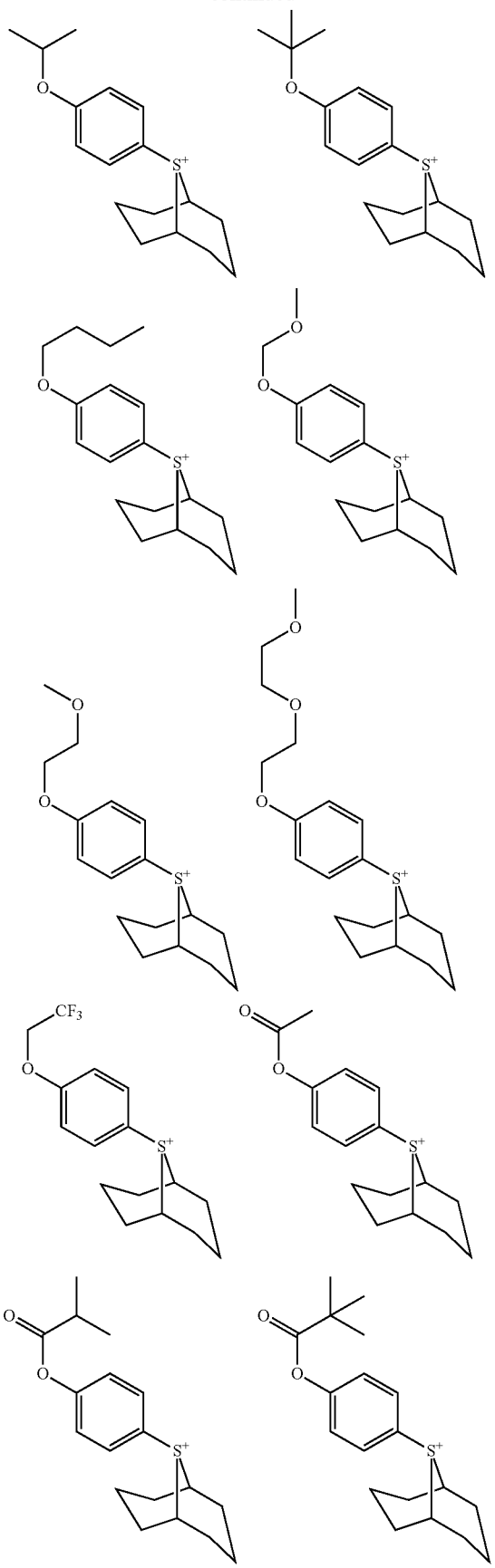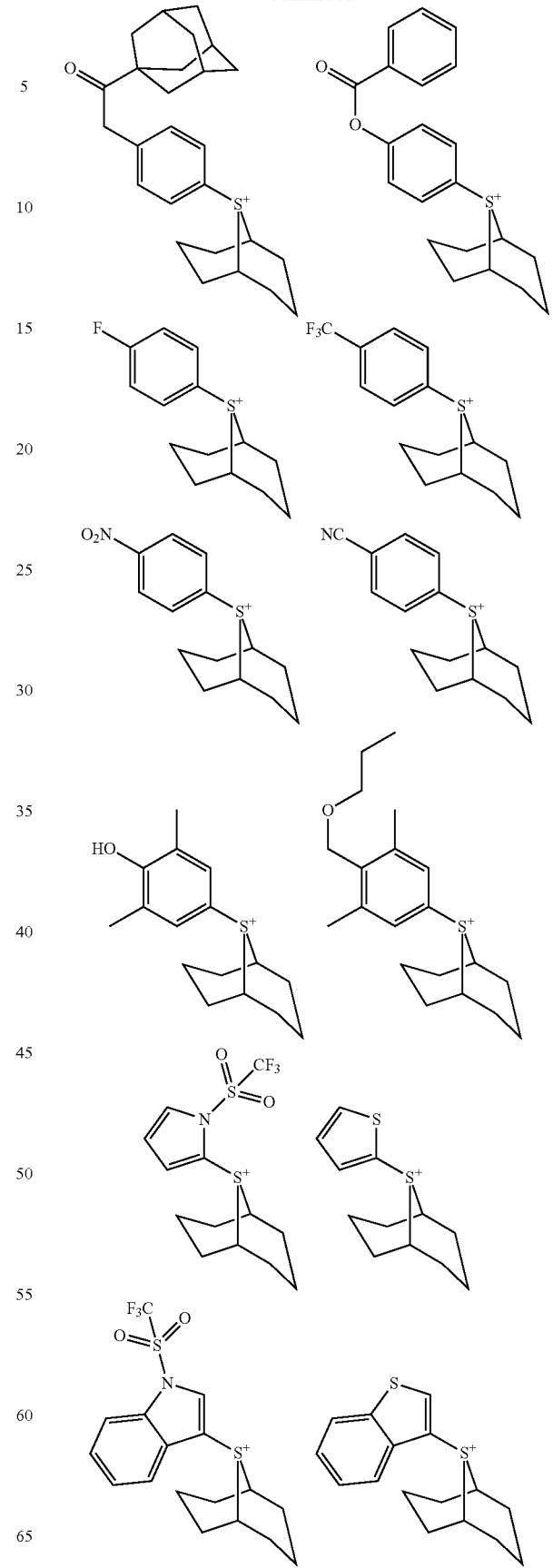

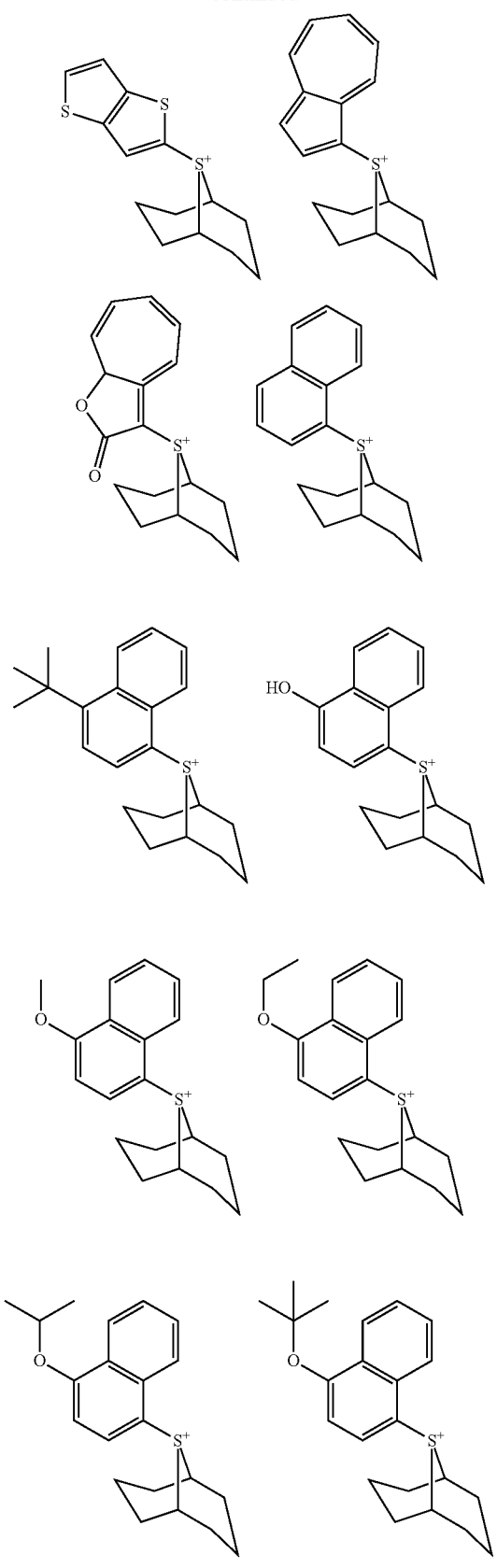
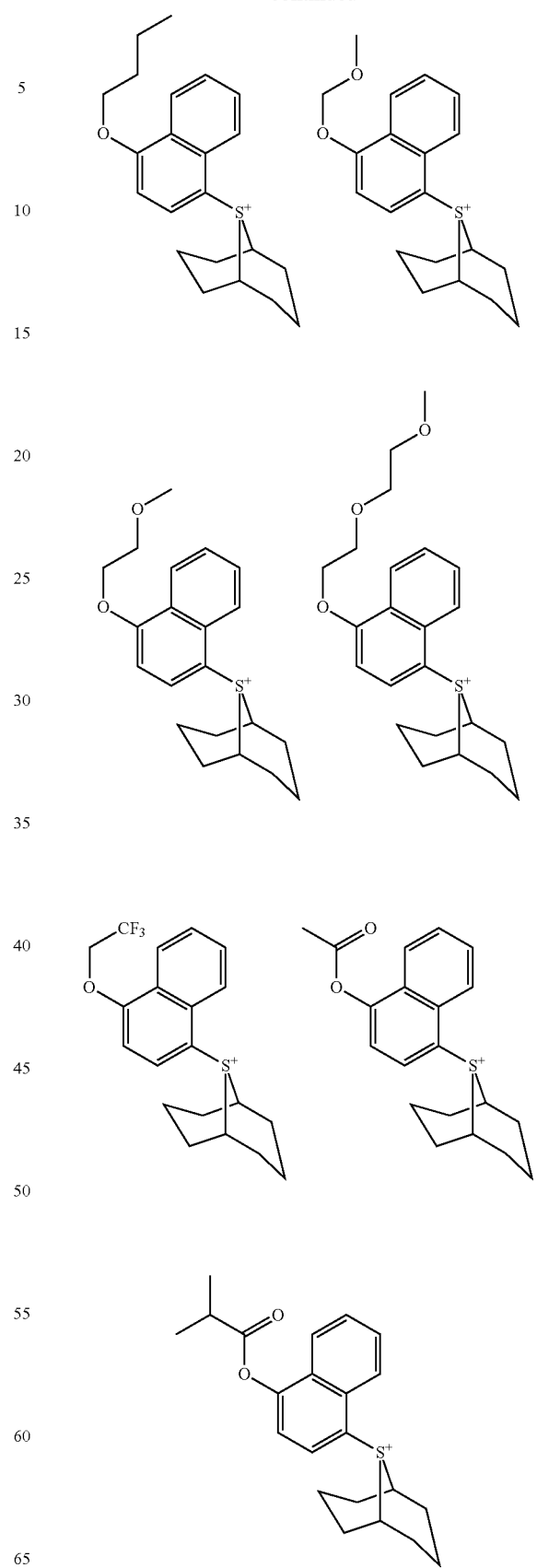

137
-continued
138
-continued
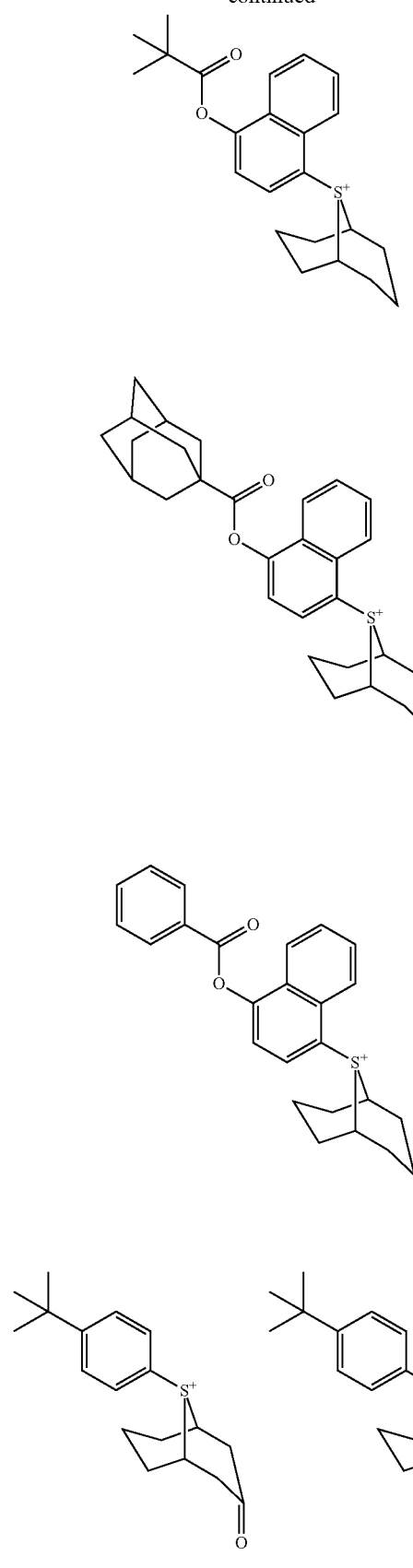

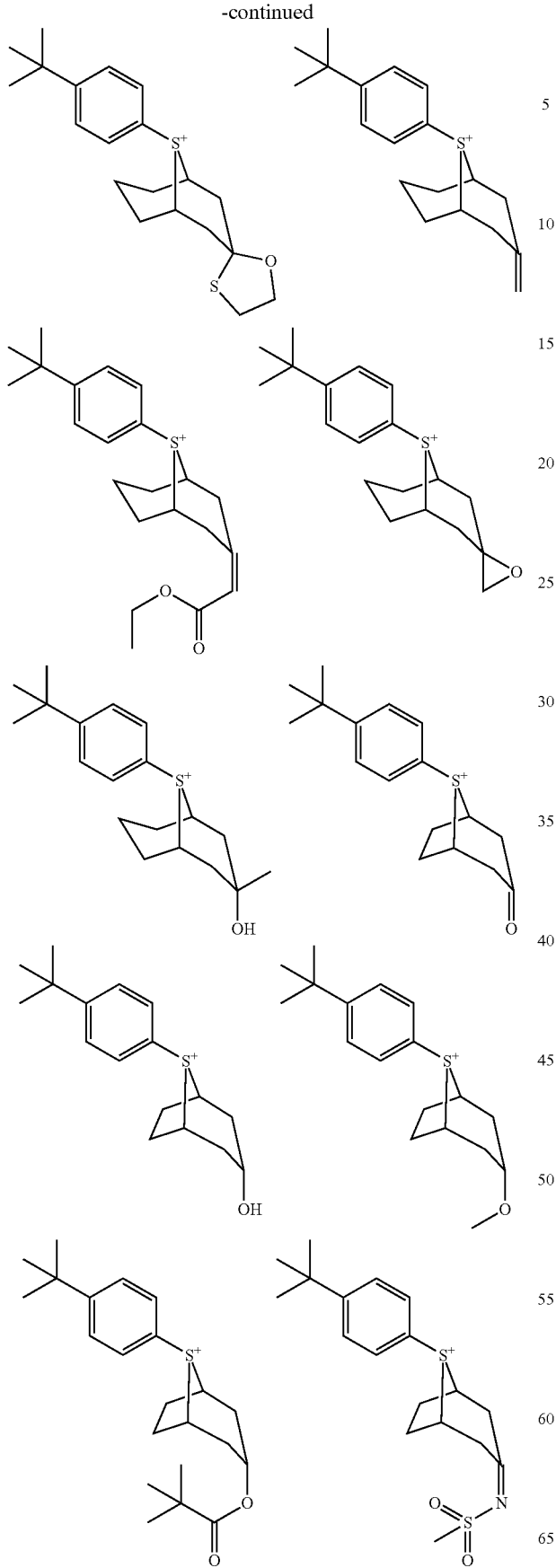
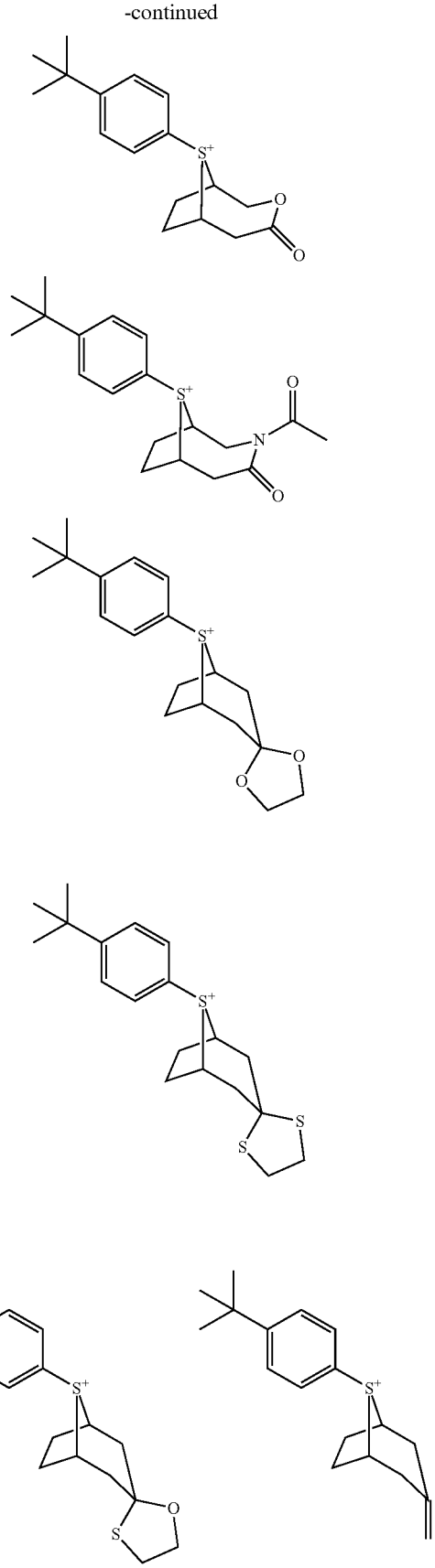

141
-continued
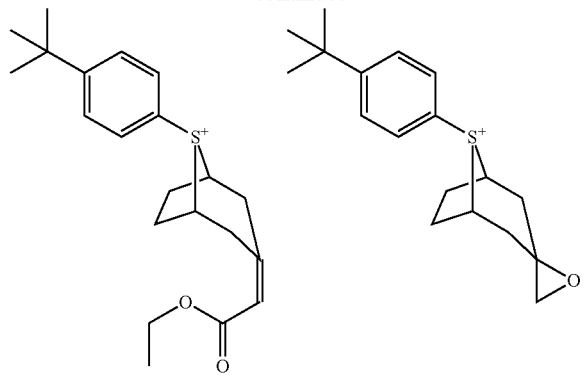
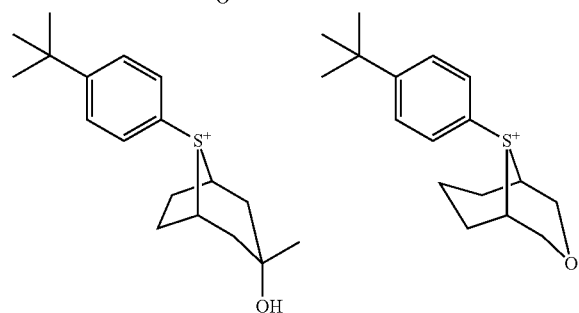
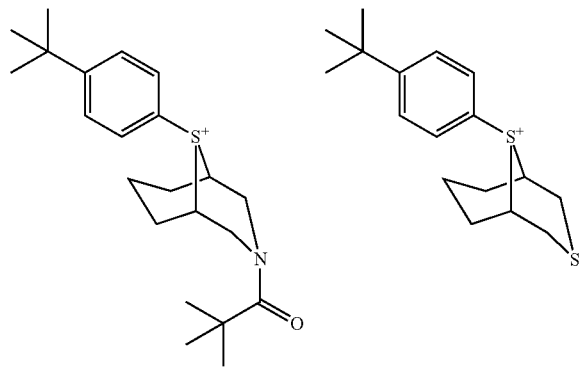
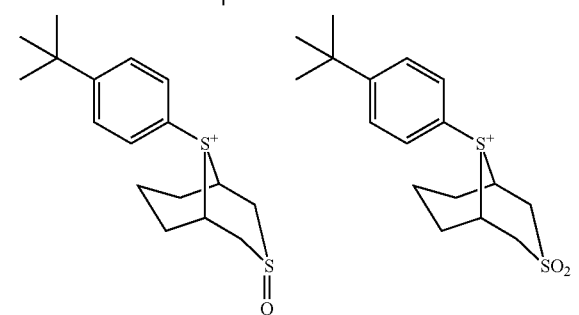
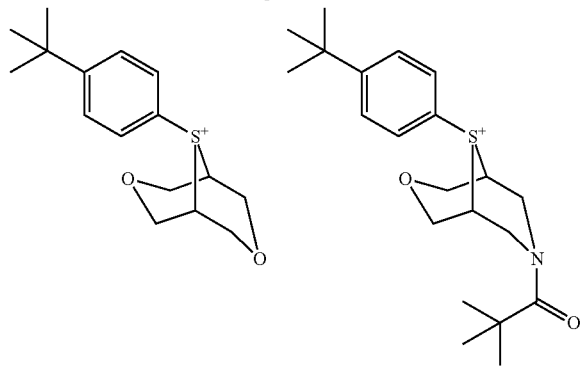
142
-continued
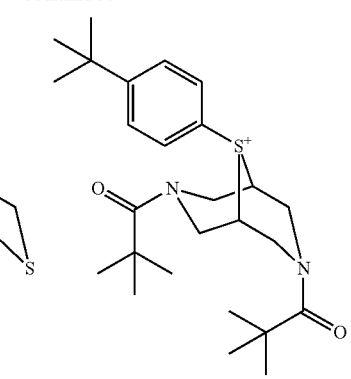
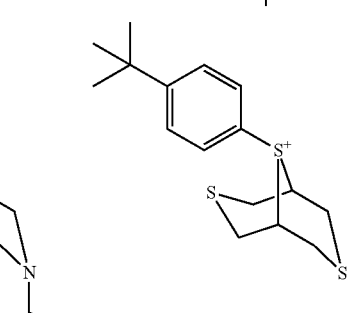
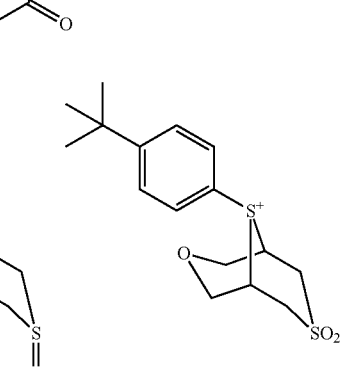
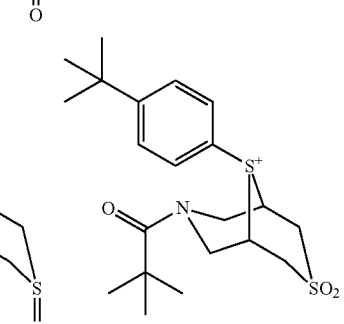
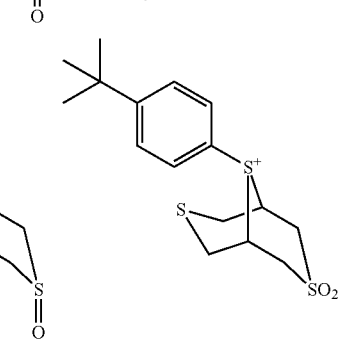

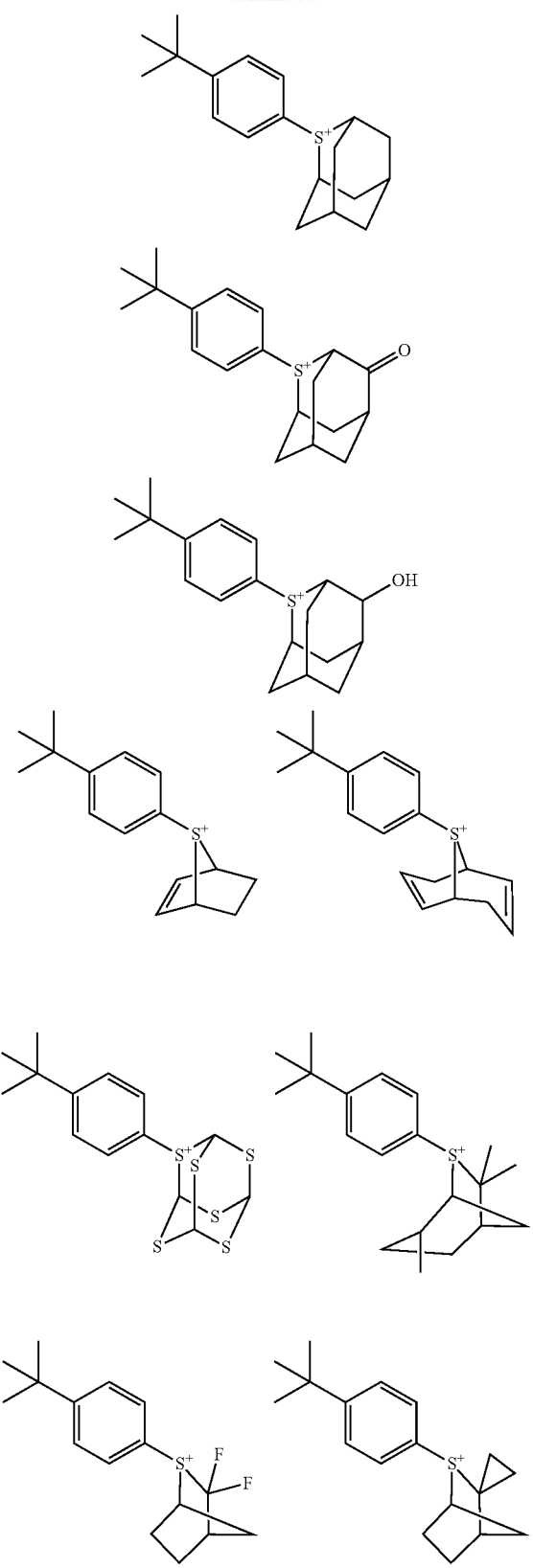
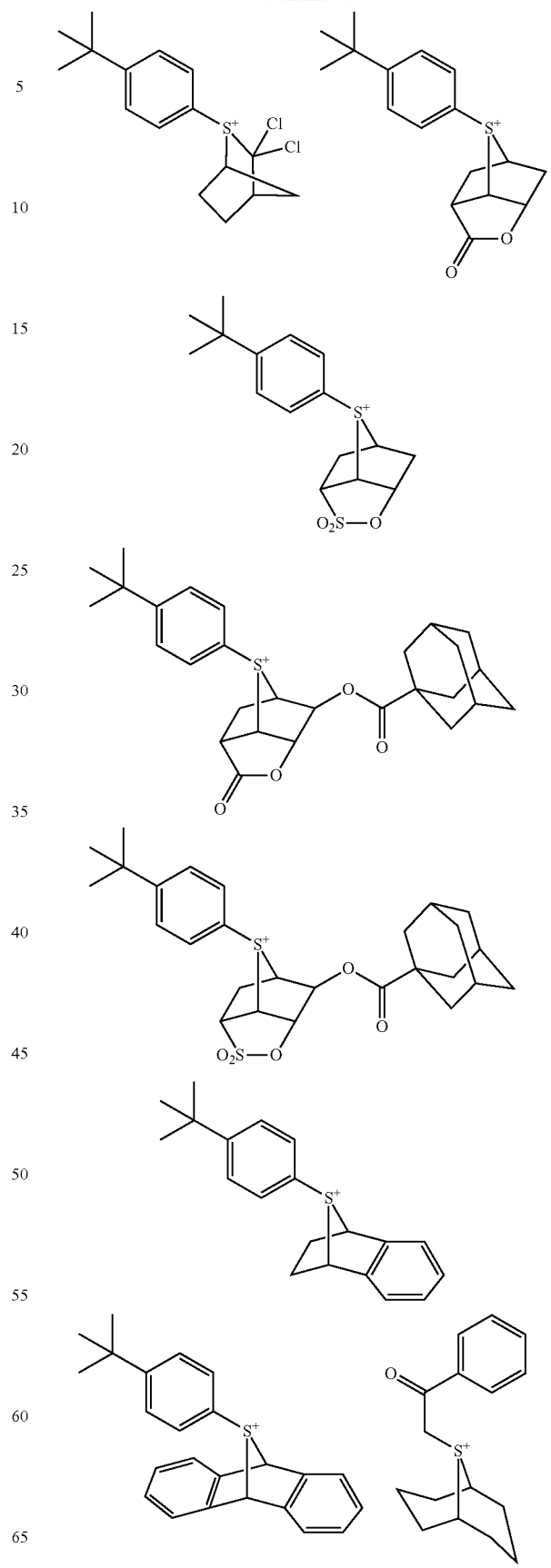

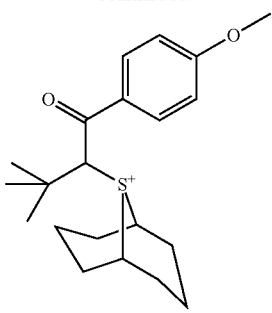

Examples of the iodonium cation having formula (c5) are given below, but not limited thereto.

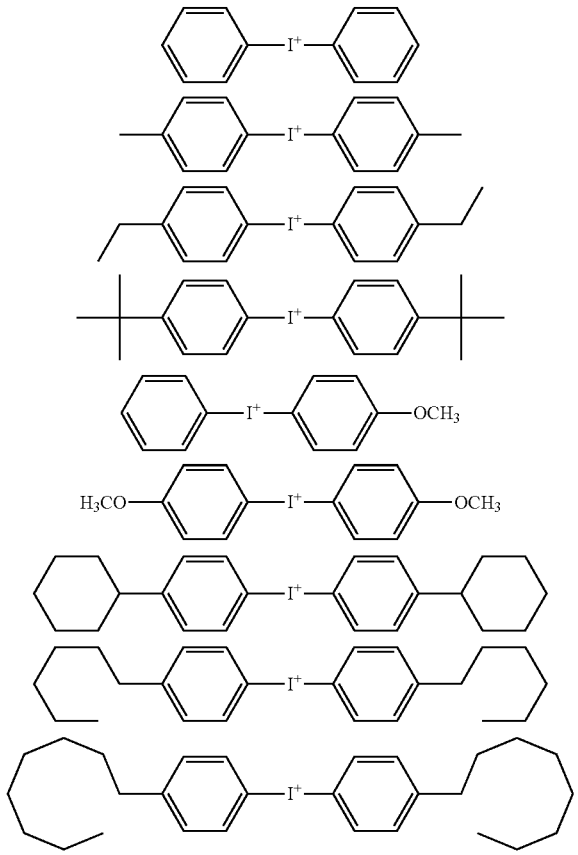

Examples of the repeat units (c1) to (c3) include arbitrary combinations of anions with cations, both as exemplified above.

The base polymer may further comprise repeat units (d) of a structure having a hydroxy group protected with an acid labile group. The repeat unit (d) is not particularly limited as long as the unit includes one or more structures having a hydroxy group protected with a protective group such that the protective group is decomposed to generate the hydroxy group under the action of acid. Repeat units having the formula (d1) are preferred.

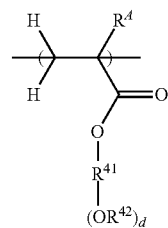

In formula (d1), $R^4$ is as defined above. $R^{41}$ is a $C_1$-$C_{30}$ (d+1)-valent hydrocarbon group which may contain a heteroatom. $R^{42}$ is an acid labile group, and d is an integer of 1 to 4.

In formula (d1), the acid labile group $R^{42}$ is deprotected under the action of acid so that a hydroxy group is generated. The structure of $R^{42}$ is not particularly limited, an acetal structure, ketal structure, alkoxycarbonyl group and alkoxymethyl group having the following formula (d2) are preferred, with the alkoxymethyl group having formula (d2) being more preferred.

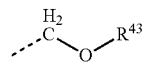

Herein $R^{43}$ is a $C_1$-$C_{15}$ hydrocarbyl group.

Illustrative examples of the acid labile group $R^{42}$, the alkoxymethyl group having formula (d2), and the repeat units (d) are as exemplified for the repeat units (d) in JP-A 2020-111564 (US 20200223796).

In addition to the foregoing units, the base polymer may further comprise repeat units is derived from other monomers, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo [6.2.1.1$^{3,6}$.0$^{2,7}$]dodecene derivatives, and unsaturated acid anhydrides such as itaconic anhydride.

The base polymer preferably has a weight average molecular weight (Mw) of 1,000 to 500,000, and more preferably 3,000 to 100,000, as measured versus polystyrene standards by gel permeation chromatography (GPC) using tetrahydrofuran (THF) solvent. The above range of Mw ensures satisfactory etch resistance and eliminates the risk of resolution being reduced due to difficulty to gain a dissolution rate difference before and after exposure.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influence of Mw/Mn becomes stronger as the pattern rule becomes finer. Therefore, the base polymer should preferably have a narrow dispersity (Mw/Mn) of 1.0 to 2.0 in order to provide a resist composition suitable for micropatterning to a small feature size.

The base polymer may be synthesized, for example, by dissolving a monomer or monomers corresponding to the above-mentioned repeat units in an organic solvent, adding a radical polymerization initiator, and heating for polymerization.

One exemplary method of synthesizing the polymer is by dissolving one or more unsaturated bond-bearing monomers in an organic solvent, adding a radical initiator, and heating for polymerization. Examples of the organic solvent which can be used for polymerization include toluene, benzene, THF, diethyl ether, dioxane, cyclohexane, cyclopentane, methyl ethyl ketone (MEK), propylene glycol monomethyl ether acetate (PGMEA), and γ-butyrolactone (GBL). Examples of the polymerization initiator used herein include 2,2'-azobisisobutyronitrile (AIBN), 2,2'-azobis(2,4-dimethylvaleronitrile), dimethyl 2,2-azobis(2-methylpropionate), 1,1'-azobis(1-acetoxy-1-phenylethane), benzoyl peroxide, and lauroyl peroxide. The initiator is preferably added in an amount of 0.01 to 25 mol % based on the total of monomers to be polymerized. The reaction temperature is preferably 50 to 150° C., more preferably 60 to 100° C. The reaction time is preferably 2 to 24 hours, more preferably 2 to 12 hours in view of production efficiency.

The polymerization initiator may be fed to the reactor either by adding the initiator to the monomer solution and feeding the solution to the reactor, or by dissolving the initiator in a solvent to form an initiator solution and feeding the initiator solution and the monomer solution independently to the reactor. Because of a possibility that in the standby duration, the initiator generates a radical which triggers polymerization reaction to form a ultra-high-molecular-weight polymer, it is preferred from the standpoint of quality control to prepare the monomer solution and the initiator solution separately and add them dropwise. The acid labile group that has been incorporated in the monomer may be kept as such, or polymerization may be followed by protection or partial protection. During the polymer synthesis, any known chain transfer agent such as dodecyl mercaptan or 2-mercaptoethanol may be added for molecular weight control purpose. The amount of chain transfer agent added is preferably 0.01 to 20 mol % based on the total of monomers.

When hydroxystyrene or hydroxyvinylnaphthalene is copolymerized, one method is by dissolving hydroxystyrene or hydroxyvinylnaphthalene and other monomers in an organic solvent, adding a radical polymerization initiator thereto, and heating the solution for polymerization. In an alternative method, acetoxystyrene or acetoxyvinylnaphthalene is used instead, and after polymerization, the acetoxy group is deprotected by alkaline hydrolysis, for thereby converting the polymer product to polyhydroxystyrene or polyhydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The amounts of monomers in the monomer solution may be determined appropriate so as to provide the preferred fractions of repeat units.

It is now described how to use the polymer obtained by the above preparation method. The reaction solution resulting from polymerization reaction may be used as the final product. Alternatively, the polymer may be recovered in powder form through a purifying step such as re-precipitation step of adding the polymerization solution to a poor solvent and letting the polymer precipitate as powder, after which the polymer powder is used as the final product. It is preferred from the standpoints of operation efficiency and consistent quality to handle a polymer solution which is obtained by dissolving the powder polymer resulting from the purifying step in a solvent, as the final product. The solvents which can be used herein are described in JP-A 2008-111103, paragraphs [0144]-[0145] (U.S. Pat. No. 7,537,880). Exemplary solvents include ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; keto-alcohols such as diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone (GBL); and high-boiling alcohols such as diethylene glycol, propylene glycol, glycerol, 1,4-butanediol, and 1,3-butanediol, which may be used alone or in admixture.

The polymer solution preferably has a polymer concentration of 0.01 to 30% by weight, more preferably 0.1 to 20% by weight.

Prior to use, the reaction solution or polymer solution is preferably filtered through a filter. Filtration is effective for consistent quality because foreign particles and gel which can cause defects are removed.

Suitable materials of which the filter is made include fluorocarbon, cellulose, nylon, polyester, and hydrocarbon base materials. Preferred for the filtration of a resist composition are filters made of fluorocarbons commonly known as Teflon®, hydrocarbons such as polyethylene and polypropylene, and nylon. While the pore size of the filter may be selected appropriate to comply with the desired cleanness, the filter preferably has a pore size of up to 100 nm, more preferably up to 20 nm. A single filter may be used or a plurality of filters may be used in combination. Although the filtering method may be single pass of the solution, preferably the filtering step is repeated by flowing the solution in a circulating manner. In the polymer preparation process, the filtering step may be carried out any times, in any order and in any stage. The reaction solution as polymerized or the polymer solution may be filtered, preferably both are filtered.

The proportion (mol %) of various repeat units in the base polymer is in the following range, but not limited thereto:
(I) preferably 1 to 60 mol %, more preferably 5 to 50 mol %, even more preferably 10 to 50 mol % of repeat units of at least one type selected from repeat units having formulae (a1) and (a2);
(II) preferably 40 to 99 mol %, more preferably 50 to 95 mol %, even more preferably 50 to 90 mol % of repeat units of at least one type selected from repeat units having formulae (b1) and (b2);
(III) preferably 0 to 30 mol %, more preferably 0 to 20 mol %, even more preferably 0 to 15 mol % of repeat units of at least one type selected from repeat units having formulae (c1) to (c3); and
(IV) preferably 0 to 80 mol %, more preferably 0 to 70 mol %, even more preferably 0 to 50 mol % of repeat units of at least one type derived from other monomers.

In the embodiment wherein the base polymer is polymer-bound photoacid generator A, the proportion (mol %) of various repeat units is in the following range, but not limited thereto:

(I) preferably 1 to 60 mol %, more preferably 5 to 50 mol %, even more preferably 10 to 50 mol % of repeat units of at least one type selected from repeat units having formulae (a1) and (a2);
(II) preferably 1 to 30 mol %, more preferably 3 to 20 mol %, even more preferably 5 to 15 mol % of repeat units of at least one type selected from repeat units having formulae (a3) and (a4);
(III) preferably 10 to 40 mol %, more preferably 30 to 40 mol %, even more preferably 35 to 40 mol % of repeat units of at least one type selected from repeat units having formulae (b1) and (b2); and
(IV) preferably 0 to 80 mol %, more preferably 0 to 70 mol %, even more preferably 0 to 50 mol % of repeat units of at least one type derived from other monomers.

The base polymer (B) may be used alone or as a blend of two or more polymers which differ in compositional ratio, Mw and/or Mw/Mn. Component (B) may also be a blend of the base polymer defined above and a hydrogenated product of ROMP. For the ROMP, reference is made to JP-A 2003-066612.

(C) Organic Solvent

The organic solvent used as component (C) is not particularly limited as long as the foregoing and other components are soluble therein. Suitable solvents include ketones such as cyclopentanone, cyclohexanone, and methyl-2-n-pentyl ketone; alcohols such as 3-methoxybutanol, 3-methyl-3-methoxybutanol, 1-methoxy-2-propanol, and 1-ethoxy-2-propanol; keto-alcohols such as diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone (GBL), and mixtures thereof.

Of the foregoing organic solvents, it is recommended to use 1-ethoxy-2-propanol, PGMEA, cyclohexanone, GBL, DAA and mixtures thereof because the base polymer (B) is most soluble therein.

The organic solvent (C) is preferably added in an amount of 200 to 5,000 parts by weight, and more preferably 400 to 3,500 parts by weight per 80 parts by weight of the base polymer (B). The organic solvent may be used alone or in admixture.

(D) Other Photoacid Generator

The chemically amplified resist composition may comprise (D) a photoacid generator other than component (A). The other PAG is not particularly limited as long as it is capable of generating an acid upon exposure to high-energy radiation. The preferred other PAG is a salt having the formula (3).

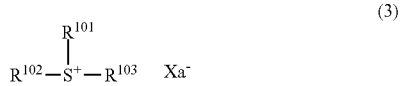

(3)

In formula (3), $R^{101}$, $R^{102}$ and $R^{103}$ are each independently a $C_1$-$C_{20}$ hydrocarbyl group which may contain a heteroatom. Any two of $R^{101}$, $R^{102}$ and $R^{103}$ may bond together to form a ring with the sulfur atom to which they are attached. Examples of the hydrocarbyl group are as exemplified above for $R^{31}$ to $R^{35}$ in formulae (c4) and (c5).

Examples of the sulfonium cation in the salt having formula (3) are as exemplified above for the sulfonium cation having formula (c4).

In formula (3), Xa⁻ is an anion selected from the formulae (3A) to (3D).

(3A)

(3B)

(3C)

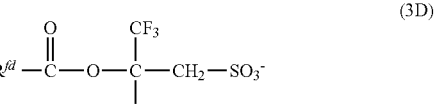

(3D)

In formula (3A), $R^{fa}$ is fluorine or a $C_1$-$C_{40}$ hydrocarbyl group which may contain a heteroatom. The hydrocarbyl group may be saturated or unsaturated and straight, branched or cyclic. Examples thereof are as will be exemplified later for $R^{111}$ in formula (3A').

Of the anions having formula (3A), anions having the formula (3A') are preferred.

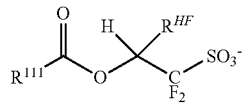

(3A')

In formula (3A'), $R^{HF}$ is hydrogen or trifluoromethyl, preferably trifluoromethyl.

$R^{111}$ is a $C_1$-$C_{38}$ hydrocarbyl group which may contain a heteroatom. Of the hydrocarbyl groups, those of 6 to 30 carbon atoms are preferred because a high resolution is available in fine pattern formation. The hydrocarbyl group $R^{111}$ may be saturated or unsaturated and straight, branched or cyclic. Examples thereof include $C_1$-$C_{30}$ alkyl groups such as methyl, ethyl, propyl, isopropyl, butyl, isobutyl, sec-butyl, tert-butyl, pentyl, neopentyl, hexyl, heptyl, octyl, 2-ethylhexyl, nonyl, decyl, undecyl, dodecyl, tridecyl, pentadecyl, heptadecyl, and icosanyl; $C_3$-$C_{30}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl; $C_2$-$C_{30}$ unsaturated aliphatic hydrocarbyl groups such as allyl and 3-cyclohexenyl; $C_6$-$C_{30}$ aryl groups such as phenyl, 1-naphthyl and 2-naphthyl; and $C_7$-$C_{30}$ aralkyl groups such as benzyl and diphenylmethyl.

In the foregoing groups, some or all of the hydrogen atoms may be substituted by a moiety containing a heteroatom such as oxygen, sulfur, nitrogen or halogen, or any constituent —CH$_2$— may be replaced by a moiety containing a heteroatom such as oxygen, sulfur or nitrogen, so that the group may contain a hydroxy, cyano, fluorine, chlorine, bromine, iodine, carbonyl, ether bond, ester bond, sulfonic ester bond, carbonate bond, lactone ring, sultone ring, carboxylic anhydride or haloalkyl moiety. Examples of the heteroatom-containing hydrocarbyl group include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, 5-hydroxy-1-adamantyl, 5-tert-butylcarbonyloxy-1-adamantyl, 4-oxatricyclo[4.2.1.0$^{3,7}$]nonan-5-on-2-yl, and 3-oxocyclohexyl.

With respect to the synthesis of the sulfonium salt having an anion of formula (3A'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (3A) are as exemplified above for the anion having formula (2A).

In formula (3B), R$^{fb1}$ and R$^{fb2}$ are each independently fluorine or a C$_1$-C$_{40}$ hydrocarbyl group which may contain a heteroatom. The hydrocarbyl group may be saturated or unsaturated and straight, branched or cyclic. Examples thereof are as exemplified above for R$^{111}$ in formula (3A'). Preferably R$^{fb1}$ and R$^{fb2}$ are fluorine or C$_1$-C$_4$ straight fluorinated alkyl groups. Also, R$^{fb1}$ and R$^{fb2}$ may bond together to form a ring with the linkage: —CF$_2$—SO$_2$—N$^-$—SO$_2$—CF$_2$— to which they are attached. It is preferred that a combination of R$^{fb1}$ and R$^{fb2}$ be a fluorinated ethylene or fluorinated propylene group.

In formula (3C), R$^{fc1}$, R$^{fc2}$ and R$^{fc3}$ are each independently fluorine or a C$_1$-C$_{40}$ hydrocarbyl group which may contain a heteroatom. The hydrocarbyl group may be saturated or unsaturated and straight, branched or cyclic. Examples thereof are as exemplified for R$^{111}$. Preferably R$^{fc1}$, R$^{fc2}$ and R$^{fc3}$ are fluorine or C$_1$-C$_4$ straight fluorinated alkyl groups. Also, R$^{fc1}$ and R$^{fc2}$ may bond together to form a ring with the linkage: —CF$_2$—SO$_2$—C$^-$—SO$_2$—CF$_2$— to which they are attached. It is preferred that a combination of R$^{fc1}$ and R$^{fc2}$ be a fluorinated ethylene or fluorinated propylene group.

In formula (3D), R$^{fd}$ is a C$_1$-C$_{40}$ hydrocarbyl group which may contain a heteroatom. The hydrocarbyl group may be saturated or unsaturated and straight, branched or cyclic. Examples thereof are as exemplified above for R$^{111}$.

With respect to the synthesis of the sulfonium salt having an anion of formula (3D), reference may be made to JP-A 2010-215608 and JP-A 2014-133723.

Examples of the anion having formula (3D) are as exemplified for the anion having formula (1D) in JP-A 2018-197853.

Notably, the compound having the anion of formula (3D) does not have fluorine at the α-position relative to the sulfo group, but two trifluoromethyl groups at the β-position. For this reason, it has a sufficient acidity to sever the acid labile groups in the base polymer. Thus the compound is an effective PAG.

Also, a compound having the formula (4) is preferred as the PAG (D).

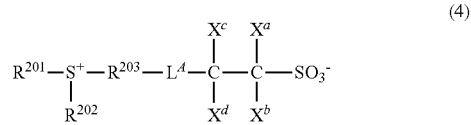

(4)

In formula (4), R$^{201}$ and R$^{202}$ are each independently a C$_1$-C$_{30}$ hydrocarbyl group which may contain a heteroatom. R$^{203}$ is a C$_1$-C$_{30}$ hydrocarbylene group which may contain a heteroatom. Any two of R$^{201}$, R$^{202}$ and R$^{203}$ may bond together to form a ring with the sulfur atom to which they are attached.

The hydrocarbyl groups R$^{201}$ and R$^{202}$ may be saturated or unsaturated and straight, branched or cyclic. Examples thereof include C$_1$-C$_{30}$ alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl; C$_3$-C$_{30}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl; and C$_6$-C$_{30}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl, and anthracenyl, and combinations thereof. In these hydrocarbyl groups, some or all of the hydrogen atoms may be substituted by a moiety containing a heteroatom such as oxygen, sulfur, nitrogen or halogen, and any constituent —CH$_2$— may be replaced by a moiety containing a heteroatom such as oxygen, sulfur or nitrogen, so that the group may contain a hydroxy, cyano, fluorine, chlorine, bromine, iodine, carbonyl, ether bond, ester bond, sulfonic ester bond, carbonate bond, lactone ring, sultone ring, carboxylic anhydride or haloalkyl moiety.

The hydrocarbylene group R$^{203}$ may be saturated or unsaturated and straight, branched or cyclic. Examples thereof include C$_1$-C$_{30}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; C$_3$-C$_{30}$ cyclic saturated hydrocarbylene groups such as cyclopentanediyl, cyclohexanediyl, norbornanediyl and adamantanediyl; and cyclic unsaturated hydrocarbylene groups such as phenylene, methylphenylene, ethylphenylene, n-propylphenylene, isopropylphenylene, n-butylphenylene, isobutylphenylene, sec-butylphenylene, tert-butylphenylene, naphthylene, methylnaphthylene, ethylnaphthylene, n-propylnaphthylene, isopropylnaphthylene, n-butylnaphthylene, isobutylnaphthylene, sec-butylnaphthylene, and tert-butylnaphthylene. In these hydrocarbylene groups, some or all of the hydrogen atoms may be substituted by a moiety containing a heteroatom such as oxygen, sulfur, nitrogen or halogen, or any constituent —CH$_2$— may be replaced by a moiety containing a heteroatom such as oxygen, sulfur or nitrogen, so that the group may contain a hydroxy, cyano, fluorine, chlorine, bromine, iodine, carbonyl, ether bond, ester bond, sulfonic ester bond, carbonate bond, lactone ring, sultone ring, carboxylic anhydride or haloalkyl moiety. Of the heteroatoms, oxygen is preferred.

In formula (4), $L^A$ is a single bond, ether bond or a $C_1$-$C_{20}$ hydrocarbylene group which may contain a heteroatom. The hydrocarbylene group may be saturated or unsaturated and straight, branched or cyclic. Examples thereof are as exemplified above for the hydrocarbylene group $R^{203}$.

In formula (4), $X^a$, $X^b$, $X^c$ and $X^d$ are each independently hydrogen, fluorine or trifluoromethyl, with the proviso that at least one of $X^a$, $X^b$, $X^c$ and $X^d$ is fluorine or trifluoromethyl.

Of the PAGs having formula (4), those having formula (4') are preferred.

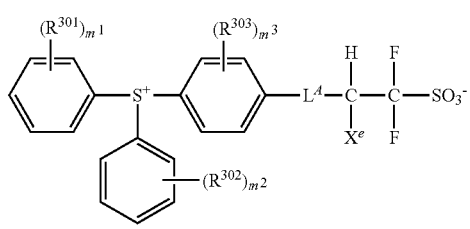

(4')

In formula (4'), $L^A$ is as defined above. $X^c$ is hydrogen or trifluoromethyl, preferably trifluoromethyl. $R^{301}$, $R^{302}$ and $R^{303}$ are each independently hydrogen or a $C_1$-$C_{20}$ hydrocarbyl group which may contain a heteroatom. The hydrocarbyl group may be saturated or unsaturated and straight, branched or cyclic. Examples thereof are as exemplified above for $R^{111}$ in formula (3A'). The subscripts $m^1$ and $m^2$ are each independently an integer of 0 to 5, and $m^3$ is an integer of 0 to 4.

Examples of the PAG having formula (4) include those exemplified for the PAG having formula (2) in JP-A 2017-026980.

Of the foregoing PAGs, those having an anion of formula (3A') or (3D) are especially preferred because of reduced acid diffusion and high solubility in solvents. Also those having formula (4') are especially preferred because of extremely reduced acid diffusion.

When used, the PAG (D) is preferably added in an amount of 0.1 to 40 parts, and more preferably 0.5 to 20 parts by weight per 80 parts by weight of the base polymer (B). As long as the amount of the PAG is in the range, good resolution is achievable and the risk of foreign particles being formed after development or during stripping of resist film is avoided. The PAG may be used alone or in admixture.

(E) Quencher

The resist composition may further comprise (E) a quencher or acid diffusion regulator. As used herein, the quencher refers to a compound capable of trapping the acid generated by the PAG in the resist composition to prevent the acid from diffusing to the unexposed region, for thereby forming the desired pattern.

Onium salts having the formulae (5) and (6) are useful as the quencher (E).

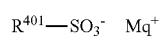  (5)

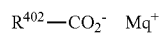  (6)

In formula (5), $R^{401}$ is hydrogen or a $C_1$-$C_{40}$ hydrocarbyl group which may contain a heteroatom, exclusive of the hydrocarbyl group in which the hydrogen atom bonded to the carbon atom at α-position of the sulfone group is substituted by fluorine or fluoroalkyl.

The hydrocarbyl group $R^{401}$ may be saturated or unsaturated and straight, branched or cyclic. Examples thereof include alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl; aryl groups such as phenyl, naphthyl and anthracenyl, and combinations thereof. In these hydrocarbyl groups, some or all hydrogen atoms may be substituted by a moiety containing a heteroatom such as oxygen, sulfur, nitrogen or halogen, or any constituent —$CH_2$— may be replaced by a moiety containing a heteroatom such as oxygen, sulfur or nitrogen, so that the group may contain a hydroxy, cyano, fluorine, chlorine, bromine, iodine, carbonyl, ether bond, ester bond, sulfonic ester bond, carbonate bond, lactone ring, sultone ring, carboxylic anhydride or haloalkyl moiety.

In formula (6), $R^{402}$ is hydrogen or a $C_1$-$C_{40}$ hydrocarbyl group which may contain a heteroatom. Examples of the hydrocarbyl group $R^{402}$ include those exemplified above for $R^{401}$ and fluoroalkyl groups such as trifluoromethyl and trifluoroethyl, and fluorinated aryl groups such as pentafluorophenyl and 4-trifluoromethylphenyl.

Examples of the anion in the onium salt having formula (5) are shown below, but not limited thereto.

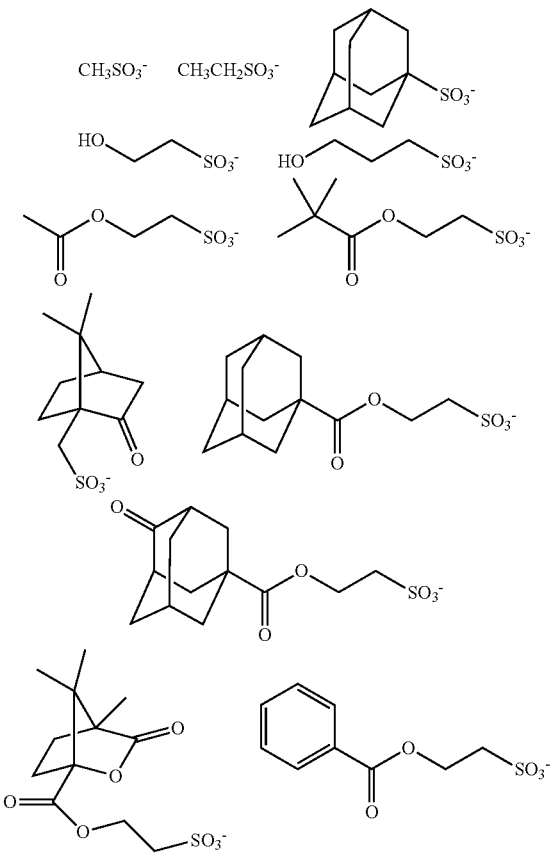

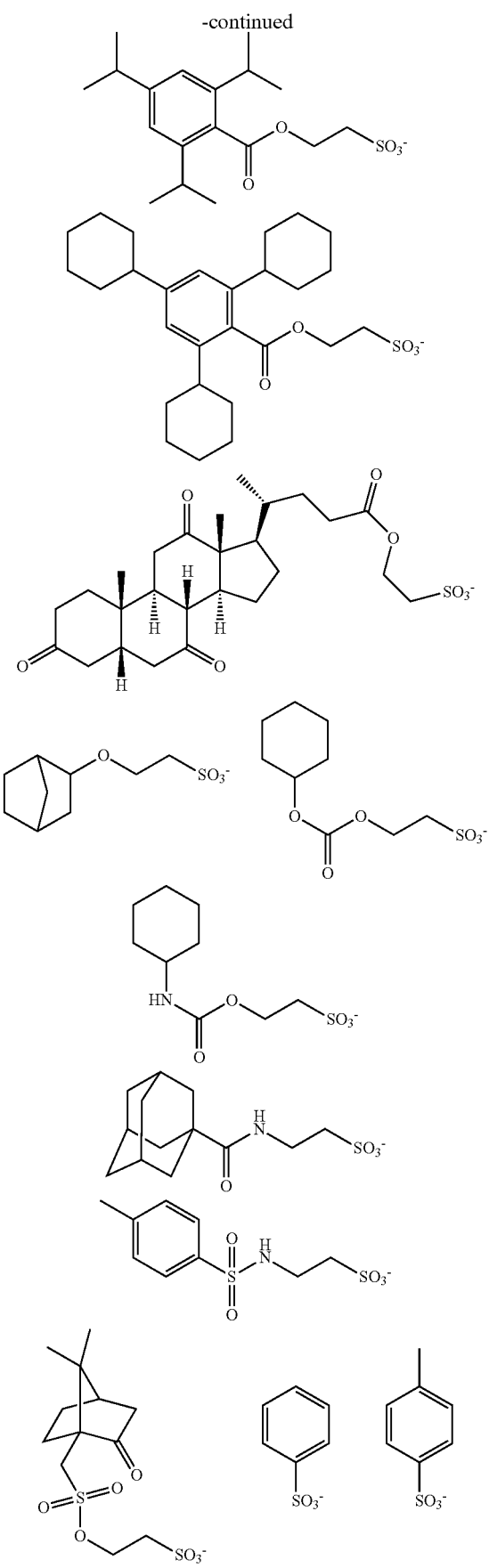
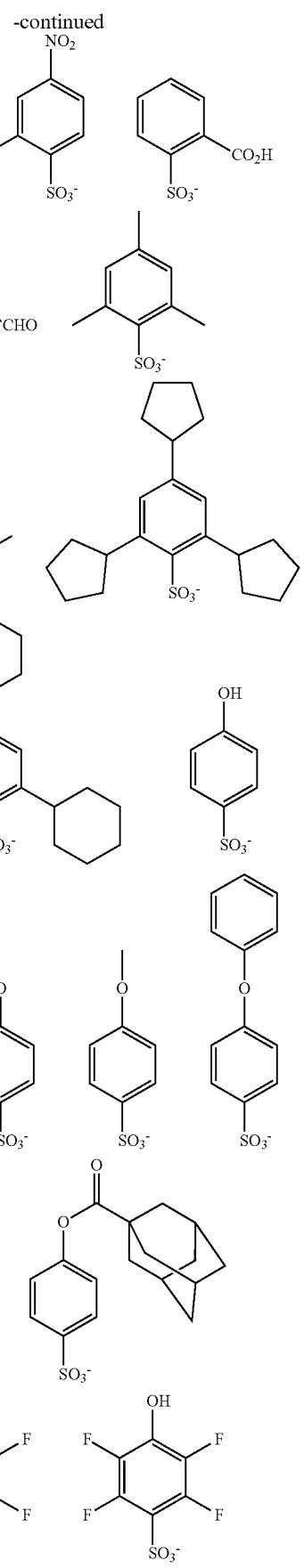

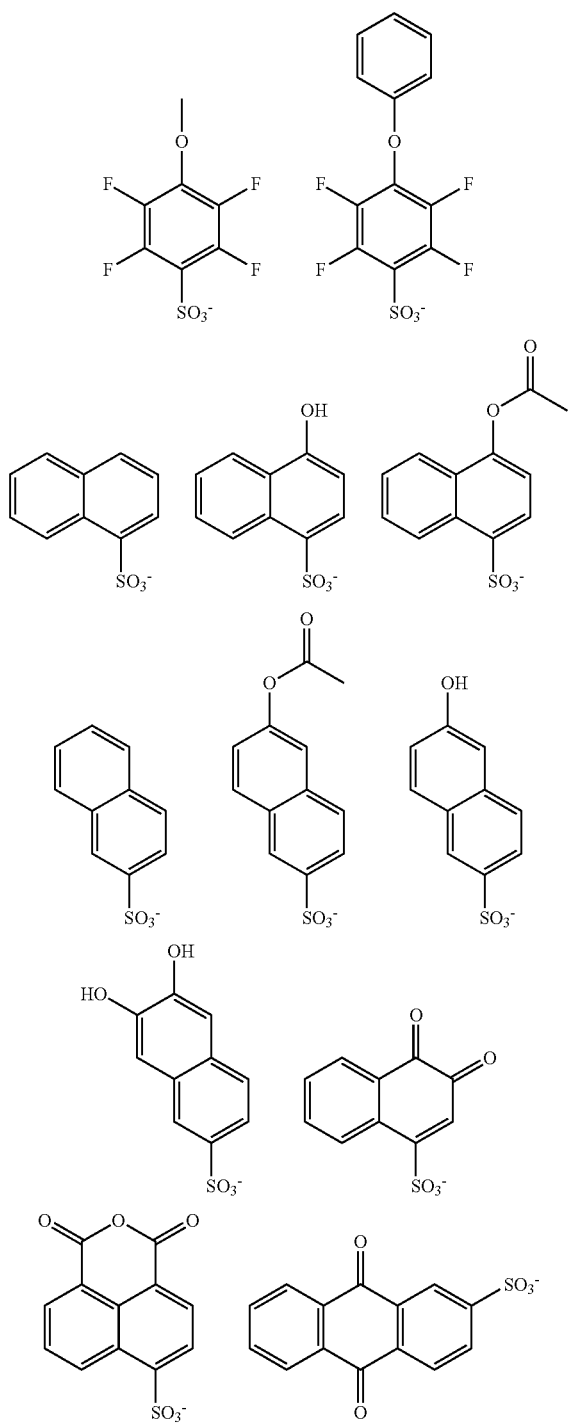
Examples of the anion in the onium salt having formula (6) are shown below, but not limited thereto.
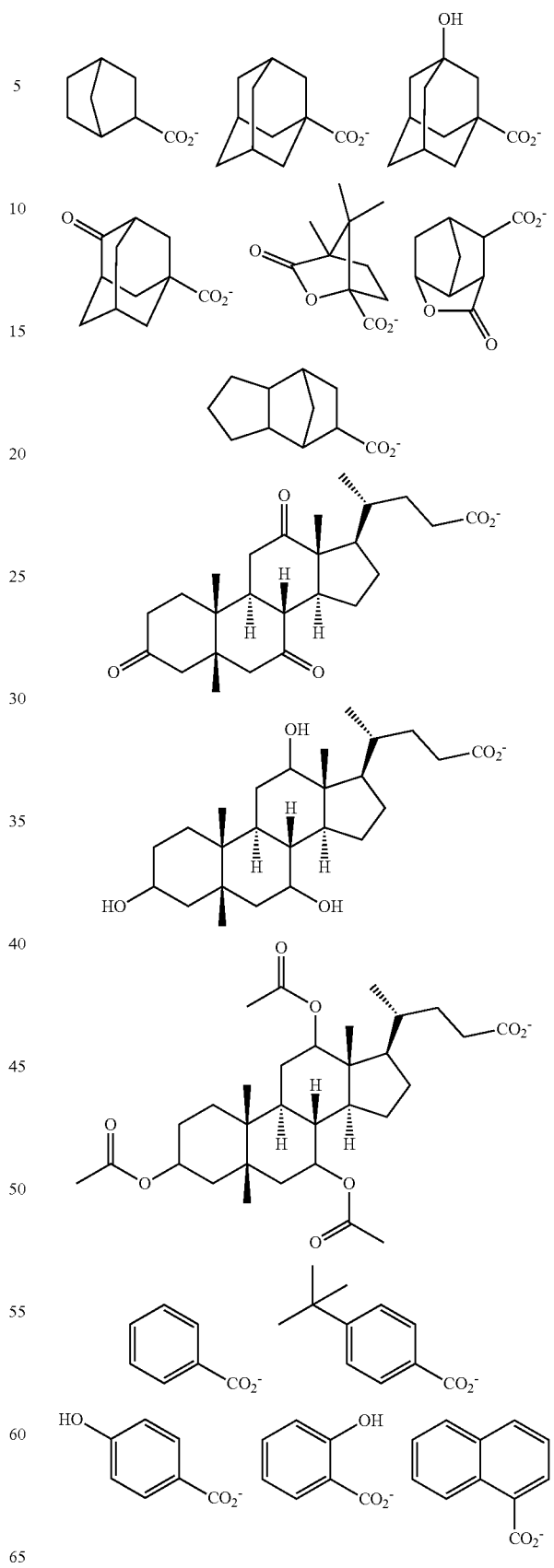

-continued

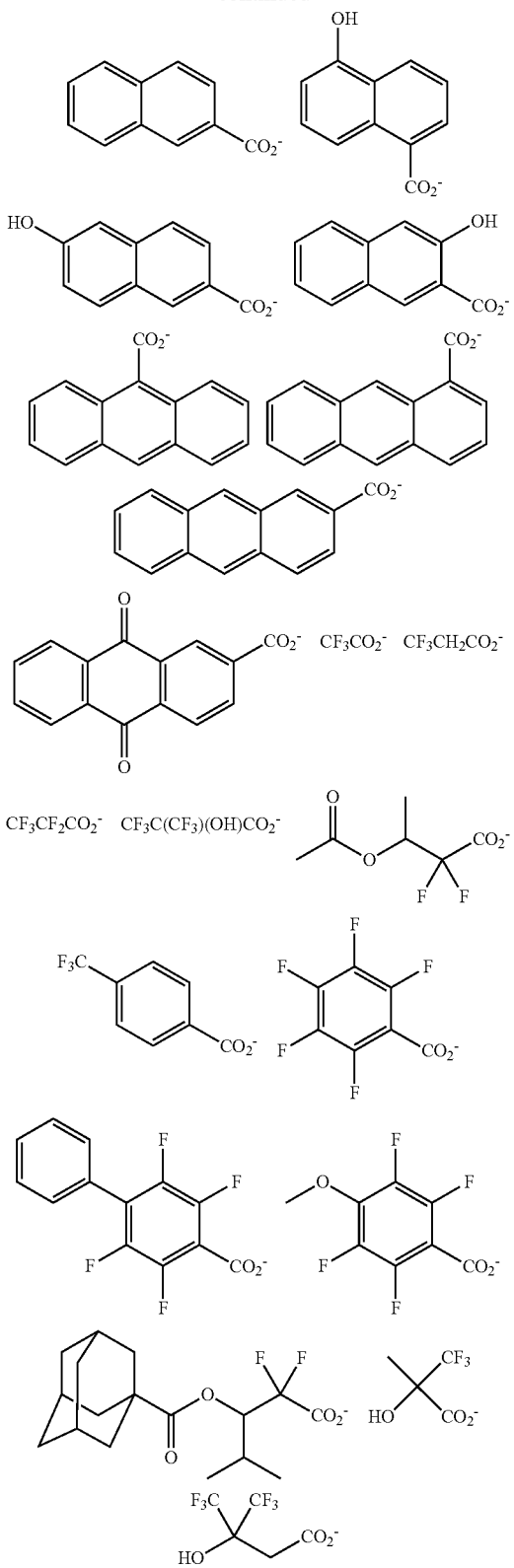

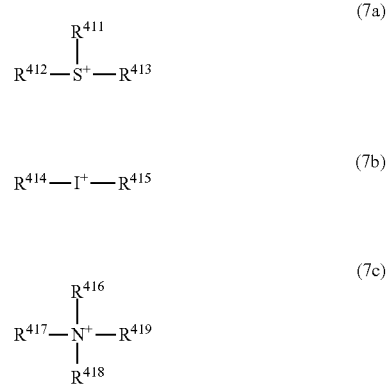

In formulae (7a) to (7c), $R^{411}$ to $R^{419}$ are each independently a $C_1$-$C_{40}$ hydrocarbyl group which may contain a heteroatom. A pair of $R^{411}$ and $R^{412}$ may bond together to form a ring with the sulfur atom to which they are attached. A pair of $R^{416}$ and $R^{417}$ may bond together to form a ring with the nitrogen atom to which they are attached. Examples of the hydrocarbyl group are as exemplified above for $R^{401}$ in formula (5).

Examples of the onium cation represented by $Mq^+$ are shown below, but not limited thereto.

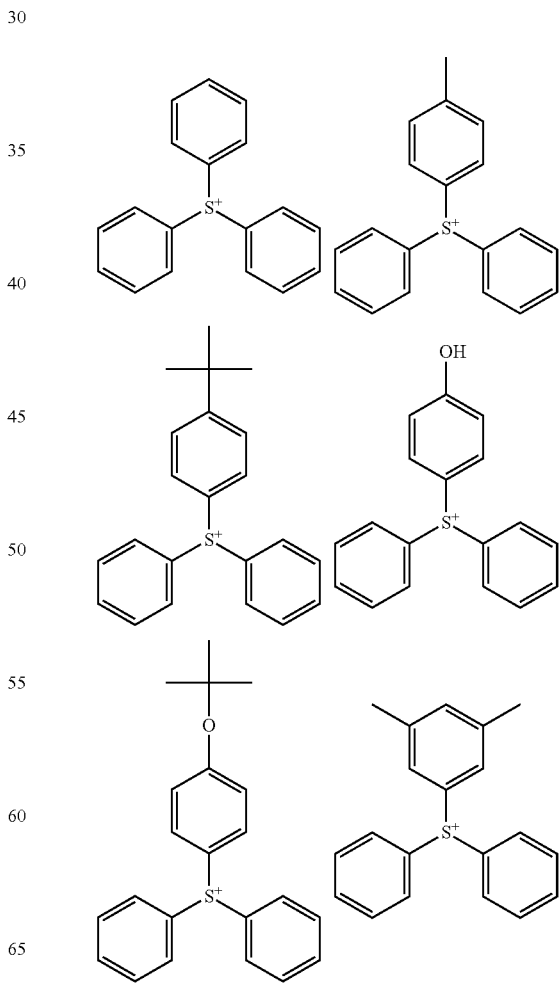

In formulae (5) and (6), $Mq^+$ is an onium cation, which is preferably selected from cations having the formulae (7a), (7b) and (7c).

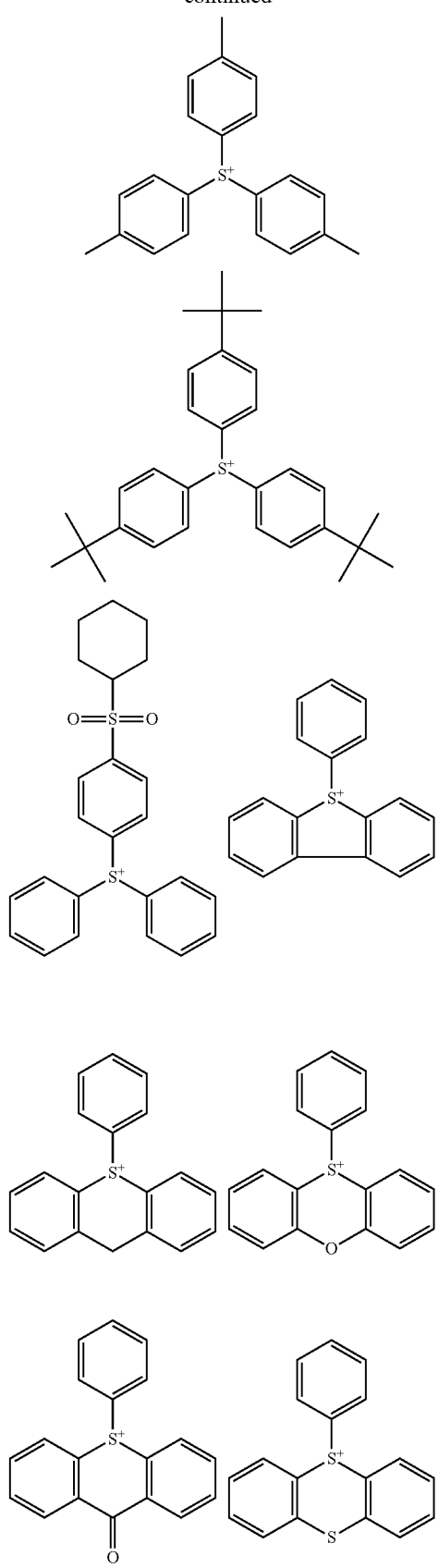
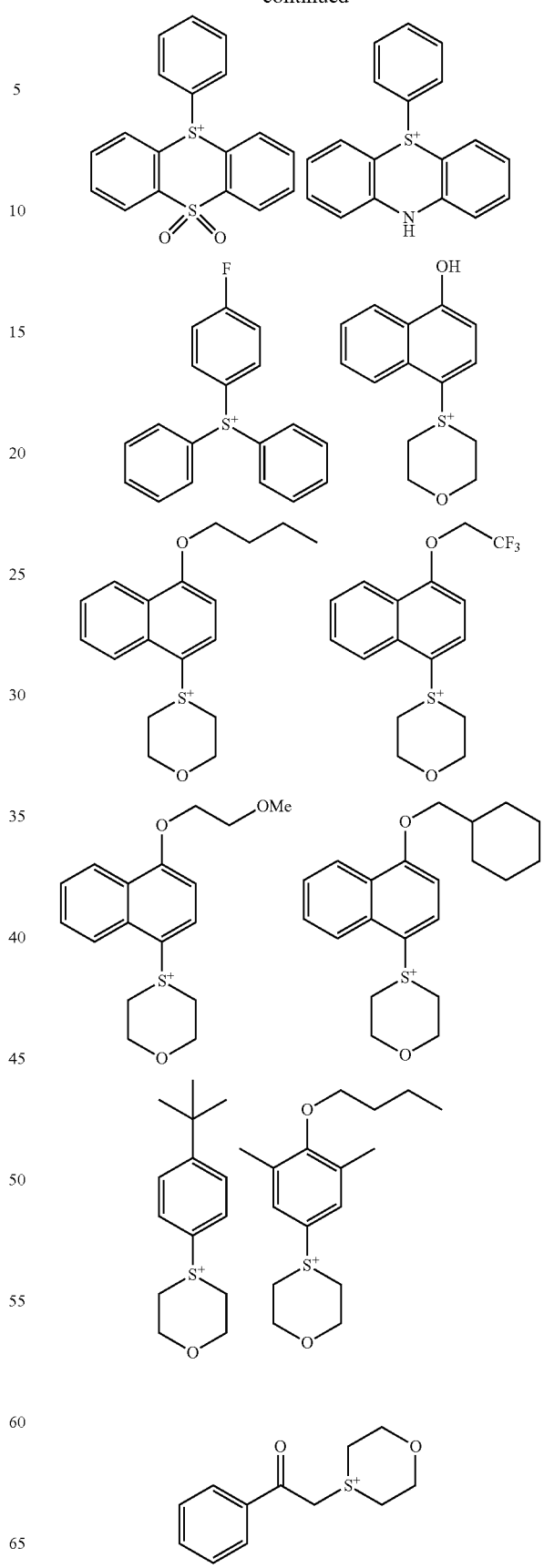

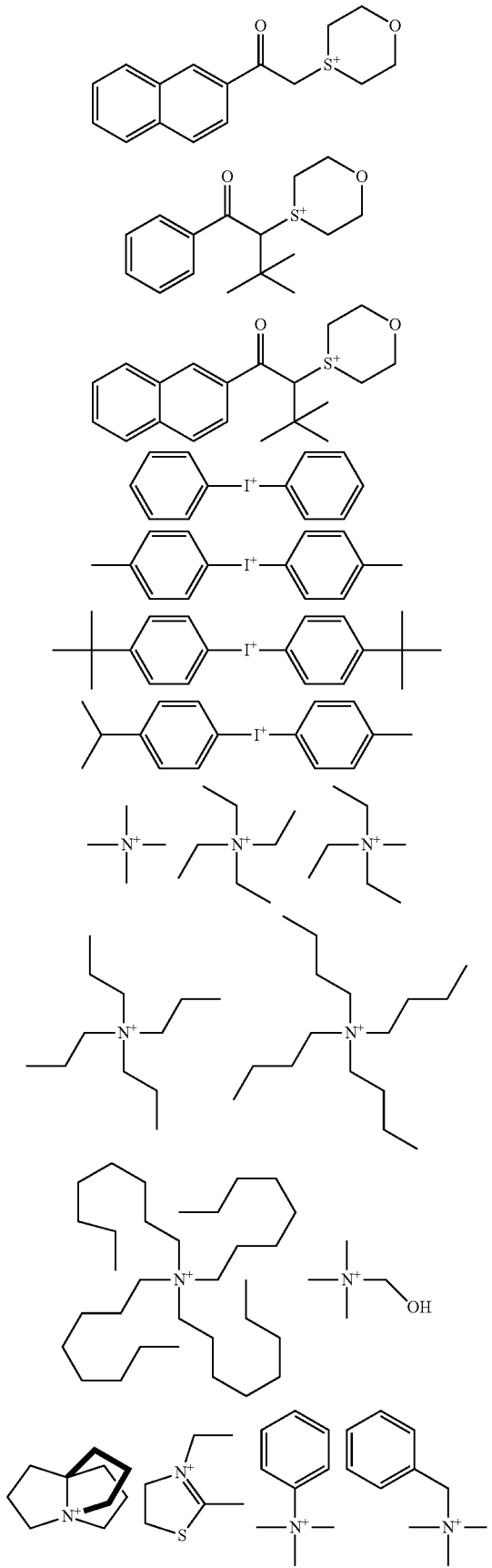

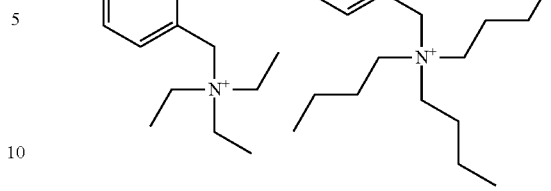

Examples of the onium salt having formula (5) or (6) include arbitrary combinations of anions with cations, both as exemplified above. These onium salts may be readily prepared by ion exchange reaction using any well-known organic chemistry technique. For the ion exchange reaction, reference may be made to JP-A 2007-145797, for example.

The onium salt having formula (5) or (6) functions as a quencher in the chemically amplified resist composition because the counter anion of the onium salt is a conjugated base of a weak acid. As used herein, the weak acid indicates an acidity insufficient to deprotect an acid labile group from an acid labile group-containing unit in the base polymer. The onium salt having formula (5) or (6) functions as a quencher when used in combination with an onium salt type PAG having a conjugated base of a strong acid (typically a sulfonic acid which is fluorinated at α-position) as the counter anion. In a system using a mixture of an onium salt capable of generating a strong acid (e.g., α-position fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If a PAG capable of generating a strong acid is an onium salt, an exchange from the strong acid generated upon exposure to high-energy radiation to a weak acid as above can take place, but it rarely happens that the weak acid generated upon exposure to high-energy radiation collides with the unreacted onium salt capable of generating a strong acid to induce a salt exchange. This is because of a likelihood of an onium cation forming an ion pair with a stronger acid anion.

When the onium salt having formula (5) or (6) is used as the quencher (E), the amount of the onium salt used is preferably 0.1 to 10 parts by weight, more preferably 0.1 to 5 parts by weight per 80 parts by weight of the base polymer (B). As long as the amount of component (E) is in the range, a satisfactory resolution is available without a substantial lowering of sensitivity. The onium salt having formula (5) or (6) may be used alone or in admixture.

Also nitrogen-containing compounds may be used as the quencher (E). Suitable nitrogen-containing compounds include primary, secondary and tertiary amine compounds, specifically amine compounds having a hydroxy group, ether bond, ester bond, lactone ring, cyano group or sulfonic ester bond, as described in JP-A 2008-111103, paragraphs [0146]-[0164] (U.S. Pat. No. 7,537,880), and primary or secondary amine compounds protected with a carbamate group, as described in JP 3790649.

A sulfonic acid sulfonium salt having a nitrogen-containing substituent may also be used as the nitrogen-containing compound. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595 and JP-A 2012-046501, for example.

When the nitrogen-containing compound is used as the quencher (E), the amount of the nitrogen-containing compound used is preferably 0.001 to 12 parts by weight, more preferably 0.01 to 8 parts by weight per 80 parts by weight of the base polymer (B). The nitrogen-containing compound may be used alone or in admixture.

(F) Surfactant

The resist composition may further include (F) a surfactant which is insoluble or substantially insoluble in water and soluble in alkaline developer, and/or a surfactant which is insoluble or substantially insoluble in water and alkaline developer. For the surfactant, reference should be made to those compounds described in JP-A 2010-215608 and JP-A 2011-016746.

While many examples of the surfactant which is insoluble or substantially insoluble in water and alkaline developer are described in the patent documents cited herein, preferred examples are surfactants FC-4430 (3M), Olfine® E1004 (Nissin Chemical Co., Ltd.), Surflon® S-381, KH-20 and KH-30 (AGC Seimi Chemical Co., Ltd.). Partially fluorinated oxetane ring-opened polymers having the formula (surf-1) are also useful.

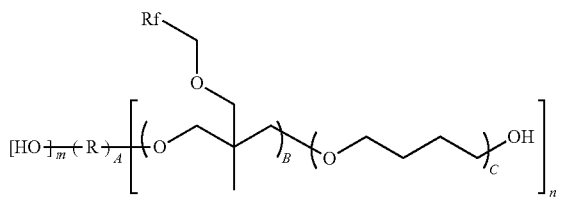

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent aliphatic groups include ethylene, 1,4-butylene, 1,2-propylene, 2,2-dimethyl-1,3-propylene and 1,5-pentylene. Exemplary tri- and tetra-valent groups are shown below.

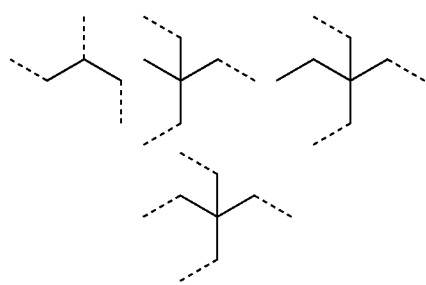

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. "A" is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water sliding.

Suitable polymeric surfactants include those containing repeat units of at least one type selected from the formulae (8A) to (8E).

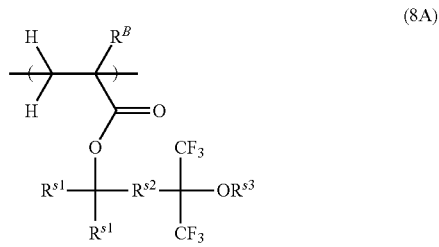

(8A)

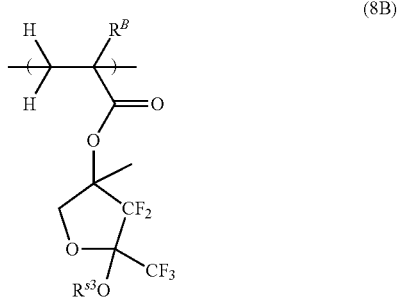

(8B)

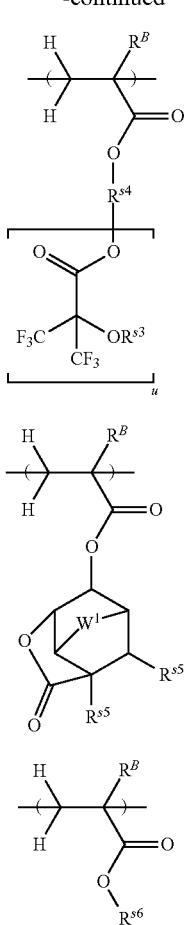

(8C)

(8D)

(8E)

Herein, $R^B$ is hydrogen, fluorine, methyl or trifluoromethyl. $W^1$ is —CH$_2$—, —CH$_2$CH$_2$— or —O—, or two separate —H. $R^{s1}$ is each independently hydrogen or a $C_1$-$C_{10}$ hydrocarbyl group. $R^{s2}$ is a single bond or a $C_1$-$C_5$ straight or branched hydrocarbylene group. $R^{s3}$ is each independently hydrogen, a $C_1$-$C_{18}$ hydrocarbyl or fluorinated hydrocarbyl group, or an acid labile group. When $R^{s3}$ is a hydrocarbyl or fluorinated hydrocarbyl group, an ether bond or carbonyl moiety may intervene in a carbon-carbon bond. $R^{s4}$ is a $C_1$-$C_{20}$ (u+1)-valent hydrocarbon or fluorinated hydrocarbon group, and u is an integer of 1 to 3. $R^{s5}$ is each independently hydrogen or a group: —C(=O)—O—$R^{s7}$ wherein $R^{s7}$ is a $C_1$-$C_{20}$ fluorinated hydrocarbyl group. $R^{s6}$ is a $C_1$-$C_{15}$ hydrocarbyl or fluorinated hydrocarbyl group in which an ether bond or carbonyl moiety may intervene in a carbon-carbon bond.

The hydrocarbyl group represented by $R^{s1}$ may be straight, branched or cyclic. Examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl, and norbornyl. Inter alia, $C_1$-$C_6$ hydrocarbyl groups are preferred.

The hydrocarbylene group represented by $R^{s2}$ may be straight, branched or cyclic. Examples thereof include methylene, ethylene, propylene, butylene and pentylene.

The hydrocarbyl group represented by $R^{s3}$ or $R^{S6}$ may be straight, branched or cyclic. Examples thereof include alkyl, alkenyl and alkynyl groups, with the alkyl groups being preferred. Suitable alkyl groups include those exemplified for the hydrocarbyl group represented by $R^{s1}$ as well as n-undecyl, n-dodecyl, tridecyl, tetradecyl, and pentadecyl. Examples of the fluorinated hydrocarbyl group represented by $R^{s3}$ or $R^{s6}$ include the foregoing hydrocarbyl groups in which some or all carbon-bonded hydrogen atoms are substituted by fluorine atoms. In these groups, an ether bond or carbonyl moiety may intervene in a carbon-carbon bond as mentioned above.

Examples of the acid labile group represented by $R^{s3}$ include groups of the above formulae (L1) to (L4), $C_4$-$C_{20}$, preferably $C_4$-$C_{15}$ tertiary hydrocarbyl groups, trialkylsilyl groups in which each alkyl moiety has 1 to 6 carbon atoms, and $C_4$-$C_{20}$ oxoalkyl groups.

The (u+1)-valent hydrocarbon or fluorinated hydrocarbon group represented by $R^{s4}$ may be straight, branched or cyclic and examples thereof include the foregoing hydrocarbyl or fluorinated hydrocarbyl groups from which the number (u) of hydrogen atoms are eliminated.

The fluorinated hydrocarbyl group represented by $R^{s7}$ may be straight, branched or cyclic. Examples thereof include the foregoing hydrocarbyl groups in which some or all hydrogen atoms are substituted by fluorine atoms. Illustrative examples include trifluoromethyl, 2,2,2-trifluoroethyl, 3,3,3-trifluoro-1-propyl, 3,3,3-trifluoro-2-propyl, 2,2,3,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7-dodecafluoroheptyl, 2-(perfluorobutyl)ethyl, 2-(perfluorohexyl)ethyl, 2-(perfluorooctyl)ethyl, and 2-(perfluorodecyl)ethyl.

Examples of the repeat units having formulae (8A) to (8E) are shown below, but not limited thereto. Herein $R^B$ is as defined above.

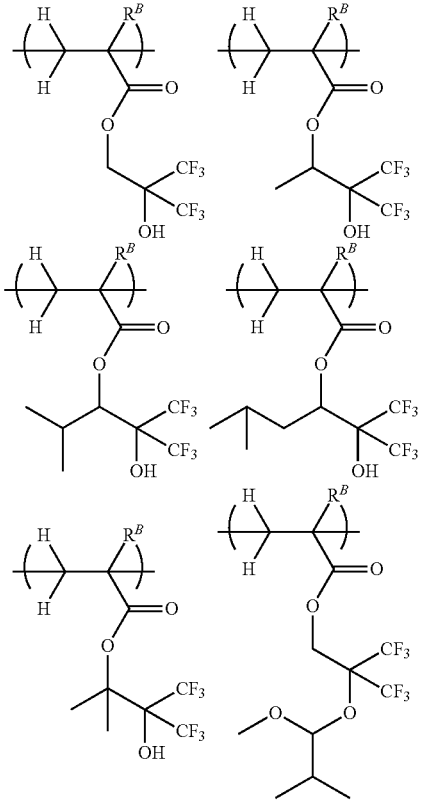

-continued
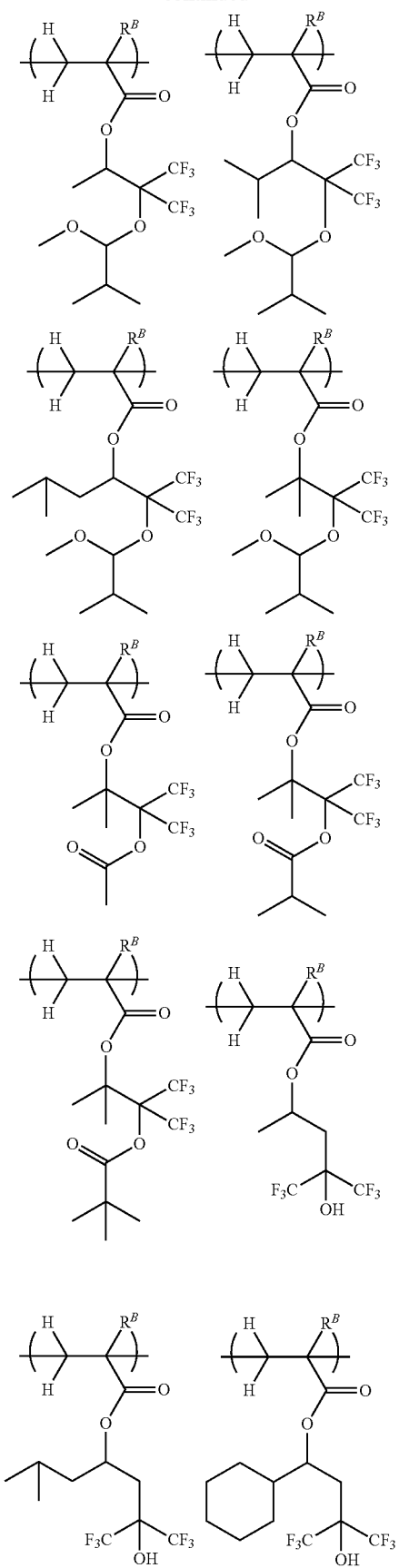
-continued
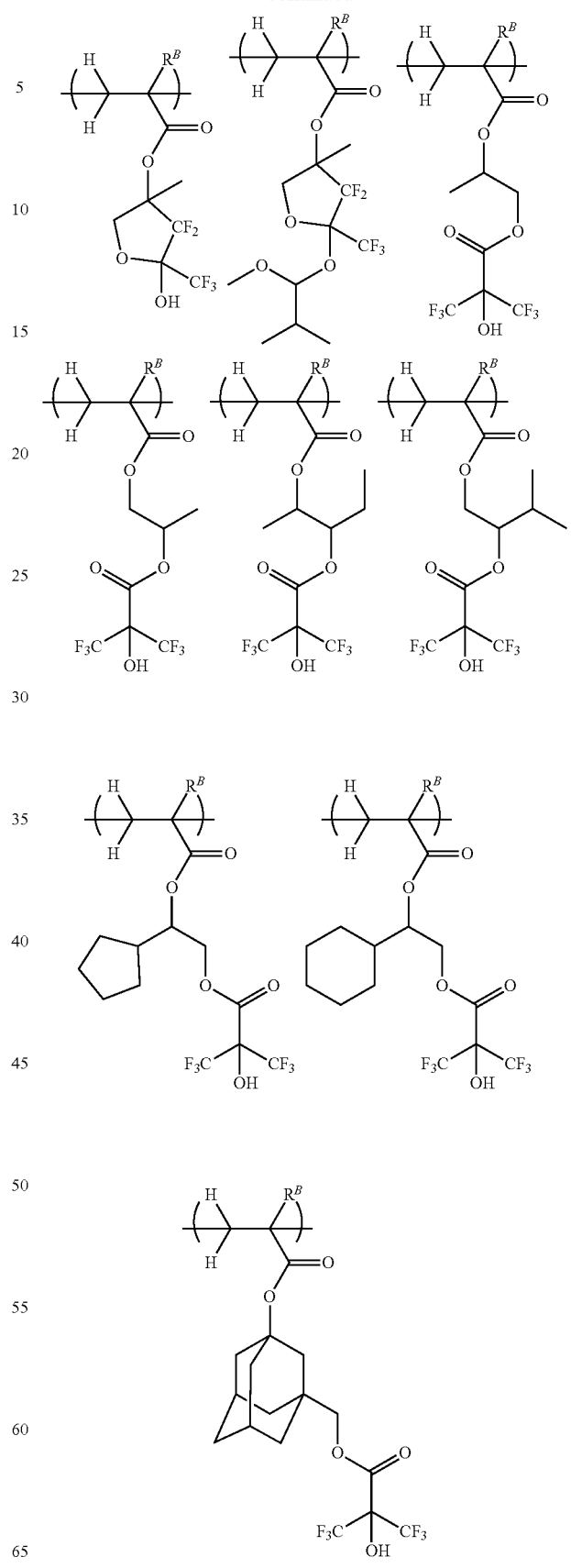

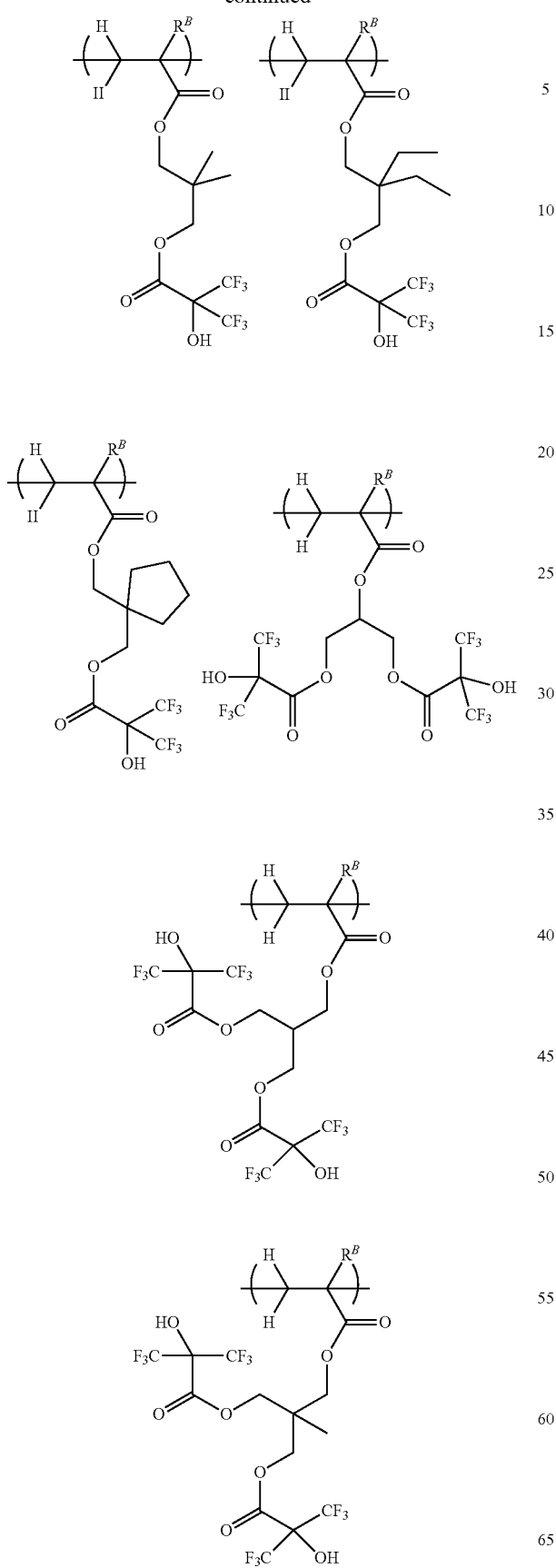
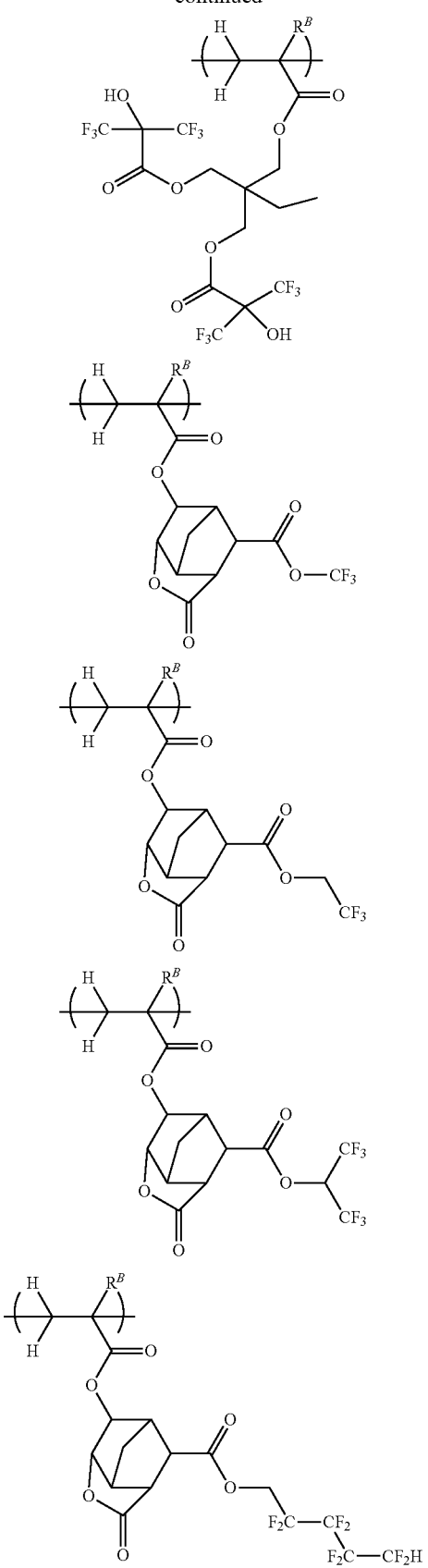

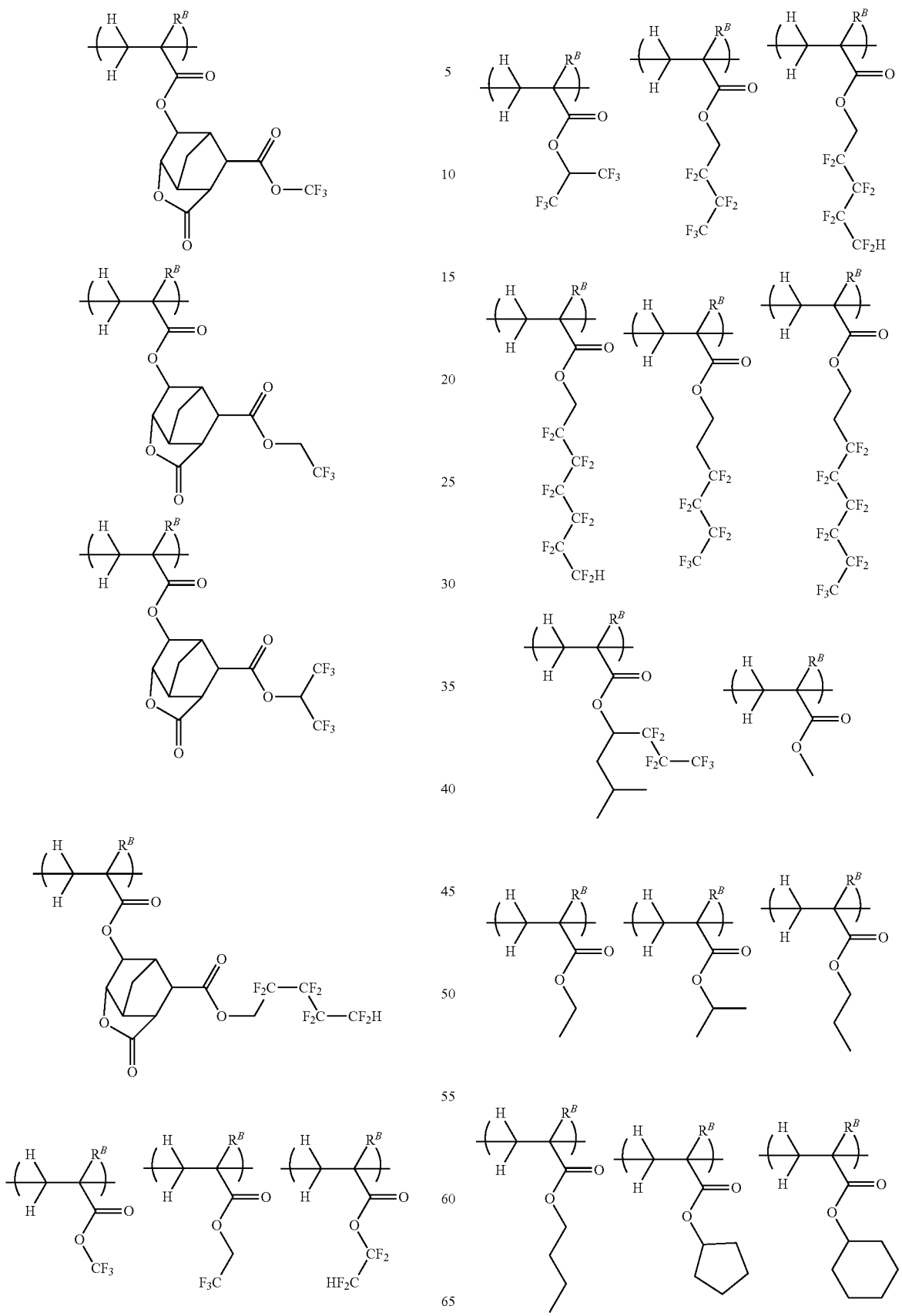

-continued

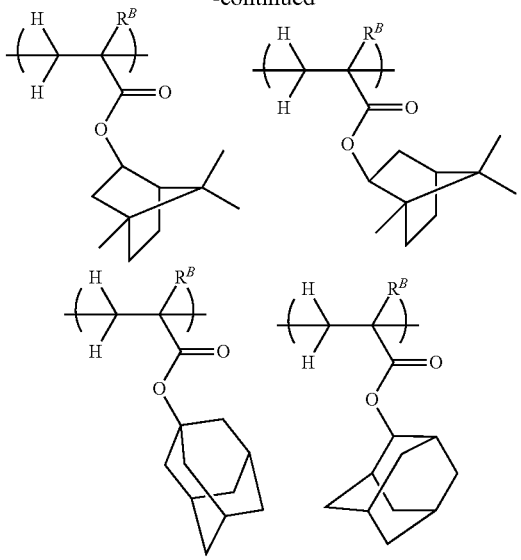

The polymeric surfactant may further contain repeat units other than the repeat units having formulae (8A) to (8E). Typical other repeat units are those derived from methacrylic acid and α-trifluoromethylacrylic acid derivatives. In the polymeric surfactant, the content of the repeat units having formulae (8A) to (8E) is preferably at least 20 mol %, more preferably at least 60 mol %, most preferably 100 mol % of the overall repeat units.

The polymeric surfactant preferably has a Mw of 1,000 to 500.000, more preferably 3,000 to 100,000 and a Mw/Mn of 1.0 to 2.0, more preferably 1.0 to 1.6.

The polymeric surfactant may be synthesized by any desired method, for example, by dissolving an unsaturated bond-containing monomer or monomers providing repeat units having formula (8A) to (8E) and optionally other repeat units in an organic solvent, adding a radical initiator, and heating for polymerization. Suitable organic solvents used herein include toluene, benzene, THF, diethyl ether, and dioxane. Examples of the polymerization initiator used herein include AIBN, 2,2'-azobis(2,4-dimethylvaleronitrile), dimethyl 2,2-azobis(2-methylpropionate), benzoyl peroxide, and lauroyl peroxide. Preferably the reaction temperature is 50 to 100° C. and the reaction time is 4 to 24 hours. The acid labile group that has been incorporated in the monomer may be kept as such, or the polymer may be protected or partially protected therewith at the end of polymerization.

During the synthesis of polymeric surfactant, any known chain transfer agent such as dodecyl mercaptan or 2-mercaptoethanol may be added for molecular weight control purpose. The amount of chain transfer agent added is preferably 0.01 to 10 mol % based on the total moles of monomers to be polymerized.

When the resist composition contains a surfactant (F), the amount thereof is preferably 0.1 to 50 parts by weight, and more preferably 0.5 to 10 parts by weight per 80 parts by weight of the base polymer (B). At least 0.1 part of the surfactant is effective in improving the receding contact angle with water of the resist film at its surface. Up to 50 parts of the surfactant is effective in forming a resist film having a low rate of dissolution in a developer and capable of maintaining the height of a fine pattern formed therein.

(G) Other Components

The resist composition may further comprise (G) another component, for example, a compound which is decomposed with an acid to generate another acid (i.e., acid amplifier compound), an organic acid derivative, a fluorinated alcohol, and a compound having a Mw of up to 3,000 which changes its solubility in developer under the action of an acid (i.e., dissolution inhibitor). Specifically, the acid amplifier compound is described in JP-A 2009-269953 and JP-A 2010-215608 and preferably used in an amount of 0 to 5 parts, more preferably 0 to 3 parts by weight per 80 parts by weight of the base polymer (B). An extra amount of the acid amplifier compound can make the acid diffusion control difficult and cause degradations to resolution and pattern profile. With respect to the remaining additives, reference should be made to JP-A 2009-269953 and JP-A 2010-215608.

Process

A further embodiment of the invention is a process of forming a pattern from the resist composition defined above by lithography. The preferred process includes the steps of applying the resist composition to form a resist film on a substrate, exposing the resist film to KrF excimer laser, ArF excimer laser, EB or EUV, and developing the exposed resist film in a developer. Any desired steps may be added to the process if necessary.

The substrate used herein may be a substrate for integrated circuitry fabrication, e.g., Si, $SiO_2$, SiN, SiON, TiN, WSi, BPSG, SOG, organic antireflective film, etc. or a substrate for mask circuitry fabrication, e.g., Cr, CrO, CrON, $MoSi_2$, $SiO_2$, etc.

The resist composition is applied onto a substrate by a suitable coating technique such as spin coating. The coating is prebaked on a hot plate preferably at a temperature of 60 to 150° C. for 1 to 10 minutes, more preferably at 80 to 140° C. for 1 to 5 minutes. The resulting resist film preferably has a thickness of 0.05 to 2 μm.

Then the resist film is exposed patternwise to KrF or ArF excimer laser, EUV or EB. On use of KrF excimer laser, ArF excimer laser or EUV of wavelength 13.5 nm, the resist film is exposed through a mask having a desired pattern, preferably in a dose of 1 to 200 mJ/cm$^2$, more preferably 10 to 100 mJ/cm$^2$. On use of EB, a pattern may be written directly or through a mask having the desired pattern, preferably in a dose of 1 to 300 μC/cm$^2$, more preferably 10 to 200 μC/cm$^2$.

The exposure may be performed by conventional lithography whereas the immersion lithography of holding a liquid having a refractive index of at least 1.0 between the resist film and the projection lens may be employed if desired. The liquid is typically water, and in this case, a protective film which is insoluble in water may be formed on the resist film.

While the water-insoluble protective film serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB), for example, on a hotplate at 60 to 150° C. for 1 to 5 minutes, preferably at 80 to 140° C. for 1 to 3 minutes.

The resist film is then developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

Any desired step may be added to the pattern forming process. For example, after the resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also, a double patterning process may be used for pattern formation. The double patterning process includes a trench process of processing an underlay to a 1:3 trench pattern by a first step of exposure and etching, shifting the position, and forming a 1:3 trench pattern by a second step of exposure, for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, negative tone development may also be used. That is, an organic solvent may be used instead of the aqueous alkaline solution as the developer for developing and dissolving away the unexposed region of the resist film.

The organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLES

Synthesis Examples, Examples and Comparative Examples are given below by way of illustration and not by way of limitation. The abbreviation "pbw" is parts by weight. For all polymers, Mw and Mn are determined by GPC versus polystyrene standards using THF solvent. THF stands for tetrahydrofuran, and PGMEA for propylene glycol monomethyl ether acetate. Analysis is made by IR, $^1$H-NMR spectroscopy and time-of-flight mass spectrometry using analytic instruments as shown below.

IR: NICOLET 6700 by Thermo Fisher Scientific Inc.

$^1$H-NMR: ECA-500 by JEOL Ltd.

MALDI TOF-MS: S3000 by JEOL Ltd.

[1] Synthesis of Onium Salts

Example 1-1

Synthesis of PAG-1

(1) Synthesis of Intermediate In-1

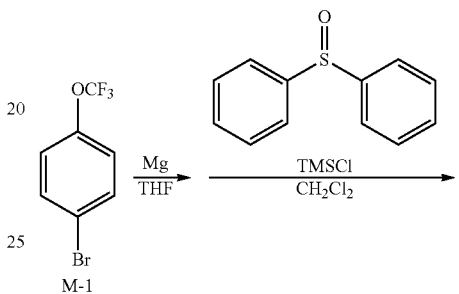

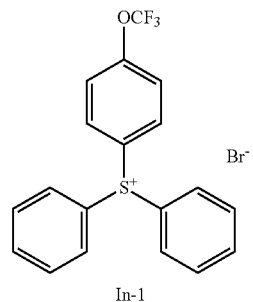

In nitrogen atmosphere, a Grignard reagent was prepared using 109.4 g of magnesium, 1084.6 g of Reactant M-1, and 2,250 g of THF. The reaction system was cooled below 10° C., to which a solution of 303.4 g of diphenyl sulfoxide in 1,500 g of methylene chloride was added. While the internal temperature was kept below 20° C., 678.2 g of chlorotrimethylsilane was added dropwise to the reaction system. The solution was aged for 2 hours at an internal temperature below 20° C. At the end of aging, the reaction system was cooled, after which an aqueous solution of 150 g of 36 wt % hydrochloric acid and 2,250 g of water was added dropwise to quench the reaction. 2,100 g of diisopropyl ether and 4,500 g of water were added to the solution, from which the water layer was taken out. The water layer was washed twice with 1,950 g of diisopropyl ether. The water layer as washed was directly used in the subsequent step.

(2) Synthesis of PAG-1

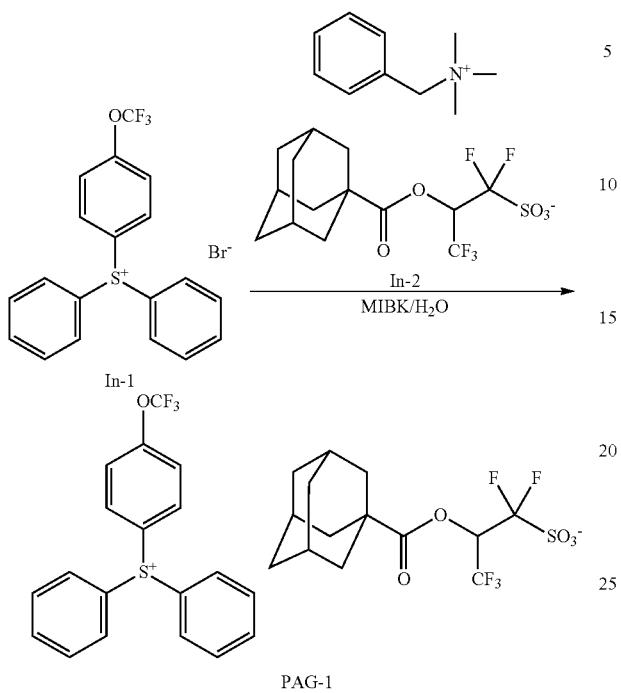

In nitrogen atmosphere, a reactor was charged with 50.0 g of the aqueous solution of Intermediate In-1, 8.1 g of Intermediate In-2, and 50 g of methyl isobutyl ketone, which were stirred at room temperature for 30 minutes. The organic layer was taken out, washed with water, and concentrated under reduced pressure, obtaining PAG-1 as colorless transparent oily matter (amount 11.5 g, yield 100%).

PAG-1 was analyzed by IR spectroscopy and TOF-MS, with the data shown below. FIG. 1 is the $^1$H-NMR/DMSO-$d_6$ spectrum of PAG-1.

IR (D-ATR): ν=3499, 3064, 2910, 2855, 1754, 1710, 1586, 1493, 1478, 1449, 1407, 1369, 1330, 1318, 1255, 1216, 1182, 1103, 1089, 1035, 1012, 993, 917, 865, 840, 751, 732, 684, 641, 615, 575, 553, 528, 517, 503 cm$^{-1}$

MALDI TOF-MS: positive M$^+$ 347 (corresponding to $C_{19}H_{14}F_3OS^+$)

negative M$^-$ 391 (corresponding to $C_{14}H_{16}F_5O_5S^-$)

Example 1-2

Synthesis of PAG-2

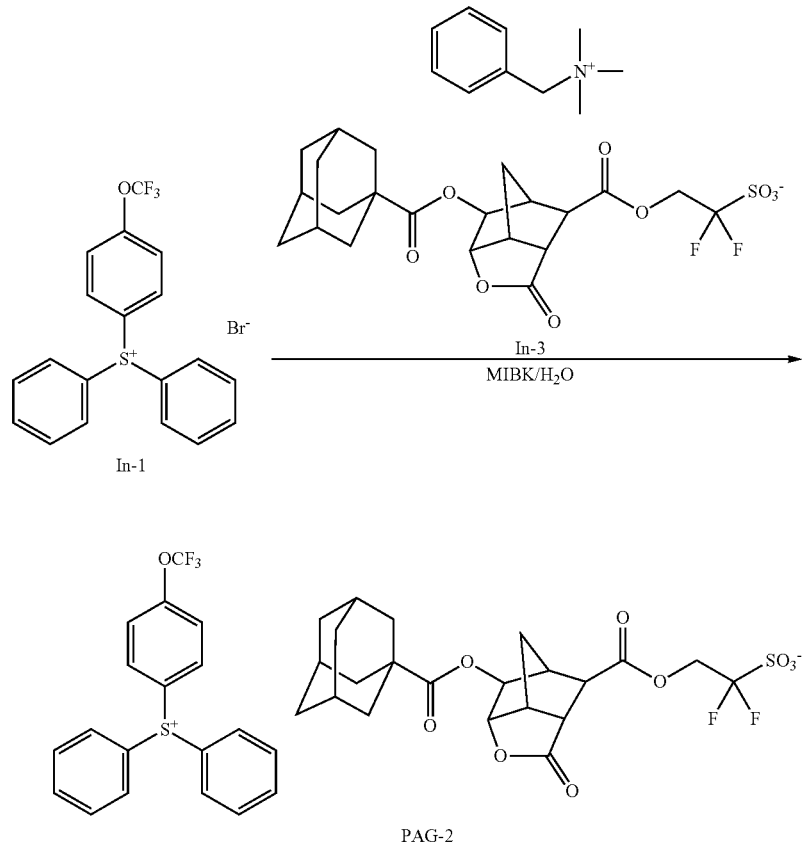

PAG-2 was synthesized by the same procedure as in Example 1-1 (2) aside from using Intermediate In-3 instead of Intermediate In-2. (amount 8.5 g, yield 98%).

Figure 2:
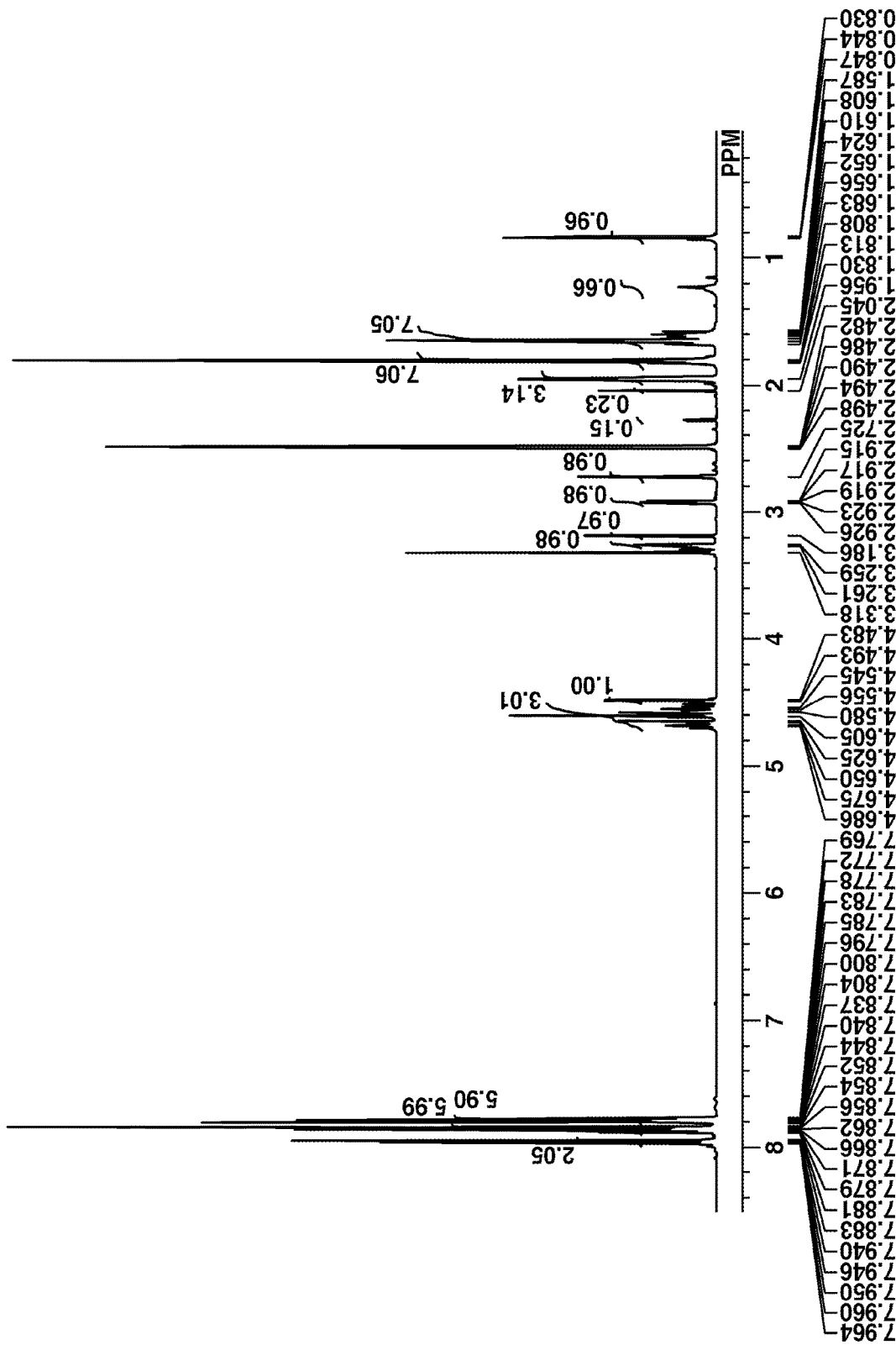
FIG. 2 is a diagram showing the $^1$H-NMR spectrum of the compound in Example 1-2.

PAG-2 was analyzed by IR spectroscopy and TOF-MS, with the data shown below. FIG. 2 is the $^1$H-NMR/DMSO-$d_6$ spectrum of PAG-2.

IR (D-ATR): ν=3477, 3098, 2908, 2853, 1785, 1729, 1586, 1492, 1478, 1448, 1344, 1252, 1177, 1104, 1075, 1035, 1010, 942, 844, 808, 751, 683, 642, 585, 551, 524, 504 cm$^{-1}$

MALDI TOF-MS: positive M$^+$ 347 (corresponding to $C_{19}H_{14}F_3OS^+$)

negative M$^-$ 503 (corresponding to $C_{22}H_{25}F_2O_9S^-$)

Example 1-3

Synthesis of PAG-3

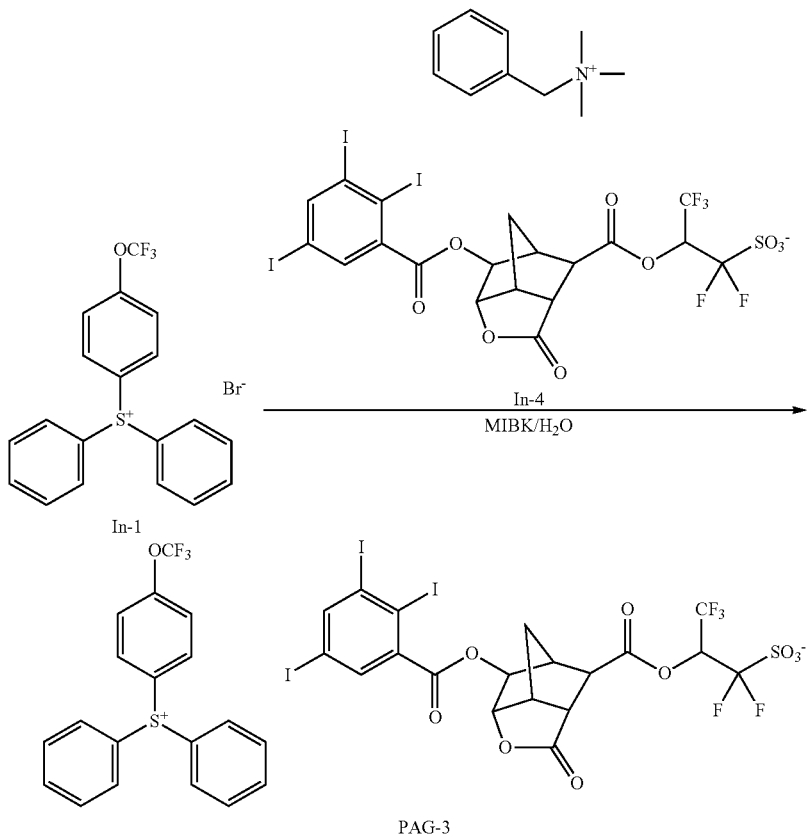

PAG-3

PAG-3 was synthesized by the same procedure as in Example 1-1 (2) aside from using Intermediate In-4 instead of Intermediate In-2. (amount 8.5 g, yield 98%).

Figure 3:
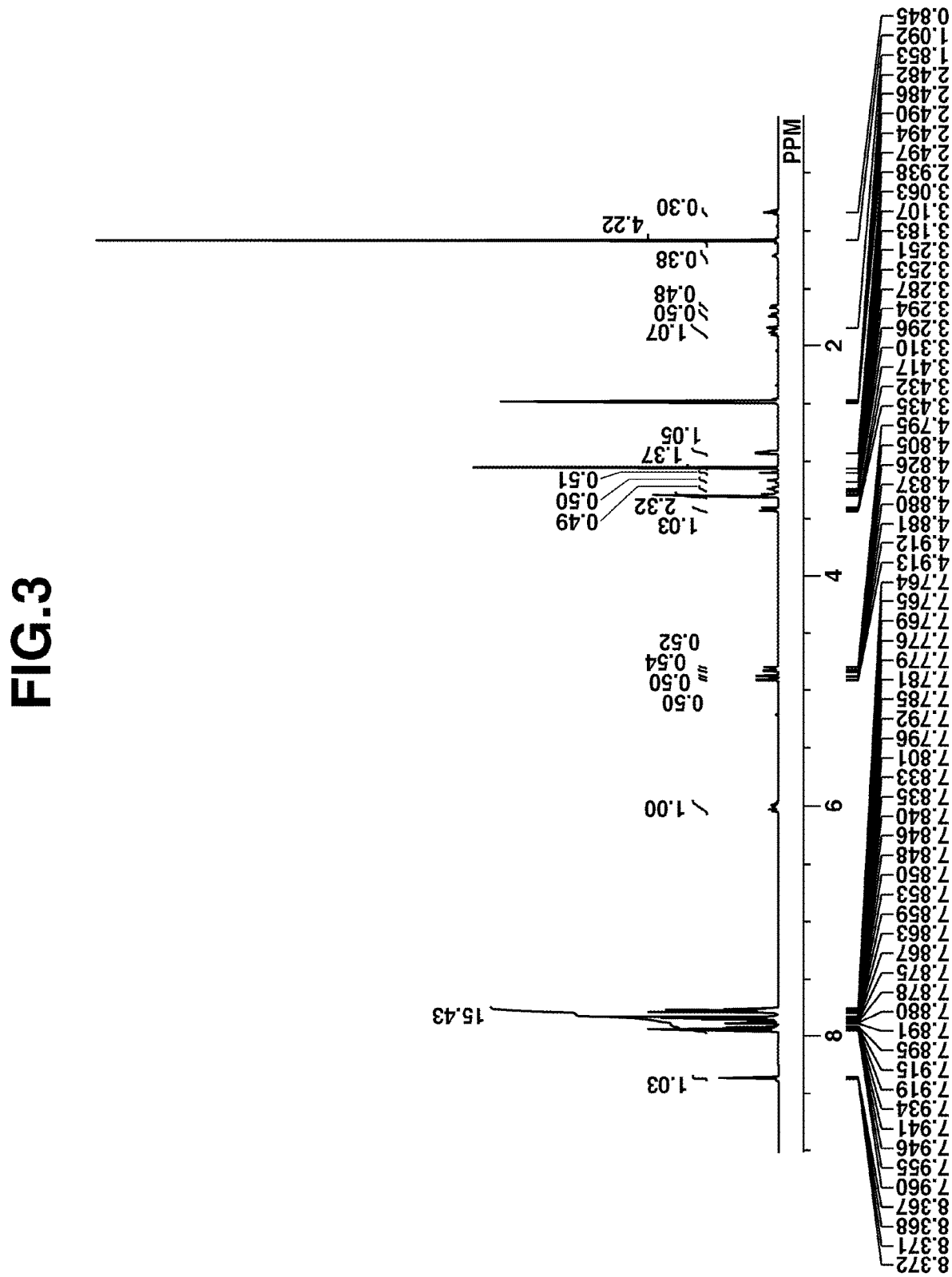
FIG. 3 is a diagram showing the $^1$H-NMR spectrum of the compound in Example 1-3.

PAG-3 was analyzed by IR spectroscopy and TOF-MS, with the data shown below. FIG. 3 is the $^1$H-NMR/DMSO-$d_6$ spectrum of PAG-3.

IR (D-ATR): ν=3476, 3064, 2974, 1785, 1730, 1586, 1522, 1493, 1477, 1448, 1366, 1252, 1212, 1177, 1111, 1075, 1037, 1005, 934, 904, 841, 748, 683, 642, 573, 552, 524, 504 cm$^{-1}$

MALDI TOF-MS: positive M$^+$ 347 (corresponding to $C_{19}H_{14}F_3OS^+$)

negative M$^-$ 891 (corresponding to $C_{19}H_{11}F_5I_3O_9S^-$)

Example 1-4

Synthesis of PAG-4

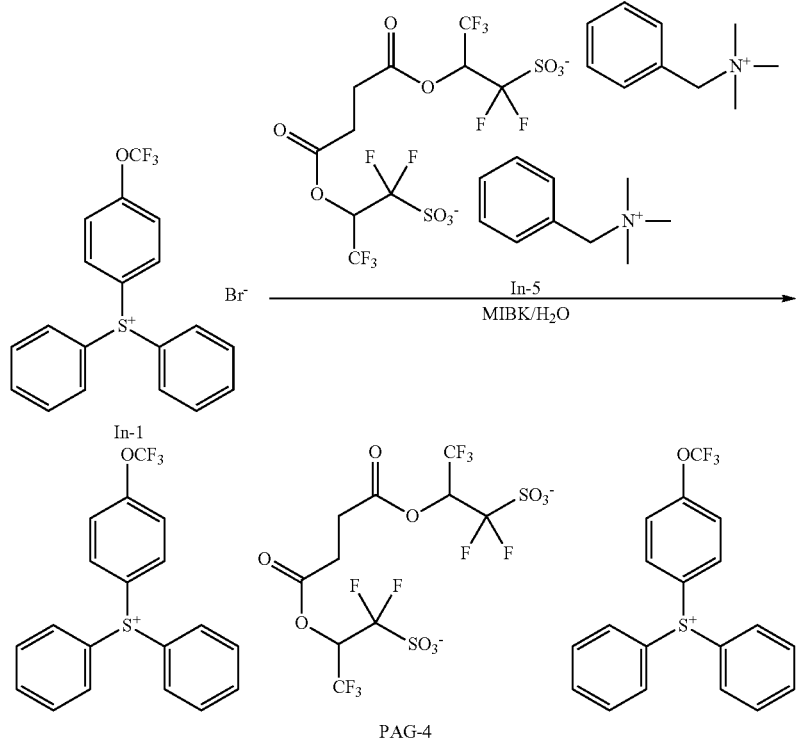

PAG-4 was synthesized by the same procedure as in Example 1-1 (2) aside from using Intermediate In-5 instead of Intermediate In-2. (amount 11.2 g, yield 91%).

Figure 4:
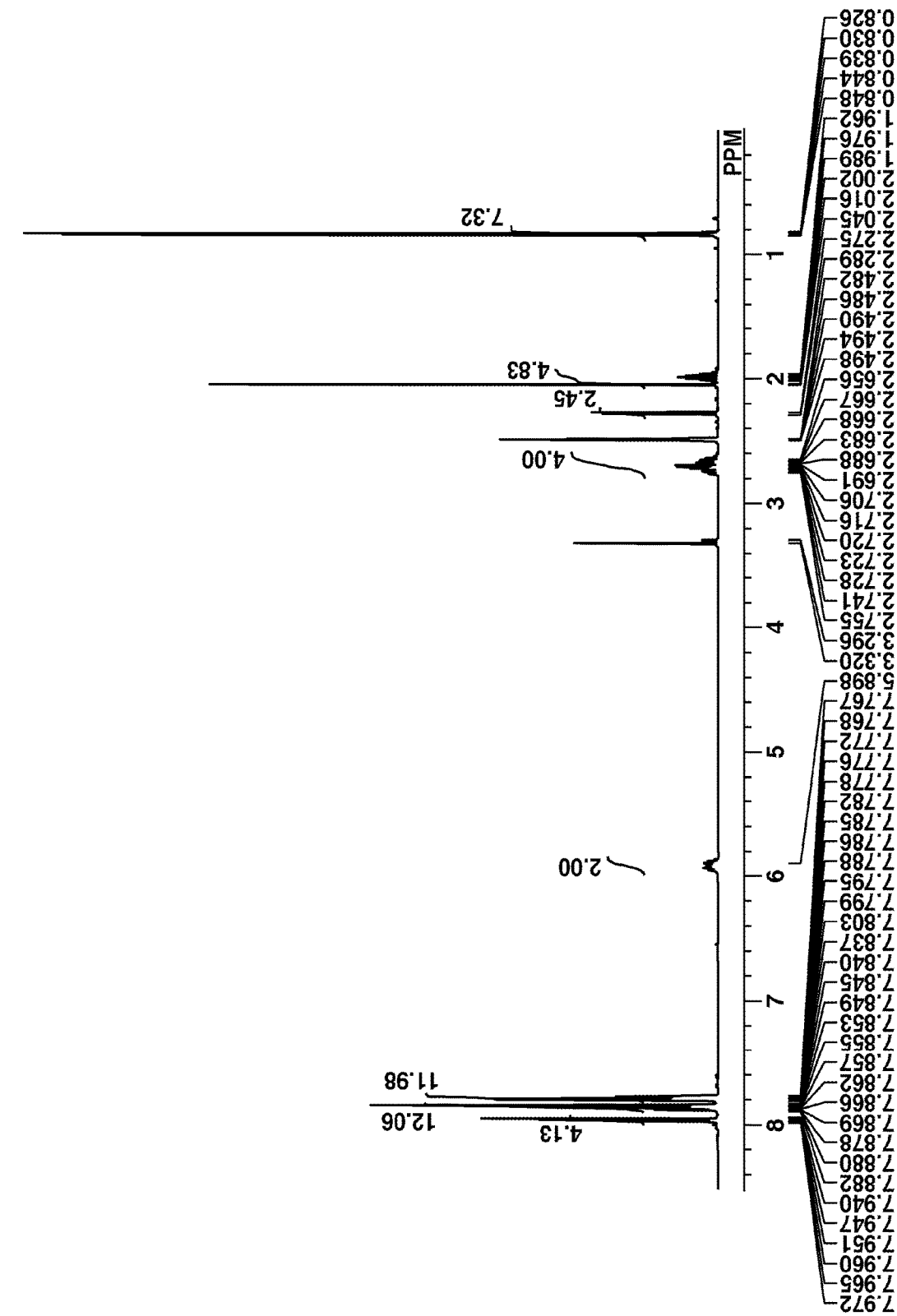
FIG. 4 is a diagram showing the $^1$H-NMR spectrum of the compound in Example 1-4.

PAG-4 was analyzed by IR spectroscopy and TOF-MS, with the data shown below. FIG. 4 is the $^1$H-NMR/DMSO-$d_6$ spectrum of PAG-4.

IR (D-ATR): ν=3556, 3065, 2969, 1771, 1709, 1586, 1493, 1478, 1448, 1409, 1370, 1255, 1214, 1173, 1128, 1073, 1012, 995, 928, 906, 842, 751, 684, 643, 553, 525, 503 cm$^{-1}$

MALDI TOF-MS: positive M$^+$ 347 (corresponding to $C_{19}H_{14}F_3OS^+$)

negative M$^-$ 887 (corresponding to $C_{29}H_{20}F_{13}O_{11}S_3^-$)

Example 1-5

Synthesis of PAG-5

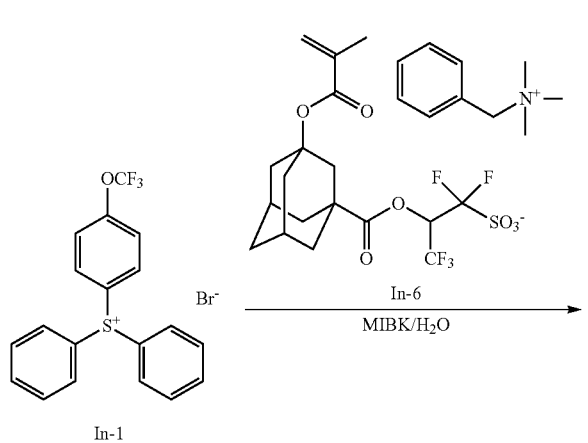

-continued

PAG-5

PAG-5 was synthesized by the same procedure as in Example 1-1 (2) aside from using Intermediate In-6 instead of Intermediate In-2. (amount 78.2 g, yield 95%).

Figure 5:
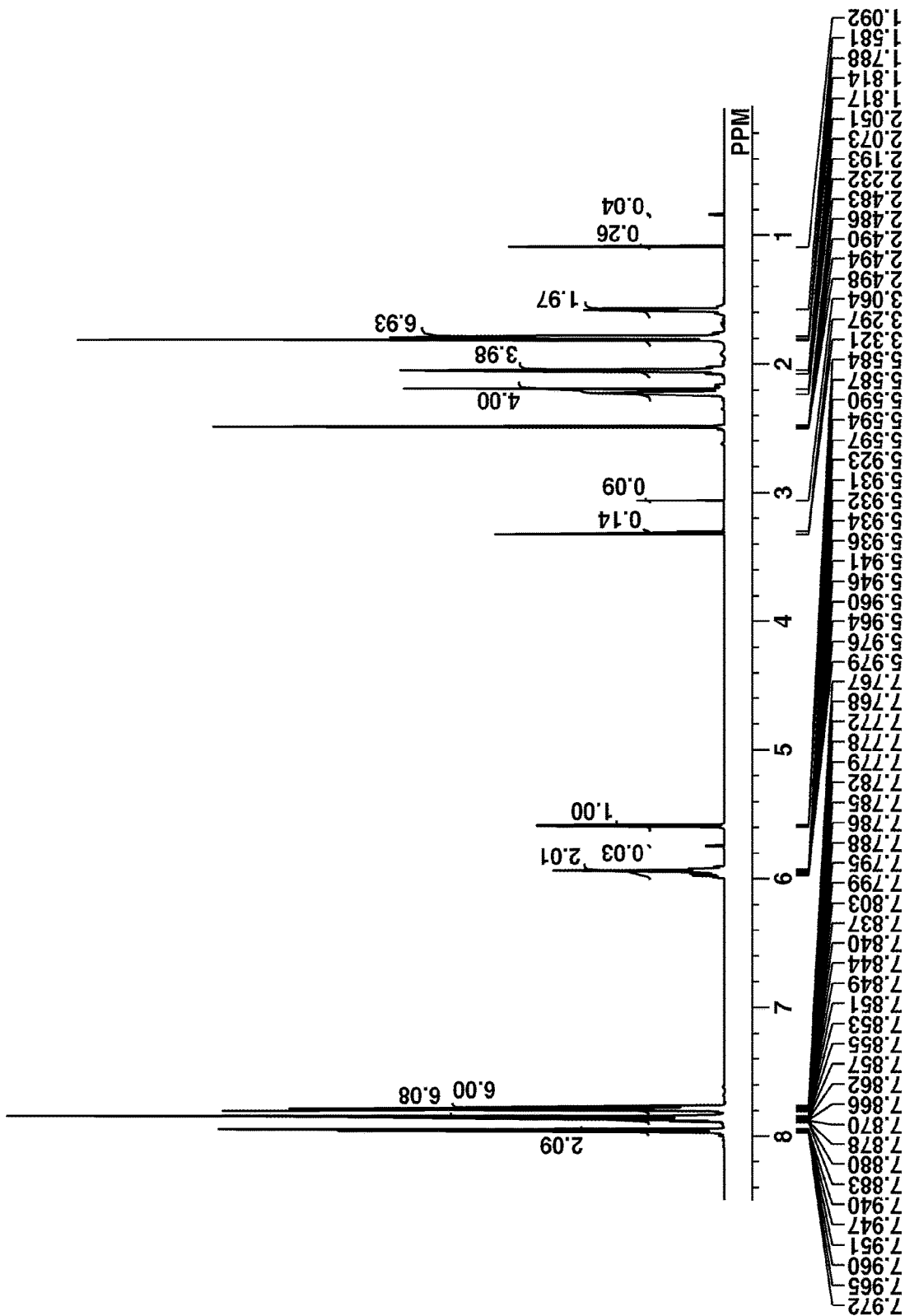
FIG. 5 is a diagram showing the $^1$H-NMR spectrum of the compound in Example 1-5.

PAG-5 was analyzed by IR spectroscopy and TOF-MS, with the data shown below. FIG. 5 is the $^1$H-NMR/DMSO-$d_6$ spectrum of PAG-5.

IR (D-ATR): ν=3110, 3088, 2935, 2865, 1747, 1711, 1637, 1585, 1496, 1477, 1450, 1406, 1377, 1328, 1316, 1303, 1263, 1253, 1212, 1192, 1166, 1109, 1091, 1076, 1008, 992, 955, 937, 930, 900, 865, 841, 815, 769, 758, 724, 687, 641, 613, 577, 551, 526, 518, 498, 471, 403 cm$^{-1}$

MALDI TOF-MS: positive M$^+$ 347 (corresponding to $C_{19}H_{14}F_3OS^+$)

negative M$^-$ 475 (corresponding to $C_{18}H_{20}F_5O_7S^-$)

Examples 1-6 to 1-11

Synthesis of PAG-6 to PAG-11

A variety of onium salts were synthesized by any organic chemistry methods before they were used in chemically amplified resist compositions. These onium salts have the following structures.

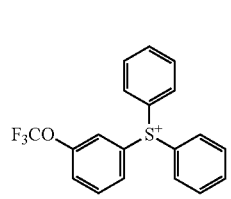

PAG-6

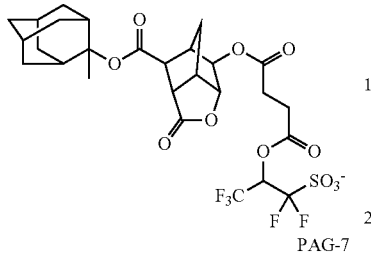

PAG-7

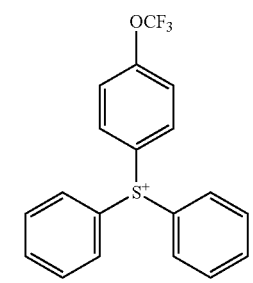

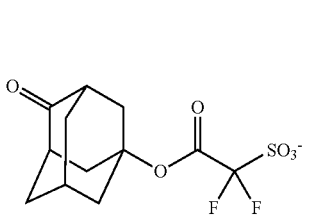

PAG-8

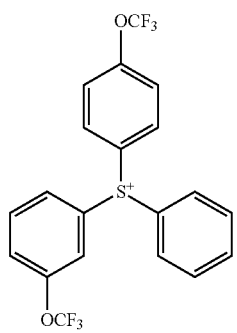

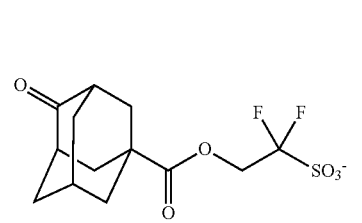

PAG-9

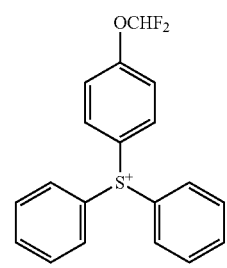

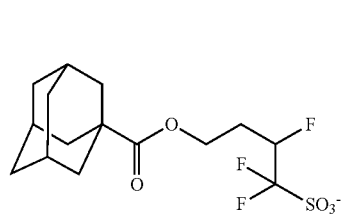

PAG-10

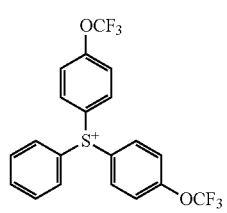

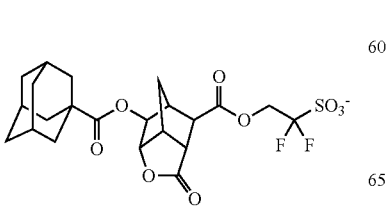

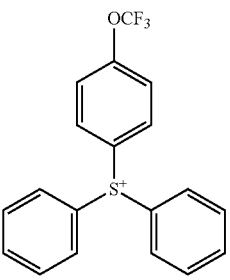

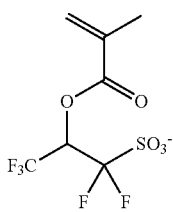

PAG-11

[2] Synthesis of Base Polymers

Base polymers used in chemically amplified resist compositions were synthesized by the following procedure.

Synthesis Example 1

Synthesis of Polymer P-1

In a flask under nitrogen atmosphere, 5.0 g of 3-hydroxy-1-adamantyl methacrylate, 14.4 g of α-methacryloxy-γ-butyrolactone, 20.8 g of 1-isopropylcyclopentyl methacrylate, 0.49 g of dimethyl 2,2'-azobis(2-methylpropionate) (V-601 by Fuji Film Wako Pure Chemical Industries, Ltd.), 0.41 g of 2-mercaptoethanol, and 56 g of PGMEA were combined to form a monomer/initiator solution. Another flask in nitrogen atmosphere was charged with 19 g of PGMEA, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining Polymer P-1 in white powder form (amount 35.3 g, yield 88%). On GPC analysis, Polymer P-1 had a Mw of 8,500 and a Mw/Mn of 1.58.

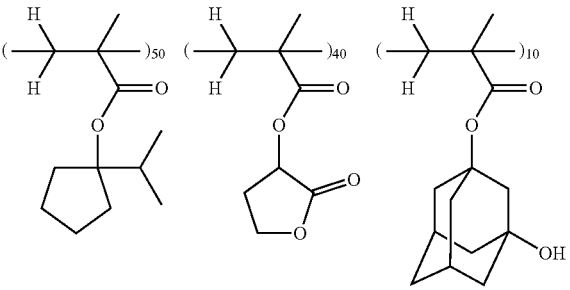

P-1

Mw = 8,500
Mw/Mn = 1.58

Synthesis Examples 2 to 13

Synthesis of Polymers P-2 to P-13

Polymers P-2 to P-13 were synthesized by the same procedure as in Synthesis Example 1 aside from changing the type and amount of monomers. Table 1 tabulates the type and molar fraction (mol %) of monomers in Polymers P-1 to P-13.
TABLE 1
| Polymer | Unit 1 (mol %) | Unit 2 (mol %) | Unit 3 (mol %) | Unit 4 (mol %) | Unit 5 (mol %) | Mw | Mw/Mn |
|---|---|---|---|---|---|---|---|
| P-1 | a1-1 (50) | b1-1 (40) | b1-4 (10) | — | — | 8,500 | 1.58 |
| P-2 | a1-2 (40) | a1-1 (10) | b1-1 (20) | b1-2 (20) | b1-4 (10) | 8,100 | 1.73 |
| P-3 | a1-2 (35) | a1-1 (15) | b1-1 (40) | b1-4 (10) | — | 8,300 | 1.67 |
| P-4 | a1-2 (10) | a1-3 (40) | b1-1 (10) | b1-3 (25) | b1-4 (15) | 9,400 | 1.71 |
| P-5 | a1-4 (55) | b2-2 (30) | PAG-5 (15) | — | — | 11,400 | 2.07 |
| P-6 | a1-4 (55) | b2-2 (30) | PAG-11 (15) | — | — | 10,200 | 2.03 |
| P-7 | a1-4 (55) | b2-2 (30) | c2-1 (15) | — | — | 10,600 | 2.05 |
| P-8 | a1-4 (55) | b2-2 (30) | c2-2 (15) | — | — | 10,800 | 2.07 |
| P-9 | a1-2 (10) | a2-1 (30) | b1-2 (30) | b2-1 (20) | PAG-5 (10) | 11,000 | 2.08 |
| P-10 | a1-2 (10) | a2-1 (30) | b1-2 (30) | b2-1 (20) | PAG-11 (10) | 10,300 | 2.02 |
| P-11 | a1-2 (10) | a2-1 (30) | b1-2 (30) | b2-1 (20) | c2-3 (10) | 11,200 | 2.05 |
| P-12 | a1-2 (10) | a2-1 (30) | b1-2 (30) | b2-1 (20) | c2-4 (10) | 11,100 | 2.04 |
| P-13 | a1-4 (50) | b2-2 (50) | — | — | — | 8,500 | 1.67 |
The monomers in Table 1 are shown below.
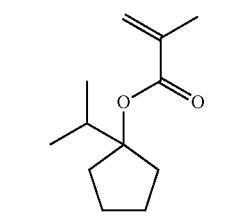
a1-1
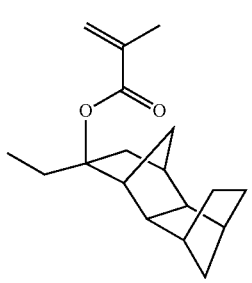
a1-2
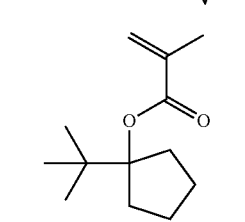
a1-3
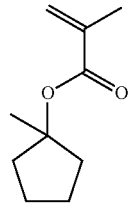
a1-4
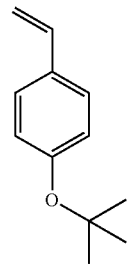
a2-1
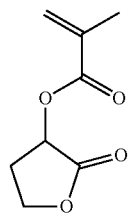
b1-1
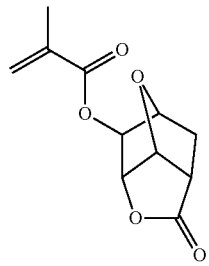
b1-2
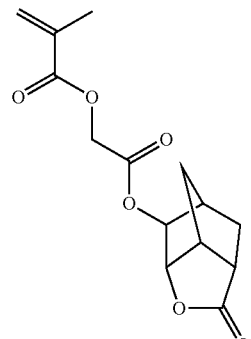
b1-3
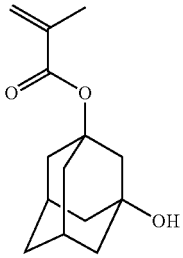
b1-4

-continued b2-1
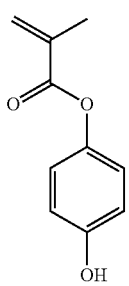

b2-2
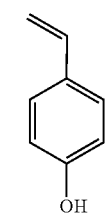

c2-1
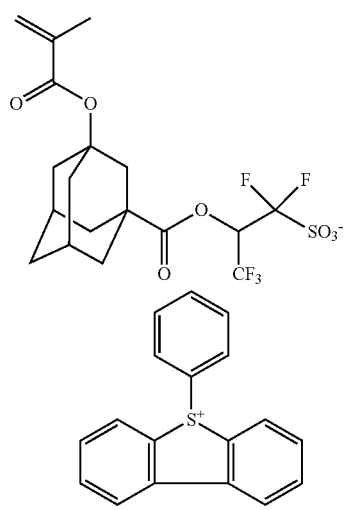

c2-2
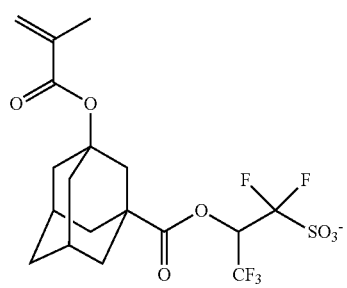

-continued
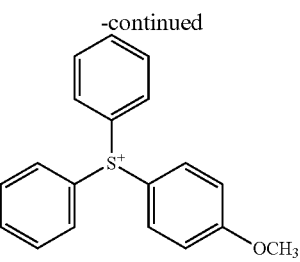

c2-3 c2-4
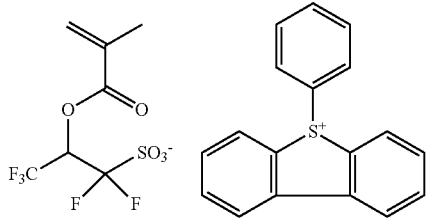

[3] Preparation of Chemically Amplified Resist Compositions

Examples 2-1 to 2-22 and Comparative Examples 1-1 to 1-12

Chemically amplified resist compositions (R-1 to R-22, CR-1 to CR-12) in solution form were prepared by dissolving a sulfonium salt (PAG-1 to PAG-11) or comparative photoacid generator (PAG-A to PAG-G), base polymer (Polymers P-1 to P-13), quencher (Q-1 to Q-5), and alkali-soluble surfactant (SF-1) in a solvent containing 0.01 wt % of surfactant A in accordance with the formulation shown in Tables 2 and 3, and filtering through a Teflon® filter with a pore size of 0.2 μm.

TABLE 2

| | Resist composition | Base polymer (pbw) | Photoacid generator (pbw) | Quencher (pbw) | Surfactant (pbw) | Solvent 1 (pbw) | Solvent 2 (pbw) |
|---|---|---|---|---|---|---|---|
| Example 2-1 | R-1 | P-1 (80) | PAG-1 (12.0) | Q-1 (5.0) | SF-1 (3.0) | PGMEA (1,400) | GBL (400) |
| 2-2 | R-2 | P-1 (80) | PAG-2 (12.0) | Q-1 (5.0) | SF-1 (3.0) | PGMEA (1,400) | GBL (400) |
| 2-3 | R-3 | P-1 (80) | PAG-4 (6.0) | Q-1 (5.0) | SF-1 (3.0) | PGMEA (1,400) | GBL (400) |
| 2-4 | R-4 | P-1 (80) | PAG-6 (12.0) | Q-1 (5.0) | SF-1 (3.0) | PGMEA (1,400) | GBL (400) |

TABLE 2-continued

| | Resist composition | Base polymer (pbw) | Photoacid generator (pbw) | Quencher (pbw) | Surfactant (pbw) | Solvent 1 (pbw) | Solvent 2 (pbw) |
|---|---|---|---|---|---|---|---|
| 2-5 | R-5 | P-1 (80) | PAG-7 (12.0) | Q-1 (5.0) | SF-1 (3.0) | PGMEA (1,400) | GBL (400) |
| 2-6 | R-6 | P-1 (80) | PAG-8 (12.0) | Q-1 (5.0) | SF-1 (3.0) | PGMEA (1,400) | GBL (400) |
| 2-7 | R-7 | P-1 (80) | PAG-9 (12.0) | Q-1 (5.0) | SF-1 (3.0) | PGMEA (1,400) | GBL (400) |
| 2-8 | R-8 | P-1 (80) | PAG-10 (12.0) | Q-1 (5.0) | SF-1 (3.0) | PGMEA (1,400) | GBL (400) |
| 2-9 | R-9 | P-1 (80) | PAG-1 (12.0) | Q-2 (5.0) | SF-1 (3.0) | PGMEA (1,400) | GBL (400) |
| 2-10 | R-10 | P-1 (80) | PAG-1 (12.0) | Q-1 (5.0) Q-5 (1.0) | SF-1 (3.0) | PGMEA (1,400) | GBL (400) |
| 2-11 | R-11 | P-2 (80) | PAG-1 (12.0) | Q-1 (5.0) | SF-1 (3.0) | PGMEA (1,400) | GBL (400) |
| 2-12 | R-12 | P-3 (80) | PAG-2 (10.0) | Q-1 (5.0) | SF-1 (3.0) | PGMEA (1,400) | GBL (400) |
| 2-13 | R-13 | P-3 (80) | PAG-6 (10.0) | Q-1 (5.0) | SF-1 (3.0) | PGMEA (1,400) | GBL (400) |
| 2-14 | R-14 | P-4 (80) | PAG-2 (10.0) | Q-1 (5.0) | SF-1 (3.0) | PGMEA (1,400) | GBL (400) |
| 2-15 | R-15 | P-9 (80) | — | Q-1 (7.0) | — | PGMEA (2,200) | DAA (900) |
| 2-16 | R-16 | P-10 (80) | — | Q-1 (7.0) | — | PGMEA (2,200) | DAA (900) |
| 2-17 | R-17 | P-5 (80) | — | Q-1 (7.0) | — | PGMEA (2,200) | DAA (900) |
| 2-18 | R-18 | P-6 (80) | — | Q-1 (7.0) | — | PGMEA (2,200) | DAA (900) |
| 2-19 | R-19 | P-6 (80) | PAG-3 (5.0) | Q-1 (7.0) | — | PGMEA (2,200) | DAA (900) |
| 2-20 | R-20 | P-6 (80) | — | Q-3 (7.0) | — | PGMEA (2,200) | DAA (900) |
| 2-21 | R-21 | P-6 (80) | — | Q-4 (7.0) | — | PGMEA (2,200) | DAA (900) |
| 2-22 | R-22 | P-13 (80) | PAG-3 (20.0) | Q-1 (10.0) | — | PGMEA (2,200) | DAA (900) |

TABLE 3

| | | Resist composition | Base polymer (pbw) | Photoacid generator (pbw) | Quencher (pbw) | Surfactant (pbw) | Solvent 1 (pbw) | Solvent 2 (pbw) |
|---|---|---|---|---|---|---|---|---|
| Comparative Example | 1-1 | CR-1 | P-1 (80) | PAG-A (12.0) | Q-1 (5.0) | SF-1 (3.0) | PGMEA (1,400) | GBL (400) |
| | 1-2 | CR-2 | P-1 (80) | PAG-B (12.0) | Q-1 (5.0) | SF-1 (3.0) | PGMEA (1,400) | GBL (400) |
| | 1-3 | CR-3 | P-1 (80) | PAG-C (12.0) | Q-1 (5.0) | SF-1 (3.0) | PGMEA (1,400) | GBL (400) |
| | 1-4 | CR-4 | P-1 (80) | PAG-D (12.0) | Q-1 (5.0) | SF-1 (3.0) | PGMEA (1,400) | GBL (400) |
| | 1-5 | CR-5 | P-1 (80) | PAG-E (12.0) | Q-1 (5.0) | SF-1 (3.0) | PGMEA (1,400) | GBL (400) |
| | 1-6 | CR-6 | P-1 (80) | PAG-G (12.0) | Q-1 (5.0) | SF-1 (3.0) | PGMEA (1,400) | GBL (400) |
| | 1-7 | CR-7 | P-3 (80) | PAG-D (10.0) | Q-1 (5.0) | SF-1 (3.0) | PGMEA (1,400) | GBL (400) |
| | 1-8 | CR-8 | P-11 (80) | — | Q-1 (7.0) | — | PGMEA (2,200) | DAA (900) |
| | 1-9 | CR-9 | P-12 (80) | — | Q-1 (7.0) | — | PGMEA (2,200) | DAA (900) |
| | 1-10 | CR-10 | P-7 (80) | — | Q-1 (7.0) | — | PGMEA (2,200) | DAA (900) |
| | 1-11 | CR-11 | P-8 (80) | — | Q-1 (7.0) | — | PGMEA (2,200) | DAA (900) |
| | 1-12 | CR-12 | P-13 (80) | PAG-F (20.0) | Q-1 (10.0) | — | PGMEA (2,200) | DAA (900) |

The solvents, alkali-soluble surfactant SF-1, comparative photoacid generators PAG-A to PAG-G, and quenchers Q-1 to Q-5 in Tables 2 and 3 are identified below.

Solvent:
  PGMEA (propylene glycol monomethyl ether acetate)
  GBL (γ-butyrolactone)
  DAA (diacetone alcohol)

Alkali-Soluble Surfactant SF-1:
  poly(2,2,3,3,4,4,4-heptafluoro-1-isobutyl-1-butyl methacrylate/9-(2,2,2-trifluoro-1-trifluoroethyloxycarbonyl)-4-oxatricyclo[4.2.1.0$^{3,7}$]nonan-5-on-2-yl methacrylate)

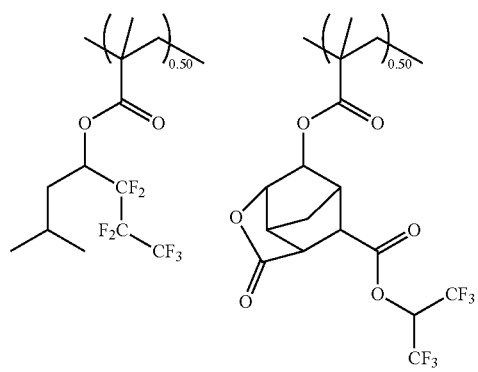

SF-1

Mw = 7,700
Mw/Mn = 1.82

Comparative Photoacid Generator: PAG-A to PAG-G

PAG-A

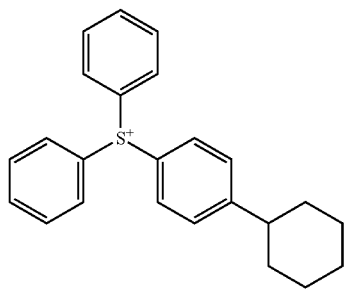

PAG-B

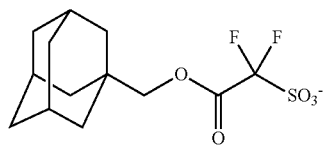

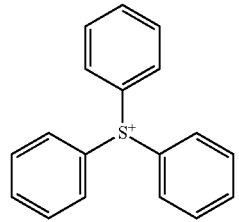

-continued

PAG-C

PAG-D

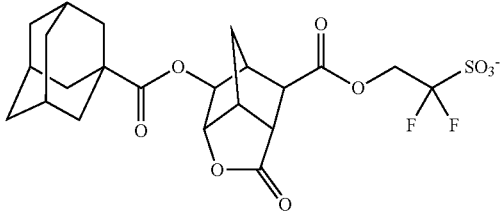

PAG-E

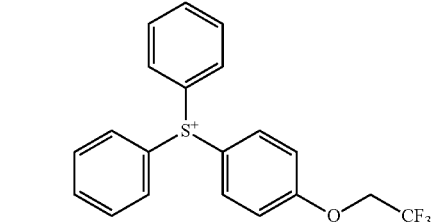

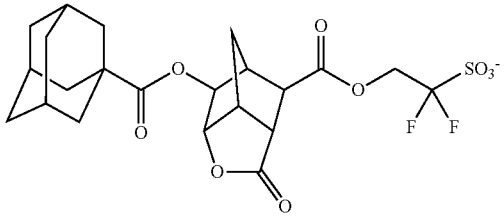

PAG-F
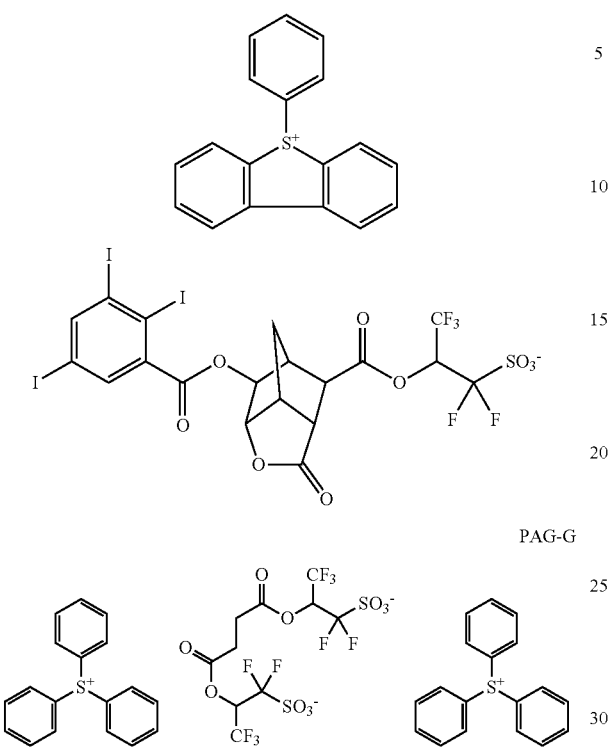
PAG-G
Quencher: Q-1 to Q-5
Q-1
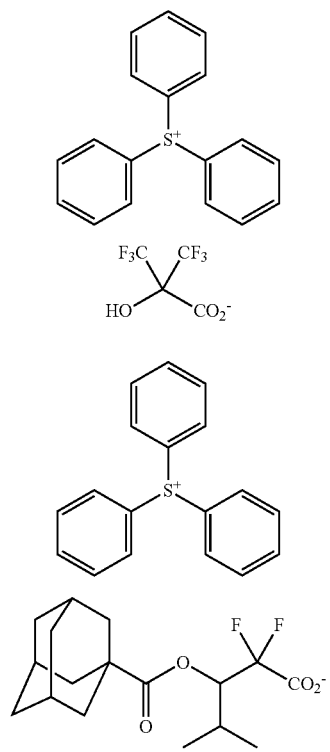
Q-2
Q-3
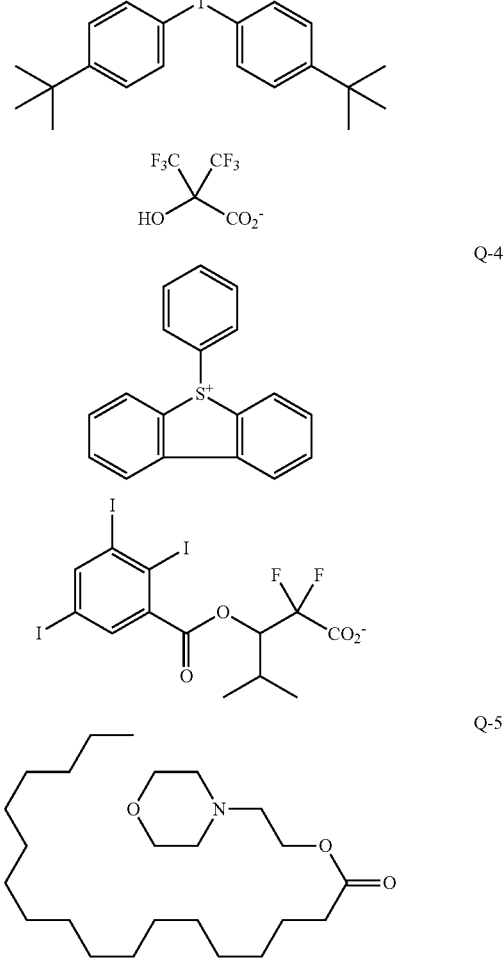
Q-4
Q-5
Surfactant A:
3-methyl-3-(2,2,2-trifluoroethoxymethyl)oxetane/tetrahydrofuran/2,2-dimethyl-1,3-propane diol copolymer (Omnova Solutions, Inc.)
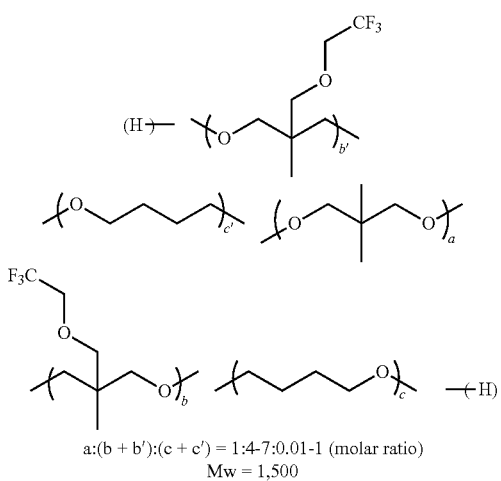
a:(b + b'):(c + c') = 1:4-7:0.01-1 (molar ratio)
Mw = 1,500

[4] Evaluation of Resist Composition: ArF Lithography Patterning Test 1

Examples 3-1 to 3-11 and Comparative Examples 2-1 to 2-6

On a silicon substrate, an antireflective coating solution (ARC29A, Nissan Chemical Corp.) was coated and baked at 200° C. for 60 seconds to form an ARC of 100 nm thick. Each of the resist compositions (R-1 to R-11, CR-1 to CR-6) was spin coated on the ARC and prebaked on a hotplate at 100° C. for 60 seconds to form a resist film of 90 nm thick on the ARC. The wafer was exposed on an ArF excimer laser immersion lithography scanner (NSR-S610C by Nikon Corp., NA 1.30, dipole illumination) through a Cr mask having a line-and-space (LS) pattern with a line width of 40 nm and a pitch of 80 nm (on-wafer size), while varying the exposure dose and focus at a dose pitch of 1 mJ/cm² and a focus pitch of 0.025 μm. The immersion liquid used herein was water. After exposure, the resist film was baked (PEB) at the temperature shown in Table 4 for 60 seconds. The resist film was puddle developed in a 2.38 wt % tetramethylammonium hydroxide (TMAH) aqueous solution for 30 seconds, rinsed with deionized water and spin dried, forming a positive pattern. The LS pattern after development was observed under CD-SEM (CG4000 by Hitachi High-Technologies Corp.), whereupon sensitivity, EL, MEF, and LWR were evaluated by the following methods. The results are shown in Table 4.

Evaluation of Sensitivity

The optimum exposure dose Eop (mJ/cm²) which provided a LS pattern having a line width of 40 nm and a pitch of 80 nm was determined as an index of sensitivity. A smaller dose value indicates a higher sensitivity.

Evaluation of Exposure Latitude (EL)

The exposure dose which provided a LS pattern with a space width of 40 nm±10% (i.e., 36 nm to 44 nm) was determined. EL (%) is calculated from the exposure doses according to the following equation:

$$EL(\%) = (|E1 - E2|/Eop) \times 100$$

wherein E1 is an optimum exposure dose which provides a LS pattern with a line width of 36 nm and a pitch of 80 nm, E2 is an optimum exposure dose which provides a LS pattern with a line width of 44 nm and a pitch of 80 nm, and Eop is an optimum exposure dose which provides a LS pattern with a line width of 40 nm and a pitch of 80 nm.

Evaluation of Mask Error Factor (MEF)

A LS pattern was formed by exposure in the optimum dose Eop through the mask with the pitch fixed and the line width varied. MEF was calculated from the mask line width and a variation of the pattern line width according to the following equation:

$$MEF = (\text{pattern line width})/(\text{mask line width}) - b$$

wherein b is a constant. A value closer to unity (1) indicates better performance.

Evaluation of Line Width Roughness (LWR)

A LS pattern was formed by exposure in the optimum dose Eop. The line width was measured at longitudinally spaced apart 10 points, from which a 3-fold value (3σ) of standard deviation (σ) was determined and reported as LWR. A smaller value of 3σ indicates a pattern having a lower roughness and more uniform line width.

TABLE 4

|  |  | Resist composition | PEB temp. (° C.) | Eop (mJ/cm²) | EL (%) | MEF | LWR (nm) |
| --- | --- | --- | --- | --- | --- | --- | --- |
| Example | 3-1 | R-1 | 95 | 55 | 18 | 2.4 | 2.2 |
|  | 3-2 | R-2 | 95 | 54 | 18 | 2.4 | 2.2 |
|  | 3-3 | R-3 | 95 | 59 | 20 | 2.2 | 2 |
|  | 3-4 | R-4 | 95 | 53 | 22 | 2.6 | 1.9 |
|  | 3-5 | R-5 | 95 | 50 | 21 | 2.8 | 2.2 |
|  | 3-6 | R-6 | 95 | 48 | 22 | 2.3 | 2.6 |
|  | 3-7 | R-7 | 95 | 52 | 19 | 2.8 | 2.2 |
|  | 3-8 | R-8 | 95 | 55 | 22 | 2.5 | 2.1 |
|  | 3-9 | R-9 | 95 | 53 | 21 | 2.5 | 2.2 |
|  | 3-10 | R-10 | 95 | 53 | 19 | 2.6 | 1.8 |
|  | 3-11 | R-11 | 95 | 50 | 18 | 2.8 | 2 |
| Comparative Example | 2-1 | CR-1 | 95 | 65 | 11 | 3.2 | 3.2 |
|  | 2-2 | CR-2 | 95 | 68 | 15 | 3.5 | 2.9 |
|  | 2-3 | CR-3 | 95 | 69 | 14 | 3.3 | 2.9 |
|  | 2-4 | CR-4 | 95 | 64 | 14 | 3.6 | 2.8 |
|  | 2-5 | CR-5 | 95 | 65 | 13 | 2.9 | 3.1 |
|  | 2-6 | CR-6 | 95 | 70 | 16 | 3.3 | 3.2 |

As is evident from Table 4, the chemically amplified resist compositions containing PAGs within the scope of the invention exhibit a satisfactory sensitivity, improved values of EL, MEF and LWR. The resist compositions are useful as the ArF immersion lithography material.

[5] Evaluation of Resist Composition: ArF Lithography Patterning Test 2

Examples 4-1 to 4-3 and Comparative Example 3-1

On a substrate, a spin-on carbon film ODL-180 (Shin-Etsu Chemical Co., Ltd.) having a carbon content of 80 wt % was deposited to a thickness of 180 nm and a silicon-containing spin-on hard mask SHB-A941 having a silicon content of 43 wt % was deposited thereon to a thickness of 35 nm. On this substrate for trilayer process, each of the resist compositions (R-12 to R-14, CR-7) was spin coated, then baked on a hot plate at 100° C. for 60 seconds to form a resist film of 100 nm thick.

Using an ArF excimer laser immersion lithography scanner NSR-S610C (Nikon Corp., NA 1.30, σ 0.90/0.72, cross-pole opening 35 deg., cross-pole illumination, azimuthally polarized illumination), exposure was performed through a 6% halftone phase shift mask bearing a contact hole (CH) pattern with a hole size of 45 nm and a pitch of 110 nm (on-wafer size) while varying the dose and focus (dose pitch: 1 mJ/cm², focus pitch: 0.025 μm). The immersion liquid used herein was water. After the exposure, the wafer was baked (PEB) at the temperature shown in Table 5 for 60 seconds. Thereafter, the resist film was puddle developed in n-butyl acetate for 30 seconds, rinsed with 4-methyl-2-pentanol, and spin dried, obtaining a negative pattern. The CH pattern after development was observed under CD-SEM CG4000 (Hitachi High Technologies Corp.) whereupon sensitivity, MEF, CDU, and DOF were evaluated by the following methods. The results are shown in Table 5.

Evaluation of Sensitivity

The optimum dose Eop (mJ/cm²) which provided a CH pattern with a hole size of 45 nm and a pitch of 110 nm was determined as an index of sensitivity. A smaller dose value indicates a higher sensitivity.

Evaluation of MEF

A CH pattern was formed by exposure at the optimum dose Eop by ArF lithography patterning test 2 with the pitch fixed and the mask size varied. MEF was calculated from the mask size and a variation of the CH pattern size according to the following equation:

$$MEF = (\text{pattern size})/(\text{mask size}) - b$$

wherein b is a constant. A value closer to unity (1) indicates better performance.

Evaluation of Critical Dimension Uniformity (CDU)

For the CH pattern formed by exposure at the optimum dose Eop, the hole size was measured at 10 areas subject to an identical dose of shot (9 contact holes per area), from which a 3-fold value (3σ) of standard deviation (σ) was determined and reported as CDU. A smaller value of 3σ indicates a CH pattern having improved CDU.

Evaluation of Depth of Focus (DOF)

As an index of DOF, a range of focus which provided a CH pattern with a size of 45 nm±10% (i.e., 40.5 to 49.5 nm) was determined. A greater value indicates a wider DOF.

TABLE 5

|  |  | Resist composition | PEB temp. (° C.) | Eop (mJ/cm$^2$) | MEF | CDU (nm) | DOF (nm) |
|---|---|---|---|---|---|---|---|
| Example | 4-1 | R-12 | 85 | 35 | 2.5 | 3.1 | 150 |
|  | 4-2 | R-13 | 85 | 36 | 2.4 | 3.3 | 150 |
|  | 4-3 | R-14 | 85 | 36 | 2.7 | 3.2 | 150 |
| Comparative Example | 3-1 | CR-7 | 85 | 48 | 3.3 | 4.5 | 80 |

As is evident from Table 5, the chemically amplified resist compositions containing PAGs within the scope of the invention exhibit a satisfactory sensitivity and improved values of MEF, CDU and DOF. The resist compositions are useful in the ArF immersion lithography process.

[6] EUV Lithography Test

Examples 5-1 to 5-8 and Comparative Examples 4-1 to 4-5

Each of the chemically amplified resist compositions (R-15 to R-22, CR-8 to CR-12) was spin coated on a silicon substrate having a 20-nm coating of silicon-containing spin-on hard mask SHB-A940 (Shin-Etsu Chemical Co., Ltd., silicon content 43 wt %) and prebaked on a hotplate at 100° C. for 60 seconds to form a resist film of 50 nm thick. Using an EUV scanner NXE3300 (ASML, NA 0.33, σ 0.9/0.6, dipole illumination), the resist film was exposed to EUV through a mask bearing a LS pattern having a size of 18 nm and a pitch of 36 nm (on-wafer size) while varying the dose and focus (dose pitch: 1 mJ/cm$^2$, focus pitch: 0.020 μm). The resist film was baked (PEB) on a hotplate at the temperature shown in Table 6 for 60 seconds and puddle developed in a 2.38 wt % TMAH aqueous solution for 30 seconds, rinsed with a rinse fluid containing surfactant, and spin dried to form a positive pattern.

The LS pattern as developed was observed under CD-SEM (CG6300, Hitachi High-Technologies Corp.) whereupon sensitivity, EL, LWR, and DOF were evaluated by the following methods. The results are shown in Table 6.

Evaluation of Sensitivity

The optimum dose Eop (mJ/cm$^2$) which provided a LS pattern with a line width of 18 nm and a pitch of 36 nm was determined as an index of sensitivity.

Evaluation of EL

The exposure dose which provided a LS pattern with a space width of 18 nm±10% (i.e., 16.2 to 19.8 nm) was determined. EL (%) is calculated from the exposure doses according to the following equation:

$$EL(\%) = (|E1 - E2|/Eop) \times 100$$

wherein E1 is an optimum exposure dose which provides a LS pattern with a line width of 16.2 nm and a pitch of 36 nm, E2 is an optimum exposure dose which provides a LS pattern with a line width of 19.8 nm and a pitch of 36 nm, and Eop is an optimum exposure dose which provides a LS pattern with a line width of 18 nm and a pitch of 36 nm.

Evaluation of LWR

For the LS pattern formed by exposure at the optimum dose Eop, the line width was measured at 10 longitudinally spaced apart points, from which a 3-fold value (3σ) of standard deviation (σ) was determined and reported as LWR. A smaller value of 3σ indicates a pattern having small roughness and uniform line width.

Evaluation of DOF

As an index of DOF, a range of focus which provided a LS pattern with a size of 18 nm±10% (i.e., 16.2 to 19.8 nm) was determined. A greater value indicates a wider DOF.

TABLE 6

|  |  | Resist composition | PEB temp. (° C.) | Eop (mJ/cm$^2$) | EL (%) | LWR (nm) | DOF (nm) |
|---|---|---|---|---|---|---|---|
| Example | 5-1 | R-15 | 95 | 50 | 20 | 3.8 | 150 |
|  | 5-2 | R-16 | 95 | 48 | 22 | 3.9 | 150 |
|  | 5-3 | R-17 | 95 | 47 | 23 | 3.8 | 135 |
|  | 5-4 | R-18 | 95 | 48 | 21 | 4.1 | 150 |
|  | 5-5 | R-19 | 95 | 51 | 21 | 4 | 135 |
|  | 5-6 | R-20 | 95 | 48 | 22 | 3.9 | 150 |
|  | 5-7 | R-21 | 95 | 50 | 23 | 4 | 150 |
|  | 5-8 | R-22 | 95 | 49 | 22 | 4.1 | 150 |
| Comparative Example | 4-1 | CR-8 | 95 | 55 | 18 | 4.6 | 100 |
|  | 4-2 | CR-9 | 95 | 54 | 20 | 4.4 | 100 |
|  | 4-3 | CR-10 | 95 | 56 | 17 | 4.5 | 100 |
|  | 4-4 | CR-11 | 95 | 55 | 18 | 4.4 | 100 |
|  | 4-5 | CR-12 | 95 | 54 | 17 | 4.5 | 80 |

It is demonstrated in Table 6 that chemically amplified resist compositions comprising PAGs within the scope of the invention exhibit a high sensitivity and improved values of EL, LWR and DOF. The resist compositions are useful in the EUV lithography process.

Japanese Patent Application No. 2020-166632 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the formula (1):

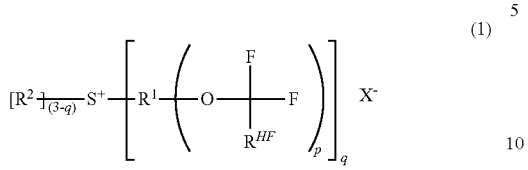
(1)

wherein p is an integer of 1 to 5, q is an integer of 1 to 3,
$R^{HF}$ is hydrogen or fluorine,
$R^1$ is a $C_1$-$C_{20}$ (p+1)-valent hydrocarbon group which may contain a heteroatom,
$R^2$ is a $C_6$-$C_{20}$ aryl group or $C_7$-$C_{20}$ aralkyl group which may contain a heteroatom,
in case of q=1, any two of $R^1$ and two $R^2$ may bond together to form a ring with the sulfur atom to which they are attached, in case of q=2, any two of two $R^1$ and $R^2$ may bond together to form a ring with the sulfur atom to which they are attached, in case of q=3, any two of three $R^1$ may bond together to form a ring with the sulfur atom to which they are attached, wherein the ring is selected from the group consisting of the following formulae:

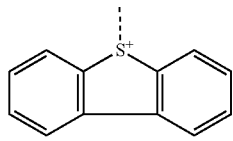

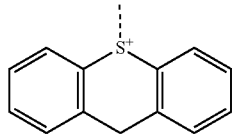

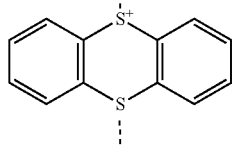

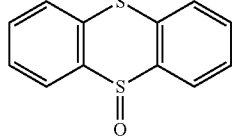

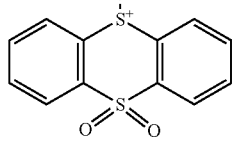

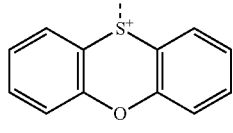

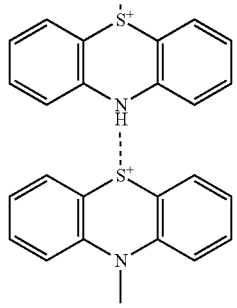

$X^-$ is a non-nucleophilic anion selected from the formulae (2A) to (2D):

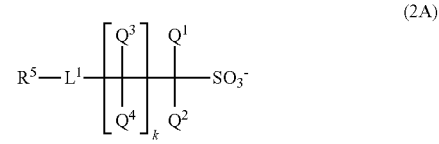
(2A)

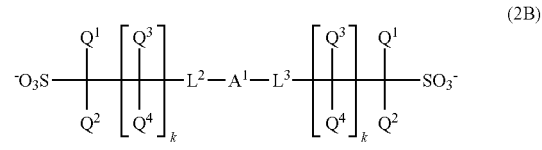
(2B)

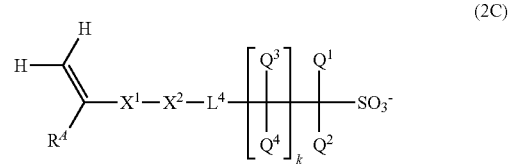
(2C)

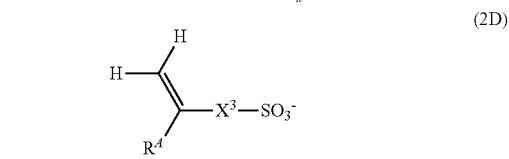
(2D)

wherein $Q^1$ and $Q^2$ are each independently fluorine or a $C_1$-$C_6$ fluorinated alkyl group,
$Q^3$ and $Q^4$ are each independently hydrogen, fluorine or a $C_1$-$C_6$ fluorinated alkyl group,
k is an integer of 0 to 4,
$L^1$ to $L^4$ are each independently a single bond, ether bond, ester bond, sulfonic ester bond, carbonate bond or carbamate bond,
$R^5$ is a $C_1$-$C_{30}$ hydrocarbyl group which may contain a heteroatom,
$A^1$ is a $C_1$-$C_{30}$ hydrocarbylene group which may contain a heteroatom,
$R^A$ is each independently hydrogen, fluorine, methyl or trifluoromethyl,
$X^1$ is a single bond, phenylene, naphthylene or (backbone)-C(=O)-O-$X^{11}$-, $X^{11}$ is a $C_1$-$C_{10}$ aliphatic hydrocarbylene group which may contain a hydroxy moiety, ether bond, ester bond or lactone ring, or phenylene or naphthylene group,
$X^2$ is a single bond or -$X^{21}$-C(=O)-O-, $X^{21}$ is a $C_1$-$C_{20}$ hydrocarbylene group which may contain a heteroatom, and
$X^3$ is a single bond, methylene, ethylene, phenylene, fluorinated phenylene, trifluoromethyl-substituted phenylene, —O—X³¹—, —C(=O)—O—X³¹—, or —C(=O)—NH—X³¹—, X³¹ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety.

2. The sulfonium salt of claim 1, having the formula (1A):

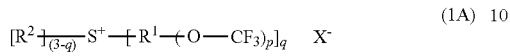
(1A)

wherein $R^1$, $R^2$, p, q, and $X^-$ are as defined above.

3. The sulfonium salt of claim 2, having the formula (1B):

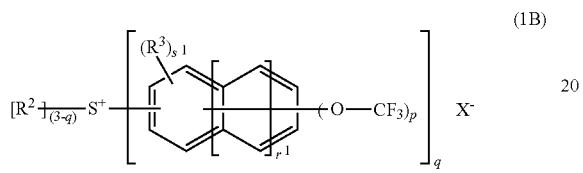
(1B)

wherein $R^2$, p, q, and $X^-$ are as defined above,
$R^3$ is a $C_1$-$C_{20}$ hydrocarbyl group which may contain a heteroatom,
$r^1$ is an integer of 0 to 2, and $s^1$ is an integer of 0 to ($2r^1+4$).

4. The sulfonium salt of claim 3, having the formula (1C):

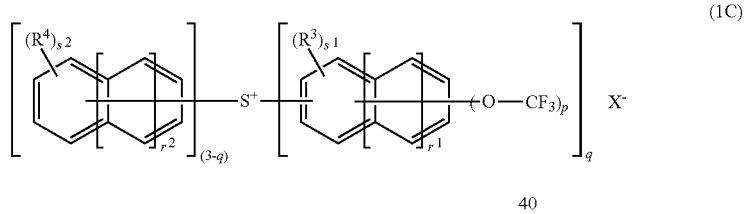
(1C)

wherein $R^3$, p, q, $r^1$, $s^1$, and $X^-$ are as defined above,
$R^4$ is a $C_1$-$C_{20}$ hydrocarbyl group which may contain a heteroatom,
$r^2$ is an integer of 0 to 2, and $s^2$ is an integer of 0 to ($2r^2+4$).

5. The sulfonium salt of claim 1 wherein $X^-$ is an anion selected from the formulae (2A-1) to (2C-1):

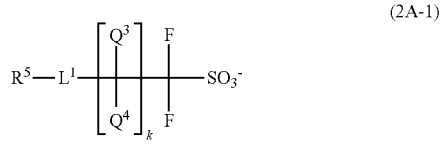
(2A-1)

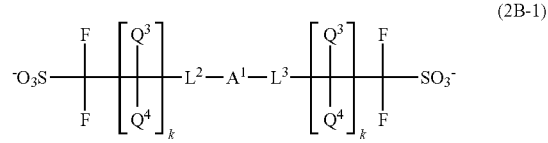
(2B-1)

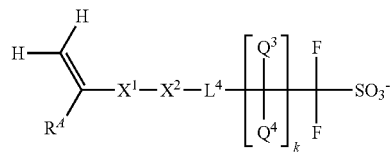
(2C-1)

wherein $Q^3$, $Q^4$, $R^5$, $L^1$ to $L^4$, $A^1$, $R^4$, $X^1$, $X^2$, and k are as defined above.

6. The sulfonium salt of claim 5 wherein $X^-$ is an anion selected from the formulae (2A-2) to (2C-2):

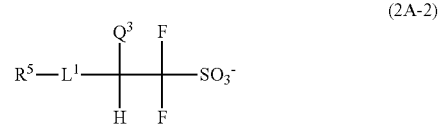
(2A-2)

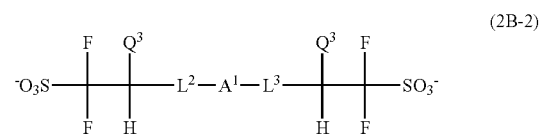
(2B-2)

-continued

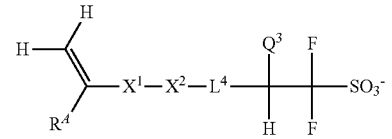
(2C-2)

wherein $Q^3$, $R^5$, $L^1$ to $L^4$, $A^1$, $R^4$, $X^1$, and $X^2$ are as defined above.

7. A photoacid generator comprising a sulfonium salt having the formula (1):

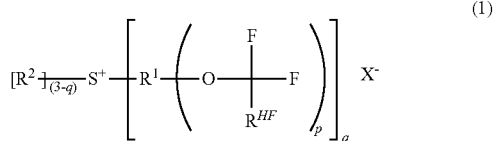
(1)

wherein p is an integer of 1 to 5, q is an integer of 1 to 3,
$R^{HF}$ is hydrogen or fluorine,
$R^1$ is a $C_1$-$C_{20}$ (p+1)-valent hydrocarbon group which may contain a heteroatom, $R^2$ is a $C_6$-$C_{20}$ aryl group or $C_7$-$C_{20}$ aralkyl group which may contain a heteroatom, in case of q=1, any two of $R^1$ and two $R^2$ may bond together to form a ring with the sulfur atom to which they are attached, in case of q=2, any two of two $R^1$ and $R^2$ may bond together to form a ring with the sulfur atom to which they are attached, in case of q=3, any two of three $R^1$ may bond together to form a ring with the sulfur atom to which they are attached, wherein the ring is selected from the group consisting of the following formulae:

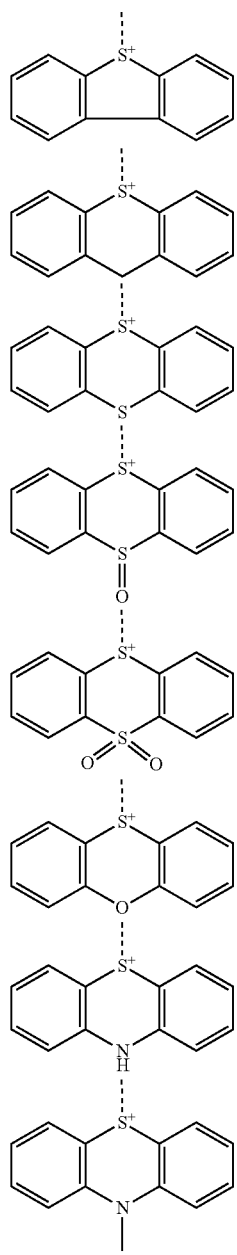

$X^-$ is a non-nucleophilic anion.

8. A chemically amplified resist composition comprising the photoacid generator of claim 7 and a base polymer comprising repeat units having the formula (a1) or (a2):

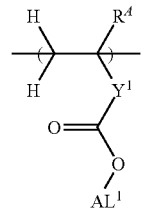
(a1)

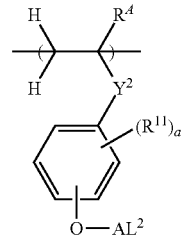
(a2)

wherein $R^A$ is each independently hydrogen, fluorine, methyl or trifluoromethyl, $Y^1$ is a single bond, phenylene, naphthylene or (backbone)-C(=O)—O—$Y^{11}$—, $Y^{11}$ is a $C_1$-$C_{10}$ alkanediyl group which may contain a hydroxy moiety, ether bond, ester bond or lactone ring, or phenylene or naphthylene group, $Y^2$ is a single bond or (backbone)-C(=O)—O—, $AL^1$ and $AL^2$ are each independently an acid labile group, $R^{11}$ is a $C_1$-$C_{20}$ hydrocarbyl group which may contain a heteroatom, and a is an integer of 0 to 4.

9. A chemically amplified resist composition comprising a base polymer comprising repeat units having the formula (a1) or (a2) and repeat units having the formula (a3) or (a4):

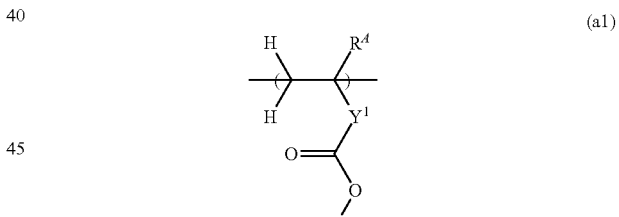

wherein $R^A$ is each independently hydrogen, fluorine, methyl or trifluoromethyl, $Y^1$ is a single bond, phenylene, naphthylene or (backbone)-C(=O)—O—$Y^{11}$—, $Y^{11}$ is a $C_1$-$C_{10}$ alkanediyl group which may contain a hydroxy moiety, ether bond, ester bond or lactone ring, or phenylene or naphthylene group, $Y^2$ is a single bond or (backbone)-C(=O)—O—, AL$^1$ and AL$^2$ are each independently an acid labile group, R$^{11}$ is a C$_1$-C$_{20}$ hydrocarbyl group which may contain a heteroatom, and a is an integer of 0 to 4,

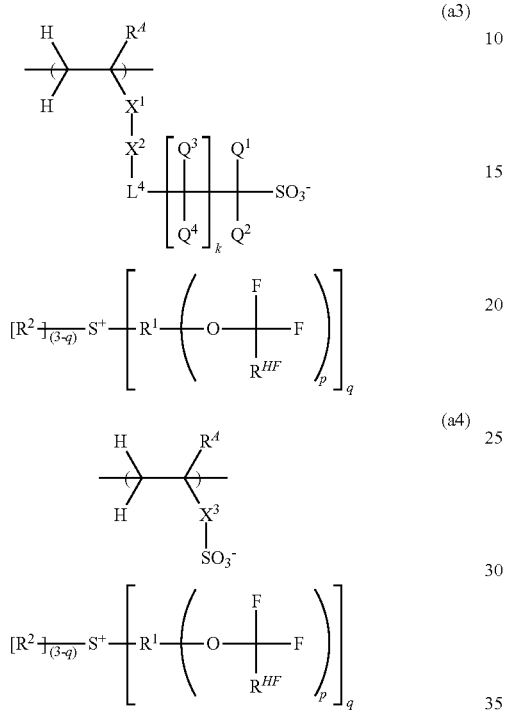

(a3)

(a4)

wherein p is an integer of 1 to 5, q is an integer of 1 to 3,

R$^{HF}$ is hydrogen or fluorine,

R$^1$ is a C$_1$-C$_{20}$ (p+1)-valent hydrocarbon group which may contain a heteroatom, R$^2$ is a C$_6$-C$_{20}$ aryl group or C$_7$-C$_{20}$ aralkyl group which may contain a heteroatom, in case of q=1, any two of R$^1$ and two R$^2$ may bond together to form a ring with the sulfur atom to which they are attached, in case of q=2, any two of two R$^1$ and R$^2$ may bond together to form a ring with the sulfur atom to which they are attached, in case of q=3, any two of three R$^1$ may bond together to form a ring with the sulfur atom to which they are attached, wherein the ring is selected from the group consisting of the following formulae:

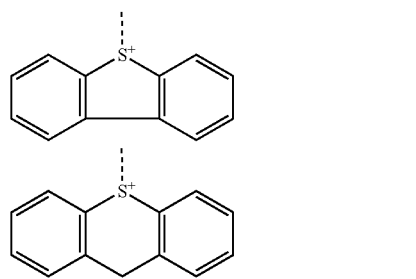

-continued

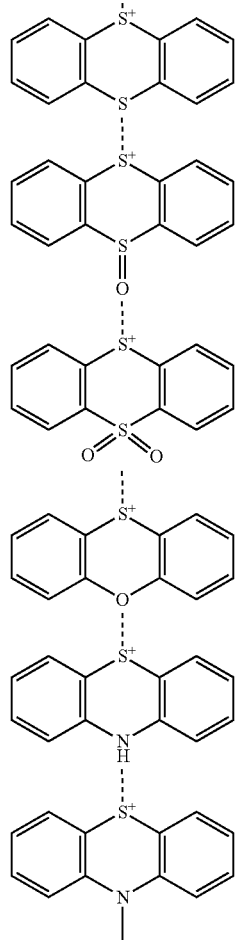

L$^4$ is each independently a single bond, ether bond, ester bond, sulfonic ester bond, carbonate bond or carbamate bond, R$^A$ is each independently hydrogen, fluorine, methyl or trifluoromethyl, X$^1$ is a single bond, phenylene, naphthylene or (backbone)-C(=O)-O-X$^{11}$-, X$^{11}$ is a C$_1$-C$_{10}$ aliphatic hydrocarbylene group which may contain a hydroxy moiety, ether bond, ester bond or lactone ring, or phenylene or naphthylene group, X$^2$ is a single bond or -X$^{21}$-C(=O)-O-, X$^{21}$ is a C$_1$-C$_{20}$ hydrocarbylene group which may contain a heteroatom, X$^3$ is a single bond, methylene, ethylene, phenylene, fluorinated phenylene, trifluoromethyl-substituted phenylene, -O-X$^{31}$-, -C(=O)-O-X$^{31}$-, or -C(=O)-NH-X$^{31}$-, X$^{31}$ is a C$_1$-C$_6$ aliphatic hydrocarbylene group, phenylene group, fluorinated phenylene group, or trifluoromethyl-substituted phenylene group, which may contain a carbonyl moiety, ester bond, ether bond or hydroxy moiety, and k is an integer of 0 to 4.

10. The resist composition of claim 8 wherein the base polymer further comprises repeat units having the formula (b1) or (b2):

(b1)

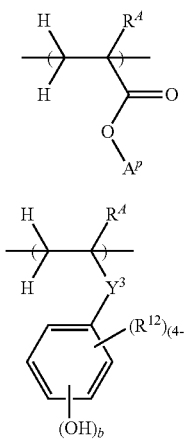

(b2)

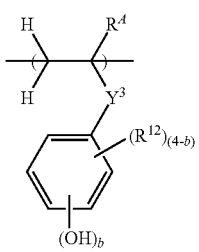

wherein $R^A$ is each independently hydrogen, fluorine, methyl or trifluoromethyl, $A^P$ is hydrogen or a polar group containing at least one structure selected from the group consisting of hydroxy, cyano, carbonyl, carboxy, ether bond, ester bond, sulfonic ester bond, carbonate bond, lactone ring, sultone ring and carboxylic anhydride, $Y^3$ is a single bond or (backbone)-C(=O)—O—, $R^{12}$ is halogen, cyano, a $C_1$-$C_{20}$ hydrocarbyl group which may contain a heteroatom, a $C_1$-$C_{20}$ hydrocarbyloxy group which may contain a heteroatom, or a $C_2$-$C_{20}$ hydrocarbylcarbonyl group which may contain a heteroatom, and b is an integer of 1 to 4.

11. The resist composition of claim 8 wherein the base polymer further comprises repeat units of at least one type selected from repeat units having the formulae (c1) to (c3):

(c1)

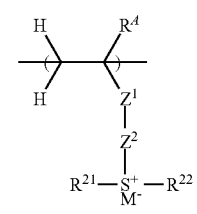

(c2)

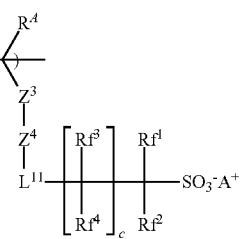

(c3)

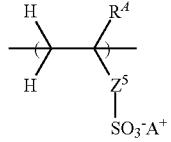

wherein $R^A$ is each independently hydrogen, fluorine, methyl or trifluoromethyl, $Z^1$ is a single bond or phenylene group, $Z^2$ is —C(=O)—O—$Z^{21}$—, —C(=O)—NH—$Z^{21}$—, —O—$Z^{21}$—, $Z^{21}$ is a $C_1$-$C_6$ aliphatic hydrocarbylene group, phenylene group or a divalent group obtained by combining the foregoing, which may contain a carbonyl moiety, ester bond, ether bond or hydroxy moiety, $Z^3$ is a single bond, phenylene, naphthylene, or (backbone)-C(=O)—O—$Z^{31}$—, $Z^{31}$ is a $C_1$-$C_{10}$ aliphatic hydrocarbylene group which may contain a hydroxy moiety, ether bond, ester bond or lactone ring, or phenylene or naphthylene group, $Z^4$ is a single bond or —$Z^{41}$—C(=O)—O—, $Z^{41}$ is a $C_1$-$C_{20}$ hydrocarbylene group which may contain a heteroatom, $Z^5$ is a single bond, methylene, ethylene, phenylene, fluorinated phenylene, trifluoromethyl-substituted phenylene, —C(=O)—O—$Z^{51}$—, —C(=O)—NH—$Z^{51}$—, or —O—$Z^{51}$—, $Z^{51}$ is a $C_1$-$C_6$ aliphatic hydrocarbylene group, phenylene group, fluorinated phenylene group or trifluoromethyl-substituted phenylene group, which may contain a carbonyl moiety, ester bond, ether bond or hydroxy moiety, $R^{21}$ and $R^{22}$ are each independently a $C_1$-$C_{20}$ hydrocarbyl group which may contain a heteroatom, $R^{21}$ and $R^{22}$ may bond together to form a ring with the sulfur atom to which they are attached, $L^{11}$ is a single bond, ether bond, ester bond, carbonyl group, sulfonic ester bond, carbonate bond or carbamate bond, $Rf^1$ and $Rf^2$ are each independently fluorine or a $C_1$-$C_6$ fluorinated alkyl group, $Rf^3$ and $Rf^4$ are each independently hydrogen, fluorine, or a $C_1$-$C_6$ fluorinated alkyl group, $M^-$ is a non-nucleophilic counter ion, $A^+$ is an onium cation, and c is an integer of 0 to 3.

12. The resist composition of claim 8, further comprising an organic solvent.

13. The resist composition of claim 8, further comprising a quencher.

14. The resist composition of claim 8, further comprising a surfactant which is insoluble or substantially insoluble in water and soluble in alkaline developer, and/or a surfactant which is insoluble or substantially insoluble in water and alkaline developer.

15. A pattern forming process comprising the steps of applying the chemically amplified resist composition of claim 8 to form a resist film on a substrate, exposing a selected region of the resist film to KrF excimer laser, ArF excimer laser, EB or EUV, and developing the exposed resist film in a developer.

16. The pattern forming process of claim 15 wherein the developing step uses an alkaline aqueous solution as the developer, thereby forming a positive pattern in which an exposed region of the resist film is dissolved away and an unexposed region of the resist film is not dissolved.

17. The pattern forming process of claim 15 wherein the developing step uses an organic solvent as the developer, thereby forming a negative pattern in which an unexposed region of the resist film is dissolved away and an exposed region of the resist film is not dissolved.

18. The process of claim 15 wherein the exposure step is carried out by immersion lithography while a liquid having a refractive index of at least 1.0 is held between the resist film and a projection lens.

19. The process of claim 18, further comprising the step of forming a protective film on the resist film prior to the exposure step, wherein immersion lithography is carried out while the liquid is held between the protective film and the projection lens.

\* \* \* \* \*